US007282578B2

(12) United States Patent
Markl et al.

(10) Patent No.: US 7,282,578 B2
(45) Date of Patent: Oct. 16, 2007

(54) NUCLEIC ACID MOLECULE COMPRISING A NUCLEIC ACID SEQUENCE WHICH CODES FOR A HAEMOCYANIN

(75) Inventors: Jürgen Markl, Gau-Bischofsheim (DE); Benjamin Altenhein, Weisbaden (DE); Bernhard Lieb, Mainz (DE); Thomas Stiefel, Stuttgart (DE)

(73) Assignee: Biosyn Arzneimittel GmbH, Fellbach (DE)

( * ) Notice: Subject to any disclaimer, the term of this patent is extended or adjusted under 35 U.S.C. 154(b) by 0 days.

(21) Appl. No.: 11/511,952

(22) Filed: Aug. 29, 2006

(65) Prior Publication Data

US 2007/0077229 A1 Apr. 5, 2007

Related U.S. Application Data

(62) Division of application No. 09/936,852, filed as application No. PCT/EP00/02410 on Mar. 17, 2000, now Pat. No. 7,125,556.

(30) Foreign Application Priority Data

Mar. 17, 1999 (DE) ................................ 199 11 971
Aug. 20, 1999 (DE) ................................ 199 39 578

(51) Int. Cl.
*C07H 21/00* (2006.01)

(52) U.S. Cl. ................................................... 536/23.1

(58) Field of Classification Search ................ 530/350, 530/857; 424/278.1; 536/23.1
See application file for complete search history.

(56) References Cited

U.S. PATENT DOCUMENTS

| | | | |
|---|---|---|---|
| 5,021,560 | A | 6/1991 | Montreuil et al. |
| 5,831,033 | A | 11/1998 | Zetter et al. |
| 5,888,775 | A | 3/1999 | Tal et al. |

FOREIGN PATENT DOCUMENTS

| | | | |
|---|---|---|---|
| EP | 0244295 | A1 | 11/1987 |
| EP | 0621039 | A1 | 10/1994 |
| EP | 0252829 | A1 | 1/1999 |
| WO | WO94/11019 | | 5/1994 |
| WO | WO 00/55192 | | 9/2000 |

OTHER PUBLICATIONS

Geyer et al., "Identification and Characterization of Keyhole Limpet Hemocyanin *N*-Glycans Mediating Cross-reactivity with *Schistosoma mansoni", J. of Biol. Chem.*, 280(49):40731-40748 (2005).

Kurokawa et al., "Hemocyanin from the keyhole dlmpet *Megathura crenulata* (KLH) carries a novel type of N-glycans with Gal(β1-6)Man-motifs", *Eur. J. Biochem*, 269:5459-5473 (2002).

J. V. Hamilton, et al., "Periodate-Sensitive Immunological Cross-Reactivity Between Keyhole Limpet Haemocyanin (KLH) and Serodiagnostic *Schistosoma mansoni* Egg Antigens." *Parasitology*, 118:83-89 (Jan. 1, 1999).

Karen I. Miller, et al., "Sequence of the *Octopus dofleini* Hemocyanin Subunit: Structural and Evoluntionary Implications," *J. Mol. Biol.* 278: 827-842 (May 15, 1998).

Stanka Stoeva, et al., "Primary Structure and Unusual Carbohydrate Moiety of Functional Unit 2-*c* of Keyhole Limpet Hemocyanin (KLH),"*Bioclinica et Biophysica Acta.*, 1435: 94-109 (Nov. 16, 1999).

Wolfgang Gebauer, et al., Keyhole Limpet Hemocyanin Type 2 (KLH2): Detection and Immunolocalization of a Labile Functional Unit *h, Journal of Structural Biology* 128: 280-286 (Dec. 30, 1999).

J. Robin Harris, et al., "Immunoelectron Microscopy of Hemocyanin from the Keyhole Limpet (*Megathura crenulata*): A Parallel Subunit Model," *Journal of Structural Biology*, 111: 96-104 (1993).

M. Rocia A. Carrera, et al., "Cocaine Vaccines: Antibody Protection Against Relapse in a Rat Model," *PNAS*, 97(11) 6202-6206 (May 23, 2000).

Sabine M. Söhngen, et al., "Mass Determination, Subunit Organization and Control of Obligomerization States of Keyhole Limpet Hemocyanin (KLH)," *Eur. J. Biochem.*, 248: 602-624 (1997).

M. Rocio A. Carrera, et al., "Suppression of Psychoactive Effects of Cocaine by Active Immunization," *NATURE*, 378: 727-730 (Dec. 14, 1995).

Bernhard Lieb, et al., The Sequence of a Gastropod Hemocyanin (HtH1 from *Haliotis tuberculata*), *The Journal of Biological Chemistry*, 275(8) 5675-5681 (Feb. 25, 2000).

Bernhard Lieb, et al., "Subunit Organization of the Abalone *Haliotis tuberculata* Hemocyanin Type 2 (HtH2), and the cDNA Sequence Encoding its Functional Units d, e, f, g and h," *Eur. J. Biochem.*265: 134-144 (Oct. 1999).

(Continued)

*Primary Examiner*—Karen Cochrane Carlson
*Assistant Examiner*—Suzanne M. Noakes
(74) *Attorney, Agent, or Firm*—Welsh & Katz, Ltd.

(57) ABSTRACT

A nucleic acid molecule or construct alone or with a promoter suitable for expression control is contemplated that codes for a KLH1 haemocyanin, a haemocyanin domain or a fragment thereof with the immunological properties of at least one domain of haemocyanin, and comprises at least one intron sequence, as well as haemocyanin fusion proteins. The construct can also comprise a nucleic acid sequence that codes for an antigen. Host cells are also contemplated that contain the nucleic acid molecule or construct and a recombinant expression product thereof. The invention further relates to a pharmaceutical composition that comprises the expression product and antibodies obtainable by immunization of an animal therewith, as well as the use of antibodies in screening methods for the identification of tumors.

31 Claims, 29 Drawing Sheets

OTHER PUBLICATIONS

Richard D. Swerdlow, et al., "Keyhole Limpet Hemocyanin: Structural and Functional Characterization of Two Different Subunits and Multimers," *Comp. Biochem. Physiol.*, 113B (3) 537-548 (1996).
Henning Keller, et al., "Abalone (*Haliotis tuberculata*) Hemocyanin Type 1 (HtH1) Organization of the =400 kDa Subunit, and Amino Acid Sequence of its Functional Units f, g and h," *Eur. J. Biochem.* 264: 27-39 (Aug. 1999).
J. Robin Harris, et al., "Keyhole Limpet Haemocyanin (KLH): Purification of Intact KLH1 Through Selective Dissociation of KLH2," *Micron*, 26(3) 201-212 (1995).
Wolfgang Gebauer, et al., "Quaternary Structure, Subunits and Domain Patterns of Two Discrete Forms of Keyhole Limpet Hemocyanin: KLH*1* and KLH*2,*" *Zoology* 98: 51-68 (1994.
Lieb et al., "Structures of two molluscan hemocyanin genes: Significance for gene evolution", *PNAS* 98(8):4546-4551 (Apr. 2001).
Drexel et al., "Complete Amino-Acid Sequence of a Functional Unit from a Molluscan Hemocyanin (*Helix pomatia*)", *Biol. Chem. Hoppe-Seyler* 386:617-635 (Jun. 1987.
International Search Report from PCT/EP00/02410, dated Jul. 3, 1999.

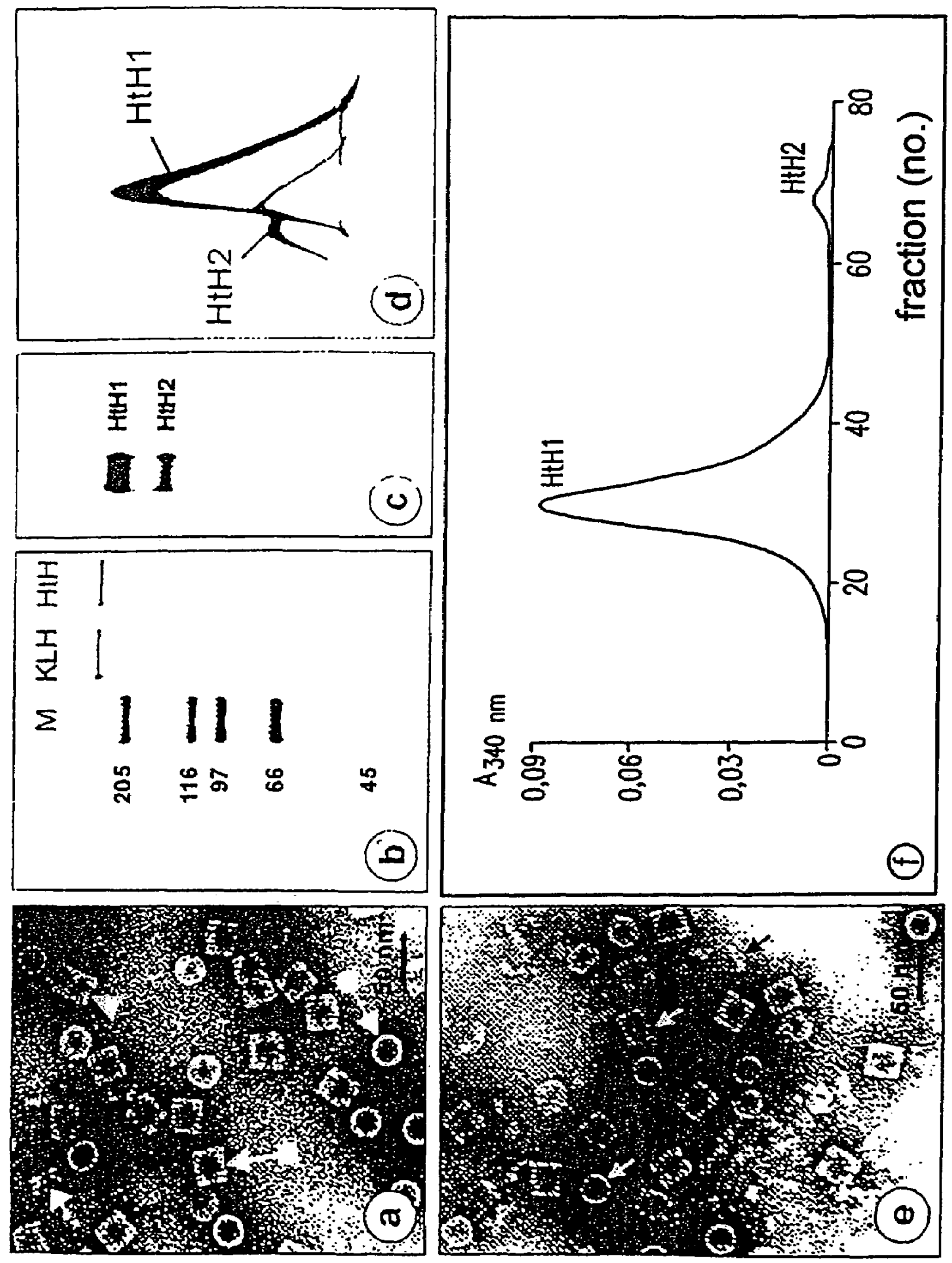
Fig. 1a-f
a
50 nm
b
M KLH HtH
205
116
97
66
45
c
HtH1
HtH2
d
HtH2
HtH1
e
50 nm
f
A340 nm
0,09
0,06
0,03
0
HtH1
HtH2
0
20
40
60
80
fraction (no.)

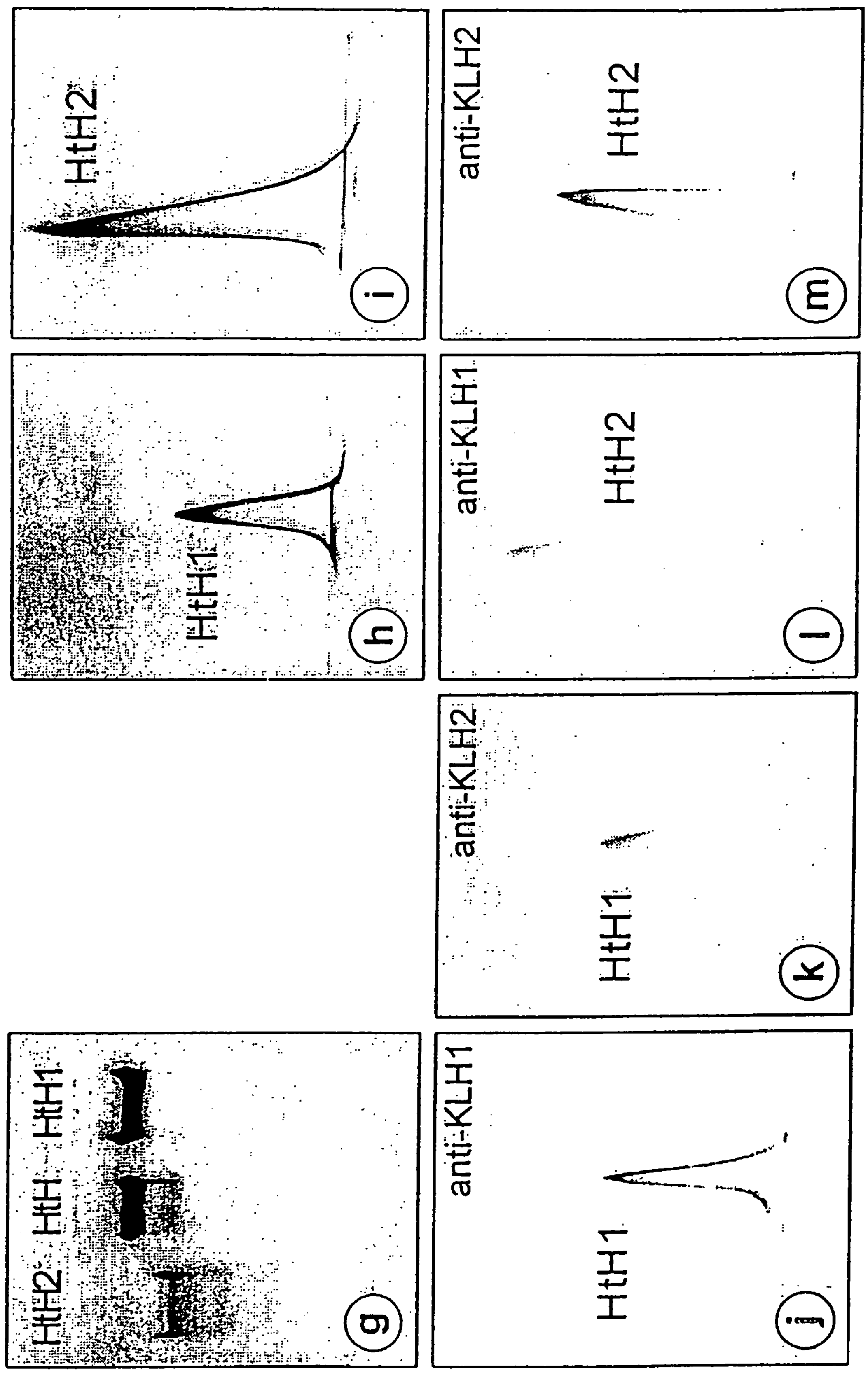
Fig. 1g-m
HtH2 HtH HtH1
g
HtH1
h
HtH2
i
anti-KLH1
HtH1
j
anti-KLH2
HtH1
k
anti-KLH1
HtH2
l
anti-KLH2
HtH2
m

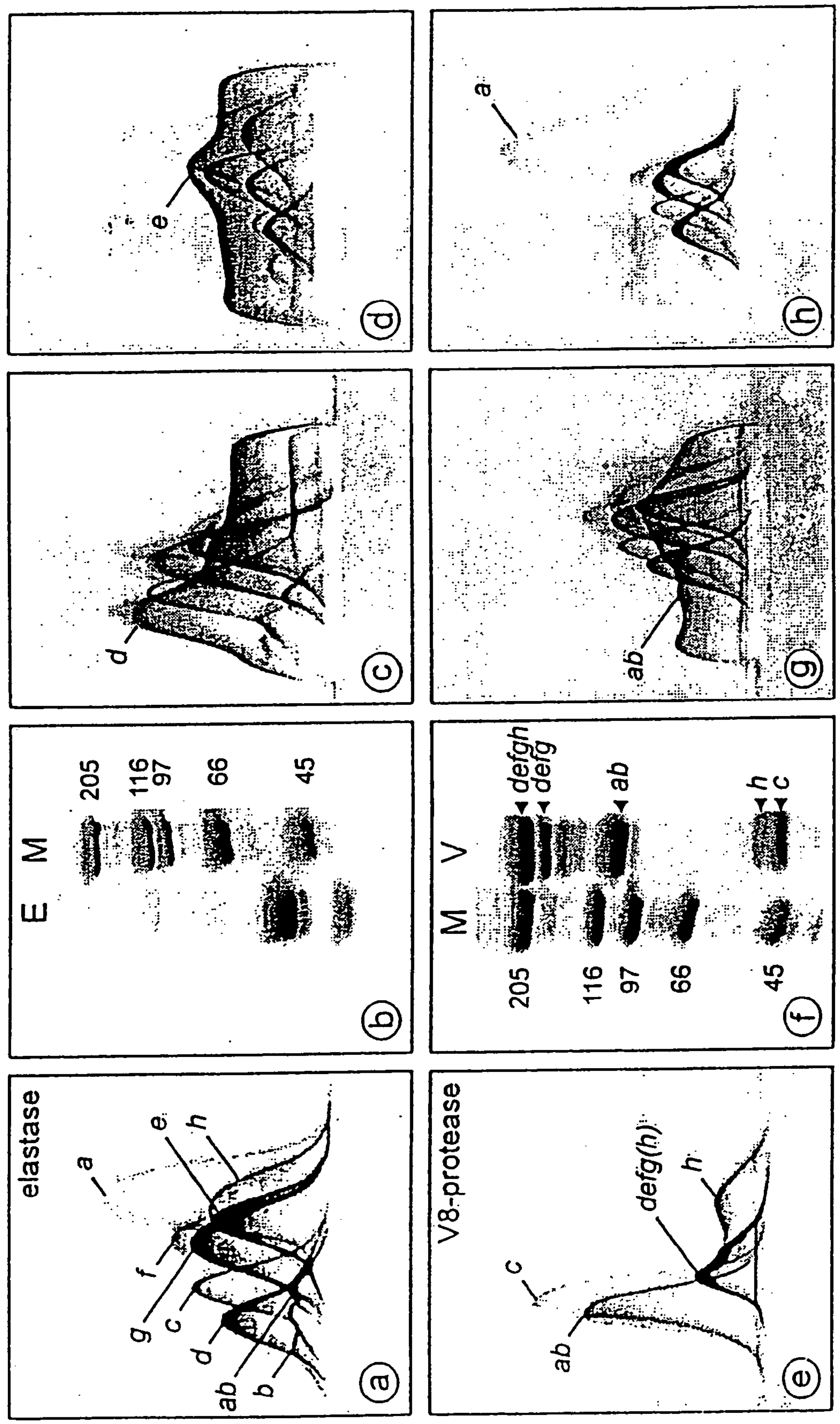
Fig. 2a-h
elastase
V8-protease
E M
M V
205
116
97
66
45
defgh
defg
ab
defg(h)

Fig. 2i-p
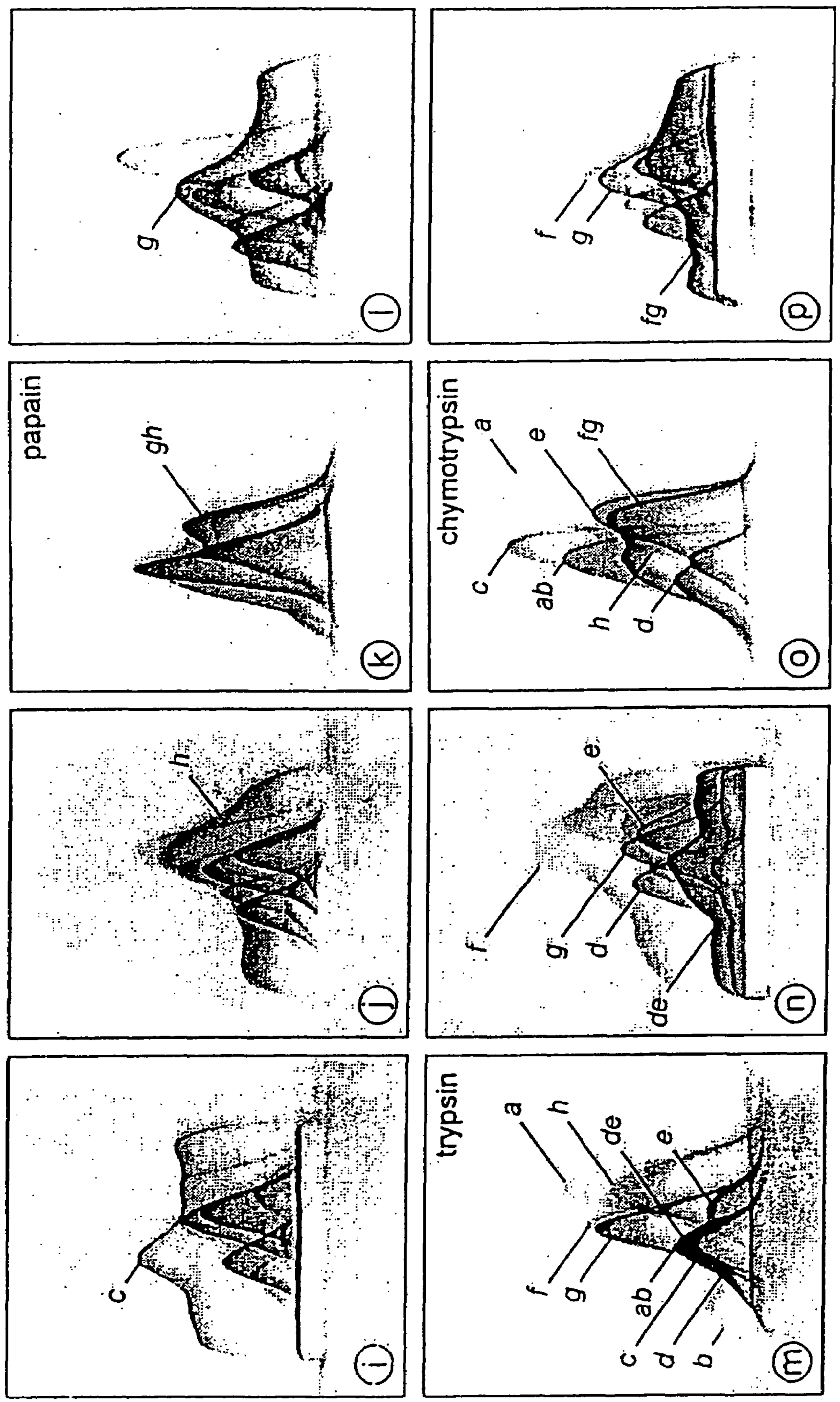

Fig. 3a-c
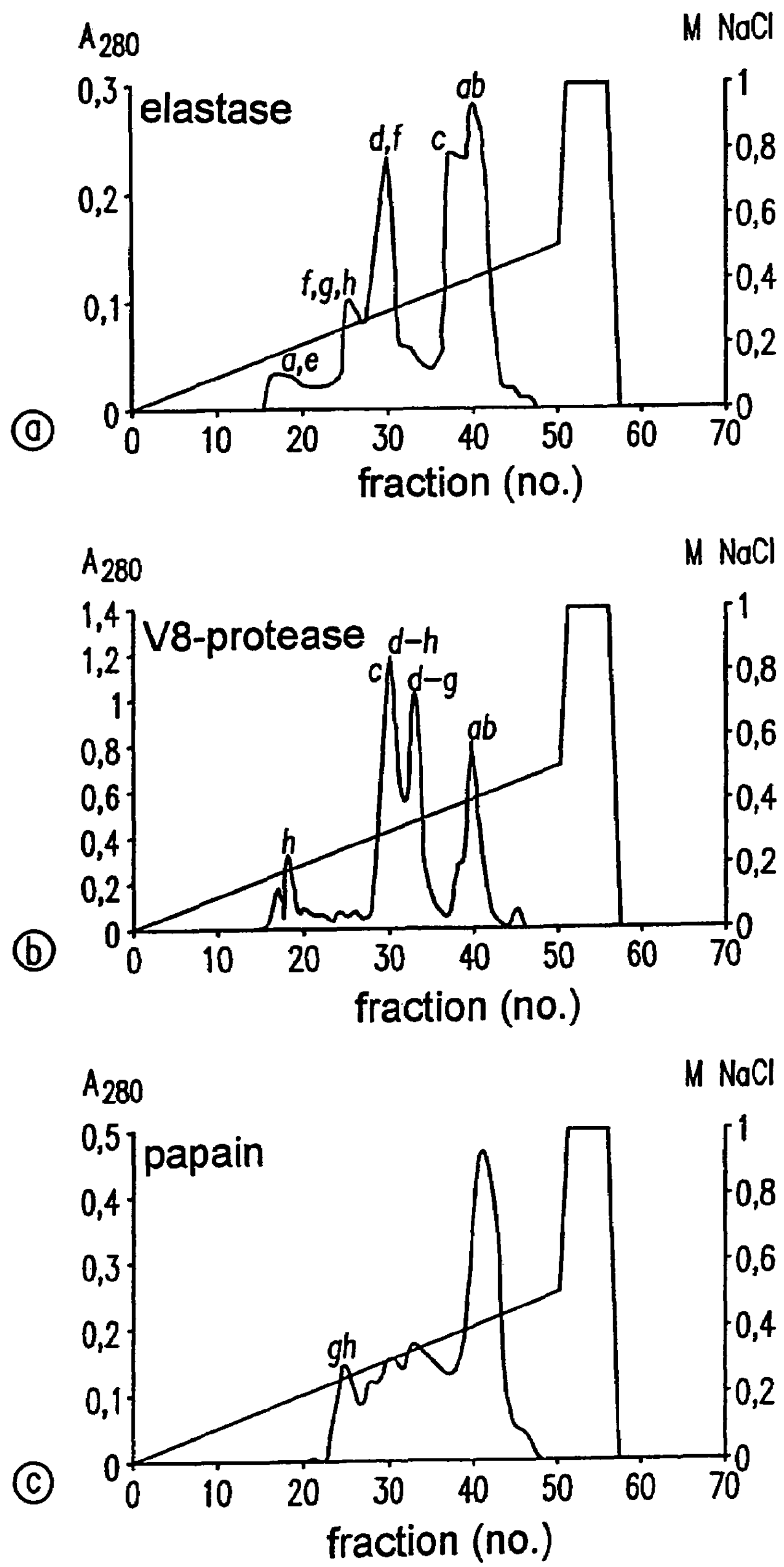

Fig. 3d-e
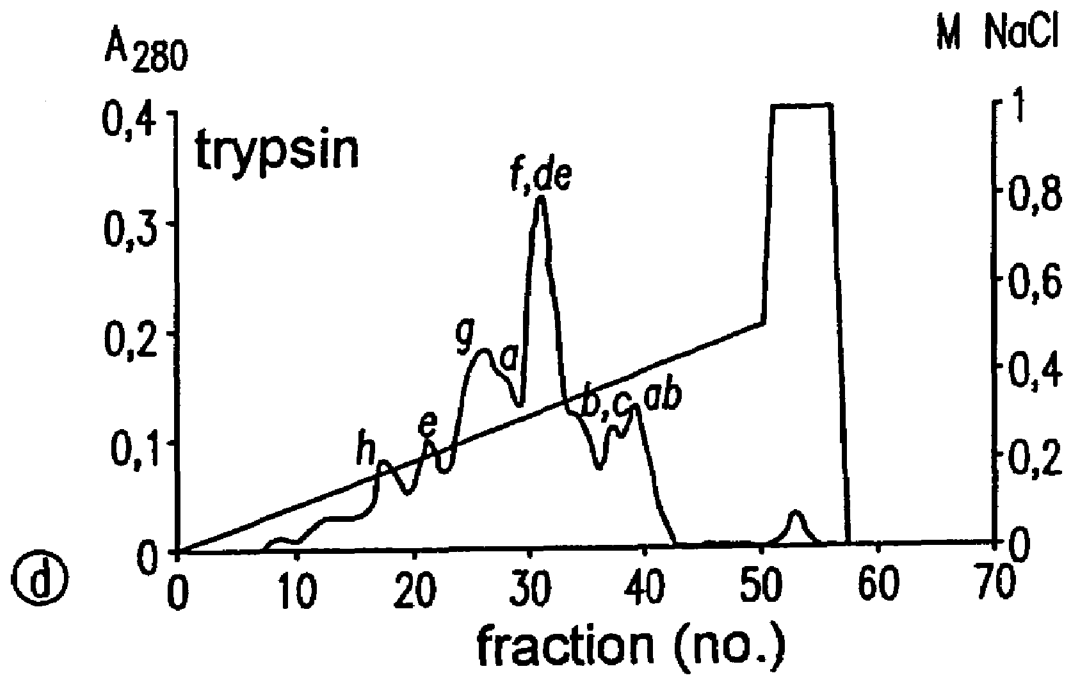
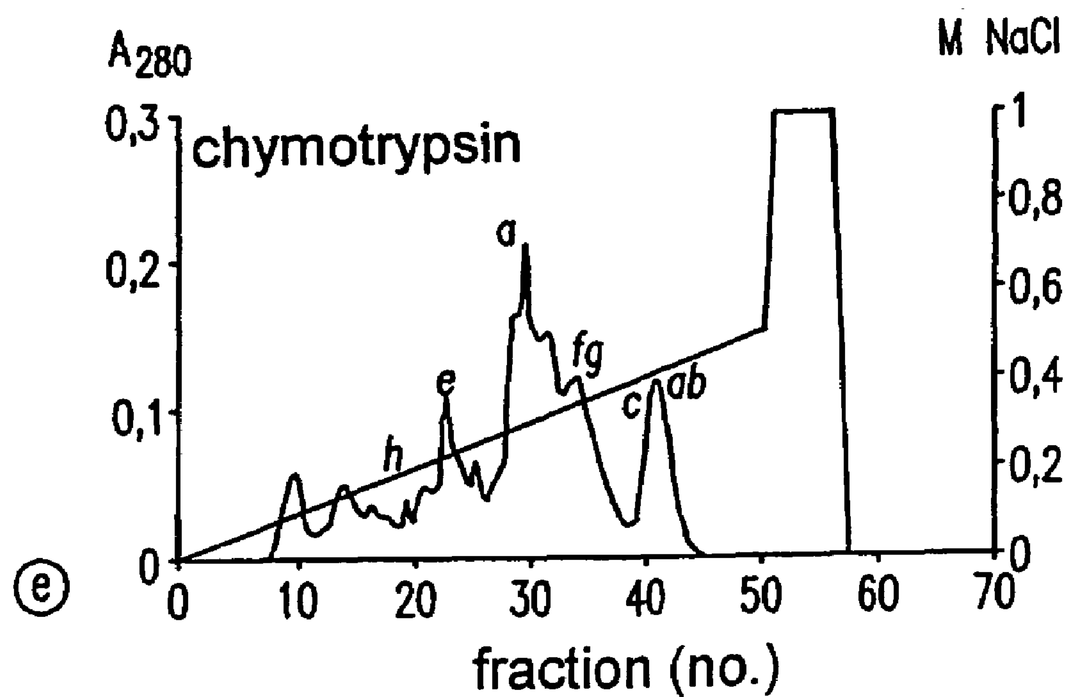

Figure 4

HtH1 cDNA sequence and intron structure

Domain a

GGCTTGTTCAGTTTCTACTCGTCGCCCTTGTGGCGGGGGCTGGAGCAGACAACGTCGTCAG
AAAGGACGTGAGTCACCTCACGGATGACGAGGTGCAAGCTCTCCACGGCGCCCTCCATGAC
GTCACTGCATCTACAGGGCCTCTGAGTTTCGAAGACATAACATCTTACCATGCCGCACCAG
CGTCGTGTGACTACAAGGGACGGAAGATCGCCTGCTGTGTCCACGGTATGCCCAGTTTCCC
CTTCTGGCACAGGGCATATGTCGTCCAAGCCGAGCGGGCACTGTTGTCCAAACGGAAGACT
GTCGGAATGCCTTACTGGGACTGGACGCAAACGCTGACTCACTTACCATCTCTTGTGACTG
AACCCATCTACATTGACAGTAAAGGTGGAAAGGCTCAAACCAACTACTGGTACCGCGGCGA
GATAGCGTTCATCAATAAGAAGACTGCGCGAGCTGTAGATGATCGCCTATTCGAGAAGGTG
GAGCCTGGTCACTACACACATCTTATGGAGACTGTCCTCGACGCTCTCGAACAGGACGAAT
TCTGTAAATTTGAAATCCAGTTCGAGTTGGCTCATAATGCTATCCATTACTTGGTTGGCGG
TAAATTTGAATATTCAATGTCAAACTTGGAATACACCTCCTACGACCCCATCTTCTTCCTC
CACCACTCCAACGTTGACCGCCTCTTCGCCATCTGGCAGCGTCTTCAGGAACTGCGAGGAA
AGAATCCCAATGCAATGGACTGTGCACATGAACTCGCTCACCAGCAACTCCAACCCTTCAA
CAGGGACAGCAATCCAGTCCAGCTCACAAAGGACCACTCGACACCTGCTGACCTCTTTGAT
TACAAACAACTTGGATACAGCTACGACAGCTTAAACCTGAATGGAATGACGCCAGAACAGC
TGAAAACAGAACTAGACGAACGCCACTCCAAAGAACGTGCGTTTGCAAGCTTCCGACTCAG
TGGCTTTGGGGGTTCTGCCAACGTTGTTGTCTATGCATGTGTCCCTGATGATGATCCACGC
AGTGATGACTACTGCGAGAAAGCAGGCGACTTCTTCATTCTTGGGGGTCAAAGCGAAATGC
CGTGGAGATTCTACAGACCCTTCTTCTATGATGTAACTGAAGCGGTACATCACCTTGGAGT
CCCGCTAAGTGGCCACTACTATGTGAAAACAGAACTCTTCAGCGTGAATGGCACAGCACTT
TCACCTGATCTTCTTCCTCAACCAACTGTTGCCTACCGACCTGGGAAAG

Domain b

GTCACCTTGACCCACCTGTGCATCATCGCCACGATGACGATCTTATTGTTCGAAAAAATAT
AGATCATTTGACTCGTGAAGAGGAATACGAGCTAAGGATGGCTCTGGAGAGATTCCAGGCC
GACACATCCGTTGATGGGTACCAGGCTACAGTAGAGTACCATGGCCTTCCTGCTCGTTGTC
CACGACCAGATGCAAAAGTCAGGTTCGCCTGTTGTATGCATGGCATGGCATCCTTCCCTCA
CTGGCACCGGCTGTTCGTTACCCAGGTGGAAGATGCTCTTGTACGGCGTGGATCGCCTATC
GGTGTTCCTTATTGGGACTGGACAAAACCTATGACTCACCTTCCAGACTTGGCATCAAATG
AGACGTACGTAGACCCGTATGGACATACACATCATAATCCATTCTTCAATGCAAATATATC
TTTTGAGGAGGGACACCATCACACGAGCAGGATGATAGATTCGAAACTGTTTGCCCCAGTC
GCTTTTGGGGAGCATTCCCATCTGTTTGATGGAATCCTGTACGCATTTGAGCAGGAAGATT
TCTGCGACTTTGAGATTCAGTTTGAGTTAGTCCATAATTCTATTCATGCGTGGATAGGCGG
TTCCGAAGATTACTCCATGGCCACCCTGCATTACACAGCCTTTGACCCCATTTTCTACCTT
CATCATTCCAATGTCGATCGTCTATGGGCAATCTGGCAAGCTCTTCAAATCAGGAGACACA
AGCCATATCAAGCCCACTGTGCACAGTCTGTGGAACAGTTGCCAATGAAGCCATTTGCTTT
CCCATCACCTCTTAACAACAACGAGAAGACACATAGTCATTCAGTCCCGACTGACATTTAT
GACTACGAGGAAGTGCTGCACTACAGCTACGATGATCTAACGTTTGGTGGGATGAACCTTG
AAGAAATAGAAGAAGCTATACATCTCAGACAACAGCATGAACGAGTCTTCGCGGGATTTCT
CCTTGCTGGAATAGGAACATCTGCACTTGTTGACATTTTCATAAATAAACCGGGGAACCAA
CCACTCAAAGCTGGAGATATTGCCATTCTTGGTGGTGCCAAGGAAATGCCTTGGGCGTTTG
ACCGCTTGTATAAGGTCGAAATAACTGACTCATTGAAGACACTTTCTCTCGATGTCGATGG
AGATTATGAAGTCACTTTTAAAATTCATGATATGCACGGAAACGCTCTTGATACGGACCTG
ATTCCACACGCAGCAGTTGTTTCTGAGCCAGCTCACC

Intron b/c

GTAAGTAAATTTACAAAATTTGGTGTTCTCTAACTATCCTAAGTATTCAATCGTTAGCGTG
TACCTATCTGCATAATGCAATACCCTGACTCCATATAAGTATAGTATATTTACTCTGGTCG
AAAACAAACAAATTGAAAACAAGAGTGGACGTGCTGTTATGATTTCTTTTTCATTCTTGGT
TCGTTGTGTAATGCCACAGCCAGCAATTCCAGATATATAGCGACGGTCTATGAATACTCCA
GTCTGGACCAGACAATCGTGTGGAATGGTTTAGGCACATTATATCAAATTCATTGTTGAAG
ATATGAGTTATGAGGTCACAATGTTGTCTTGTTACCCCGTGTCAGTAGTGACGTCATTTCA
TGACTGAAATCTCTTCAACGCCGTTTAGCAATAATAGGCTCAGTAGTATTCAACCAATTAC
AATCAGTAGAAAATTCTCTATACTATTCTTATGTTGCATCCTGATATCCCTATGCAAAAAT
TAGTCATCTAATATAATCATTTTCGATAAATACTTTGGGCAAACAAATCAATGTAACATCT
ATTTTCTTTCAG

Domain c

CTACCTTTGAGGATGAAAAGCACAGCTTACGAATCAGAAAAAATGTCGACAGCTTGACTCC
TGAAGAAACAAATGAACTGCGTAAAGCCCTGGAGCTTCTTGAAAATGATCATACTGCAGGT
GGATTCAATCAGCTTGGCGCCTTCCATGGAGAGCCTAAATGGTGCCCTAATCCTGAAGCGG
AGCACAAGGTTGCATGCTGTGTTCATGGCATGGCTGTTTTCCCTCATTGGCACAGGCTTCT
TGCTCTCCAGGCGGAGAATGCTCTTAGAAAGCATGGGTACAGTGGTGCTCTACCATACTGG
GATTGGACTCGCCCCCTTTCCCAACTTCCTGATCTGGTTAGTCATGAGCAGTATACAGATC
CTTCCGACCATCACGTGAAGCATAACCCGTGGTTCAATGGCCACATCGATACAGTAAATCA
GGATACCACCAGAAGCGTACGGGAGGATCTTTATCAACAACCTGAATTTGGACATTTCACG
GATATTGCTCAACAAGTCCTCTTAGCATTAGAACAAGATGACTTCTGTTCGTTTGAAGTGC
AGTATGAGATTTCCCATAATTTTATCCATGCACTTGTAGGAGGAACCGACGCTTATGGCAT
GGCATCGCTGAGATATACAGCATACGATCCAATCTTTTTCTTGCATCATTCAAACACCGAC
AGGATCTGGGCTATTTGGCAATCCCTGCAAAAATACAGAGGCAAACCGTACAACACTGCCA
ACTGCGCCATAGAATCTATGAGAAGGCCCCTGCAACCATTTGGACTAAGCAGTGCCATTAA
CCCTGACAGAATCACCAGAGAGCATGCTATCCCGTTTGATGTCTTCAACTATAGAGATAAC
CTTCATTACGTATATGATACCCTGGAATTTAATGGTTTGTCGATTTCACAACTTGATAGAG
AGCTGGAAAAAATCAAGAGTCACGAAAGAGTATTTGCTGGATTCTTGCTGTCGGGGATTAA
AAAATCTGCTCTTGTGAAATTCGAAGTTTGTACTCCACCTGATAATTGTCATAAAGCAGGG
GAGTTTTATCTACTCGGGGACGAAAACGAGATGGCTTGGGCCTATGACCGACTTTTCAAGT
ATGATATTACTCAGGTTCTGGAAGCAAACCATCTACACTTCTATGATCATCTCTTCATTCG
CTACGAAGTCTTTGATCTTAAAGGAGTGAGTTTGGGAACTGACCTGTTCCACACTGCAAAT
GTGGTACATGATTCCGGCACAG

Intron c/d

GTACGTGGATTTGATTACATAGCAATGCTATATGATTTCAGTAATTACAACCTCAAGTCAT
GTAGCCGTTTTAGATTGCATTACATCAAACAGCATTGGATTAAATTGGGGGATTGTCCAGG
CCGCATTATGTTGCATTCCGAAAATAGTTTGTGTCCAGTGTCCACGTTTAAAATTAAACCA
TTTTAATCATATTAGGGATAATTTTAATAGATGTTATAGTGCTTTATTTCATATTGTTACA
GTGGACAGTCACCAAGGACATATTTTACTCTATAGATACACAAACACCAATTAAAACCCTG
CTTTGGAAAGTCTAACTTTTTCCCCACAG

Domain d

GCACCCGTGATCGTGATAACTACGTTGAAGAAGTTACTGGGGCCAGTCATATCAGGAAGAA
TTTGAACGACCTCAATACCGGAGAAATGGAAAGCCTTAGAGCTGCTTTCCTGCATATTCAG
GACGACGGAACATATGAATCTATTGCCCAGTACCATGGCAAACCAGGCAAATGTCAATTGA
ATGATCATAATATTGCGTGTTGTGTCCATGGTATGCCTACCTTCCCCCAGTGGCACAGACT
GTATGTGGTTCAGGTGGAGAATGCTCTCCTAAACAGGGGATCTGGTGTGGCTGTTCCTTAC

TGGGAGTGGACTGCTCCCATAGACCATCTACCTCATTTCATTGATGATGCAACATACTTCA
ATTCCCGACAACAGCGGTACGACCCTAACCCTTTCTTCAGGGGAAAGGTTACTTTTGAAAA
CGCAGTCACAACAAGGGACCCACAAGCCGGGCTCTTCAACTCAGATTATATGTATGAGAAT
GTTTTACTTGCACTGGAGCAGGAAAATTATTGTGACTTTGAAATTCAGTTTGAGCTTGTTC
ATAACGCACTTCATTCCATGCTGGGAGGTAAAGGGCAGTACTCCATGTCCTCCCTGGACTA
TTCTGCGTTTGATCCCGTCTTCTTCCTACATCATGCCAACACGGACAGACTGTGGGCAATC
TGGCAGGAACTACAAAGATTCCGAGAACTGCCTTATGAAGAAGCGAACTGTGCAATCAACC
TCATGCATCAACCACTGAAGCCGTTCAGTGATCCACATGAGAATCACGACAATGTCACTTT
GAAATACTCAAAACCACAGGACGGATTCGACTACCAGAACCACTTCGGATACAAGTATGAC
AACCTTGAGTTCCATCACTTATCTATCCCAAGTCTTGATGCTACCCTGAAGCAAAGGAGAA
ATCACGACAGAGTGTTTGCGGGCTTCCTTCTTCATAACATAGGAACTTCTGCTGACATAAC
TATCTACATATGTCTGCCTGACGGACGGCGTGGCAATGACTGCAGTCATGAGGCGGGAACA
TTCTATATCCTCGGAGGCGAAACAGAGATGCCTTTTATCTTTGACCGTTTGTATAAATTTG
AAATCACCAAACCACTGCAACAGTTAGGAGTCAAGCTGCATGGTGGAGTTTTCGAACTGGA
GCTTGAGATCAAGGCATACAACGGTTCCTATCTGGATCCCCATACCTTTGATCCAACTATC
ATCTTTGAACCTGGAACAG

Intron d/e

GTAATGCCATCTTAATACAGTTCGTTCGTTAAATTATATATGTTCGTTTACAACACCATAC
CTTGAATTGAGGTAATACATCACTTGATATTGATAATGTAATGGTAATTGTTCTTGTTTGT
AAAACCGTTTCTGGGGTGTTTATTCACTATCCACCTGGTGGATAGTGAGTAAACACATTCG
GTTTAATATGGGTATCTAATGGACAGTGAAGTGTGCTGGCTAGGCAGATACCTTGGTTTCT
GTGAATGGAGGTAGTAGAAAGGGGTTTTGATGATTGCAG

Domain e

ATACCCATATCTTGGACCACGACCATGAGGAAGAGATACTTGTCAGGAAGAATATAATTGA
TTTGAGCCCAAGGGAGAGGGTTTCTCTAGTCAAAGCTTTGCAAAGAATGAAGAATGATCGC
TCCGCTGATGGGTACCAAGCCATTGCCTCTTTCCATGCCCTGCCACCACTCTGTCCCAATC
CATCTGCAGCTCACCGTTATGCTTGCTGTGTCCATGGCATGGCTACATTTCCCCAGTGGCA
CAGACTGTACACTGTTCAGGTTCAGGATGCCCTGAGGAGACATGGTTCACTTGTTGGTATT
CCTTACTGGGACTGGACAAAACCAGTCAACGAGTTACCCGAGCTTCTTTCTTCAGCAACAT
TTTATCATCCAATCCGGAATATTAATATTTCAAATCCATTCCTCGGGGCTGACATAGAATT
TGAAGGACCGGGCGTTCATACAGAGAGGCACATAAATACTGAGCGCCTGTTTCACAGTGGG
GATCATGACGGATACCACAACTGGTTCTTCGAAACTGTTCTCTTTGCTTTGGAACAGGAAG
ATTACTGCGATTTTGAAATACAATTTGAGATAGCCCATAATGGCATCCACACATGGATTGG
TGGAAGCGCAGTATATGGCATGGGACACCTTCACTATGCATCATATGATCCAATTTTCTAC
ATCCACCATTCACAGACGGACAGAATATGGGCTATTTGGCAAGAGCTGCAGAAGTACAGGG
GTCTATCTGGTTCGGAAGCAAACTGTGCCATTGAACATATGAGAACACCCTTGAAGCCTTT
CAGCTTTGGGCCACCCTACAATTTGAATAGTCATACGCAAGAATATTCAAAGCCTGAGGAC
ACGTTTGACTATAAGAAGTTTGGATACAGATATGATAGTCTGGAATTGGAGGGGCGATCAA
TTTCTCGCATTGATGAACTTATCCAGCAGAGACAGGAGAAAGACAGAACTTTTGCAGGGTT
CCTCCTTAAAGGTTTTGGTACATCCGCATCTGTGTCATTGCAAGTTTGCAGAGTTGATCAC
ACCTGTAAAGATGCGGGCTATTTCACTATTCTGGGAGGATCAGCCGAAATGCCATGGGCAT
TCGACAGGCTTTATAAGTATGACATTACTAAAACTCTTCACGACATGAACCTGAGGCACGA
GGACACTTTCTCTATAGACGTAACTATCACGTCTTACAATGGAACAGTACTCTCGGGAGAC
CTCATTCAGACGCCCTCCATTATATTTGTACCTGGACGCC

Intron e/f

GTGAGTACCTGTTTGCACTAAGACTTCTGTAGGCTAAAAGTGTAAGAAATATCAATTAATT
TCAATTCACCCAAACTTGAAAACGGTACCTATATAGGTTAACTTTTTGTCTACAGTAAACT
GAACATACCTACACATTTCATGAAATGATCTCTCAATATTTTCCACCAACAG

Domain f

ATAAACTCAACTCACGGAAACATACACCTAACAGAGTCCGCCATGAGCTAAGTAGCCTTAG
TTCCCGTGACATAGCAAGCTTGAAGGCAGCTTTGACAAGCCTTCAACATGATAATGGGACT
GATGGTTATCAAGCTATTGCTGCCTTCCATGGCGTTCCTGCGCAGTGCCACGAGCCATCTG
GACGTGAG

Intron f(1)

GTAAATTTACAGAGCTTTATGAAGTGTGTTCAGAGTGAAGAGACCAAGATATACTTATACC
CAAAACTAGCTAGCAACAGACGATTTCACTTGTTTCGGACACTTTGTATTATACGTTGGAT
CCCAAGGTAAACGGAAACGTAACCGAGAATCAGTCCGTAAAGTGAGTGAGTGAGTTTGGGG
CTTAACGTCGCACTCAGCAATACCCCAGCTATGTGGCGACTCTCAGATTTACTGCTGGAGG
AGAACCTACATAGCCCGGTTTAACCCGTGTGGTATGTAGTAAGACCAGCGCGGCATGGCTG
GTATCTGACGGACGAAGGGTGGCGCTGCACGTATTCCAGTGGTACAACACTGCACCCCAAT
TTCACCGACCGGAGAACTGATCTCCCCTTCGGAGATATCGCCTGCCTTCCACGGGATTCGA
ACTCGGTGACCTTCAAGCCAGCGCGCTTCTAGCGGGGGCGATTAGAGGTTNAAGGCCGACG
GCTCTACCACCTTAACTATCCCCCGGCCCCACTCCTGACGGAAATGTTTATAATTCAGCCT
TTGTTTTCTTATTAAACACTCTTGGCAGATTTTCTATAGATAATGGATTCACATGTAGACA
GTCTCCCATTGTTGTAACTGGTAGTCAAGAGTTAGAATCTGAATACATTCTCCAAGATGGA
TCAAGGAAAACAATAATTACTTGATGTTGCAG

Domain f(2)

ATCGCCTGTTGCATCCACGGCATGGCGACGTTTCCTCACTGGCACCGGTTGTACACTCTGC
AGTTGGAGCAAGCGCTGCGCAGACACGGGTCCAGTGTTGCTGTTCCATACTGGGACTGGAC
CAAGCCAATCACCGAACTGCCACACATTCTGACAGACGGAGAATATTATGACGTTTGGCAA
AATGCCGTCTTGGCCAATCCGTTTGCAAGAGGTTATGTGAAAATTAAAGATGCATTTACGG
TGAGAAATGTCCAGGAAAGTCTGTTCAAAATGTCAAGTTTTGGAAAGCACTCGCTTCTGTT
TGACCAGGCTTTGTTGGCTCTTGAACAAACTGACTACTGTGACTTCGAAGTTCAGTTTGAA
GTGATGCATAACACGATCCATTATCTCGTAGGAGGGCGTCAAACGTACGCCTTCTCCTCTC
TCGAGTATTCCTCATACGATCCAATCTTCTTTATTCACCACTCGTTTGTTGACAAAATATG
GGCTGTATGGCAAGAACTGCAAAGCAGGAGACATCTACAGTTTAGAACAGCTGATTGTGCT
GTGGGCCTCATGGGTCAGGCAATGAGGCCTTTCAACAAGGATTTCAACCACAACTCGTTCA
CCAAGAAGCACGCAGTCCCTAATACAGTATTTGATTATGAAGATCTTGGCTATAACTATGA
CAACCTTGAAATCAGTGGTTTAAACTTAAATGAGATCGAGGCGTTAATAGCAAAACGCAAG
TCACATGCTAGAGTCTTTGCTGGGTTCCTGTTGTTTGGATTAGGAACTTCGGCTGATATAC
ATCTGGAAATTTGCAAGACATCGGAAAACTGCCATGATGCTGGTGTGATTTTCATCCTTGG
AGGTTCTGCAGAGATGCATTGGGCATACAACCGCCTCTACAAGTATGACATTACAGAAGCA
TTGCAGGAATTTGACATCAACCCTGAAGATGTTTTCCATGCTGATGAACCATTTTTCCTGA
GGCTGTCGGTTGTTGCTGTGAATGGAACTGTCATTCCATCGTCTCATCTTCACCAGCCAAC
GATAATCTATGAACCAGGCGAAG

Intron f/g

GTGAGATATATGCAAATTGAATGTTGTCCAGATGCGTTGTTTACATTTATATGCTTGGAAT
TGTCCTGAACGAATACAGTGGAATAACCAAAAGCTGAAAAATAAAAAGATATATACTTCAT
TCTGAATTTGTCAGTATTGCTGACCCAAAAACACGTTATCCATGTCGACACTATATTTGCC
TTTCTGAATCTGAGACTGCGTTATGTTTCTAATAATCACGAAATATGGTATACAGGTTGTG
TATCTGTAGAATACCCAAGGCAGAATTTAAAGGGTCACACCCTGTTTAATACAG

Domain g(1)

ATCACCATGACGACCATCAGTCGGGAAGCATAGCAGGATCCGGGGTCCGCAAGGACGTGAA
CACCTTGACTAAGGCTGAGACCGACAACCTGAGGGAGGCGCTGTGGGGTGTCATGGCAGAC
CACGGTCCCAATGGCTTTCAAGCTATTGCTGCTTTCCATGGAAAACCAGCTTTGTGTCCCA
TGCCTGATGGCCACAACTACTCATGTTGTACTCACGGCATGGCTACCTTCCCACACTGGCA
TCGCCTCTACACCAAGCAGATGGAGGATGCAATGAGGGCGCATGGGTCTCATGTCGGCCTG
CCCTACTGGGACTGGACTGCTGCCTTCACCCACCTGCCAACACTGGTCACCGACACGGACA
ACAACCCCTTCCAACAT

Intron g(2)

GTAAGAGCGGGGTAGGGATGGGGTGGTAGGGGGTGGGTTGTTCTATTACTTCCCGCTTCAC
TTGTATGAAATGGATAACCTTGGCTGCATCCCAATTGCGTGATCGATTCTCTTTCGATTCA
CTCGTGCGATTAGACTGCCTTATTTACTATAGTAGTTAGAATGTTGCTCAGTGCGCCGTTA
AACAACTAATACACAAAACCGCATTTGTTTTATATGGTCACTCTACTGTTTATCACGTATA
TGTATGTTCCGACTCACTGGTTGGTGCGTACCATTCTACTGTCACACTGAGAGCCAATGTT
CTCAGATGTGTGAAATGTTTGAAAGCCGTTTCTACATAATATTGCAGGAATACCATTGTAG
AATGTAGTCAAACAGGTAACAATCTGTTAGTGAGCCCAGTTCGAGGTTGCGTTGTAGGGTG
TAGTCCAACAGGTAGGCAGTCCATAAGCATAGTTTTTAAGCATTTTAGATCATCTATAATT
AACCACATGGTTAGCCGCTATGTTTAGTTTAATCCAGTATAAGTTAGAACTGTTATATTTC
GAAGGGAAGTGAGTAAATCCTTATTCCTTGACTACCATTTAATAGATTTCCCAATGACTCC
ATTCAACTCCTAACTTTCACATCACTGCTCTCTTCAACAG

Domain g(2)

GGACACATTGATTATCTCAATGTCAGCACAACTCGATCTCCCCGAGACATGCTGTTCAACG
ACCCCGAGCATGGATCAGAGTCGTTCTTCTACAGACAAGTCCTCTTAGCTCTGGAACAAAC
TGATTTCTGCAAATTCGAAGTTCAGTTTGAGATAACCCACAATGCCATCCATTCCTGGACA
GGTGGCCACAGCCCCTACGGAATGTCCACTCTCGACTTCACTGCCTACGATCCTCTCTTCT
GGCTTCACCACTCCAACACCGACAGAATCTGGGCTGTCTGGCAAGCTTTGCAAGAATACAG
AGGACTTCCATACAACCATGCCAATTGTGAGATCCAGGCAATGAAAACGCCCCTGAGGCCT
TTCAGTGACGATATCAACCACAACCCAGTCACAAAGGCTAACGCGAAGCCATTAGATGTGT
TCGAGTATAATCGGTTGAGCTTCCAGTACGACAACCTCATCTTCCATGGATACAGTATTCC
GGAACTTGATCGCGTGCTTGAAGAAAGAAAGGAGGAGGACAGAATATTTGCTGCCTTCCTT
CTCAGTGGAATCAAGCGTAGTGCTGATGTAGTGTTCGACATATGCCAGCCAGAACACGAAT
GTGTGTTCGCAGGGACTTTTGCGATTTTGGGAGGGGAGCTAGAAATGCCCTGGTCCTTCGA
CAGACTGTTCCGCTATGATATCACCAAGGTGATGAAGCAGCTACACCTGAGGCATGACTCT
GACTTTACCTTCAGGGTGAAGATTGTCGGCACCGACGACCACGAGCTTCCTTCAGACAGTG
TCAAAGCACCAACTATTGAATTTGAACCGGGCG

Intron g/h

GTGAGTACGACAGGCATTTCTAGTAAAAACCTACTTTTGGTAAAAGGTTCGAGAAATCACT
TGAAGCAACAACATGATTTTGTAACGCCTATTACACGTGAACATGTCACACCCGGTGATGC
CGTTTAATGGACATGCCTCTGTTAATGAAAGGGGTAAGTACATGTGTATGGGGATGGGATG
GGAGCCACCTGTCCCAATTTCATAGGTCCCTAGGATCCCAGTTGCGTAGGAATCCCCTGAT
TAATGCCTTGTGAATTCCTCCTGGAATTGTCCTGGCCCAAATTTTTACAAACCCGCCCCGA
TATACCTTGGAAATAATTGGGCCTAAGGGTGGGGCTTTTAAGGACCAAGAACCCAACCTAA
ACCCCAACCCATTTTTTCCCACCCATTCCAGGTTTGTTTTACCAAATAAAAAGGTTTCCA
CTTTGAGGAAACCCTTTAAGGGTTCTTTTCAGGGCTTTTTTTCTTTTCTGGGAATTCCAAT
TCCGGGGGAACAAAATACATATATTTCACAGACCTTTGGTCAAATTTATATAATTTCCGAC
TTCATGTCATAGGTTTGTCTTTCTTCCTACACAG

Domain h

TGCACAGAGGCGGAAACCACGAAGATGAACACCATGATGACAGACTCGCAGATGTCCTGAT
CAGGAAAGAAGTTGACTTCCTCTCCCTGCAAGAGGCCAACGCAATTAAGGATGCACTGTAC
AAGCTCCAGAATGACGACAGTAAAGGGGGCTTTGAGGCCATAGCTGGCTATCACGGGTATC
CTAATATGTGTCCAGAAAGAGGTACCGACAAGTATCCCTGCTGTGTCCACGGAATGCCCGT
GTTCCCCCACTGGCACCGCCTGCATACCATTCAGATGGAGAGAGCTCTGAAAAACCATGGC
TCTCCAATGGGCATTCCTTACTGGGATTGGACAAAGAAGATGTCGAGTCTTCCATCTTTCT
TTGGAGATTCCAGCAACAACAACCCTTTCTACAAATATTACATCCGGGGCGTGCAGCACGA
AACAACCAGGGACATTAATCAGAGACTCTTTAATCAAACCAAGTTTGGTGAATTTGATTAC
CTATATTACCTAACTCTGCAAGTCCTGGAGGAAAACTCGTACTGTGACTTTGAAGTTCAGT
ATGAGATCCTCCATAACGCCGTCCACTCCTGGCTTGGAGGAACTGGAAAGTATTCCATGTC
TACCCTGGAGCATTCGGCCTTTGACCCTGTCTTCATGATTCACCACTCGAGTTTGGATAGA
ATCTGGATCCTTTGGCAGAAGTTGCAAAAGATAAGAATGAAGCCTTACTACGCATTGGATT
GTGCTGGCGACAGACTTATGAAAGACCCCCTGCATCCCTTCAACTACGAAACCGTTAATGA
AGATGAATTCACCCGCATCAACTCTTTCCCAAGCATACTGTTTGACCACTACAGGTTCAAC
TATGAATACGATAACATGAGAATCAGGGGTCAGGACATACATGAACTTGAAGAGGTAATTC
AGGAATTAAGAAACAAAGATCGCATATTTGCTGGTTTTGTTTTGTCGGGCTTACGGATATC
AGCTACAGTGAAAGTATTCATTCATTCGAAAAACGATACAAGTCACGAAGAATATGCAGGA
GAATTTGCAGTTTTGGGAGGTGAGAAGGAGATGCCGTGGGCATATGAAAGAATGCTGAAAT
TGGACATCTCCGATGCTGTACACAAGCTTCACGTGAAAGATGAAGACATCCGTTTTAGAGT
GGTTGTTACTGCCTACAACGGTGACGTTGTTACCACCAGGCTGTCTCAGCCATTCATCGTC
CACCGTCCAGCCCATGTGGCTCACGACATCTTGGTAATCCCAGTAGGTGCGGGCCATGACC
TTCCGCCTAAAGTCGTAGTAAAGAGCGGCACCAAAGTCGAGTTTACACCAATAGATTCGTC
GGTGAACAAAGCAATGGTGGAGCTGGGCAGCTATACTGCTATGGCTAAATGCATCGTTCCC
CCTTTCTCTTACCACGGCTTTGAACTGGACAAAGTCTACAGCGTCGATCACGGAGACTACT
ACATTGCTGCAGGTACCCACGCGTTGTGTGAGCAGAACCTCAGGCTCCACATCCACGTGGA
ACACGAGTAG

3´UTR

TTCACAG

Intron UTR

GTGAGGAGAAGGCCCCAGGCTAGCAGGGCAATGGATGAAGGAAATAGGGGCAAAGGGAATA
GCAGTTACACCATCGACATTTCCAACCTCCTCAGAAACTAATATATAGCCTTAATACAACC
AGCCAAGACTCAACGGGCAGCCGGGGTGGGGGATTTGGTGGTCGCTGTTTCAGACCAGGG
TGCAAAATATCAGTGCGCAAATCAACATGTTGCGTGTCAGACACTGACACAGCAGTCATTG
AACCTGCAGACCCATAACAGGAAAATGGGGCAGATACGATCAAAGACAGTGTAAAATAGGG
ATAAGTAGGCATATGCAACCACCTGATGGAAATGAAAAGGGGTAAGTTTAAACCCCGGCTA
CCAAAGGTCCAATGGTTCCTTAACCCAGCTTACGCTATCCCTCTAATTTCAGTATTGAGCT
GATTTCTGTCGAGTTCATGTAAACTGTATACTTTCTGTATTATTACAG

3´UTR

GTTGCTATGCCGACTGCGCTATATTGGTGAACGAGACGATGAGGACATCTCTGAAAGAGTT
CGCCAAGTGATGTGTAGGTCACGGAAGTATTGTTGAGCTAACAATATGATGATTTCAAAAT
GACTTGGCGCTCTAGGACAAAGACATAATTCATCAGCACCCTGTGCACCAACTCTTTGTTT
GCTGCAAACGTCTGACAAGCGACACGTCAATCAACAAGCTGTTCAAACTCAAGTGGATGTA
ACTAGAATCGTTGGGCCATCGTTCACAAAGTATTGACAGATGTCACACATGATGGCGAGAA
ACACTTTAGAACTTTTAATGACCTAGAGTGACTTGTAAATATGTAAATATATTCTTCAAAG
ACTCAGCTGAACTATTGTTGGATAACACATCAATTCCCTCAACAAAATGCTTTATCTTCAC
ATGGATGTATGTAATGTGGCCGGCAATAAAGTATATATATGTATAAAAAAAAAAAAAAAAA
A

Figure 5

Derived primary structure of HtH1

Signal peptide

LVQFLLVALVAGAGA

Domain a

DNVVRKDVSHLTDDEVQALHGALHDVTASTGPLSFEDITSYHAAPASCDYKGRKIACCVHG
MPSFPFWHRAYVVQAERALLSKRKTVGMPYWDWTQTLTHLPSLVTEPIYIDSKGGKAQTNY
WYRGEIAFINKKTARAVDDRLFEKVEPGHYTHLMETVLDALEQDEFCKFEIQFELAHNAIH
YLVGGKFEYSMSNLEYTSYDPIFFLHHSNVDRLFAIWQRLQELRGKNPNAMDCAHELAHQQ
LQPFNRDSNPVQLTKDHSTPADLFDYKQLGYSYDSLNLNGMTPEQLKTELDERHSKERAFA
SFRLSGFGGSANVVVYACVPDDDPRSDDYCEKAGDFFILGGQSEMPWRFYRPFFYDVTEAV
HHLGVPLSGHYYVKTELFSVNGTALSPDLLPQPTVAYRPGK

Domain b

GHLDPPVHHRHDDDLIVRKNIDHLTREEEYELRMALERFQADTSVDGYQATVEYHGLPARC
PRPDAKVRFACCMHGMASFPHWHRLFVTQVEDALVRRGSPIGVPYWDWTKPMTHLPDLASN
ETYVDPYGHTHHNPFFNANISFEEGHHHTSRMIDSKLFAPVAFGEHSHLFDGILYAFEQED
FCDFEIQFELVHNSIHAWIGGSEDYSMATLHYTAFDPIFYLHHSNVDRLWAIWQALQIRRH
KPYQAHCAQSVEQLPMKPFAFPSPLNNNEKTHSHSVPTDIYDYEEVLHYSYDDLTFGGMNL
EEIEEAIHLRQQHERVFAGFLLAGIGTSALVDIFINKPGNQPLKAGDIAILGGAKEMPWAF
DRLYKVEITDSLKTLSLDVDGDYEVTFKIHDMHGNALDTDLIPHAAVVSEPAH

Domain c

PTFEDEKHSLRIRKNVDSLTPEETNELRKALELLENDHTAGGFNQLGAFHGEPKWCPNPEA
EHKVACCVHGMAVFPHWHRLLALQAENALRKHGYSGALPYWDWTRPLSQLPDLVSHEQYTD
PSDHHVKHNPWFNGHIDTVNQDTTRSVREDLYQQPEFGHFTDIAQQVLLALEQDDFCSFEV
QYEISHNFIHALVGGTDAYGMASLRYTAYDPIFFLHHSNTDRIWAIWQSLQKYRGKPYNTA
NCAIESMRRPLQPFGLSSAINPDRITREHAIPFDVFNYRDNLHYVYDTLEFNGLSISQLDR
ELEKIKSHERVFAGFLLSGIKKSALVKFEVCTPPDNCHKAGEFYLLGDENEMAWAYDRLFK
YDITQVLEANHLHFYDHLFIRYEVFDLKGVSLGTDLFHTANVVHDSGT

Domain d

GTRDRDNYVEEVTGASHIRKNLNDLNTGEMESLRAAFLHIQDDGTYESIAQYHGKPGKCQL
NDHNIACCVHGMPTFPQWHRLYVVQVENALLNRGSGVAVPYWEWTAPIDHLPHFIDDATYF
NSRQQRYDPNPFFRGKVTFENAVTTRDPQAGLFNSDYMYENVLLALEQENYCDFEIQFELV
HNALHSMLGGKGQYSMSSLDYSAFDPVFFLHHANTDRLWAIWQELQRFRELPYEEANCAIN
LMHQPLKPFSDPHENHDNVTLKYSKPQDGFDYQNHFGYKYDNLEFHHLSIPSLDATLKQRR
NHDRVFAGFLLHNIGTSADITIYICLPDGRRGNDCSHEAGTFYILGGETEMPFIFDRLYKF
EITKPLQQLGVKLHGGVFELELEIKAYNGSYLDPHTFDPTIIFEPGT

Domain e

DTHILDHDHEEEILVRKNIIDLSPRERVSLVKALQRMKNDRSADGYQAIASFHALPPLCPN
PSAAHRYACCVHGMATFPQWHRLYTVQVQDALRRHGSLVGIPYWDWTKPVNELPELLSSAT
FYHPIRNINISNPFLGADIEFEGPGVHTERHINTERLFHSGDHDGYHNWFFETVLFALEQE
DYCDFEIQFEIAHNGIHTWIGGSAVYGMGHLHYASYDPIFYIHHSQTDRIWAIWQELQKYR
GLSGSEANCAIEHMRTPLKPFSFGPPYNLNSHTQEYSKPEDTFDYKKFGYRYDSLELEGRS
ISRIDELIQQRQEKDRTFAGFLLKGFGTSASVSLQVCRVDHTCKDAGYFTILGGSAEMPWA
FDRLYKYDITKTLHDMNLRHEDTFSIDVTITSYNGTVLSGDLIQTPSIIFVPGR

Domain f

HKLNSRKHTPNRVRHELSSLSSRDIASLKAALTSLQHDNGTDGYQAIAAFHGVPAQCHEPS
GREIACCIHGMATFPHWHRLYTLQLEQALRRHGSSVAVPYWDWTKPITELPHILTDGEYYD
VWQNAVLANPFARGYVKIKDAFTVRNVQESLFKMSSFGKHSLLFDQALLALEQTDYCDFEV
QFEVMHNTIHYLVGGRQTYAFSSLEYSSYDPIFFIHHSFVDKIWAVWQELQSRRHLQFRTA
DCAVGLMGQAMRPFNKDFNHNSFTKKHAVPNTVFDYEDLGYNYDNLEISGLNLNEIEALIA
KRKSHARVFAGFLLFGLGTSADIHLEICKTSENCHDAGVIFILGGSAEMHWAYNRLYKYDI
TEALQEFDINPEDVFHADEPFFLRLSVVAVNGTVIPSSHLHQPTIIYEPGE

Domain g

DHHDDHQSGSIAGSGVRKDVNTLTKAETDNLREALWGVMADHGPNGFQAIAAFHGKPALCP
MPDGHNYSCCTHGMATFPHWHRLYTKQMEDAMRAHGSHVGLPYWDWTAAFTHLPTLVTDTD
NNPFQHGHIDYLNVSTTRSPRDMLFNDPEHGSESFFYRQVLLALEQTDFCKFEVQFEITHN
AIHSWTGGHSPYGMSTLDFTAYDPLFWLHHSNTDRIWAVWQALQEYRGLPYNHANCEIQAM
KTPLRPFSDDINHNPVTKANAKPLDVFEYNRLSFQYDNLIFHGYSIPELDRVLEERKEEDR
IFAAFLLSGIKRSADVVFDICQPEHECVFAGTFAILGGELEMPWSFDRLFRYDITKVMKQL
HLRHDSDFTFRVKIVGTDDHELPSDSVKAPTIEFEPG

Domain h

VHRGGNHEDEHHDDRLADVLIRKEVDFLSLQEANAIKDALYKLQNDDSKGGFEAIAGYHGY
PNMCPERGTDKYPCCVHGMPVFPHWHRLHTIQMERALKNHGSPMGIPYWDWTKKMSSLPSF
FGDSSNNNPFYKYYIRGVQHETTRDVNQRLFNQTKFGEFDYLYYLTLQVLEENSYCDFEVQ
YEILHNAVHSWLGGTGQYSMSTLEYSAFDPVFMIHHSSLDRIWILWQKLQKIRMKPYYALD
CAGDRLMKDPLHPFNYETVNEDEFTRINSFPSILFDHYRFNYEYDNMRIRGQDIHELEEVI
QELRNKDRIFAGFVLSGLRISATVKVFIHSKNDTSHEEYAGEFAVLGGEKEMPWAYERMLK
LDISDAVHKLHVKDEDIRFRVVVTAYNGDVVTTRLSQPFIVHRPAHVAHDILVIPVGAGHD
LPPKVVVKSGTKVEFTPIDSSVNKAMVELGSYTAMAKCIVPPFSYHGFELDKVYSVDHGDY
YIAAGTHALCEQNLRLHIHVEHE

Figure 6

HtH2 cDNA sequence and intron structure

Domain b

CACAGACTGTTCGTCACCCAGGTGGAAGATGCTCTGATCAGGCGAGGATCGCCTATAGGGG
TCCCCTACTGGGACTGGACTCAGCCTATGGCGCATCTCCCAGGACTTGCAGACAACGCCAC
CTATAGAGATCCCATCAGCGGGGACAGCAGACACAACCCCTTCCACGATGTTGAAGTTGCC
TTTGAAAATGGACGTACAGAACGTCACCCAGATAGTAGATTGTTTGAACAACCTTTATTTG
GCAAACATACGCGTCTCTTCGACAGTATAGTCTATGCTTTTGAGCAGGAGGACTTCTGCGA
TTTTGAAGTTCAATTTGAGATGACCCATAATAATATTCACGCCTGGATTGGTGGCGGCGAG
AAGTATTCCATGTCTTCTCTACACTACACAGCCTTCGACCCTATCTTCTACCTTCGTCACT
CCAACACTGACCGGCTCTGGGCAATTTGGCAAGCGTTGCAGATACGAAGAAACAGGCCTTA
CAAGGCTCATTGTGCTTGGTCTGAGGAACGCCAGCCTCTCAAACCTTTCGCCTTCAGTTCC
CCACTGAACAACAACGAAAAAACCTACGAAAACTCGGTGCCCACCAACGTTTACGACTACG
AAGGAGTCCTTGGCTATACTTATGATGACCTCAACTTCGGGGGCATGGACCTGGGTCAGCT
TGAGGAATACATCCAGAGGCAGAGACAGAGAGACAGGACCTTTGCTGGTTTCTTTCTGTCA
CATATTGGTACATCAGCGAATGTTGAAATCATTATAGACCATGGGACTCTTCATACCTCCG
TGGGCACGTTTGCTGTTCTTGGCGGAGAGAAGGAGATGAAATGGGGATTTGACCGTTTGTA
CAAATATGAGATTACAGATGAACTGAGGCAACTTAATCTCCGTGCTGATGATGTTTTCAGC
ATCTCTGTTAAAGTAACTGATGTTGATGGCAGTGAGCTGTCCTCTGAACTCATCCCATCTG
CTGCTATCATCTTCGAACGAAGCCATA

Intron b/c

GTAAGTAGCTACCTGTTTATTCAATTTTTTCGCTTTGCCAATCAATTCATTCAGCTTGAAA
TTCAATAATTGTGTTTTGCATGGCTGAAAACCAATTTGAACTCTTTTCTTTTCTCAGGTCG
AACTCAAATAAATAATCACTAATTGTTATGCACGCGGGTAGGGCATACATACTATATCCAC
ATCGGTCATCTCAAAATGCAAACAAATTGTCTTATTTCCGTTGGGACAAGCAAACCCCCTT
TCCTGTAATCTTGCCTTTGGCATCCACTGGAATTAATGTTGACTGGTAATTGATACTGGCT
CTCTTCTTGCATAGAGTTAATATCTATAGTTTGTAAATCTTTATGATTTTGCTATTTATAT
TTCGACAGCATGCTATAGACACCCTAGACTATTGTATAGCCACTTGTATTGTTTTTCCATT
TATTATTTATAACAGAACATGGCTTGTAATTTTTATTTACCTTCCAG

Domain c

TTGACCATCAGGACCCGCATCATGACACAATCATTAGGAAAAATGTTGATAATCTTACACC
CGAGGAAATTAATTCTCTGAGGCGGGCAATGGCAGACCTTCAATCAGACAAAACCGCCGGT
GGATTCCAGCAAATTGCTGCTTTTCACGGGGAACCCAAATGGTGCCCAAGTCCCGATGCTG
AGAAGAAGTTCTCCTGCTGTGTCCATGGAATGGCTGTCTTCCCTCACTGGCACAGACTCCT
GACCGTGCAAGGCGAGAATGCCCTGAGAAAGCATGGATGTCTCGGAGCTCTCCCCTACTGG
GACTGGACTCGGCCCCTGTCTCACCTACCTGATTTGGTTTTGGTAAGTAGCAGAACTACAC
CGATGCCATATTCCACCGTGGAAGCCCGAAACCCCTGGTACAGCGGCCATATTGATACAGT
TGGTGTTGACACAACAAGAAGCGTCCGTCAAGAACTGTATGAAGCTCCTGGATTTGGCCAT
TATACTGGGGTCGCTAAGCAAGTGCTTCTGGCTTTGGAGCAGGATGACTTCTGTGATTTTG
AAGTCCAGTTTGAGATAGCTCACAATTTCATTCACGCTCTTGTCGGCGGAAGCGAGCCATA
TGGTATGGCGTCACTCCGTTACACTACTTATGATCCAATTTTCTACCTCCATCATTCTAAC
ACTGACAGACTCTGGGCTATATGGCAGGCTCTACAAAAGTACAGGGGCAAACCTTACAATT
CCGCCAACTGCGCCATTGCTTCTATGAGAAAACCCCTACAACCCTTTGGTCTGACTGATGA
GATCAACCCGGATGATGAGACAAGACAGCATGCTGTTCCTTTCAGTGTCTTTGATTACAAG
AACAACTTCAATTATGAATATGACACCCTTGACTTCAACGGACTATCAATCTCCCAGCTGG
ACCGTGAACTGTCACGGAGAAAGTCTCATGACAGAGTATTTGCCGGATTTTTGCTGCATGG

TATTCAGCAGTCTGCACTAGTTAAATTCTTTGTCTGCAAATCAGATGATGACTGTGACCAC
TATGCTGGTGAATTCTACATCCTTGGTGATGAAGCTGAAATGCCATGGGGCTATGATCGTC
TTTACAAATATGAGATCACTGAGCAGCTCAATGCCCTGGATCTACACATCGGAGATAGATT
CTTCATCAGATACGAAGCGTTTGATCTTCATGGTACAAGTCTTGGAAGCAACATCTTCCCC
AAACCTTCTGTCATACATGACGAAGGGGCAG

Intron c/d

GTGAGAACATTGATAATAGTTCAAATgAAGTATATCCGATTCAAGCTGTCGATACAAGATg
AGATACATAATCACAATGTTTGTATTAGATATCTCTCTTAATTTAATGCCGCTTTTATCAA
TATTCGAGCAATCCTTCAGCAACATACACCAGCAAATGTTTCATCAACAGACTATATTATT
TAATCTTTTAAAAATCCTTTTCTGTTGTTATAAATACTTAAAGTATCGAATTCCTTGAATG
CGTCTTCTCTGCAGCATATAGTTAAGTTGTTGTGTTTCTCTGTCAG

Domain d

GTCACCATCAGGCTGACGAGTACGACGAAGTTGTAACTGCTGCAAGCCACATCAGAAAGAA
TTTAAAAGATCTGTCAAAGGGAGAAGTAGAGAGCCTAAGGTCTGCCTTCCTGCAACTTCAG
AACGACGGAGTCTATGAGAATATTGCCAAGTTCCACGGCAAGCCTGGGTTGTGTGATGATA
ACGGTCGCAAGGTTGCCTGTTGTGTCCATGGAATGCCCACCTTCCCCCAGTGGCACAGGCT
CTATGTCCTCCAGGTGGAGAATGCTTTGCTGGAGAGAGGATCTGCCGTCTCTGTGCCATAC
TGGGACTGGACTGAAACATTTACAGAGCTGCCATCTTTGATTGCTGAGGCTACCTATTTCA
ATTCCCGTCAACAAACGTTTGACCCTAATCCTTTCTTCAGAGGTAAAATCAGTTTTGAGAA
TGCTGTTACAACACGTGATCCCCAGCCTGAGCTGTACGTTAACAGGTACTACTACCAAAAC
GTCATGTTGGTTTTTGAACAGGACAACTACTGCGACTTCGAGATACAGTTTGAGATGGTTC
ACAATGTTCTCCATGCTTGGCTTGGTGGAAGAGCTACTTATTCTATTTCTTCTCTTGATTA
TTCTGCATTCGACCCTGTGTTTTTCCTTCACCATGCGAACACAGATAGATTGTGGGCCATC
TGGCAGGAGCTGCAGAGGTACAGGAAGAAGCCATACAATGAAGCGGATTGTGCCATTAACC
TAATGCGCAAACCTCTACATCCCTTCGACAACAGTGATCTCAATCATGATCCTGTAACCTT
TAAATACTCAAAACCCACTGATGGCTTTGACTACCAGAACAACTTTGGATACAAGTATGAC
AACCTTGAGTTCAATCATTTCAGTATTCCCAGGCTTGAAgAAATCATTCGtATTAGACAAC
GTCAAGATCGTGTGTTTGCAGGATTCCTCCTTCACAACATTGGGACATCCGCAACTGTTGA
GATATTCGTCTGTGTCCCTACCACCAGCGGTGAGCAAAACTGTGAAAACAAAGCCGGAACA
TTTGCCGTACTCGGAGGAGAAACAGAGATGGCGTTTCATTTTGACAGACTCTACAGGTTTG
ACATCAGTGAAACACTGAGGGACCTCGGCATACAGCTGGACAGCCATGACTTTGACCTCAG
CATCAAGATTCAAGGAGTAAATGGATCCTACCTTGATCCACACATCCTGCCAGAGCCATCC
TTGATTTTTGTGCCTGGTTCAAGT

Intron d/e

AAGAAAGTTTCACTGTCTAAATCTTTTTTTATGATAGAGGGTAGAGAAGTGGAGACAATGT
GACAATATATTGAATAAAGTTGTTTAAAATTTATAACTCTCATAAGTTCATATTATGCTGA
AGCTGTAGCCATCTATAACTGTGTAACATGAAATGTTAAGACATTAACCTAAATACTTCAG
CTGATAACAAAACAATGTTAATACATACGTCAATGTAACATTTTCTTATCTTTAGGTTATA
GCATAAACACTTCAGAGATACAGTGACGAAAACCTCTATTTAAATATTTCAGGT

Domain e

TCTTTCCTGCGTCCTGATGGGCATTCAGATGACATCCTTGTGAGAAAAGAAGTGAACAGCC
TGACAACCAGGGAGACTGCATCTCTGATCCATGCTCTGAAAAGTATGCAGGAAGACCATTC
ACCTGACGGGTTCCAAGCCATTGCCTCTTTCCATGCTCTGCCACCACTCTGCCCTTCACCA
TCTGCAGCTCACCGTTATGCTTGCTGTGTCCACGGCATGGCTACATTTCCCCAGTGGCACA
GATTGTACACTGTACAGTTCCAGGATGCACTGAGGAGACATGGAGCTACGGTAGGTGTACC
GTATTGGGATTGGCTGCGACCGCAGTCTCACCTACCAGAGCTTGTCACCATGGAGACATAC

CATGATATTTGGAGTAACAGAGATTTCCCCAATCCTTTCTACCAAGCCAATATTGAGTTTG
AAGGAGAAAACATTACAACAGAGAGAGAAGTCATTGCAGACAAACTTTTTGTCAAAGGTGG
ACACGTTTTTGATAAACTGGTTCTTCAAACAAGCCATCCTAGCGCTGAGCAGGAAAACTAC
TGTGACTTTGAGATTCAGTTTGAAATTCTTCACAACGGCGTTCACACGTGGGTCGGAGGCA
GTCGTACCTACTCTATCGGACATCTTCATTACGCATTCTACGACCCTCTTTTCTACCTTCA
CCATTTCCAGACAGACCGTATTTGgGCAATCTGGCAAGAACTCCAGGAACAGAGAGGGCTC
TCGGGTGATGAGGCTCACTGTGCTCTCGAGCAAATGAGAGAACCATTGAAGCCTTTCAGCT
TCGGCGCTCCTTATAACTGGAATCAGCTCACACAGGATTTCTCCCGACCCGAGGACACCTT
CGACTACAGGAAGTTTGGTTATGAATATGACAATTTAGAATTCCTGGGAATGTCAGTTGCT
GAACTGGATCAATACATTATTGAACATCAAGAAAATGATAGAGTATTCGCTGGGTTCCTGT
TGAGTGGATTCGGAGGTTCCGCATCAGTTAATTTCCAGGTTTGTAGAGCTGATTCCACATG
TCAGGATGCTGGGTACTTCACCGTTCTTGGTGGCAGTGCTGAGATGGCGTGGGCATTTGAC
AGGCTTTACAAATATGACATTACTGAAACTCTGGAGAAAATGCACCTTCGATATGATGATG
ACTTCACAATCTCTGTCAGTCTGACCGCCAACAACGGAACTGTCCTGAGCAGCAGTCTAAT
CCCAACACCGAGTGTCATATTCCAGCGGGGACATC

Intron e/f

AAGTAGTAAACTGCTCAGATTGTTTTCATAATTACTCCACTATTAAGTAAAAAGTACTAGT
AATTCAATAGTACTGTTCACAGAGAAATGTAACACAATAGACCACAGAGTCCATTTGTTAA
ACGCCTTTGGCTTGGTAAGTCTGAGGTTTTGGTGACTGATGGAAAGCTAAAATATATTTTG
ACAG

Domain f(1)

GTGACATAAATACCAGGAGCATGTCACCGAACCGTGTTCGCCGTGAGCTGAGCGATCTGTC
TGCGAGGGACCTGTCTAGTCTCAAGTCTGCTCTGCGAGACCTACAGGAGGATGATGGCCCC
AACGGATACCAGGCTCTTGCAGCCTTCCATGGGCTACCAGCAGGCTGCCATGATAGCCGGG
GAAATGAGAT

Intron f

ATATTTAAAGTATTTTATCTTACGCATGACCCTGACCCTATTATTTTTTTAATCCTATGAT
GAAACATTTACTTAGACTGGCTTGTGAGCCCCAGGCAAAATGCACTGTAAAAAATACACTGA
CAGAGGATTAGGCATTCTTGGGAGTACTGTATAGTTAGTTGCATACATATTAGCGTTCCCT
CACTAAAACGAATCTCTGAATGCTATCAATTAAAGATCATGATGCTTTGATTGTGTCTACT
GTATTTAAAATGGTGTTAAGATTTGCAATTACAATATACACAAACACGTTTCCTGCATCTC
GGAGAATGCAATCTTTCGTTGTACGCGTCTGTTTTCATATTTTTATGCATGTAGTTTGCAC
TACTTAGCGTCCAATAAATCCATTCACAAAATCACACAAACAAACGATTTTAGGAATGTGA
CTGTAGCTGCAACGAATATACCTGATCCTTTCTTGTTCCAGAT

Domain f(2)

CGCATGTTGCATTCACGGGATGCCGACCTTCCCCCAGTGGCACAGACTGTACACCCTGCAG
TTGGAGATGGCTCTGAGGAGACATGGATCATCTGTCGCCATCCCCTACTGGGACTGGACAA
AGCCTATCTCCGAACTCCCCTCGCTCTTCACCAGCCCTGAGTATTATGACCCATGGCATGA
TGCTGTGGTAAACAACCCATTCTCCAAAGGTTTTGTCAAATTTGCAAATACCTACACAGTA
AGAGACCCACAGGAGATGCTGTTCCAGCTTTGTGAACATGGAGAGTCAATCCTCTATGAGC
AAACTCTTCTTGCTCTTGAGCAAACCGACTACTGTGATTTTGAGGTACAGTTTGAGGTCCT
CCATAACGTGATCCACTACCTTGTTGGTGGACGTCAGACCTACGCATTGTCTTCTCTGCAT
TATGCCTCCTACGACCCATTCTTCTTTATACACCATTCCTTTGTGGATAAGATGTGGGTAG
TATGGCAAGCTCTTCAAAAGAGGAGGAAACTTCCATACAAGCGAGCTGACTGTgcTGTCAA
CCTAATGACTAAACCAATGAGGCCATTTGACTCCGATATGAATCAGAACCCATTCACAAAG
ATGCACGCAGTTCCCAACACACTCTATGACTACGAGACACTGTACTACAGCTACGATAATC
TCGAAATAGGTGGCAGGAATCTCGACCAGCTTCAGGCTGAAATTGACAGAAGCAGAAGCCA

CGATCGCGTTTTTGCTGGATTCTTGCTTCGTGGAATCGGAACTTCTGCTGATGTCAGGTTT
TGGATTTGTAGAAATGAAAATGACTGCCACAGGGGTGGAATAATTTTCATCTTAGGTGGAG
CCAAGGAAATGCCATGGTCATTTGACAGAAACTTCAAGTTTGATATCACCCATGTACTCGA
GAATGCTGGCATTAGCCCAGAGGACGTGTTTGATGCTGAGGAGCCATTTTATATCAAGGTT
GAGATCCATGCTGTTAACAAGACCATGATACCGTCGTCTGTGATCCCAGCCCCAACTATCA
TCTATTCTCCTGGGGAAG

Intron f/g

GTGAGAGAACCAGTAATAGCTACTGTCTACAAAGAATGTGTTCATTTAAAGACCTGACTGT
AGGCCGATGGCTGCTGTCATCTCCTCCGCCTCCTCCTCCTGTTCCTCCTCCGAAGGGGTCA
GCTTCAGGTTCTCTTGCCAATATGCCAAGCAGACCTCCTGAGCAGGCAGTATATATACGTA
AGGGAAGCAAGTATGGACCATCGCGCGGCATGTAGAGATACAATGATCAGCTGTCTGCTGT
TCCACTCCTGTCAGACAATGAGATAAACATGAATACAGTATTACTCAGCAGCGTTCCAATT
TTCAACCCTCGTATTTATTAAAAAAAGGAATTTTTAATATATTTTTCTCCTTGTTGAAATA
TTTTAGTAACTGTTAATCGATATAGAGTGGAGTAGTGACGCTTTATTTCGGtTCATTCTCG
AAACAAAAATATAATAGTCCACTGAACTCTCTTAAATTGTTTTTACAACCTTCAACTGCCA
CAGACGTAATCCCTCACGTTATTTGAGCTGACAACGTGTTGAATTGAGTGTGTTCCGAAT
TCTAAATAAGCATGTATATATTTACGTCTCATGCAAGTAATATATGTTTAACTGATGACGT
CACTTGGTGACCACTGATTTAGTTCCTTTGTCATAATTGCAGTTTCTGTTGTCACGGGGAC
GGTGGGGAAGCCAGGTTCCTCCTGTCACGCTGAATATCCCGTTCGAATCCCCCACATGGGT
ACAAAGTGTGATGCCTATTTCTGGTGTCCCCCACCGTGATATTGCTGGAATAAGTGGCTTA
ATACCATATACACTCACTCTATTGTCACACTACTGCCACCGGCTCACACCTCTGATGCTTC
TGTTCTATCCAG

Domain g(1)

GTCGCGCTGCTGACAGTGCGCACTCTGCCAACATTGCTGGCTCTGGGGTGAGGAAGGACGT
CACGACCCTCACTGTGTCTGAGACCGAGAACCTAAGACAGGCTCTTCAAGGTGTCATCGAT
GATACTGGTCCCAATGGTTACCAAGCAATAGCATCCTTCCACGGAAGTCCTCCAATGTGCG
AGATGAACGGCCGCAAGGTTGCCTGTTGTGCTCACG

Intron g(1)

GTAATTAATGGATGTGAAGTCAATGTCCGAGGGTATAATAAGGATTTAAATACTTCAGTCG
TGTAATACTGTATGACATGTGTATTGGATGGTGTAGGTATTACAGGTTATAAGGCCAGTGT
GTGTTGGGACGGTTACTTTCCTGCACTAGTAATAAGCATTGTATTTAGCTAGCTTTTATCA
TATAACTTTAGTTTCAGGTTTGtGGCAATTGAAATCGAAATTTTCTTTCATTTCAAGGTTA
TCGCACTCGTGTGTNAGAATAGTTACTATGCTGCATTGAGAATAACACTATAGTAATAAAG
CATATCATACAGTAAGAATAACACTATAGTAATAAAGTATATCATNCAGTAAGAATGTCAT
TGTATGATAAATAGGTTATCACACTCGTGTGTTTTAGAATGGTTACTATCCCAGGAATAAC
CACTATGTATTACATGTATATTGGCAGTGTAAGTAGTAGCATTGTATATTAAATCAGTAT
ATCGTGCTTCAAAACACCAGGATATATGGGGTATACAGTGGCAGTGTAAGTAGCAACATT
GTATATTAAATCAGTATATCGTACTTCAAAACACCAGGATTATGGGGTATACAGTGGCAG
TGTAAGTAGTAGCATTGTATATTAAATCAGTATATCGTACTTCAAAACACCAGGATATAAT
TCAGTATATCGTGCTTCAAAACACCAGGATATAATTCAGTATATCGTGCTTCAAAACACCA
GGATATATGGGATATACAGTGCGGGTTTGCATACAACCTCCACCCTTTACAG

Domain g(2)

GTATGGcCTCCTTCCcACACTGGCACAGACTGTATGTGAAGCAGATGGAAGATGCCCTGGC
TGACCACGGGTCACATATCGGCATCCCTTACTGGGACTGGACAACTGCCTTCACAGAGTTA
CCCGCCCTTGTCACAGACTCCGAGAACAATCCCTTCCATGAG

Intron g(2)

GTCAGTTTAGTCTCCTGTCTGAGCTAACGATACCAATTTCCTATTTTCGAGAACCACGATG
ACGAGAAAACAAGCAATATAGATATAGATGCAGTATAGATCAAGTTAATGAATTCATTGCT
ATATGTTTGCTTGTAATAAACTTTAAGAAAACGAGAGCATGCACACAAATGAAACAAACAA
TTATGTGTTTGATAGGAATATGATATATGTATTTGGGGGCTGACGTGAGCAGGGTTGAAGG
GACAGTTTACATTGTCAGTAACACTGGGAGTATTCTTTGATCCACAATATATAGTTTCATT
GTGTTCAGCAGTTACAACTAACATTATATCATACATTACGTCGtAACATGCTTCTTTTGTC
CTCTTTTGCCAG

Domain g(3)

GGTCGCATTGATCATCTCGGTGTAACCACGTCACGTTCCCCCAGAGACATGCTGTTTAACG
ACCCAGAGCAAGGATCAGAGTCGTTCTTCTATAGACAAGTCCTCCTGGCTTTGGAGCAGAC
TGACTACTGCCAGTTCGAAGTCCAGTTTGAGCTGACCCACAACGCCATTCACTCCTGGACA
GGTGGACGTAGCCCTTACGGAATGTCGACCCTCGAGTTCACAGCCTACGATCCTCTCTTCT
GGCTTCACCACTCCAACACCGACAGAATCTGGGCTGTCTGGCAAGCACTGCAGAAATACCG
AGGACTCCCATACAACGAAGCACACTGTGAAATCCAGGTTCTGAAACAGCCCTTGAGGCCA
TTCAACGATGACATCAACCACAATCCAATCACCAAGACTAATGCCAGGCCTATCGATTCAT
TTGATTATGAGAGGtTTAACTATCAGTATGACACCCTTAGCTTCCATGGTAAGAGCATCCC
TGAACTGAATGACCTGCTCGAGGAAAGAAAAAGAGAAGAGAGAACATTTGCTGcCTTCCTT
CTTCGTGGAATCGGTTGCAGTGCTGATGTCGTCTTTGACATCTGCCGgCCCAATGGTGACT
GTGTCTTTGCAGGAACCTTTGCTGTGCTGGGAGGGGAGCTaGAAATGCCTTGGTCCTTCGA
CAGACTGTTCCGCTATGACATCACCAGAGTCATGAATCAGCTCCATCTCCAGTATGATTCA
GATTTCAGTTTCAGGGTGAAGCTTGTTGCCACCAATGGCACTGAGCTTTCATCAGACCTtC
TCAAGTCACCAACAATTGAACATGAACTTGG

Intron g/h

GTATGTTATCTTATCATCAAATGTGTGATCAGATACTGGAGACGTTTTCATATTAACTTGG
TCAGCATTAGTTGATGATTTTGGTGCGATGTTGACGACAAGGAGTCAAGCATTAACACATT
CAACACATCTTTAATCTGATATGAGAAGGGAATAAATTGATCCAGTATTGATGATTGAAGT
TAGATTAACAGTGAAAGATATACCAGTTTTGATAATCGTATAAAACAGTAGCAGAATTGTA
TCGTGAAAACTAAATGTGGGAAGGCGAACGCCAAGCAGATTTTAGATTACGATCGTGTGCT
AGAATAATTCACAATAACCCAGACGTCGGAAATGTGGTTGTCTATGGCAATGGTTACGATT
AATTGCTAACATGCACGATTTACCTATTTCAG

Domain h

AGCCCACAGAGGACCAGTTGAAGAAACAGAAGTCACTCGCCAACATACTGACGGCAATGCA
CACTTTCATCGTAAGGAAGTTGATTCGCTGTCCCTGGATGAAGCAAACAACTTGAAGAATG
CCCTTTACAAGCTACAGAACGACCACAGTCTAACGGGATACGAAGCAATCTCTGGTTACCA
TGGATACCCCAATCTGTGTCCGGAAGAAGGCGATGACAAAATACCCCTGCTGCGTCCCCGG
ATGGGCATCTTTCCTTACTGGCACAGACTCTTGACCATTCAACTGGAAAGAGCTCTTGAGC
ACAATGGTGCACTGCTTGGTGTTCCTTACTGGGACTGGAACAAGGACCTGTCGTCACTGCC
GGCGTTCTTCTCCGACTCCAGCAACAACAATCCCTACTTCAAGTACCACATCGCCGGTGTT
GGTCACGACACCGTCAGAGAGCCAACTAGTCTTATATATAACCAGCCCCAAATCCATGGTT
ATGATTATCTCTATTACCTAGCATTGACCACGCTTGAAGAAAACAATTACTGGGACTTTGA
GGTTCAGTATGAGATCCTCCACAACGCCGTCCACTCCTGGCTTGGAGGATCCCAGAAGTAT
TCCATGTCTACCCTGGAGTATTCGGCCTTTGACCCTGTCTTTATGATCCTTCACTCGGGTC
TAGACAGACTTTGGATCATCTGGCAAGAACTTCAGAAGATCAGGAGAAAGCCCTACAACTT
CGCTAAATGTGCTTATCATATGATGGAAGAGCCACTGGCGCCCTTCAGCTATCCATCTATC
AACCAGGACGAGTTCACCCGTGCCAACTCCAAGCCTTCTACAGTTTTTGACAGCCATAAGT

TCGGCTACCATTACGATAACCTGAATGTTAGAGGTCACAGCATCCAAGAACTCAACACAAT
CATCAATGACTTGAGAAACACAGACAGAATCTACGCAGGATTTGTTTTGTCAGGCATCGGT
ACGTCTGCTAGTGTCAAGATCTATCTCCGAACAGATGACAATGACGAAGAAGTTGGAACTT
TCACTGTCCTGGGAGGAGAGAGGGAAATGCCATGGGCCTACGAGCGAGTTTTCAAGTATGA
CATCACAGAGGTTGCAGATAGACTTAAAATTAAGTTATGGGGACACCCTTTAACTTCCGGA
ACTGGAGATCACATCCTTACGAATGGAATCGGTGGTAAACAAGAGCCTACCCAAATCCTTT
CATCATCTACAGACCTGCCAATCATGACTACGATGTTCTTGTTATCCCAGTANGGAAGAAA
CCTTCACATCCCTCCCAAAGTTGTCGTCAAGAAAGGCACCCGCATCGAGTTCCACCCAGTC
GATGATTCAGTTACGAGACCAGTTGTTGATCTTGGAAGCTACACTGCACTCTTCAACTGTG
TGGTACCACCGTTCACATACCACGGATTCGAACTGAACCACGTCTATTCTGTCAAGCCTGG
TGACTACTATGTTACTGGACCCACGAGAGACCTTTGCCAGAATGCAGATGTCAGGATTCAT
ATCCATGTTGAGGATGAGTAA

3´UTR

CGCAACAGGT

Intron UTR

GAGATAAGAAACCCTTCTAACAGTAATACGACACCACATTACAGCTTAAACATGATTGCCA
TCGATGTTTTCATGTGTAGTATACGCTTTTCAGTTCTACATAATTTTGTTTTTCAAATCAA
GTTTAGCAAATGAATCTATCACTGGAAAATAGGGTAGGGTAGCCAAGTGGTTAAAGCGGTC
ACTGATCACGCCAAAGACGAGTGTCCTAACCTGCATGGGTACAAAAGTGAAGACCATTGCT
GGTGTCTACCGCCGTAATATTGTTTTTAGTATTGCTAAAACTTATACTCACCCATGCGCTG
TAAAAGTGGAATAATAATCATATTTCAACAAAAGCACAAAACCATTTCATTTTCATGAAAG
CCTCTTGTTCACCTGAAAGACGCAAGAGAACAATAGTTCCTAACATTATTTCAGACATTG
GAAATGTCCTGCACGTGTAAACCATATATCCTTTGAAATTTTTACGACTGCATCGTATACA
ATTTATGATATAAATTTAAAACTTTAT

3`UTR

TTCTTGGTCTCCACATATTCACATATCAGCACCAAATGGTTTCGAAGGACATTGGCGTTCT
TCTCTGGCAATGCATTTCAATACAACATTGAAAATGACTTCAGCATATCAGTGTGCTTCGA
ACGTGTTCCGGAAGTACTCAAATGTGCTATGACTGAATTATTGTACATACATAACTTATTG
ATGTTCAATAAATAAATGTTGAAACGAAAAAAAAAAAAAAAAAAAAAAAA

Figure 7

Derived primary structure of HtH2

Domain b

HRLFVTQVEDALIRRGSPIGVPYWDWTQPMAHLPGLADNATYRDPISGDSRHNPFHDVEVA
FENGRTERHPDSRLFEQPLFGKHTRLFDSIVYAFEQEDFCDFEVQFEMTHNNIHAWIGGGE
KYSMSSLHYTAFDPIFYLRHSNTDRLWAIWQALQIRRNRPYKAHCAWSEERQPLKPFAFSS
PLNNNEKTYENSVPTNVYDYEGVLGYTYDDLNFGGMDLGQLEEYIQRQRQRDRTFAGFFLS
HIGTSANVEIIIDHGTLHTSVGTFAVLGGEKEMKWGFDRLYKYEITDELRQLNLRADDVFS
ISVKVTDVDGSELSSELIPSAAIIFERSH

Domain c

IDHQDPHHDTIIRKNVDNLTPEEINSLRRAMADLQSDKTAGGFQQIAAFHGEPKWCPSPDA
EKKFSCCVHGMAVFPHWHRLLTVQGENALRKHGCLGALPYWDWTRPLSHLPDLVLVSSRTT
PMPYSTVEARNPWYSGHIDTVGVDTTRSVRQELYEAPGFGHYTGVAKQVLLALEQDDFCDF
EVQFEIAHNFIHALVGGSEPYGMASLRYTTYDPIFYLHHSNTDRLWAIWQALQKYRGKPYN
SANCAIASMRKPLQPFGLTDEINPDDETRQHAVPFSVFDYKNNFNYEYDTLDFNGLSISQL
DRELSRRKSHDRVFAGFLLHGIQQSALVKFFVCKSDDDCDHYAGEFYILGDEAEMPWGYDR
LYKYEITEQLNALDLHIGDRFFIRYEAFDLHGTSLGSNIFPKPSVIHDEGA

Domain d

GHHQADEYDEVVTAASHIRKNLKDLSKGEVESLRSAFLQLQNDGVYENIAKFHGKPGLCDD
NGRKVACCVHGMPTFPQWHRLYVLQVENALLERGSAVSVPYWDWTETFTELPSLIAEATYF
NSRQQTFDPNPFFRGKISFENAVTTRDPQPELYVNRYYYQNVMLVFEQDNYCDFEIQFEMV
HNVLHAWLGGRATYSISSLDYSAFDPVFFLHHANTDRLWAIWQELQRYRKKPYNEADCAIN
LMRKPLHPFDNSDLNHDPVTFKYSKPTDGFDYQNNFGYKYDNLEFNHFSIPRLEEIIRIRQ
RQDRVFAGFLLHNIGTSATVEIFVCVPTTSGEQNCENKAGTFAVLGGETEMAFHFDRLYRF
DISETLRDLGIQLDSHDFDLSIKIQGVNGSYLDPHILPEPSLIFVPGSS

Domain e

SFLRPDGHSDDILVRKEVNSLTTRETASLIHALKSMQEDHSPDGFQAIASFHALPPLCPSP
SAAHRYACCVHGMATFPQWHRLYTVQFQDALRRHGATVGVPYWDWLRPQSHLPELVTMETY
HDIWSNRDFPNPFYQANIEFEGENITTEREVIADKLFVKGGHVFDKLVLQTSHPSAEQENY
CDFEIQFEILHNGVHTWVGGSRTYSIGHLHYAFYDPLFYLHHFQTDRIWAIWQELQEQRGL
SGDEAHCALEQMREPLKPFSFGAPYNWNQLTQDFSRPEDTFDYRKFGYEYDNLEFLGMSVA
ELDQYIIEHQENDRVFAGFLLSGFGGSASVNFQVCRADSTCQDAGYFTVLGGSAEMAWAFD
RLYKYDITETLEKMHLRYDDDFTISVSLTANNGTVLSSSLIPTPSVIFQRGH

Domain f

RDINTRSMSPNRVRRELSDLSARDLSSLKSALRDLQEDDGPNGYQALAAFHGLPAGCHDSR
GNEIACCIHGMPTFPQWHRLYTLQLEMALRRHGSSVAIPYWDWTKPISELPSLFTSPEYYD
PWHDAVVNNPFSKGFVKFANTYTVRDPQEMLFQLCEHGESILYEQTLLALEQTDYCDFEVQ
FEVLHNVIHYLVGGRQTYALSSLHYASYDPFFFIHHSFVDKMWVVWQALQKRRKLPYKRAD
CAVNLMTKPMRPFDSDMNQNPFTKMHAVPNTLYDYETLYYSYDNLEIGGRNLDQLQAEIDR

SRSHDRVFAGFLLRGIGTSADVRFWICRNENDCHRGGIIFILGGAKEMPWSFDRNFKFDIT
HVLENAGISPEDVFDAEEPFYIKVEIHAVNKTMIPSSVIPAPTIIYSPGE

Domain g

GRAADSAHSANIAGSGVRKDVTTLTVSETENLRQALQGVIDDTGPNGYQAIASFHGSPPMC
EMNGRKVACCAHGMASFPHWHRLYVKQMEDALADHGSHIGIPYWDWTTAFTELPALVTDSE
NNPFHEGRIDHLGVTTSRSPRDMLFNDPEQGSESFFYRQVLLALEQTDYCQFEVQFELTHN
AIHSWTGGRSPYGMSTLEFTAYDPLFWLHHSNTDRIWAVWQALQKYRGLPYNEAHCEIQVL
KQPLRPFNDDINHNPITKTNARPIDSFDYERFNYQYDTLSFHGKSIPELNDLLEERKREER
TFAAFLLRGIGCSADVVFDICRPNGDCVFAGTFAVLGGELEMPWSFDRLFRYDITRVMNQL
HLQYDSDFSFRVKLVATNGTELSSDLLKSPTIEHEL

Domain h

GAHRGPVEETEVTRQHTDGNAHFHRKEVDSLSLDEANNLKNALYKLQNDHSLTGYEAISGY
HGYPNLCPEEGDDKIPLLRPRMGIFPYWHRLLTIQLERALEHNGALLGVPYWDWNKDLSSL
PAFFSDSSNNNPYFKYHIAGVGHDTVREPTSLIYNQPQIHGYDYLYYLALTTLEENNYWDF
EVQYEILHNAVHSWLGGSQKYSMSTLEYSAFDPVFMILHSGLDRLWIIWQELQKIRRKPYN
FAKCAYHMMEEPLAPFSYPSINQDEFTRANSKPSTVFDSHKFGYHYDNLNVRGHSIQELNT
IINDLRNTDRIYAGFVLSGIGTSASVKIYLRTDDNDEEVGTFTVLGGEREMPWAYERVFKY
DITEVADRLKIKLWGHPLTSGTGDHILTNGIGGKQEPTQILSSSTDLPIMTTMFLLSQXGR
NLHIPPKVVVKKGTRIEFHPVDDSVTRPVVDLGSYTALFNCVVPPFTYHGFELNHVYSVKP
GDYYVTGPTRDLCQNADVRIHIHVEDE

Figure 8

*KLH1 cDNA sequence and intron structure*

Domain b

GGCCTACCGTACTGGGACTGGACTGAACCCATGACACACATTCCGGGTCTGGCAGGAAACA
AAACTTATGTGGATTCTCATGGTGCATCCCACACAAATCCTTTTCATAGTTCAGTGATTGC
ATTTGAAGAAAATGCTCCCCACACCAAAAGACAAATAGATCAAAGACTCTTTAAACCCGCT
ACCTTTGGACACCACACAGACCTGTTCAACCAGATTTTGTATGCCTTTGAACAAGAAGATT
ACTGTGACTTTGAAGTCCAATTTGAGATTACCCATAACACGATTCACGCTTGGACAGGAGG
AAGCGAACATTTCTCAATGTCGTCCCTACATTACACAGCTTTCGATCCTTTGTTTTACTTT
CACCATTCTAACGTTGATCGTCTTTGGGCCGTTTGGCAAGCCTTACAGATGAGACGGCATA
AACCCTACAGGGCCCACTGCGCCATATCTCTGGAACATATGCATCTGAAACCATTCGCCTT
TTCATCTCCCCTTAACAATAACGAAAAGACTCATGCCAATGCCATGCCAAACAAGATCTAC
GACTATGAAAATGTCCTCCATTACACATACGAAGATTTAACATTTGGAGGCATCTCTCTGG
AAAACATAGAAAAGATGATCCACGAAAACCAGCAAGAAGACAGAATATATGCCGGTTTTCT
CCTGGCTGGCATACGTACTTCAGCAAATGTTGATATCTTCATTAAAACTACCGATTCCGTG
CAACATAAGGCTGGAACATTTGCAGTGCTCGGTGGAAGCAAGGAAATGAAGTGGGGATTTG
ATCGCGTTTTCAAGTTTGACATCACGCACGTTTTGAAAGATCTCGATCTCACTGCTGATGG
CGATTTCGAAGTTACTGTTGACATCACTGAAGTCGATGGAACTAAACTTGCATCCAGTCTT
ATTCCACATGCTTCTGTCATTCGTGAGCATGCACGTGGTAAGCTGAATAGAG

Intron b/c

GTTTTGTAATAATTATGTAGAATTCTTTACCTCAGAATAAGATGAGGTCACATGGGTTTTG
CAAAACTATTACGTTCGAATTAATATTAATAATACCGGACCCTCCACTGGTACATATTTAT
CTTTATAACGATAATAGCGATGATGATGATGATGATGATGATGATGATGATGATgATAATg
ATgATGCCGGTATTGCACGTAATCCAGCCGAcTTAGATGACACCCTAAGGGTGCAGAAAGT
ATAaCAATTAGATTGCGTTtGCATCTGTGTATGCGTGTGCTTTAaCCAAAAGTCAAAATAA
AAGTGCAAACCCTTAGTTTATTCATTTGATAGAGCCTTTTACGATAAGAACAATGTAATAA
ATTAGAACATAACTGAAACCTCCGAAAGAAGGCCTGTTTGTCAAGAGAGGTATCGACATGA
TTGACTTATAAACCTGTGCTTCTATATTTTGGAACTGTCCACTTTCTTGTTGTGTGTACTG
TAATCACATCGCACTATGGCTGCAAGACGTGTACGAGTACACTATATACTTACCTAATGAC
CAACCACAAGGCTGGCTTTGTTAATATTGTTATTTCACAGAAATAAACACAGAATTCCAGC
ATTTGGCTGGTGTATTTAGCAAAACACCGATATGACACTCATGTTTTATTACATTTTTTC
AG

Domain c

TTAAATTTGACAAAGTGCCAAGGAGTCGTCTTATTCGAAAAAATGTAGACCGTTTGAGCCC
CGAGGAGATGAATGAACTTCGTAAAGCCCTAGCCTTACTGAAAGAGGACAAAAGTGCCGGT
GGATTTCAGCAGCTTGGTGCATTCCATGGGGAGCCAAAATGGTGTCCTAGTCCCGAAGCAT
CTAAAAAATTTGCCTGCTGTGTTCACGGCATGTCTGTGTTCCCTCACTGGCATCGACTGTT
GACGGTTCAGAGTGAAAATGCTTTGAGACGACATGGCTACGATGGAGCTTTGCCGTACTGG
GATTGGACCTCTCCTCTTAATCACCTTCCCGAACTGGCAGATCATGAGAAGTACGTCGACC
CTGAAGATGGGGTAGAGAAGCATAACCCTTGGTTCGATGGTCATATAGATACAGTCGACAA
AACAACAACAAGAAGTGTTCAGAATAAACTCTTCGAACAGCCTGAGTTTGGTCATTATACA
AGCATTGCCAAACAAGTACTGCTAGCGTTGGAACAGGACAATTTCTGTGACTTTGAAATCC
AATATGAGATTGCCCATAACTACATCCATGCACTTGTAGGAGGCGCTCAGCCTTATGGTAT
GGCATCGCTTCGCTACACTGCTTTTGATCCACTATTCTACTTGCATCACTCTAATACAGAT
CGTATATGGGCAATATGGCAGGCTTTACAGAAGTACAGAGGAAAACCGTACAACGTTGCTA
ACTGTGCTGTTACATCGATGAGAGAACCTTTGCAACCATTTGGCCTCTCTGCCAATATCAA
CACAGACCATGTAACCAAGGAGCATTCAGTGCCATTCAACGTTTTTGATTACAAGACCAAT

TTCAATTATGAATATGACACTTTGGAATTTAACGGTCTCTCAATCTCTCAGTTGAATAAAA
AGCTCGAAGCGATAAAGAGCCAAGACAGGTTCTTTGCAGGCTTCCTGTTATCTGGTTTCAA
GAAATCATCTCTTGTTAAATTCAATATTTGCACCGATAGCAGCAACTGTCACCCCGCTGGA
GAGTTTTACCTTCTGGGTGATGAAAACGAGATGCCATGGGCATACGATAGAGTCTTCAAAT
ATGACATAACCGAAAAACTCCACGATCTAAAGCTGCATGCAGAAGACCACTTCTACATTGA
CTATGAAGTATTTGACCTTAAACCAGCAAGCCTGGGAAAAGATTTGTTCAAGCAGCCTTCA
GTCATTCATGAACCAAGAATAG

Intron c/d

GTACTTGTTATATGTTTCGAATATTGCCGATACCTTCAATATATATACTTTATCAAAGTAA
TTGATTAATCTGAAGTAATTTTCCTTTCCAGTAGAGATTCAGTTGATACAACAAGAATTCG
CCCTGTTGTATGTCACTTTATTTTCATCAAACGATTCGAAGTGAGCTGTCCATGCCACAAT
GGGGTCTCTGTAACTTTCTCGTATGGGGTATAGATTATATAGACGTGGCAGACCTTACGTA
TAACTAATATTTGTGTAATGTCGTTTCAG

Domain d

GTCACCATGAAGGCGAAGTATATCAAGCTGAAGTAACTTCTGCCAACCGTATTCGAAAAAA
CATTGAAAATCTGAGCCTTGGTGAACTCGAAAGTCTGAGAGCTGCCTTCCTGGAAATTGAA
AACGATGGAACTTACGAATCAATAGCTAAATTCCATGGTAGCCCTGGTTTGTGCCAGTTAA
ATGGTAACCCCATCTCTTGTTGTGTCCATGGCATGCCAACTTTCCCTCACTGGCACAGACT
GTACGTGGTTGTCGTTGAGAATGCCCTCCTGAAAAAAGGATCATCTGTAGCTGTTCCCTAT
TGGGACTGGACAAAACGAATCGAACATTTACCTCACCTGATTTCAGACGCCACTTACTACA
ATTCCAGGCAACATCACTATGAGACAAACCCATTCCATCATGGCAAAATCACACACGAGAA
TGAAATCACTACTAGGGATCCCAAGGACAGCCTCTTCCATTCAGACTACTTTTACGAGCAG
GTCCTTTACGCCTTGGAGCAGGATAACTTCTGTGATTTCGAGATTCAGTTGGAGATATTAC
ACAATGCATTGCATTCTTTACTTGGTGGCAAAGGTAAATATTCCATGTCAAACCTTGATTA
CGCTGCTTTTGATCCTGTGTTCTTCCTTCATCACGCAACGACTGACAGAATCTGGGCAATC
TGGCAAGACCTTCAGAGGTTCCGAAAACGGCCATACCGAGAAGCGAATTGCGCTATCCAAT
TGATGCACACGCCACTCCAGCCGTTTGATAAGAGCGACAACAATGACGAGGCAACGAAAAC
GCATGCCACTCCACATGATGGTTTTGAATATCAAAACAGCTTTGGTTATGCTTACGATAAT
CTGGAACTGAATCACTACTCGATTCCTCAGCTTGATCACATGCTGCAAGAAAGAAAAAGGC
ATGACAGAGTATTCGCTGGCTTCCTCcTTCACAATATTGGAACatCTGCCGATGGCCATGT
ATTTGTATGTCTCCCAACTGGGGAACACACGAAGGACTGCAGTCATGAGGCTGGTATGTTC
TCCATCTTAGGCGGTCAAACGGAgATGTCCTTTGTATTTGACAGACTTTACAAACTTGACA
TAACTAAAGCCTTGAAAAAGAACGGTGTGCACCTGCAAGGGGATTTCGATCTGGAAATTGA
GATTACGGCTGTGAATGGATCTCATCTAGACAGTCATGTCATCCACTCTCCCACTATACTG
TTTGAGGCCGGAACAG

Intron d/e

GTAACTATTTTGTCACTGTAACCAACAACTGCAGTCTATTTTGCAATTACGATAATAACAA
TTTTTGAAATATATCTTTATTAAAGCAAAGGTTTCTAGAGACAAACAGCCGGCTCTAATTA
TTTTTTCGAACTTACGCTTGAGTAAAGATCTGCAAATGGCAACCCTACCTATACTATTAAA
AATATAATGTTACATTCGTATCTGAATGTTTAATAAATCACTTCATATTCTGTTGCAG

Domain e

ATTCTGCCCACACAGATGATGGACACACTGAACCAGTGATGATTCGCAAAGATATCACACA
ATTGGACAAGCGTCAACAACTGTCACTGGTGAAAGCCCTCGAGTCCATGAAAGCCGACCAT
TCATCTGATGGGTTCCAGGCAATCGCTTCCTTCCATGCTCTTCCTCCTCTTTGTCCATCAC
CAGCTGCTTCAAAGAGGTTTGCGTGCTGCGTCCATGGCATGCCAACCTTCCCGCAATG

Figure 9

Derived primary structure of KLH1

Domain b

GLPYWDWTEPMTHIPGLAGNKTYVDSHGASHTNPFHSSVIAFEENAPHTKRQIDQRLFKPA
TFGHHTDLFNQILYAFEQEDYCDFEVQFEITHNTIHAWTGGSEHFSMSSLHYTAFDPLFYF
HHSNVDRLWAVWQALQMRRHKPYRAHCAISLEHMHLKPFAFSSPLNNNEKTHANAMPNKIY
DYENVLHYTYEDLTFGGISLENIEKMIHENQQEDRIYAGFLLAGIRTSANVDIFIKTTDSV
QHKAGTFAVLGGSKEMKWGFDRVFKFDITHVLKDLDLTADGDFEVTVDITEVDGTKLASSL
IPHASVIREHARGKLNR

Domain c

VKFDKVPRSRLIRKNVDRLSPEEMNELRKALALLKEDKSAGGFQQLGAFHGEPKWCPSPEA
SKKFACCVHGMSVFPHWHRLLTVQSENALRRHGYDGALPYWDWTSPLNHLPELADHEKYVD
PEDGVEKHNPWFDGHIDTVDKTTTRSVQNKLFEQPEFGHYTSIAKQVLLALEQDNFCDFEI
QYEIAHNYIHALVGGAQPYGMASLRYTAFDPLFYLHHSNTDRIWAIWQALQKYRGKPYNVA
NCAVTSMREPLQPFGLSANINTDHVTKEHSVPFNVFDYKTNFNYEYDTLEFNGLSISQLNK
KLEAIKSQDRFFAGFLLSGFKKSSLVKFNICTDSSNCHPAGEFYLLGDENEMPWAYDRVFK
YDITEKLHDLKLHAEDHFYIDYEVFDLKPASLGKDLFKQPSVIHEPRI

Domain d

GHHEGEVYQAEVTSANRIRKNIENLSLGELESLRAAFLEIENDGTYESIAKFHGSPGLCQL
NGNPISCCVHGMPTFPHWHRLYVVVVENALLKKGSSVAVPYWDWTKRIEHLPHLISDATYY
NSRQHHYETNPFHHGKITHENEITTRDPKDSLFHSDYFYEQVLYALEQDNFCDFEIQLEIL
HNALHSLLGGKGKYSMSNLDYAAFDPVFFLHHATTDRIWAIWQDLQRFRKRPYREANCAIQ
LMHTPLQPFDKSDNNDEATKTHATPHDGFEYQNSFGYAYDNLELNHYSIPQLDHMLQERKR
HDRVFAGFLLHNIGTSADGHVFVCLPTGEHTKDCSHEAGMFSILGGQTEMSFVFDRLYKLD
ITKALKKNGVHLQGDFDLEIEITAVNGSHLDSHVIHSPTILFEAG

Domain e

DSAHTDDGHTEPVMIRKDITQLDKRQQLSLVKALESMKADHSSDGFQAIASFHALPPLCPS
PAASKRFACCVHGMPTFPQWHRLYTVQFQDSLRKHGAVVGLPYWDWTLPR

Figure 10

KLH2 cDNA sequence and intron structure

Domain b

GGCCTGCCCTACTGGGATTGGACCATGCCAATGAGTCATTTGCCAGAACTGGCTACAAGTG
AGACCTACCTCGATCCAGTTACTGGGGAAACTAAAAACAACCCTTTCCATCACGCCCAAGT
GGCGTTTGAAAATGGTGTAACAAGCAGGAATCCTGATGCCAAACTTTTTATGAAACCAACT
TACGGAGACCACACTTACCTCTTCGACAGCATGATCTACGCATTTGAGCAGGAAGACTTCT
GCGACTTTGAAGTCCAATATGAGCTCACGCATAATGCAATACATGCATGGGTTGGAGGCAG
TGAAAAGTATTCAATGTCTTCTCTTCACtacacTGCTTTTGATCCTATATTTTACCTCCAT
CACTCAAATGTTGATCGTCTCTGGGCCATTTGGCAAGCTCTTCAAATCAGGAGAGGCAAGT
CTTACAAGGCCCACTGCGCCTCGTCTCAAGAAAGAGAACCATTAAAGCCTTTTGCATTCAG
TTCCCCACTGAACAACAACGAGAAAACGTACCACAACTCTGTCCCCACTAACGTTTATGAC
TATGTGGGAGTTTTGCACTATCGATATGATGACCTTCAGTTTGGCGGTATGACCATGTCAG
AACTTGAGGAATATATTCACAAGCAGACACAACATGATAGAACCTTTGCAGGATTCTTCCT
TTCATATATTGGAACATCAGCAAGCGTAGATATCTTCATCAATCGAGAAGGTCATGATAAA
TACAAAGTGGGAAGTTTTGTAGTACTTGGTGGATCCAAAGAAATGAAATGGGGCTTTGATA
GAATGTACAAGTATGAGATCACTGAGGCTCTGAAGACGCTGAATGTTGCAGTGGATGATGG
GTTCAGCATTACTGTTGAGATCACCGATGTTGATGGATCTCCCCCATCTGCAGATCTCATT
CCACCTCCTGCTATAATCtTTGaACGTGGTCaTG Intron 2b/c AGGTATTTAAAAAAGTAATAAAACCaTATTTTCGAATGCGCTTTATGAAATATCGTGTGAC
TGGTTCTTTAGTTTACATGGAGTGTAACAACATGCTCCATCAGTTGACATATACTGCTCAC
ACAAAGTAAGGGATATTTGATAATGATAACAAATATAATCAAAGCGGTTATACTATCAAGA
CTTATTCACATAATTACAGGTGAAGGGAGGTGTGATCGTGTTCACTGATCAGGTTGAGGCC
AGAGAAGTCCCAGTTTGAGTCTTGCAGAAGATGATGTTTAGGCATGGGGTCGAATCACCAA
AATCACATGACTTCAATAACGGGTTGGACCACCTCGAGCGACgATGCAAGCAGTAGAGCGT
CTACGCATGCTCCTGATAAGGCGACCAATCTGTTCCTGGGGAATCAGtCGCCACTCCTCTT
GTAGTGCCACGCTCATTTCTGCTACGGTCCTGGGTACCTGCTATCGGgTCTTGATCCGTAT
CCCAAGGATGTCCCACACATGTTCAAgGTGAGAGGTCGGGGAACATCGCTGGCCACGGTaA
GGtCTGAATTTGATGCCGTTGAAAGTGAGCTCTGACAACcTGAGCATGGtGAGCTCTGACG
TTGTCGTCCTGAAAGATGAATcCAGCTcCaTGaCAGCGAGCAAaGGGCAGGACGTGTTGGT
CAATGCAGTTGTCTCTGCAGTACACACCTGTCACTCGCCACTCACAAGCGTGTAGATCTGT
ACGACCAGTCATGGAGATCCCAGCCCACATCATAACGGACCCCTATCCATACCGATCATGA
GCCACCATAGCAGCGTCTTGATGACGTTCTCCCTGTCGCCTCGACATCCTcACACGGCCAA
AAGGAACGTGGACTCGTCACTGAACATGACATTAGCCAACCTGGCACTTGTCCACCGCTGA
TGTTGGCGAGACCATTCCAGTCGAGCTCTTCGGTGTCTGGCTTTCATCGATAACACGACGT
AAGGTCTGCGGGCGTGCAAGACGGCTCTATGCAGGCGATTTCGGATTGTCTGGGTGCTAAC
TCTGATCCCAGGTGCCTGCTGAAGTTGATGCTGGATCTGTGTGGCATTGAGATGGCGATTC
CTTAGGACTGTGGAGATGATGAATCGATCTTGACTTATGGTGGTGACATTAGGACGTCGGG
TTCGTGTCCTATCCTGCACTCTTCCAGTTGTTCGGTGACGCTCTGGTACCCGGCTGATTAC
TGACTGAGAATATCCATCTGCCGTGCGACATGAGCCTGTGTTGGCCCAGCCTGAAGCATTG
CAATCGCCAGAGACGCTCTTCAAAAGTCATTCGACGCATGGtTTTCTGTTCACAAATGACA
GCGTAAAACAGtTTTTGGtGCTTTTATGCTTCCCAAGAGCATGAAAAACACGTTCTATgGG
TCGtGCACACCTTACATGACAAGtGtGAAAAGtGACTTGcACCCCCTTGtGtGTTCGGATG
CACACTCTGTTTACGTACTGATGCGATTTGGCGTCTAAACATGTTTTGGCGTCTAAACATG
TTTTCCTGCATGATTCATATACTATTTTGTCATATTCCTGGCATCAAACCAAACTACAGTG
AAATATATTTCAATATCCCCTACTTTGTGTGAGTAGTATAGATCACTGCAGACAACATATA GACAAtGCAgtTaCaCCGTCAACAATCCCAGTCATTAATTATGATGaCaCTTCCACACATA
GTGTCAGTGATTGTAATTCAaCTGTACACACTTTTCCCGTGAACATTCAGGATCTATATGA
CTAAATATATAACATTAGTATACGTGCAGTTTTGTATCGCTACGACATTGTTGTAACTCTT
TGTTTAATCATTTaACAG Domain c CTGATGCCAAAGaCTTTGgCCATAGCAGAAAAATCAGgAAAGcCGTTGATTcTcTGACAGT
CgAAGAACAAAcTTCGTTGAGgCGAGcTATGgCAGATcTACAGGACGACAAAACATCAGGG
GGTTTCCAGCAGATTGCAGCATTCCACGGAGAACCAAAATGGTGTCCAAGCCCCgAAGCGG
AGAAAAAATTTGCATGCTGTGTTCATGGAATGGCTGTTTTCCCTCACTGGCACAGATTGCT
GACAGTTCAAGGAGAAAATGCTCTGAGGAAACATGGCTTTACTGGTGGACTGCCCTACTGG
GACTGGACTCGATCAATGAGCGCCCTTCCACATTTTGTTGCTGATCCTACTTACAATGATG
CTATTTCCAGCCAGGAAGAAGATAACCCATGGCATCATGGTCACATAGACTCTGTTGGGCA
TGATACTACAAGAGATGTGCGTGATGATCTTTATCAATCTCCTGGTTTCGGTCACTACACA
GATATTGCACAACAAGTCCTTCTGGCCTTTGAGCAGGACAGTTTCTGTGATTTTGAGGTAC
AATTTGAAATTGCCCATAATTTCATACATGCACTGATTGGTGGTAACGAACCATACAGTAT
GTCATCTTTGAGGTATACTACATACGATCCAATCTTCTTCTTGCACCACTCCAGTACAGAC
CGACTTTGGGCCATCTGGCAAGCAATCACTAGTGCGGCCGCCTGCAGGTCGACCATAAGGG
AGAGCTCCCAACGCgtTGGAtGCAATCT Domain g ATGGCTGTGTTTCCGCACTGGCACAGACTGTTTGTGAAACAGATGGAGGACGCACTTGCTG
CTCATGGAGCTCATATTGGCATACCATACTGGGATTGGACAAGTGCGTTTAGTCATCTGCC
CGCCCTAGTGACTGACCACGAGAACAATCCCTTCCACCAC Intron g(2)

GTATGTGTCAAATCGTTTTAGGAACTGCCTTATCCATTTTACAATTACGAGTACAAAATGA
AAACGGAAACTGTGTGACCTCGAAAAGTGCAATCTTTAAAGGATGCAATGTACACAATAAA
ATGCTCCGATCAAAAGCGATGGCTAGAAATCATTTTCCCTCTAATTCCCTTTCACACAGCT
CGGTTCGTTTTAAGTAGGAACAAGTCTCTGCAAAAACATCACAAATAAAGAGAACACAGAA
AAAACCTCATTCTCGTTTCTGTATTCCGAAAATGAAATTTACAATTTCTTTCATTTATAG

Domain g

GGCCATATTGGTCATCTGAATGTGGATACATCTCGATCTCCAAGAGACATGCTGTTTAATG
ATCCTGAACAAGGCTCAGAATCATTCTTCTACAGACAGGTTCTCTTGACTCTAGAACAGAC
AGACTTCTGCCAATTTGAAGTTCAGTTTGAACTTACACACAATGCCATCCACTCTTGGACT
GGAGGACATACTCCATATGGAATGTCATCACTGGAATATACAGCATATGATCCACTCTTTT
ATCTCCACCATTCCAACACTGATCGTATCTGGGCCATCTGGCAGGCACTCCAGAAATATAG
AGGTCTTCCATACAACGCAGCTCACTGCGATATccaagttctgaaacaacctcTTAAACCA
TTCAGCGAGTCCAGGAATCCAAACCCAGTCACCAGAGCCAATTCTAGGGCCGTTGATTCAT
TTGATTATGAGAAATTCAATTATCAATATGACACACTTACCTTCCACGGACTTTCTATCCC
AGAACTTGATGCCATGCTTCAAGAGAGAAAGAAGGAAGAGAGAACATTTGCAGCCTTCCTG
TTGCACGGATTTGGCGCCAGTGCTGATGTTTCGTTTGATGTCTGCACACCTGATGGTCATT
GTGCCTTTGCTGGAACCTTCGCGGTACTTGGTGGGGAGCTTGAGATGCCCTGGTCCTTTGA
AAGATTGTTCCGTTACGATATCACAAAGGTTCTCAAGCAGATGAATCTTCACTATGATTCT
GAGTTCCACTTTGAGTTGAAGATTGTTGGCACAGATGGAACAGAACTGCCATCGGATCGTA
TCAAGAGCCCTACCATTGAACACCATGGAGGAG Intron g/h GTATGTTTTGAGATCCACATAATCTTCTACCCTGTCTCATTTCTAATGCTCTTCAATACAC
AATTTATATAGCCTTTGAGCTTCAGATGTATTACGGACAGGCATTACAGTATACATGTAAT
ATGGTTTTCTGCTATTTGCAAAAATTGTGTCCTATCTCTGTTCAGATCATCATGGCGGTGA
CACCTAG Domain h GTCACGATCACAGTGAACGTCACGATGGATTTTTCAGGAAGGAAGTCGGTTCCCTGTCCCT
GGATGAAGCCAATGACCTTAAAAATGCACTGTACAAGCTGCAGAATGATCAGGGTCCCAAT
GGATATGAATCAATAGCCGGTTACCATGGCTATCCATTCCTCTGCCCTGAACATGGTGAAG
ACCAGTACGCATGCTGTGTCCACGGAATGCCTGTATTTCCACATTGGCACAGACTTCATAC
AATCCAGTTTGAGAGAGCTCTCAAAGAACATGGTTCTCATTTGGGTCTGCCATACTGGGAC
TGGAC

Figure 11

Derived primary structure of KLH2

Domain b

GLPYWDWTMPMSHLPELATSETYLDPVTGETKNNPFHHAQVAFENGVTSRNPDAKLFMKPT
YGDHTYLFDSMIYAFEQEDFCDFEVQYELTHNAIHAWVGGSEKYSMSSLHYTAFDPIFYLH
HSNVDRLWAIWQALQIRRGKSYKAHCASSQEREPLKPFAFSSPLNNNEKTYHNSVPTNVYD
YVGVLHYRYDDLQFGGMTMSELEEYIHKQTQHDRTFAGFFLSYIGTSASVDIFINREGHDK
YKVGSFVVLGGSKEMKWGFDRMYKYEITEALKTLNVAVDDGFSITVEITDVDGSPPSADLI
PPPAIIFERGHA

Domain c

DAKDFGHSRKIRKAVDSLTVEEQTSLRRAMADLQDDKTSGGFQQIAAFHGEPKWCPSPEAE
KKFACCVHGMAVFPHWHRLLTVQGENALRKHGFTGGLPYWDWTRSMSALPHFVADPTYNDA
ISSQEEDNPWHHGHIDSVGHDTTRDVRDDLYQSPGFGHYTDIAQQVLLAFEQDSFCDFEVQ
FEIAHNFIHALIGGNEPYSMSSLRYTTYDPIFFLHHSSTDRLWAIWQALQKYRGKPYNTAN
CAIASMRKPLQPFGLDSVINPDDETREHSVPFRVFDYKNNFDYEYESLAFNGLSIAQLDRE
LQRRKSHDRVFAGFLLHEIGQSAKHNVSDCDHYAGEFYILGDEAEMPWRYDRVYKYEITQQ
LHDLDLHVGDNFFLKYEAFDLNGGSLGGSIFSQPSVIFEPAAGMF

Domain d

GSHQADEYREAVTSASHIRKNIRDLSEGEIESIRSAFLQIQKEGIYENIAKFHGKPGLCEH
DGHPVACCVHGMPTFPHWHRLYVLQVENALLERGSAVAVPYWDWTLPR

Domain g

MAVFPHWHRLFVKQMEDALAAHGAHIGIPYWDWTSAFSHLPALVTDHENNPFHHGHIGHLN
VDTSRSPRDMLFNDPEQGSESFFYRQVLLTLEQTDFCQFEVQFELTHNAIHSWTGGHTPYG
MSSLEYTAYDPLFYLHHSNTDRIWAIWQALQKYRGLPYNAAHCDIQVLKQPLKPFSESRNP
NPVTRANSRAVDSFDYEKFNYQYDTLTFHGLSIPELDAMLQERKKEERTFAAFLLHGFGAS
ADVSFDVCTPDGHCAFAGTFAVLGGELEMPWSFERLFRYDITKVLKQMNLHYDSEFHFELK
IVGTDGTELPSDRIKSPTIEHHGG

Domain h

GHDHSERHDGFFRKEVGSLSLDEANDLKNALYKLQNDQGPNGYESIAGYHGYPFLCPEHGE
DQYACCVHGMPVFPHWHRLHTIQFERALKEHGSHLGLPYWDW

SEQUENCE LISTING

```
<160> NUMBER OF SEQ ID NOS: 108

<210> SEQ ID NO 1
<211> LENGTH: 1269
<212> TYPE: DNA
<213> ORGANISM: HALIOTIS TUBERCULATA

<400> SEQUENCE: 1

ggcttgttca gtttctactc gtcgcccttg tggcgggggc tggagcagac aacgtcgtca     60

gaaaggacgt gagtcacctc acggatgacg aggtgcaagc tctccacggc gccctccatg    120

acgtcactgc atctacaggg cctctgagtt tcgaagacat aacatcttac catgccgcac    180

cagcgtcgtg tgactacaag ggacggaaga tcgcctgctg tgtccacggt atgcccagtt    240

tcccctctg gcacagggca tatgtcgtcc aagccgagcg ggcactgttg tccaaacgga     300

agactgtcgg aatgccttac tgggactgga cgcaaacgct gactcactta ccatctcttg    360

tgactgaacc catctacatt gacagtaaag gtggaaaggc tcaaaccaac tactggtacc    420

gcggcgagat agcgttcatc aataagaaga ctgcgcgagc tgtagatgat cgcctattcg    480

agaaggtgga gcctggtcac tacacacatc ttatggagac tgtcctcgac gctctcgaac    540

aggacgaatt ctgtaaattt gaaatccagt tcgagttggc tcataatgct atccattact    600
```

-continued

```
tggttggcgg taaatttgaa tattcaatgt caaacttgga atacacctcc tacgacccca    660

tcttcttcct ccaccactcc aacgttgacc gcctcttcgc catctggcag cgtcttcagg    720

aactgcgagg aaagaatccc aatgcaatgg actgtgcaca tgaactcgct caccagcaac    780

tccaaccctt caacagggac agcaatccag tccagctcac aaaggaccac tcgacacctg    840

ctgacctctt tgattacaaa caacttggat acagctacga cagcttaaac ctgaatggaa    900

tgacgccaga acagctgaaa acagaactag acgaacgcca ctccaaagaa cgtgcgtttg    960

caagcttccg actcagtggc tttggggggtt ctgccaacgt tgttgtctat gcatgtgtcc   1020

ctgatgatga tccacgcagt gatgactact gcgagaaagc aggcgacttc ttcattcttg   1080

ggggtcaaag cgaaatgccg tggagattct acagaccctt cttctatgat gtaactgaag   1140

cggtacatca ccttggagtc ccgctaagtg gccactacta tgtgaaaaca gaactcttca   1200

gcgtgaatgg cacagcactt tcacctgatc ttcttcctca accaactgtt gcctaccgac   1260

ctgggaaag                                                            1269
```

<210> SEQ ID NO 2
<211> LENGTH: 1257
<212> TYPE: DNA
<213> ORGANISM: HALIOTIS TUBERCULATA

<400> SEQUENCE: 2

```
gtcaccttga cccacctgtg catcatcgcc acgatgacga tcttattgtt cgaaaaaata     60

tagatcattt gactcgtgaa gaggaatacg agctaaggat ggctctggag agattccagg    120

ccgacacatc cgttgatggg taccaggcta cagtagagta ccatggcctt cctgctcgtt    180

gtccacgacc agatgcaaaa gtcaggttcg cctgttgtat gcatggcatg gcatccttcc    240

ctcactggca ccggctgttc gttacccagg tggaagatgc tcttgtacgg cgtggatcgc    300

ctatcggtgt tccttattgg gactggacaa aacctatgac tcaccttcca gacttggcat    360

caaatgagac gtacgtagac ccgtatggac atacacatca taatccattc ttcaatgcaa    420

atatatcttt tgaggaggga caccatcaca cgagcaggat gatagattcg aaactgtttg    480

ccccagtcgc ttttggggag cattcccatc tgtttgatgg aatcctgtac gcatttgagc    540

aggaagattt ctgcgacttt gagattcagt ttgagttagt ccataattct attcatgcgt    600

ggataggcgg ttccgaagat tactccatgg ccaccctgca ttacacagcc tttgacccca    660

ttttctacct tcatcattcc aatgtcgatc gtctatgggc aatctggcaa gctcttcaaa    720

tcaggagaca caagccatat caagcccact gtgcacagtc tgtggaacag ttgccaatga    780

agccatttgc tttcccatca cctcttaaca acaacgagaa gacacatagt cattcagtcc    840

cgactgacat ttatgactac gaggaagtgc tgcactacag ctacgatgat ctaacgtttg    900

gtgggatgaa ccttgaagaa atagaagaag ctatacatct cagacaacag catgaacgag    960

tcttcgcggg atttctcctt gctggaatag gaacatctgc acttgttgac attttcataa   1020

ataaaccggg gaaccaacca ctcaaagctg gagatattgc cattcttggt ggtgccaagg   1080

aaatgccttg ggcgtttgac cgcttgtata aggtcgaaat aactgactca ttgaagacac   1140

tttctctcga tgtcgatgga gattatgaag tcacttttaa aattcatgat atgcacggaa   1200

acgctcttga tacggacctg attccacacg cagcagttgt ttctgagcca gctcacc       1257
```

<210> SEQ ID NO 3
<211> LENGTH: 1242
<212> TYPE: DNA
<213> ORGANISM: HALIOTIS TUBERCULATA

-continued

<400> SEQUENCE: 3

```
ctacctttga ggatgaaaag cacagcttac gaatcagaaa aaatgtcgac agcttgactc      60
ctgaagaaac aaatgaactg cgtaaagccc tggagcttct tgaaaatgat catactgcag     120
gtggattcaa tcagcttggc gccttccatg gagagcctaa atggtgccct aatcctgaag     180
cggagcacaa ggttgcatgc tgtgttcatg gcatggctgt tttccctcat tggcacaggc     240
ttcttgctct ccaggcggag aatgctctta gaaagcatgg gtacagtggt gctctaccat     300
actgggattg gactcgcccc ctttcccaac ttcctgatct ggttagtcat gagcagtata     360
cagatccttc cgaccatcac gtgaagcata acccgtggtt caatggccac atcgatacag     420
taaatcagga taccaccaga agcgtacggg aggatcttta tcaacaacct gaatttggac     480
atttcacgga tattgctcaa caagtcctct tagcattaga acaagatgac ttctgttcgt     540
ttgaagtgca gtatgagatt tcccataatt ttatccatgc acttgtagga ggaaccgacg     600
cttatggcat ggcatcgctg agatatacag catacgatcc aatctttttc ttgcatcatt     660
caaacaccga caggatctgg gctatttggc aatccctgca aaaatacaga ggcaaaccgt     720
acaacactgc caactgcgcc atagaatcta tgagaaggcc cctgcaacca tttggactaa     780
gcagtgccat taaccctgac agaatcacca gagagcatgc tatcccgttt gatgtcttca     840
actatagaga taaccttcat tacgtatatg ataccctgga atttaatggt ttgtcgattt     900
cacaacttga tagagagctg gaaaaaatca agagtcacga aagagtattt gctggattct     960
tgctgtcggg gattaaaaaa tctgctcttg tgaaattcga agtttgtact ccacctgata    1020
attgtcataa agcaggggag ttttatctac tcggggacga aaacgagatg gcttgggcct    1080
atgaccgact tttcaagtat gatattactc aggttctgga agcaaaccat ctacacttct    1140
atgatcatct cttcattcgc tacgaagtct ttgatcttaa aggagtgagt ttgggaactg    1200
acctgttcca cactgcaaat gtggtacatg attccggcac ag                       1242
```

<210> SEQ ID NO 4
<211> LENGTH: 1239
<212> TYPE: DNA
<213> ORGANISM: HALIOTIS TUBERCULATA

<400> SEQUENCE: 4

```
gcacccgtga tcgtgataac tacgttgaag aagttactgg ggccagtcat atcaggaaga      60
atttgaacga cctcaatacc ggagaaatgg aaagccttag agctgctttc ctgcatattc     120
aggacgacgg aacatatgaa tctattgccc agtaccatgg caaaccaggc aaatgtcaat     180
tgaatgatca taatattgcg tgttgtgtcc atggtatgcc taccttcccc cagtggcaca     240
gactgtatgt ggttcaggtg gagaatgctc tcctaaacag gggatctggt gtggctgttc     300
cttactggga gtggactgct cccatagacc atctacctca tttcattgat gatgcaacat     360
acttcaattc ccgacaacag cggtacgacc ctaacccttt cttcagggga aaggttactt     420
ttgaaaacgc agtcacaaca agggacccac aagccgggct cttcaactca gattatatgt     480
atgagaatgt tttacttgca ctggagcagg aaaattattg tgactttgaa attcagtttg     540
agcttgttca taacgcactt cattccatgc tgggaggtaa agggcagtac tccatgtcct     600
ccctggacta ttctgcgttt gatcccgtct tcttcctaca tcatgccaac acggacagac     660
tgtgggcaat ctggcaggaa ctacaaagat tccgagaact gccttatgaa gaagcgaact     720
gtgcaatcaa cctcatgcat caaccactga agccgttcag tgatccacat gagaatcacg     780
```

-continued

```
acaatgtcac tttgaaatac tcaaaaccac aggacggatt cgactaccag aaccacttcg    840

gatacaagta tgacaacctt gagttccatc acttatctat cccaagtctt gatgctaccc    900

tgaagcaaag gagaaatcac gacagagtgt ttgcgggctt ccttcttcat aacataggaa    960

cttctgctga cataactatc tacatatgtc tgcctgacgg acggcgtggc aatgactgca   1020

gtcatgaggc gggaacattc tatatcctcg gaggcgaaac agagatgcct tttatctttg   1080

accgtttgta taaatttgaa atcaccaaac cactgcaaca gttaggagtc aagctgcatg   1140

gtggagtttt cgaactggag cttgagatca aggcatacaa cggttcctat ctggatcccc   1200

atacctttga tccaactatc atctttgaac ctggaacag                         1239
```

<210> SEQ ID NO 5
<211> LENGTH: 1260
<212> TYPE: DNA
<213> ORGANISM: HALIOTIS TUBERCULATA

<400> SEQUENCE: 5

```
atacccatat cttggaccac gaccatgagg aagagatact tgtcaggaag aatataattg     60

atttgagccc aagggagagg gtttctctag tcaaagcttt gcaaagaatg aagaatgatc    120

gctccgctga tgggtaccaa gccattgcct ctttccatgc cctgccacca ctctgtccca    180

atccatctgc agctcaccgt tatgcttgct gtgtccatgg catggctaca tttccccagt    240

ggcacagact gtacactgtt caggttcagg atgccctgag gagacatggt tcacttgttg    300

gtattcctta ctgggactgg acaaaaccag tcaacgagtt acccgagctt ctttcttcag    360

caacatttta tcatccaatc cggaatatta atatttcaaa tccattcctc ggggctgaca    420

tagaatttga aggaccgggc gttcatacag agaggcacat aaatactgag cgcctgtttc    480

acagtgggga tcatgacgga taccacaact ggttcttcga aactgttctc tttgctttgg    540

aacaggaaga ttactgcgat tttgaaatac aatttgagat agcccataat ggcatccaca    600

catggattgg tggaagcgca gtatatggca tgggacacct tcactatgca tcatatgatc    660

caattttcta catccaccat tcacagacgg acagaatatg ggctatttgg caagagctgc    720

agaagtacag ggtctatct ggttcggaag caaactgtgc cattgaacat atgagaacac    780

ccttgaagcc tttcagcttt gggccaccct acaatttgaa tagtcatacg caagaatatt    840

caaagcctga ggacacgttt gactataaga agtttggata cagatatgat agtctggaat    900

tggaggggcg atcaatttct cgcattgatg aacttatcca gcagagacag gagaaagaca    960

gaacttttgc agggttcctc cttaaaggtt ttggtacatc cgcatctgtg tcattgcaag   1020

tttgcagagt tgatcacacc tgtaaagatg cgggctattt cactattctg ggaggatcag   1080

ccgaaatgcc atgggcattc gacaggcttt ataagtatga cattactaaa actcttcacg   1140

acatgaacct gaggcacgag gacactttct ctatagacgt aactatcacg tcttacaatg   1200

gaacagtact ctcgggagac ctcattcaga cgccctccat tatatttgta cctggacgcc   1260
```

<210> SEQ ID NO 6
<211> LENGTH: 1251
<212> TYPE: DNA
<213> ORGANISM: HALIOTIS TUBERCULATA

<400> SEQUENCE: 6

```
ataaactcaa ctcacggaaa catacaccta acagagtccg ccatgagcta agtagcctta     60

gttcccgtga catagcaagc ttgaaggcag ctttgacaag ccttcaacat gataatggga    120

ctgatggtta tcaagctatt gctgccttcc atggcgttcc tgcgcagtgc cacgagccat    180
```

```
ctggacgtga gatcgcctgt tgcatccacg gcatggcgac gtttcctcac tggcaccggt    240
tgtacactct gcagttggag caagcgctgc gcagacacgg gtccagtgtt gctgttccat    300
actgggactg gaccaagcca atcaccgaac tgccacacat tctgacagac ggagaatatt    360
atgacgtttg gcaaaatgcc gtcttggcca atccgtttgc aagaggttat gtgaaaatta    420
aagatgcatt tacggtgaga aatgtccagg aaagtctgtt caaaatgtca agttttggaa    480
agcactcgct tctgtttgac caggctttgt tggctcttga acaaactgac tactgtgact    540
tcgaagttca gtttgaagtg atgcataaca cgatccatta tctcgtagga gggcgtcaaa    600
cgtacgcctt ctcctctctc gagtattcct catacgatcc aatcttcttt attcaccact    660
cgtttgttga caaaatatgg gctgtatggc aagaactgca aagcaggaga catctacagt    720
ttagaacagc tgattgtgct gtgggcctca tgggtcaggc aatgaggcct ttcaacaagg    780
atttcaacca caactcgttc accaagaagc acgcagtccc taatacagta tttgattatg    840
aagatcttgg ctataactat gacaaccttg aaatcagtgg tttaaactta aatgagatcg    900
aggcgttaat agcaaaacgc aagtcacatg ctagagtctt tgctgggttc ctgttgtttg    960
gattaggaac ttcggctgat atacatctgg aaatttgcaa gacatcggaa aactgccatg   1020
atgctggtgt gattttcatc cttggaggtt ctgcagagat gcattgggca tacaaccgcc   1080
tctacaagta tgacattaca gaagcattgc aggaatttga catcaaccct gaagatgttt   1140
tccatgctga tgaaccattt ttcctgaggc tgtcggttgt tgctgtgaat ggaactgtca   1200
ttccatcgtc tcatcttcac cagccaacga taatctatga accaggcgaa g            1251
```

<210> SEQ ID NO 7
<211> LENGTH: 1209
<212> TYPE: DNA
<213> ORGANISM: HALIOTIS TUBERCULATA

<400> SEQUENCE: 7

```
atcaccatga cgaccatcag tcgggaagca tagcaggatc cggggtccgc aaggacgtga     60
acaccttgac taaggctgag accgacaacc tgagggaggc gctgtggggt gtcatggcag    120
accacggtcc caatggcttt caagctattg ctgctttcca tggaaaacca gctttgtgtc    180
ccatgcctga tggccacaac tactcatgtt gtactcacgg catggctacc ttcccacact    240
ggcatcgcct ctacaccaag cagatggagg atgcaatgag ggcgcatggg tctcatgtcg    300
gcctgcccta ctgggactgg actgctgcct tcacccacct gccaacactg gtcaccgaca    360
cggacaacaa ccccttccaa catggacaca ttgattatct caatgtcagc acaactcgat    420
ctccccgaga catgctgttc aacgaccccg agcatggatc agagtcgttc ttctacagac    480
aagtcctctt agctctggaa caaactgatt tctgcaaatt cgaagttcag tttgagataa    540
cccacaatgc catccattcc tggacaggtg gccacagccc ctacggaatg tccactctcg    600
acttcactgc ctacgatcct ctcttctggc ttcaccactc caacaccgac agaatctggg    660
ctgtctggca agctttgcaa gaatacagag gacttccata caaccatgcc aattgtgaga    720
tccaggcaat gaaaacgccc ctgaggcctt tcagtgacga tatcaaccac aacccagtca    780
caaaggctaa cgcgaagcca ttagatgtgt tcgagtataa tcggttgagc ttccagtacg    840
acaacctcat cttccatgga tacagtattc cggaacttga tcgcgtgctt gaagaaagaa    900
aggaggagga cagaatattt gctgccttcc ttctcagtgg aatcaagcgt agtgctgatg    960
tagtgttcga catatgccag ccagaacacg aatgtgtgtt cgcagggact tttgcgattt   1020
```

-continued tgggaggggga gctagaaatg ccctggtcct tcgacagact gttccgctat gatatcacca 1080
aggtgatgaa gcagctacac ctgaggcatg actctgactt taccttcagg gtgaagattg 1140
tcggcaccga cgaccacgag cttccttcag acagtgtcaa agcaccaact attgaatttg 1200
aaccgggcg 1209

<210> SEQ ID NO 8
<211> LENGTH: 1535
<212> TYPE: DNA
<213> ORGANISM: HALIOTIS TUBERCULATA

<400> SEQUENCE: 8
tgcacagagg cggaaaccac gaagatgaac accatgatga cagactcgca gatgtcctga 60
tcaggaaaga agttgacttc ctctccctgc aagaggccaa cgcaattaag gatgcactgt 120
acaagctcca gaatgacgac agtaaagggg gctttgaggc catagctggc tatcacgggt 180
atcctaatat gtgtccagaa agaggtaccg acaagtatcc ctgctgtgtc cacggaatgc 240
ccgtgttccc ccactggcac cgcctgcata ccattcagat ggagagagct ctgaaaaacc 300
atggctctcc aatgggcatt ccttactggg attggacaaa gaagatgtcg agtcttccat 360
ctttctttgg agattccagc aacaacaacc ctttctacaa atattacatc cggggcgtgc 420
agcacgaaac aaccagggac attaatcaga gactctttaa tcaaaccaag tttggtgaat 480
ttgattacct atattaccta actctgcaag tcctggagga aaactcgtac tgtgactttg 540
aagttcagta tgagatcctc cataacgccg tccactcctg gcttggagga actggaaagt 600
attccatgtc taccctggag cattcggcct ttgaccctgt cttcatgatt caccactcga 660
gtttggatag aatctggatc ctttggcaga agttgcaaaa gataagaatg aagccttact 720
acgcattgga ttgtgctggc gacagactta tgaaagaccc cctgcatccc ttcaactacg 780
aaaccgttaa tgaagatgaa ttcacccgca tcaactcttt cccaagcata ctgtttgacc 840
actacaggtt caactatgaa tacgataaca tgagaatcag ggtcaggac atacatgaac 900 ttgaagaggt aattcaggaa ttaagaaaca aagatcgcat atttgctggt tttgttttgt 960
cgggcttacg gatatcagct acagtgaaag tattcattca ttcgaaaaac gatacaagtc 1020
acgaagaata tgcaggagaa tttgcagttt tgggaggtga gaaggagatg ccgtgggcat 1080
atgaaagaat gctgaaattg gacatctccg atgctgtaca caagcttcac gtgaaagatg 1140
aagacatccg ttttagagtg gttgttactg cctacaacgg tgacgttgtt accaccaggc 1200
tgtctcagcc attcatcgtc caccgtccag cccatgtggc tcacgacatc ttggtaatcc 1260
cagtaggtgc gggccatgac cttccgccta aagtcgtagt aaagagcggc accaaagtcg 1320
agtttacacc aatagattcg tcggtgaaca aagcaatggt ggagctgggc agctatactg 1380
ctatggctaa atgcatcgtt ccccctttct cttaccacgg ctttgaactg gacaaagtct 1440
acagcgtcga tcacggagac tactacattg ctgcaggtac ccacgcgttg tgtgagcaga 1500
acctcaggct ccacatccac gtggaacacg agtag 1535

<210> SEQ ID NO 9
<211> LENGTH: 1003
<212> TYPE: DNA
<213> ORGANISM: HALIOTIS TUBERCULATA

<400> SEQUENCE: 9
cacagactgt tcgtcaccca ggtggaagat gctctgatca ggcgaggatc gcctataggg 60
gtcccctact gggactggac tcagcctatg gcgcatctcc caggacttgc agacaacgcc 120

-continued

```
acctatagag atcccatcag cggggacagc agacacaacc ccttccacga tgttgaagtt    180

gcctttgaaa atggacgtac agaacgtcac ccagatagta gattgtttga acaaccttta    240

tttggcaaac atacgcgtct cttcgacagt atagtctatg cttttgagca ggaggacttc    300

tgcgattttg aagttcaatt tgagatgacc cataataata ttcacgcctg gattggtggc    360

ggcgagaagt attccatgtc ttctctacac tacacagcct tcgaccctat cttctacctt    420

cgtcactcca acactgaccg gctctgggca atttggcaag cgttgcagat acgaagaaac    480

aggccttaca aggctcattg tgcttggtct gaggaacgcc agcctctcaa acctttcgcc    540

ttcagttccc cactgaacaa caacgaaaaa acctacgaaa actcggtgcc caccaacgtt    600

tacgactacg aaggagtcct tggctatact tatgatgacc tcaacttcgg gggcatggac    660

ctgggtcagc ttgaggaata catccagagg cagagacaga gagacaggac ctttgctggt    720

ttctttctgt cacatattgg tacatcagcg aatgttgaaa tcattataga ccatgggact    780

cttcatacct ccgtgggcac gtttgctgtt cttggcggag agaaggagat gaaatgggga    840

tttgaccgtt tgtacaaata tgagattaca gatgaactga ggcaacttaa tctccgtgct    900

gatgatgttt tcagcatctc tgttaaagta actgatgttg atggcagtga gctgtcctct    960

gaactcatcc catctgctgc tatcatcttc gaacgaagcc ata                     1003
```

<210> SEQ ID NO 10
<211> LENGTH: 1251
<212> TYPE: DNA
<213> ORGANISM: HALIOTIS TUBERCULATA

<400> SEQUENCE: 10

```
ttgaccatca ggacccgcat catgacacaa tcattaggaa aaatgttgat aatcttacac     60

ccgaggaaat taattctctg aggcgggcaa tggcagacct tcaatcagac aaaaccgccg    120

gtggattcca gcaaattgct gcttttcacg gggaacccaa atggtgccca agtcccgatg    180

ctgagaagaa gttctcctgc tgtgtccatg gaatggctgt cttccctcac tggcacagac    240

tcctgaccgt gcaaggcgag aatgccctga gaaagcatgg atgtctcgga gctctcccct    300

actgggactg gactcggccc ctgtctcacc tacctgattt ggttttggta agtagcagaa    360

ctacaccgat gccatattcc accgtggaag cccgaaaccc ctggtacagc ggccatattg    420

atacagttgg tgttgacaca acaagaagcg tccgtcaaga actgtatgaa gctcctggat    480

ttggccatta tactggggtc gctaagcaag tgcttctggc tttggagcag gatgacttct    540

gtgattttga agtccagttt gagatagctc acaatttcat tcacgctctt gtcggcggaa    600

gcgagccata tggtatggcg tcactccgtt acactactta tgatccaatt ttctacctcc    660

atcattctaa cactgacaga ctctgggcta tatggcaggc tctacaaaag tacaggggca    720

aaccttacaa ttccgccaac tgcgccattg cttctatgag aaaaccccta caaccctttg    780

gtctgactga tgagatcaac ccggatgatg agacaagaca gcatgctgtt cctttcagtg    840

tctttgatta caagaacaac ttcaattatg aatatgacac ccttgacttc aacggactat    900

caatctccca gctggaccgt gaactgtcac ggagaaagtc tcatgacaga gtatttgccg    960

gatttttgct gcatggtatt cagcagtctg cactagttaa attctttgtc tgcaaatcag   1020

atgatgactg tgaccactat gctggtgaat tctacatcct tggtgatgaa gctgaaatgc   1080

catggggcta tgatcgtctt tacaaatatg agatcactga gcagctcaat gccctggatc   1140

tacacatcgg agatagattc ttcatcagat acgaagcgtt tgatcttcat ggtacaagtc   1200
```

-continued ttggaagcaa catcttcccc aaaccttctg tcatacatga cgaaggggca g 1251

<210> SEQ ID NO 11
<211> LENGTH: 1244
<212> TYPE: DNA
<213> ORGANISM: HALIOTIS TUBERCULATA

<400> SEQUENCE: 11
gtcaccatca ggctgacgag tacgacgaag ttgtaactgc tgcaagccac atcagaaaga 60
atttaaaaga tctgtcaaag ggagaagtag agagcctaag gtctgccttc ctgcaacttc 120
agaacgacgg agtctatgag aatattgcca agttccacgg caagcctggg ttgtgtgatg 180
ataacggtcg caaggttgcc tgttgtgtcc atggaatgcc caccttcccc cagtggcaca 240
ggctctatgt cctccaggtg gagaatgctt tgctggagag aggatctgcc gtctctgtgc 300
catactggga ctggactgaa acatttacag agctgccatc tttgattgct gaggctacct 360
atttcaattc ccgtcaacaa acgtttgacc ctaatccttt cttcagaggt aaaatcagtt 420
ttgagaatgc tgttacaaca cgtgatcccc agcctgagct gtacgttaac aggtactact 480
accaaaacgt catgttggtt tttgaacagg acaactactg cgacttcgag atacagtttg 540
agatggttca caatgttctc catgcttggc ttggtggaag agctacttat tctatttctt 600
ctcttgatta ttctgcattc gaccctgtgt tttccttca ccatgcgaac acagatagat 660
tgtgggccat ctggcaggag ctgcagaggt acaggaagaa gccatacaat gaagcggatt 720
gtgccattaa cctaatgcgc aaacctctac atcccttcga caacagtgat ctcaatcatg 780
atcctgtaac ctttaaatac tcaaaaccca ctgatggctt tgactaccag aacaactttg 840
gatacaagta tgacaacctt gagttcaatc atttcagtat tcccaggctt gaagaaatca 900
ttcgtattag acaacgtcaa gatcgtgtgt ttgcaggatt cctccttcac aacattggga 960
catccgcaac tgttgagata ttcgtctgtg tccctaccac cagcggtgag caaaactgtg 1020
aaaacaaagc cggaacattt gccgtactcg gaggagaaac agagatggcg tttcattttg 1080
acagactcta caggtttgac atcagtgaaa cactgaggga cctcggcata cagctggaca 1140
gccatgactt tgacctcagc atcaagattc aaggagtaaa tggatcctac cttgatccac 1200
acatcctgcc agagccatcc ttgatttttg tgcctggttc aagt 1244

<210> SEQ ID NO 12
<211> LENGTH: 1255
<212> TYPE: DNA
<213> ORGANISM: HALIOTIS TUBERCULATA

<400> SEQUENCE: 12
tctttcctgc gtcctgatgg gcattcagat gacatccttg tgagaaaaga agtgaacagc 60
ctgacaacca gggagactgc atctctgatc catgctctga aaagtatgca ggaagaccat 120
tcacctgacg ggttccaagc cattgcctct ttccatgctc tgccaccact ctgcccttca 180
ccatctgcag ctcaccgtta tgcttgctgt gtccacggca tggctacatt tccccagtgg 240
cacagattgt acactgtaca gttccaggat gcactgagga gacatggagc tacggtaggt 300
gtaccgtatt gggattggct gcgaccgcag tctcacctac cagagcttgt caccatggag 360
acataccatg atatttggag taacagagat ttccccaatc ctttctacca agccaatatt 420
gagtttgaag gagaaaacat tacaacagag agagaagtca ttgcagacaa actttttgtc 480
aaaggtggac acgtttttga taaactggtt cttcaaacaa gccatcctag cgctgagcag 540
gaaaactact gtgactttga gattcagttt gaaattcttc acaacggcgt tcacacgtgg 600

-continued

```
gtcggaggca gtcgtaccta ctctatcgga catcttcatt acgcattcta cgaccctctt    660

ttctaccttc accatttcca gacagaccgt atttgggcaa tctggcaaga actccaggaa    720

cagagagggc tctcgggtga tgaggctcac tgtgctctcg agcaaatgag agaaccattg    780

aagcctttca gcttcggcgc tccttataac tggaatcagc tcacacagga tttctcccga    840

cccgaggaca ccttcgacta caggaagttt ggttatgaat atgacaattt agaattcctg    900

ggaatgtcag ttgctgaact ggatcaatac attattgaac atcaagaaaa tgatagagta    960

ttcgctgggt tcctgttgag tggattcgga ggttccgcat cagttaattt ccaggtttgt   1020

agagctgatt ccacatgtca ggatgctggg tacttcaccg ttcttggtgg cagtgctgag   1080

atggcgtggg catttgacag gctttacaaa tatgacatta ctgaaactct ggagaaaatg   1140

caccttcgat atgatgatga cttcacaatc tctgtcagtc tgaccgccaa caacggaact   1200

gtcctgagca gcagtctaat cccaacaccg agtgtcatat tccagcgggg acatc        1255
```

<210> SEQ ID NO 13
<211> LENGTH: 1248
<212> TYPE: DNA
<213> ORGANISM: HALIOTIS TUBERCULATA

<400> SEQUENCE: 13

```
gtgacataaa taccaggagc atgtcaccga accgtgttcg ccgtgagctg agcgatctgt     60

ctgcgaggga cctgtctagt ctcaagtctg ctctgcgaga cctacaggag gatgatggcc    120

ccaacggata ccaggctctt gcagccttcc atgggctacc agcaggctgc catgatagcc    180

ggggaaatga gatcgcatgt tgcattcacg ggatgccgac cttcccccag tggcacagac    240

tgtacaccct gcagttggag atggctctga ggagacatgg atcatctgtc gccatcccct    300

actgggactg gacaaagcct atctccgaac tcccctcgct cttcaccagc cctgagtatt    360

atgacccatg gcatgatgct gtggtaaaca acccattctc caaaggtttt gtcaaatttg    420

caaataccta cacagtaaga gacccacagg agatgctgtt ccagctttgt gaacatggag    480

agtcaatcct ctatgagcaa actcttcttg ctcttgagca aaccgactac tgtgattttg    540

aggtacagtt tgaggtcctc cataacgtga tccactacct tgttggtgga cgtcagacct    600

acgcattgtc ttctctgcat tatgcctcct acgacccatt cttctttata caccattcct    660

ttgtggataa gatgtgggta gtatggcaag ctcttcaaaa gaggaggaaa cttccataca    720

agcgagctga ctgtgctgtc aacctaatga ctaaaccaat gaggccattt gactccgata    780

tgaatcagaa cccattcaca aagatgcacg cagttcccaa cacactctat gactacgaga    840

cactgtacta cagctacgat aatctcgaaa taggtggcag gaatctcgac cagcttcagg    900

ctgaaattga cagaagcaga agccacgatc gcgtttttgc tggattcttg cttcgtggaa    960

tcggaacttc tgctgatgtc aggttttgga tttgtagaaa tgaaaatgac tgccacaggg   1020

gtggaataat tttcatctta ggtggagcca aggaaatgcc atggtcattt gacagaaact   1080

tcaagtttga tatcacccat gtactcgaga atgctggcat tagcccagag gacgtgtttg   1140

atgctgagga gccattttat atcaaggttg agatccatgc tgttaacaag accatgatac   1200

cgtcgtctgt gatcccagcc ccaactatca tctattctcc tggggaag                1248
```

<210> SEQ ID NO 14
<211> LENGTH: 1207
<212> TYPE: DNA
<213> ORGANISM: HALIOTIS TUBERCULATA

-continued

<400> SEQUENCE: 14

```
gtcgcgctgc tgacagtgcg cactctgcca acattgctgg ctctggggtg aggaaggacg     60
tcacgaccct cactgtgtct gagaccgaga acctaagaca ggctcttcaa ggtgtcatcg    120
atgatactgg tcccaatggt taccaagcaa tagcatcctt ccacggaagt cctccaatgt    180
gcgagatgaa cggccgcaag gttgcctgtt gtgctcacgg tatggcctcc ttcccacact    240
ggcacagact gtatgtgaag cagatggaag atgccctggc tgaccacggg tcacatatcg    300
gcatccctta ctgggactgg acaactgcct tcacagagtt acccgccctt gtcacagact    360
ccgagaacaa tcccttccat gagggtcgca ttgatcatct cggtgtaacc acgtcacgtt    420
cccccagaga catgctgttt aacgacccag agcaaggatc agagtcgttc ttctatagac    480
aagtcctcct ggctttggag cagactgact actgccagtt cgaagtccag tttgagctga    540
cccacaacgc cattcactcc tggacaggtg gacgtagccc ttacggaatg tcgaccctcg    600
agttcacagc ctacgatcct ctcttctggc ttcaccactc caacaccgac agaatctggg    660
ctgtctggca agcactgcag aaataccgag gactcccata caacgaagca cactgtgaaa    720
tccaggttct gaaacagccc ttgaggccat tcaacgatga catcaaccac aatccaatca    780
ccaagactaa tgccaggcct atcgattcat ttgattatga gaggtttaac tatcagtatg    840
acacccttag cttccatggt aagagcatcc ctgaactgaa tgacctgctc gaggaaagaa    900
aaagagaaga gagaacattt gctgccttcc ttcttcgtgg aatcggttgc agtgctgatg    960
tcgtctttga catctgccgg cccaatggtg actgtgtctt tgcaggaacc tttgctgtgc   1020
tgggagggga gctagaaatg ccttggtcct tcgacagact gttccgctat gacatcacca   1080
gagtcatgaa tcagctccat ctccagtatg attcagattt cagtttcagg gtgaagcttg   1140
ttgccaccaa tggcactgag ctttcatcag accttctcaa gtcaccaaca attgaacatg   1200
aacttgg                                                             1207
```

<210> SEQ ID NO 15
<211> LENGTH: 1546
<212> TYPE: DNA
<213> ORGANISM: HALIOTIS TUBERCULATA
<220> FEATURE:
<221> NAME/KEY: misc_feature
<222> LOCATION: (1273)..(1273)
<223> OTHER INFORMATION: n is a,g,c, or t

<400> SEQUENCE: 15

```
agcccacaga ggaccagttg aagaaacaga agtcactcgc caacatactg acggcaatgc     60
acactttcat cgtaaggaag ttgattcgct gtccctggat gaagcaaaca acttgaagaa    120
tgccctttac aagctacaga acgaccacag tctaacggga tacgaagcaa tctctggtta    180
ccatggatac cccaatctgt gtccggaaga aggcgatgac aaaatacccc tgctgcgtcc    240
ccggatgggc atctttcctt actggcacag actcttgacc attcaactgg aaagagctct    300
tgagcacaat ggtgcactgc ttggtgttcc ttactgggac tggaacaagg acctgtcgtc    360
actgccggcg ttcttctccg actccagcaa caacaatccc tacttcaagt accacatcgc    420
cggtgttggt cacgacaccg tcagagagcc aactagtctt atatataacc agccccaaat    480
ccatggttat gattatctct attacctagc attgaccacg cttgaagaaa acaattactg    540
ggactttgag gttcagtatg agatcctcca caacgccgtc cactcctggc ttggaggatc    600
ccagaagtat tccatgtcta ccctggagta ttcggccttt gaccctgtct ttatgatcct    660
tcactcgggt ctagacagac tttggatcat ctggcaagaa cttcagaaga tcaggagaaa    720
```

```
gccctacaac ttcgctaaat gtgcttatca tatgatggaa gagccactgg cgcccttcag    780

ctatccatct atcaaccagg acgagttcac ccgtgccaac tccaagcctt ctacagtttt    840

tgacagccat aagttcggct accattacga taacctgaat gttagaggtc acagcatcca    900

agaactcaac acaatcatca atgacttgag aaacacagac agaatctacg caggatttgt    960

tttgtcaggc atcggtacgt ctgctagtgt caagatctat ctccgaacag atgacaatga   1020

cgaagaagtt ggaactttca ctgtcctggg aggagagagg gaaatgccat gggcctacga   1080

gcgagttttc aagtatgaca tcacagaggt tgcagataga cttaaaatta agttatgggg   1140

acaccettta acttccggaa ctggagatca catccttacg aatggaatcg gtggtaaaca   1200

agagcctacc caaatccttt catcatctac agacctgcca atcatgacta cgatgttctt   1260

gttatcccag tanggaagaa accttcacat ccctcccaaa gttgtcgtca agaaaggcac   1320

ccgcatcgag ttccacccag tcgatgattc agttacgaga ccagttgttg atcttggaag   1380

ctacactgca ctcttcaact gtgtggtacc accgttcaca taccacggat tcgaactgaa   1440

ccacgtctat tctgtcaagc ctggtgacta ctatgttact ggacccacga gagacctttg   1500

ccagaatgca gatgtcagga ttcatatcca tgttgaggat gagtaa                  1546
```

<210> SEQ ID NO 16
<211> LENGTH: 967
<212> TYPE: DNA
<213> ORGANISM: MEGATHURA CRENULATA

<400> SEQUENCE: 16

```
ggcctaccgt actgggactg gactgaaccc atgacacaca ttccgggtct ggcaggaaac     60

aaaacttatg tggattctca tggtgcatcc cacacaaatc cttttcatag ttcagtgatt    120

gcatttgaag aaaatgctcc ccacaccaaa agacaaatag atcaaagact ctttaaaccc    180

gctacctttg gacaccacac agacctgttc aaccagattt tgtatgcctt tgaacaagaa    240

gattactgtg actttgaagt ccaatttgag attacccata acacgattca cgcttggaca    300

ggaggaagcg aacatttctc aatgtcgtcc ctacattaca cagctttcga tcctttgttt    360

tactttcacc attctaacgt tgatcgtctt tgggccgttt ggcaagcctt acagatgaga    420

cggcataaac cctacagggc ccactgcgcc atatctctgg aacatatgca tctgaaacca    480

ttcgcctttt catctcccct taacaataac gaaaagactc atgccaatgc catgccaaac    540

aagatctacg actatgaaaa tgtcctccat tacacatacg aagatttaac atttggaggc    600

atctctctgg aaaacataga aaagatgatc cacgaaaacc agcaagaaga cagaatatat    660

gccggttttc tcctggctgg catacgtact tcagcaaatg ttgatatctt cattaaaact    720

accgattccg tgcaacataa ggctggaaca tttgcagtgc tcggtggaag caaggaaatg    780

aagtggggat ttgatcgcgt tttcaagttt gacatcacgc acgttttgaa agatctcgat    840

ctcactgctg atggcgattt cgaagttact gttgacatca ctgaagtcga tggaactaaa    900

cttgcatcca gtcttattcc acatgcttct gtcattcgtg agcatgcacg tggtaagctg    960

aatagag                                                              967
```

<210> SEQ ID NO 17
<211> LENGTH: 1242
<212> TYPE: DNA
<213> ORGANISM: MEGATHURA CRENULATA

<400> SEQUENCE: 17

-continued

```
ttaaatttga caaagtgcca aggagtcgtc ttattcgaaa aaatgtagac cgtttgagcc     60

ccgaggagat gaatgaactt cgtaaagccc tagccttact gaaagaggac aaaagtgccg    120

gtggatttca gcagcttggt gcattccatg gggagccaaa atggtgtcct agtcccgaag    180

catctaaaaa atttgcctgc tgtgttcacg gcatgtctgt gttccctcac tggcatcgac    240

tgttgacggt tcagagtgaa aatgctttga gacgacatgg ctacgatgga gctttgccgt    300

actgggattg gacctctcct cttaatcacc ttcccgaact ggcagatcat gagaagtacg    360

tcgaccctga agatggggta gagaagcata acccttggtt cgatggtcat atagatacag    420

tcgacaaaac aacaacaaga agtgttcaga ataaactctt cgaacagcct gagtttggtc    480

attatacaag cattgccaaa caagtactgc tagcgttgga acaggacaat ttctgtgact    540

ttgaaatcca atatgagatt gcccataact acatccatgc acttgtagga ggcgctcagc    600

cttatggtat ggcatcgctt cgctacactg cttttgatcc actattctac ttgcatcact    660

ctaatacaga tcgtatatgg gcaatatggc aggctttaca gaagtacaga ggaaaaccgt    720

acaacgttgc taactgtgct gttacatcga tgagagaacc tttgcaacca tttggcctct    780

ctgccaatat caacacagac catgtaacca aggagcattc agtgccattc aacgtttttg    840

attacaagac caatttcaat tatgaatatg acactttgga atttaacggt ctctcaatct    900

ctcagttgaa taaaaagctc gaagcgataa agagccaaga caggttcttt gcaggcttcc    960

tgttatctgg tttcaagaaa tcatctcttg ttaaattcaa tatttgcacc gatagcagca   1020

actgtcaccc cgctggagag ttttaccttc tgggtgatga aaacgagatg ccatgggcat   1080

acgatagagt cttcaaatat gacataaccg aaaaactcca cgatctaaag ctgcatgcag   1140

aagaccactt ctacattgac tatgaagtat ttgaccttaa accagcaagc ctgggaaaag   1200

atttgttcaa gcagccttca gtcattcatg aaccaagaat ag                      1242
```

<210> SEQ ID NO 18
<211> LENGTH: 1236
<212> TYPE: DNA
<213> ORGANISM: MEGATHURA CRENULATA

<400> SEQUENCE: 18

```
gtcaccatga aggcgaagta tatcaagctg aagtaacttc tgccaaccgt attcgaaaaa     60

acattgaaaa tctgagcctt ggtgaactcg aaagtctgag agctgccttc ctggaaattg    120

aaaacgatgg aacttacgaa tcaatagcta aattccatgg tagccctggt ttgtgccagt    180

taaatggtaa ccccatctct tgttgtgtcc atggcatgcc aactttccct cactggcaca    240

gactgtacgt ggttgtcgtt gagaatgccc tcctgaaaaa aggatcatct gtagctgttc    300

cctattggga ctggacaaaa cgaatcgaac atttacctca cctgatttca gacgccactt    360

actacaattc caggcaacat cactatgaga caaacccatt ccatcatggc aaaatcacac    420

acgagaatga aatcactact agggatccca aggacagcct cttccattca gactactttt    480

acgagcaggt cctttacgcc ttggagcagg ataacttctg tgatttcgag attcagttgg    540

agatattaca caatgcattg cattctttac ttggtggcaa aggtaaatat tccatgtcaa    600

accttgatta cgctgctttt gatcctgtgt tcttccttca tcacgcaacg actgacagaa    660

tctgggcaat ctggcaagac cttcagaggt tccgaaaacg gccataccga gaagcgaatt    720

gcgctatcca attgatgcac acgccactcc agccgtttga taagagcgac aacaatgacg    780

aggcaacgaa aacgcatgcc actccacatg atggttttga atatcaaaac agctttggtt    840

atgcttacga taatctggaa ctgaatcact actcgattcc tcagcttgat cacatgctgc    900
```

-continued

```
aagaaagaaa aaggcatgac agagtattcg ctggcttcct ccttcacaat attggaacat    960

ctgccgatgg ccatgtattt gtatgtctcc caactgggga acacacgaag gactgcagtc   1020

atgaggctgg tatgttctcc atcttaggcg gtcaaacgga gatgtccttt gtatttgaca   1080

gactttacaa acttgacata actaaagcct tgaaaaagaa cggtgtgcac ctgcaagggg   1140

atttcgatct ggaaattgag attacggctg tgaatggatc tcatctagac agtcatgtca   1200

tccactctcc cactatactg tttgaggccg gaacag                             1236
```

<210> SEQ ID NO 19
<211> LENGTH: 241
<212> TYPE: DNA
<213> ORGANISM: MEGATHRUA CRENULATA

<400> SEQUENCE: 19

```
attctgccca cacagatgat ggacacactg aaccagtgat gattcgcaaa gatatcacac     60

aattggacaa gcgtcaacaa ctgtcactgg tgaaagccct cgagtccatg aaagccgacc    120

attcatctga tgggttccag gcaatcgctt ccttccatgc tcttcctcct ctttgtccat    180

caccagctgc ttcaaagagg tttgcgtgct gcgtccatgg catgccaacc ttcccgcaat    240

g                                                                    241
```

<210> SEQ ID NO 20
<211> LENGTH: 949
<212> TYPE: DNA
<213> ORGANISM: MEGATHURA CRENULATA

<400> SEQUENCE: 20

```
ggcctgccct actgggattg gaccatgcca atgagtcatt tgccagaact ggctacaagt     60

gagacctacc tcgatccagt tactggggaa actaaaaaca accctttcca tcacgcccaa    120

gtggcgtttg aaaatggtgt aacaagcagg aatcctgatg ccaaactttt tatgaaacca    180

acttacggag accacactta cctcttcgac agcatgatct acgcatttga gcaggaagac    240

ttctgcgact ttgaagtcca atatgagctc acgcataatg caatacatgc atgggttgga    300

ggcagtgaaa agtattcaat gtcttctctt cactacactg cttttgatcc tatattttac    360

ctccatcact caaatgttga tcgtctctgg gccatttggc aagctcttca aatcaggaga    420

ggcaagtctt acaaggccca ctgcgcctcg tctcaagaaa gagaaccatt aaagcctttt    480

gcattcagtt ccccactgaa caacaacgag aaaacgtacc acaactctgt ccccactaac    540

gtttatgact atgtgggagt tttgcactat cgatatgatg accttcagtt tggcggtatg    600

accatgtcag aacttgagga atatattcac aagcagacac aacatgatag aacctttgca    660

ggattcttcc tttcatatat tggaacatca gcaagcgtag atatcttcat caatcgagaa    720

ggtcatgata aatacaaagt gggaagtttt gtagtacttg gtggatccaa agaaatgaaa    780

tggggctttg atagaatgta caagtatgag atcactgagg ctctgaagac gctgaatgtt    840

gcagtggatg atgggttcag cattactgtt gagatcaccg atgttgatgg atctccccca    900

tctgcagatc tcattccacc tcctgctata atctttgaac gtggtcatg                949
```

<210> SEQ ID NO 21
<211> LENGTH: 760
<212> TYPE: DNA
<213> ORGANISM: MEGATHURA CRENULATA

<400> SEQUENCE: 21

-continued

```
ctgatgccaa agactttggc catagcagaa aaatcaggaa agccgttgat tctctgacag    60

tcgaagaaca aacttcgttg aggcgagcta tggcagatct acaggacgac aaaacatcag   120

ggggtttcca gcagattgca gcattccacg gagaaccaaa atggtgtcca agccccgaag   180

cggagaaaaa atttgcatgc tgtgttcatg gaatggctgt tttccctcac tggcacagat   240

tgctgacagt tcaaggagaa aatgctctga ggaaacatgg ctttactggt ggactgccct   300

actgggactg gactcgatca atgagcgccc ttccacattt tgttgctgat cctacttaca   360

atgatgctat ttccagccag gaagaagata acccatggca tcatggtcac atagactctg   420

ttgggcatga tactacaaga gatgtgcgtg atgatcttta tcaatctcct ggtttcggtc   480

actacacaga tattgcacaa caagtccttc tggcctttga gcaggacagt ttctgtgatt   540

ttgaggtaca atttgaaatt gcccataatt tcatacatgc actgattggt ggtaacgaac   600

catacagtat gtcatctttg aggtatacta catacgatcc aatcttcttc ttgcaccact   660

ccagtacaga ccgactttgg gccatctggc aagcaatcac tagtgcggcc gcctgcaggt   720

cgaccataag ggagagctcc caacgcgttg gatgcaatct                         760
```

```
<210> SEQ ID NO 22
<211> LENGTH: 323
<212> TYPE: DNA
<213> ORGANISM: MEGATHURA CRENULATA

<400> SEQUENCE: 22

gttcacacca ggctgatgaa tatcgtgagg cagtaacaag cgctagccac ataagaaaaa    60

atatccggga cctctcagag ggagaaattg agagcatcag atctgctttc ctccaaattc   120

aaaaagaggg tatatatgaa aacattgcaa agttccatgg aaaaccagga ctttgtgaac   180

atgatggaca tcctgttgct tgttgtgtcc atggcatgcc cacctttccc cactggcaca   240

gactgtacgt tcttcaggtg gagaatgcgc tcttagaacg agggtctgca gttgctgttc   300

cttactggga ctggacccta cct                                           323
```

```
<210> SEQ ID NO 23
<211> LENGTH: 988
<212> TYPE: DNA
<213> ORGANISM: MEGATHURA CRENULATA

<400> SEQUENCE: 23

atggctgtgt ttccgcactg gcacagactg tttgtgaaac agatggagga cgcacttgct    60

gctcatggag ctcatattgg cataccatac tgggattgga caagtgcgtt tagtcatctg   120

cccgccctag tgactgacca cgagaacaat cccttccacc acggccatat tggtcatctg   180

aatgtggata catctcgatc tccaagagac atgctgttta atgatcctga acaaggctca   240

gaatcattct tctacagaca ggttctcttg actctagaac agacagactt ctgccaattt   300

gaagttcagt ttgaacttac acacaatgcc atccactctt ggactggagg acatactcca   360

tatggaatgt catcactgga atatacagca tatgatccac tcttttatct ccaccattcc   420

aacactgatc gtatctgggc catctggcag gcactccaga aatatagagg tcttccatac   480

aacgcagctc actgcgatat ccaagttctg aaacaacctc ttaaaccatt cagcgagtcc   540

aggaatccaa acccagtcac cagagccaat tctagggccg ttgattcatt tgattatgag   600

aaattcaatt atcaatatga cacacttacc ttccacggac tttctatccc agaacttgat   660

gccatgcttc aagagagaaa gaaggaagag agaacatttg cagccttcct gttgcacgga   720

tttggcgcca gtgctgatgt ttcgtttgat gtctgcacac ctgatggtca ttgtgccttt   780
```

-continued

```
gctggaacct tcgcggtact tggtggggag cttgagatgc cctggtcctt tgaaagattg    840

ttccgttacg atatcacaaa ggttctcaag cagatgaatc ttcactatga ttctgagttc    900

cactttgagt tgaagattgt tggcacagat ggaacagaac tgccatcgga tcgtatcaag    960

agccctacca ttgaacacca tggaggag                                       988


<210> SEQ ID NO 24
<211> LENGTH: 310
<212> TYPE: DNA
<213> ORGANISM: MEGATHURA CRENULATA

<400> SEQUENCE: 24

gtcacgatca cagtgaacgt cacgatggat ttttcaggaa ggaagtcggt tccctgtccc     60

tggatgaagc caatgacctt aaaaatgcac tgtacaagct gcagaatgat cagggtccca    120

atggatatga atcaatagcc ggttaccatg gctatccatt cctctgccct gaacatggtg    180

aagaccagta cgcatgctgt gtccacggaa tgcctgtatt tccacattgg cacagacttc    240

atacaatcca gtttgagaga gctctcaaag aacatggttc tcatttgggt ctgccatact    300

gggactggac                                                           310


<210> SEQ ID NO 25
<211> LENGTH: 422
<212> TYPE: PRT
<213> ORGANISM: HALIOTIS TUBERCULATA

<400> SEQUENCE: 25

Leu Val Gln Phe Leu Leu Val Ala Leu Val Ala Gly Ala Gly Ala Asp
1               5                   10                  15

Asn Val Val Arg Lys Asp Val Ser His Leu Thr Asp Asp Glu Val Gln
            20                  25                  30

Ala Leu His Gly Ala Leu His Asp Val Thr Ala Ser Thr Gly Pro Leu
        35                  40                  45

Ser Phe Glu Asp Ile Thr Ser Tyr His Ala Ala Pro Ala Ser Cys Asp
    50                  55                  60

Tyr Lys Gly Arg Lys Ile Ala Cys Cys Val His Gly Met Pro Ser Phe
65                  70                  75                  80

Pro Phe Trp His Arg Ala Tyr Val Val Gln Ala Glu Arg Ala Leu Leu
                85                  90                  95

Ser Lys Arg Lys Thr Val Gly Met Pro Tyr Trp Asp Trp Thr Gln Thr
            100                 105                 110

Leu Thr His Leu Pro Ser Leu Val Thr Glu Pro Ile Tyr Ile Asp Ser
        115                 120                 125

Lys Gly Gly Lys Ala Gln Thr Asn Tyr Trp Tyr Arg Gly Glu Ile Ala
    130                 135                 140

Phe Ile Asn Lys Lys Thr Ala Arg Ala Val Asp Asp Arg Leu Phe Glu
145                 150                 155                 160

Lys Val Glu Pro Gly His Tyr Thr His Leu Met Glu Thr Val Leu Asp
                165                 170                 175

Ala Leu Glu Gln Asp Glu Phe Cys Lys Phe Glu Ile Gln Phe Glu Leu
            180                 185                 190

Ala His Asn Ala Ile His Tyr Leu Val Gly Gly Lys Phe Glu Tyr Ser
        195                 200                 205

Met Ser Asn Leu Glu Tyr Thr Ser Tyr Asp Pro Ile Phe Phe Leu His
    210                 215                 220
```

-continued

```
His Ser Asn Val Asp Arg Leu Phe Ala Ile Trp Gln Arg Leu Gln Glu
225                 230                 235                 240

Leu Arg Gly Lys Asn Pro Asn Ala Met Asp Cys Ala His Glu Leu Ala
                245                 250                 255

His Gln Gln Leu Gln Pro Phe Asn Arg Asp Ser Asn Pro Val Gln Leu
            260                 265                 270

Thr Lys Asp His Ser Thr Pro Ala Asp Leu Phe Asp Tyr Lys Gln Leu
        275                 280                 285

Gly Tyr Ser Tyr Asp Ser Leu Asn Leu Asn Gly Met Thr Pro Glu Gln
    290                 295                 300

Leu Lys Thr Glu Leu Asp Glu Arg His Ser Lys Glu Arg Ala Phe Ala
305                 310                 315                 320

Ser Phe Arg Leu Ser Gly Phe Gly Gly Ser Ala Asn Val Val Val Tyr
                325                 330                 335

Ala Cys Val Pro Asp Asp Asp Pro Arg Ser Asp Asp Tyr Cys Glu Lys
            340                 345                 350

Ala Gly Asp Phe Phe Ile Leu Gly Gly Gln Ser Glu Met Pro Trp Arg
        355                 360                 365

Phe Tyr Arg Pro Phe Phe Tyr Asp Val Thr Glu Ala Val His His Leu
    370                 375                 380

Gly Val Pro Leu Ser Gly His Tyr Tyr Val Lys Thr Glu Leu Phe Ser
385                 390                 395                 400

Val Asn Gly Thr Ala Leu Ser Pro Asp Leu Leu Pro Gln Pro Thr Val
                405                 410                 415

Ala Tyr Arg Pro Gly Lys
            420


<210> SEQ ID NO 26
<211> LENGTH: 419
<212> TYPE: PRT
<213> ORGANISM: HALIOTIS TUBERCULATA

<400> SEQUENCE: 26

Gly His Leu Asp Pro Pro Val His His Arg His Asp Asp Asp Leu Ile
1               5                   10                  15

Val Arg Lys Asn Ile Asp His Leu Thr Arg Glu Glu Glu Tyr Glu Leu
            20                  25                  30

Arg Met Ala Leu Glu Arg Phe Gln Ala Asp Thr Ser Val Asp Gly Tyr
        35                  40                  45

Gln Ala Thr Val Glu Tyr His Gly Leu Pro Ala Arg Cys Pro Arg Pro
    50                  55                  60

Asp Ala Lys Val Arg Phe Ala Cys Cys Met His Gly Met Ala Ser Phe
65                  70                  75                  80

Pro His Trp His Arg Leu Phe Val Thr Gln Val Glu Asp Ala Leu Val
                85                  90                  95

Arg Arg Gly Ser Pro Ile Gly Val Pro Tyr Trp Asp Trp Thr Lys Pro
            100                 105                 110

Met Thr His Leu Pro Asp Leu Ala Ser Asn Glu Thr Tyr Val Asp Pro
        115                 120                 125

Tyr Gly His Thr His His Asn Pro Phe Phe Asn Ala Asn Ile Ser Phe
    130                 135                 140

Glu Glu Gly His His His Thr Ser Arg Met Ile Asp Ser Lys Leu Phe
145                 150                 155                 160

Ala Pro Val Ala Phe Gly Glu His Ser His Leu Phe Asp Gly Ile Leu
                165                 170                 175
```

-continued

Tyr Ala Phe Glu Gln Glu Asp Phe Cys Asp Phe Glu Ile Gln Phe Glu
180 185 190

Leu Val His Asn Ser Ile His Ala Trp Ile Gly Gly Ser Glu Asp Tyr
195 200 205

Ser Met Ala Thr Leu His Tyr Thr Ala Phe Asp Pro Ile Phe Tyr Leu
210 215 220

His His Ser Asn Val Asp Arg Leu Trp Ala Ile Trp Gln Ala Leu Gln
225 230 235 240

Ile Arg Arg His Lys Pro Tyr Gln Ala His Cys Ala Gln Ser Val Glu
245 250 255

Gln Leu Pro Met Lys Pro Phe Ala Phe Pro Ser Pro Leu Asn Asn Asn
260 265 270

Glu Lys Thr His Ser His Ser Val Pro Thr Asp Ile Tyr Asp Tyr Glu
275 280 285

Glu Val Leu His Tyr Ser Tyr Asp Asp Leu Thr Phe Gly Gly Met Asn
290 295 300

Leu Glu Glu Ile Glu Glu Ala Ile His Leu Arg Gln Gln His Glu Arg
305 310 315 320

Val Phe Ala Gly Phe Leu Leu Ala Gly Ile Gly Thr Ser Ala Leu Val
325 330 335

Asp Ile Phe Ile Asn Lys Pro Gly Asn Gln Pro Leu Lys Ala Gly Asp
340 345 350

Ile Ala Ile Leu Gly Gly Ala Lys Glu Met Pro Trp Ala Phe Asp Arg
355 360 365

Leu Tyr Lys Val Glu Ile Thr Asp Ser Leu Lys Thr Leu Ser Leu Asp
370 375 380

Val Asp Gly Asp Tyr Glu Val Thr Phe Lys Ile His Asp Met His Gly
385 390 395 400

Asn Ala Leu Asp Thr Asp Leu Ile Pro His Ala Ala Val Val Ser Glu
405 410 415

Pro Ala His

<210> SEQ ID NO 27
<211> LENGTH: 414
<212> TYPE: PRT
<213> ORGANISM: HALIOTIS TUBERCULATA

<400> SEQUENCE: 27

Pro Thr Phe Glu Asp Glu Lys His Ser Leu Arg Ile Arg Lys Asn Val
1 5 10 15

Asp Ser Leu Thr Pro Glu Glu Thr Asn Glu Leu Arg Lys Ala Leu Glu
20 25 30

Leu Leu Glu Asn Asp His Thr Ala Gly Gly Phe Asn Gln Leu Gly Ala
35 40 45

Phe His Gly Glu Pro Lys Trp Cys Pro Asn Pro Glu Ala Glu His Lys
50 55 60

Val Ala Cys Cys Val His Gly Met Ala Val Phe Pro His Trp His Arg
65 70 75 80

Leu Leu Ala Leu Gln Ala Glu Asn Ala Leu Arg Lys His Gly Tyr Ser
85 90 95

Gly Ala Leu Pro Tyr Trp Asp Trp Thr Arg Pro Leu Ser Gln Leu Pro
100 105 110

Asp Leu Val Ser His Glu Gln Tyr Thr Asp Pro Ser Asp His His Val
115 120 125

```
Lys His Asn Pro Trp Phe Asn Gly His Ile Asp Thr Val Asn Gln Asp
    130                 135                 140

Thr Thr Arg Ser Val Arg Glu Asp Leu Tyr Gln Gln Pro Glu Phe Gly
145                 150                 155                 160

His Phe Thr Asp Ile Ala Gln Gln Val Leu Leu Ala Leu Glu Gln Asp
                165                 170                 175

Asp Phe Cys Ser Phe Glu Val Gln Tyr Glu Ile Ser His Asn Phe Ile
            180                 185                 190

His Ala Leu Val Gly Gly Thr Asp Ala Tyr Gly Met Ala Ser Leu Arg
        195                 200                 205

Tyr Thr Ala Tyr Asp Pro Ile Phe Phe Leu His His Ser Asn Thr Asp
    210                 215                 220

Arg Ile Trp Ala Ile Trp Gln Ser Leu Gln Lys Tyr Arg Gly Lys Pro
225                 230                 235                 240

Tyr Asn Thr Ala Asn Cys Ala Ile Glu Ser Met Arg Arg Pro Leu Gln
                245                 250                 255

Pro Phe Gly Leu Ser Ser Ala Ile Asn Pro Asp Arg Ile Thr Arg Glu
            260                 265                 270

His Ala Ile Pro Phe Asp Val Phe Asn Tyr Arg Asp Asn Leu His Tyr
        275                 280                 285

Val Tyr Asp Thr Leu Glu Phe Asn Gly Leu Ser Ile Ser Gln Leu Asp
    290                 295                 300

Arg Glu Leu Glu Lys Ile Lys Ser His Glu Arg Val Phe Ala Gly Phe
305                 310                 315                 320

Leu Leu Ser Gly Ile Lys Lys Ser Ala Leu Val Lys Phe Glu Val Cys
                325                 330                 335

Thr Pro Pro Asp Asn Cys His Lys Ala Gly Glu Phe Tyr Leu Leu Gly
            340                 345                 350

Asp Glu Asn Glu Met Ala Trp Ala Tyr Asp Arg Leu Phe Lys Tyr Asp
        355                 360                 365

Ile Thr Gln Val Leu Glu Ala Asn His Leu His Phe Tyr Asp His Leu
    370                 375                 380

Phe Ile Arg Tyr Glu Val Phe Asp Leu Lys Gly Val Ser Leu Gly Thr
385                 390                 395                 400

Asp Leu Phe His Thr Ala Asn Val Val His Asp Ser Gly Thr
                405                 410


<210> SEQ ID NO 28
<211> LENGTH: 413
<212> TYPE: PRT
<213> ORGANISM: HALIOTIS TUBERCULATA

<400> SEQUENCE: 28

Gly Thr Arg Asp Arg Asp Asn Tyr Val Glu Glu Val Thr Gly Ala Ser
1               5                   10                  15

His Ile Arg Lys Asn Leu Asn Asp Leu Asn Thr Gly Glu Met Glu Ser
            20                  25                  30

Leu Arg Ala Ala Phe Leu His Ile Gln Asp Asp Gly Thr Tyr Glu Ser
        35                  40                  45

Ile Ala Gln Tyr His Gly Lys Pro Gly Lys Cys Gln Leu Asn Asp His
    50                  55                  60

Asn Ile Ala Cys Cys Val His Gly Met Pro Thr Phe Pro Gln Trp His
65                  70                  75                  80

Arg Leu Tyr Val Val Gln Val Glu Asn Ala Leu Leu Asn Arg Gly Ser
```

-continued

```
                85                  90                  95

Gly Val Ala Val Pro Tyr Trp Glu Trp Thr Ala Pro Ile Asp His Leu
            100                 105                 110

Pro His Phe Ile Asp Asp Ala Thr Tyr Phe Asn Ser Arg Gln Gln Arg
        115                 120                 125

Tyr Asp Pro Asn Pro Phe Phe Arg Gly Lys Val Thr Phe Glu Asn Ala
    130                 135                 140

Val Thr Thr Arg Asp Pro Gln Ala Gly Leu Phe Asn Ser Asp Tyr Met
145                 150                 155                 160

Tyr Glu Asn Val Leu Leu Ala Leu Glu Gln Glu Asn Tyr Cys Asp Phe
                165                 170                 175

Glu Ile Gln Phe Glu Leu Val His Asn Ala Leu His Ser Met Leu Gly
            180                 185                 190

Gly Lys Gly Gln Tyr Ser Met Ser Ser Leu Asp Tyr Ser Ala Phe Asp
        195                 200                 205

Pro Val Phe Phe Leu His His Ala Asn Thr Asp Arg Leu Trp Ala Ile
    210                 215                 220

Trp Gln Glu Leu Gln Arg Phe Arg Glu Leu Pro Tyr Glu Glu Ala Asn
225                 230                 235                 240

Cys Ala Ile Asn Leu Met His Gln Pro Leu Lys Pro Phe Ser Asp Pro
                245                 250                 255

His Glu Asn His Asp Asn Val Thr Leu Lys Tyr Ser Lys Pro Gln Asp
            260                 265                 270

Gly Phe Asp Tyr Gln Asn His Phe Gly Tyr Lys Tyr Asp Asn Leu Glu
        275                 280                 285

Phe His His Leu Ser Ile Pro Ser Leu Asp Ala Thr Leu Lys Gln Arg
    290                 295                 300

Arg Asn His Asp Arg Val Phe Ala Gly Phe Leu Leu His Asn Ile Gly
305                 310                 315                 320

Thr Ser Ala Asp Ile Thr Ile Tyr Ile Cys Leu Pro Asp Gly Arg Arg
                325                 330                 335

Gly Asn Asp Cys Ser His Glu Ala Gly Thr Phe Tyr Ile Leu Gly Gly
            340                 345                 350

Glu Thr Glu Met Pro Phe Ile Phe Asp Arg Leu Tyr Lys Phe Glu Ile
        355                 360                 365

Thr Lys Pro Leu Gln Gln Leu Gly Val Lys Leu His Gly Gly Val Phe
    370                 375                 380

Glu Leu Glu Leu Glu Ile Lys Ala Tyr Asn Gly Ser Tyr Leu Asp Pro
385                 390                 395                 400

His Thr Phe Asp Pro Thr Ile Ile Phe Glu Pro Gly Thr
                405                 410


<210> SEQ ID NO 29
<211> LENGTH: 420
<212> TYPE: PRT
<213> ORGANISM: HALIOTIS TUBERCULATA

<400> SEQUENCE: 29

Asp Thr His Ile Leu Asp His Asp His Glu Glu Glu Ile Leu Val Arg
1               5                   10                  15

Lys Asn Ile Ile Asp Leu Ser Pro Arg Glu Arg Val Ser Leu Val Lys
            20                  25                  30

Ala Leu Gln Arg Met Lys Asn Asp Arg Ser Ala Asp Gly Tyr Gln Ala
        35                  40                  45
```

-continued

```
Ile Ala Ser Phe His Ala Leu Pro Pro Leu Cys Pro Asn Pro Ser Ala
    50                  55                  60

Ala His Arg Tyr Ala Cys Cys Val His Gly Met Ala Thr Phe Pro Gln
65                  70                  75                  80

Trp His Arg Leu Tyr Thr Val Gln Val Gln Asp Ala Leu Arg Arg His
                85                  90                  95

Gly Ser Leu Val Gly Ile Pro Tyr Trp Asp Trp Thr Lys Pro Val Asn
            100                 105                 110

Glu Leu Pro Glu Leu Leu Ser Ser Ala Thr Phe Tyr His Pro Ile Arg
        115                 120                 125

Asn Ile Asn Ile Ser Asn Pro Phe Leu Gly Ala Asp Ile Glu Phe Glu
    130                 135                 140

Gly Pro Gly Val His Thr Glu Arg His Ile Asn Thr Glu Arg Leu Phe
145                 150                 155                 160

His Ser Gly Asp His Asp Gly Tyr His Asn Trp Phe Phe Glu Thr Val
                165                 170                 175

Leu Phe Ala Leu Glu Gln Glu Asp Tyr Cys Asp Phe Glu Ile Gln Phe
            180                 185                 190

Glu Ile Ala His Asn Gly Ile His Thr Trp Ile Gly Gly Ser Ala Val
        195                 200                 205

Tyr Gly Met Gly His Leu His Tyr Ala Ser Tyr Asp Pro Ile Phe Tyr
    210                 215                 220

Ile His His Ser Gln Thr Asp Arg Ile Trp Ala Ile Trp Gln Glu Leu
225                 230                 235                 240

Gln Lys Tyr Arg Gly Leu Ser Gly Ser Glu Ala Asn Cys Ala Ile Glu
                245                 250                 255

His Met Arg Thr Pro Leu Lys Pro Phe Ser Phe Gly Pro Pro Tyr Asn
            260                 265                 270

Leu Asn Ser His Thr Gln Glu Tyr Ser Lys Pro Glu Asp Thr Phe Asp
        275                 280                 285

Tyr Lys Lys Phe Gly Tyr Arg Tyr Asp Ser Leu Glu Leu Glu Gly Arg
    290                 295                 300

Ser Ile Ser Arg Ile Asp Glu Leu Ile Gln Gln Arg Gln Glu Lys Asp
305                 310                 315                 320

Arg Thr Phe Ala Gly Phe Leu Leu Lys Gly Phe Gly Thr Ser Ala Ser
                325                 330                 335

Val Ser Leu Gln Val Cys Arg Val Asp His Thr Cys Lys Asp Ala Gly
            340                 345                 350

Tyr Phe Thr Ile Leu Gly Gly Ser Ala Glu Met Pro Trp Ala Phe Asp
        355                 360                 365

Arg Leu Tyr Lys Tyr Asp Ile Thr Lys Thr Leu His Asp Met Asn Leu
    370                 375                 380

Arg His Glu Asp Thr Phe Ser Ile Asp Val Thr Ile Thr Ser Tyr Asn
385                 390                 395                 400

Gly Thr Val Leu Ser Gly Asp Leu Ile Gln Thr Pro Ser Ile Ile Phe
                405                 410                 415

Val Pro Gly Arg
            420
```

```
<210> SEQ ID NO 30
<211> LENGTH: 417
<212> TYPE: PRT
<213> ORGANISM: HALIOTIS TUBERCULATA

<400> SEQUENCE: 30
```

-continued

```
His Lys Leu Asn Ser Arg Lys His Thr Pro Asn Arg Val Arg His Glu
1               5                   10                  15

Leu Ser Ser Leu Ser Ser Arg Asp Ile Ala Ser Leu Lys Ala Ala Leu
            20                  25                  30

Thr Ser Leu Gln His Asp Asn Gly Thr Asp Gly Tyr Gln Ala Ile Ala
        35                  40                  45

Ala Phe His Gly Val Pro Ala Gln Cys His Glu Pro Ser Gly Arg Glu
    50                  55                  60

Ile Ala Cys Cys Ile His Gly Met Ala Thr Phe Pro His Trp His Arg
65                  70                  75                  80

Leu Tyr Thr Leu Gln Leu Glu Gln Ala Leu Arg Arg His Gly Ser Ser
                85                  90                  95

Val Ala Val Pro Tyr Trp Asp Trp Thr Lys Pro Ile Thr Glu Leu Pro
            100                 105                 110

His Ile Leu Thr Asp Gly Glu Tyr Tyr Asp Val Trp Gln Asn Ala Val
        115                 120                 125

Leu Ala Asn Pro Phe Ala Arg Gly Tyr Val Lys Ile Lys Asp Ala Phe
    130                 135                 140

Thr Val Arg Asn Val Gln Glu Ser Leu Phe Lys Met Ser Ser Phe Gly
145                 150                 155                 160

Lys His Ser Leu Leu Phe Asp Gln Ala Leu Leu Ala Leu Glu Gln Thr
                165                 170                 175

Asp Tyr Cys Asp Phe Glu Val Gln Phe Glu Val Met His Asn Thr Ile
            180                 185                 190

His Tyr Leu Val Gly Gly Arg Gln Thr Tyr Ala Phe Ser Ser Leu Glu
        195                 200                 205

Tyr Ser Ser Tyr Asp Pro Ile Phe Phe Ile His His Ser Phe Val Asp
    210                 215                 220

Lys Ile Trp Ala Val Trp Gln Glu Leu Gln Ser Arg Arg His Leu Gln
225                 230                 235                 240

Phe Arg Thr Ala Asp Cys Ala Val Gly Leu Met Gly Gln Ala Met Arg
                245                 250                 255

Pro Phe Asn Lys Asp Phe Asn His Asn Ser Phe Thr Lys Lys His Ala
            260                 265                 270

Val Pro Asn Thr Val Phe Asp Tyr Glu Asp Leu Gly Tyr Asn Tyr Asp
        275                 280                 285

Asn Leu Glu Ile Ser Gly Leu Asn Leu Asn Glu Ile Glu Ala Leu Ile
    290                 295                 300

Ala Lys Arg Lys Ser His Ala Arg Val Phe Ala Gly Phe Leu Leu Phe
305                 310                 315                 320

Gly Leu Gly Thr Ser Ala Asp Ile His Leu Glu Ile Cys Lys Thr Ser
                325                 330                 335

Glu Asn Cys His Asp Ala Gly Val Ile Phe Ile Leu Gly Gly Ser Ala
            340                 345                 350

Glu Met His Trp Ala Tyr Asn Arg Leu Tyr Lys Tyr Asp Ile Thr Glu
        355                 360                 365

Ala Leu Gln Glu Phe Asp Ile Asn Pro Glu Asp Val Phe His Ala Asp
    370                 375                 380

Glu Pro Phe Phe Leu Arg Leu Ser Val Val Ala Val Asn Gly Thr Val
385                 390                 395                 400

Ile Pro Ser Ser His Leu His Gln Pro Thr Ile Ile Tyr Glu Pro Gly
                405                 410                 415
```

```
Glu

<210> SEQ ID NO 31
<211> LENGTH: 403
<212> TYPE: PRT
<213> ORGANISM: HALIOTIS TUBERCULATA

<400> SEQUENCE: 31

Asp His His Asp Asp His Gln Ser Gly Ser Ile Ala Gly Ser Gly Val
1               5                   10                  15

Arg Lys Asp Val Asn Thr Leu Thr Lys Ala Glu Thr Asp Asn Leu Arg
            20                  25                  30

Glu Ala Leu Trp Gly Val Met Ala Asp His Gly Pro Asn Gly Phe Gln
        35                  40                  45

Ala Ile Ala Ala Phe His Gly Lys Pro Ala Leu Cys Pro Met Pro Asp
    50                  55                  60

Gly His Asn Tyr Ser Cys Cys Thr His Gly Met Ala Thr Phe Pro His
65                  70                  75                  80

Trp His Arg Leu Tyr Thr Lys Gln Met Glu Asp Ala Met Arg Ala His
                85                  90                  95

Gly Ser His Val Gly Leu Pro Tyr Trp Asp Trp Thr Ala Ala Phe Thr
            100                 105                 110

His Leu Pro Thr Leu Val Thr Asp Thr Asp Asn Asn Pro Phe Gln His
        115                 120                 125

Gly His Ile Asp Tyr Leu Asn Val Ser Thr Thr Arg Ser Pro Arg Asp
    130                 135                 140

Met Leu Phe Asn Asp Pro Glu His Gly Ser Glu Ser Phe Phe Tyr Arg
145                 150                 155                 160

Gln Val Leu Leu Ala Leu Glu Gln Thr Asp Phe Cys Lys Phe Glu Val
                165                 170                 175

Gln Phe Glu Ile Thr His Asn Ala Ile His Ser Trp Thr Gly Gly His
            180                 185                 190

Ser Pro Tyr Gly Met Ser Thr Leu Asp Phe Thr Ala Tyr Asp Pro Leu
        195                 200                 205

Phe Trp Leu His His Ser Asn Thr Asp Arg Ile Trp Ala Val Trp Gln
    210                 215                 220

Ala Leu Gln Glu Tyr Arg Gly Leu Pro Tyr Asn His Ala Asn Cys Glu
225                 230                 235                 240

Ile Gln Ala Met Lys Thr Pro Leu Arg Pro Phe Ser Asp Asp Ile Asn
                245                 250                 255

His Asn Pro Val Thr Lys Ala Asn Ala Lys Pro Leu Asp Val Phe Glu
            260                 265                 270

Tyr Asn Arg Leu Ser Phe Gln Tyr Asp Asn Leu Ile Phe His Gly Tyr
        275                 280                 285

Ser Ile Pro Glu Leu Asp Arg Val Leu Glu Glu Arg Lys Glu Glu Asp
    290                 295                 300

Arg Ile Phe Ala Ala Phe Leu Leu Ser Gly Ile Lys Arg Ser Ala Asp
305                 310                 315                 320

Val Val Phe Asp Ile Cys Gln Pro Glu His Glu Cys Val Phe Ala Gly
                325                 330                 335

Thr Phe Ala Ile Leu Gly Gly Glu Leu Glu Met Pro Trp Ser Phe Asp
            340                 345                 350

Arg Leu Phe Arg Tyr Asp Ile Thr Lys Val Met Lys Gln Leu His Leu
        355                 360                 365
```

-continued

```
Arg His Asp Ser Asp Phe Thr Phe Arg Val Lys Ile Val Gly Thr Asp
    370                 375                 380

Asp His Glu Leu Pro Ser Asp Ser Val Lys Ala Pro Thr Ile Glu Phe
385                 390                 395                 400

Glu Pro Gly


<210> SEQ ID NO 32
<211> LENGTH: 511
<212> TYPE: PRT
<213> ORGANISM: HALIOTIS TUBERCULATA

<400> SEQUENCE: 32

Val His Arg Gly Gly Asn His Glu Asp Glu His His Asp Asp Arg Leu
1               5                   10                  15

Ala Asp Val Leu Ile Arg Lys Glu Val Asp Phe Leu Ser Leu Gln Glu
            20                  25                  30

Ala Asn Ala Ile Lys Asp Ala Leu Tyr Lys Leu Gln Asn Asp Asp Ser
        35                  40                  45

Lys Gly Gly Phe Glu Ala Ile Ala Gly Tyr His Gly Tyr Pro Asn Met
    50                  55                  60

Cys Pro Glu Arg Gly Thr Asp Lys Tyr Pro Cys Cys Val His Gly Met
65                  70                  75                  80

Pro Val Phe Pro His Trp His Arg Leu His Thr Ile Gln Met Glu Arg
                85                  90                  95

Ala Leu Lys Asn His Gly Ser Pro Met Gly Ile Pro Tyr Trp Asp Trp
            100                 105                 110

Thr Lys Lys Met Ser Ser Leu Pro Ser Phe Phe Gly Asp Ser Ser Asn
        115                 120                 125

Asn Asn Pro Phe Tyr Lys Tyr Tyr Ile Arg Gly Val Gln His Glu Thr
    130                 135                 140

Thr Arg Asp Val Asn Gln Arg Leu Phe Asn Gln Thr Lys Phe Gly Glu
145                 150                 155                 160

Phe Asp Tyr Leu Tyr Tyr Leu Thr Leu Gln Val Leu Glu Glu Asn Ser
                165                 170                 175

Tyr Cys Asp Phe Glu Val Gln Tyr Glu Ile Leu His Asn Ala Val His
            180                 185                 190

Ser Trp Leu Gly Gly Thr Gly Gln Tyr Ser Met Ser Thr Leu Glu Tyr
        195                 200                 205

Ser Ala Phe Asp Pro Val Phe Met Ile His His Ser Ser Leu Asp Arg
    210                 215                 220

Ile Trp Ile Leu Trp Gln Lys Leu Gln Lys Ile Arg Met Lys Pro Tyr
225                 230                 235                 240

Tyr Ala Leu Asp Cys Ala Gly Asp Arg Leu Met Lys Asp Pro Leu His
                245                 250                 255

Pro Phe Asn Tyr Glu Thr Val Asn Glu Asp Glu Phe Thr Arg Ile Asn
            260                 265                 270

Ser Phe Pro Ser Ile Leu Phe Asp His Tyr Arg Phe Asn Tyr Glu Tyr
        275                 280                 285

Asp Asn Met Arg Ile Arg Gly Gln Asp Ile His Glu Leu Glu Glu Val
    290                 295                 300

Ile Gln Glu Leu Arg Asn Lys Asp Arg Ile Phe Ala Gly Phe Val Leu
305                 310                 315                 320

Ser Gly Leu Arg Ile Ser Ala Thr Val Lys Val Phe Ile His Ser Lys
                325                 330                 335
```

-continued

```
Asn Asp Thr Ser His Glu Glu Tyr Ala Gly Glu Phe Ala Val Leu Gly
            340                 345                 350

Gly Glu Lys Glu Met Pro Trp Ala Tyr Glu Arg Met Leu Lys Leu Asp
        355                 360                 365

Ile Ser Asp Ala Val His Lys Leu His Val Lys Asp Glu Asp Ile Arg
    370                 375                 380

Phe Arg Val Val Val Thr Ala Tyr Asn Gly Asp Val Val Thr Thr Arg
385                 390                 395                 400

Leu Ser Gln Pro Phe Ile Val His Arg Pro Ala His Val Ala His Asp
                405                 410                 415

Ile Leu Val Ile Pro Val Gly Ala Gly His Asp Leu Pro Pro Lys Val
            420                 425                 430

Val Val Lys Ser Gly Thr Lys Val Glu Phe Thr Pro Ile Asp Ser Ser
        435                 440                 445

Val Asn Lys Ala Met Val Glu Leu Gly Ser Tyr Thr Ala Met Ala Lys
    450                 455                 460

Cys Ile Val Pro Pro Phe Ser Tyr His Gly Phe Glu Leu Asp Lys Val
465                 470                 475                 480

Tyr Ser Val Asp His Gly Asp Tyr Tyr Ile Ala Ala Gly Thr His Ala
                485                 490                 495

Leu Cys Glu Gln Asn Leu Arg Leu His Ile His Val Glu His Glu
            500                 505                 510


<210> SEQ ID NO 33
<211> LENGTH: 334
<212> TYPE: PRT
<213> ORGANISM: HALIOTIS TUBERCULATA

<400> SEQUENCE: 33

His Arg Leu Phe Val Thr Gln Val Glu Asp Ala Leu Ile Arg Arg Gly
1               5                   10                  15

Ser Pro Ile Gly Val Pro Tyr Trp Asp Trp Thr Gln Pro Met Ala His
            20                  25                  30

Leu Pro Gly Leu Ala Asp Asn Ala Thr Tyr Arg Asp Pro Ile Ser Gly
        35                  40                  45

Asp Ser Arg His Asn Pro Phe His Asp Val Glu Val Ala Phe Glu Asn
    50                  55                  60

Gly Arg Thr Glu Arg His Pro Asp Ser Arg Leu Phe Glu Gln Pro Leu
65                  70                  75                  80

Phe Gly Lys His Thr Arg Leu Phe Asp Ser Ile Val Tyr Ala Phe Glu
                85                  90                  95

Gln Glu Asp Phe Cys Asp Phe Glu Val Gln Phe Glu Met Thr His Asn
            100                 105                 110

Asn Ile His Ala Trp Ile Gly Gly Gly Glu Lys Tyr Ser Met Ser Ser
        115                 120                 125

Leu His Tyr Thr Ala Phe Asp Pro Ile Phe Tyr Leu Arg His Ser Asn
    130                 135                 140

Thr Asp Arg Leu Trp Ala Ile Trp Gln Ala Leu Gln Ile Arg Arg Asn
145                 150                 155                 160

Arg Pro Tyr Lys Ala His Cys Ala Trp Ser Glu Glu Arg Gln Pro Leu
                165                 170                 175

Lys Pro Phe Ala Phe Ser Ser Pro Leu Asn Asn Asn Glu Lys Thr Tyr
            180                 185                 190

Glu Asn Ser Val Pro Thr Asn Val Tyr Asp Tyr Glu Gly Val Leu Gly
        195                 200                 205
```

```
Tyr Thr Tyr Asp Asp Leu Asn Phe Gly Gly Met Asp Leu Gly Gln Leu
    210                 215                 220

Glu Glu Tyr Ile Gln Arg Gln Arg Gln Arg Asp Arg Thr Phe Ala Gly
225                 230                 235                 240

Phe Phe Leu Ser His Ile Gly Thr Ser Ala Asn Val Glu Ile Ile Ile
                245                 250                 255

Asp His Gly Thr Leu His Thr Ser Val Gly Thr Phe Ala Val Leu Gly
            260                 265                 270

Gly Glu Lys Glu Met Lys Trp Gly Phe Asp Arg Leu Tyr Lys Tyr Glu
        275                 280                 285

Ile Thr Asp Glu Leu Arg Gln Leu Asn Leu Arg Ala Asp Asp Val Phe
    290                 295                 300

Ser Ile Ser Val Lys Val Thr Asp Val Asp Gly Ser Glu Leu Ser Ser
305                 310                 315                 320

Glu Leu Ile Pro Ser Ala Ala Ile Ile Phe Glu Arg Ser His
                325                 330


<210> SEQ ID NO 34
<211> LENGTH: 417
<212> TYPE: PRT
<213> ORGANISM: HALIOTIS TUBERCULATA

<400> SEQUENCE: 34

Ile Asp His Gln Asp Pro His His Asp Thr Ile Ile Arg Lys Asn Val
1               5                   10                  15

Asp Asn Leu Thr Pro Glu Glu Ile Asn Ser Leu Arg Arg Ala Met Ala
            20                  25                  30

Asp Leu Gln Ser Asp Lys Thr Ala Gly Gly Phe Gln Gln Ile Ala Ala
        35                  40                  45

Phe His Gly Glu Pro Lys Trp Cys Pro Ser Pro Asp Ala Glu Lys Lys
    50                  55                  60

Phe Ser Cys Cys Val His Gly Met Ala Val Phe Pro His Trp His Arg
65                  70                  75                  80

Leu Leu Thr Val Gln Gly Glu Asn Ala Leu Arg Lys His Gly Cys Leu
                85                  90                  95

Gly Ala Leu Pro Tyr Trp Asp Trp Thr Arg Pro Leu Ser His Leu Pro
            100                 105                 110

Asp Leu Val Leu Val Ser Ser Arg Thr Thr Pro Met Pro Tyr Ser Thr
        115                 120                 125

Val Glu Ala Arg Asn Pro Trp Tyr Ser Gly His Ile Asp Thr Val Gly
    130                 135                 140

Val Asp Thr Thr Arg Ser Val Arg Gln Glu Leu Tyr Glu Ala Pro Gly
145                 150                 155                 160

Phe Gly His Tyr Thr Gly Val Ala Lys Gln Val Leu Leu Ala Leu Glu
                165                 170                 175

Gln Asp Asp Phe Cys Asp Phe Glu Val Gln Phe Glu Ile Ala His Asn
            180                 185                 190

Phe Ile His Ala Leu Val Gly Gly Ser Glu Pro Tyr Gly Met Ala Ser
        195                 200                 205

Leu Arg Tyr Thr Thr Tyr Asp Pro Ile Phe Tyr Leu His His Ser Asn
    210                 215                 220

Thr Asp Arg Leu Trp Ala Ile Trp Gln Ala Leu Gln Lys Tyr Arg Gly
225                 230                 235                 240

Lys Pro Tyr Asn Ser Ala Asn Cys Ala Ile Ala Ser Met Arg Lys Pro
```

-continued

```
                245                 250                 255

Leu Gln Pro Phe Gly Leu Thr Asp Glu Ile Asn Pro Asp Asp Glu Thr
            260                 265                 270

Arg Gln His Ala Val Pro Phe Ser Val Phe Asp Tyr Lys Asn Asn Phe
        275                 280                 285

Asn Tyr Glu Tyr Asp Thr Leu Asp Phe Asn Gly Leu Ser Ile Ser Gln
    290                 295                 300

Leu Asp Arg Glu Leu Ser Arg Arg Lys Ser His Asp Arg Val Phe Ala
305                 310                 315                 320

Gly Phe Leu Leu His Gly Ile Gln Gln Ser Ala Leu Val Lys Phe Phe
                325                 330                 335

Val Cys Lys Ser Asp Asp Asp Cys Asp His Tyr Ala Gly Glu Phe Tyr
            340                 345                 350

Ile Leu Gly Asp Glu Ala Glu Met Pro Trp Gly Tyr Asp Arg Leu Tyr
        355                 360                 365

Lys Tyr Glu Ile Thr Glu Gln Leu Asn Ala Leu Asp Leu His Ile Gly
    370                 375                 380

Asp Arg Phe Phe Ile Arg Tyr Glu Ala Phe Asp Leu His Gly Thr Ser
385                 390                 395                 400

Leu Gly Ser Asn Ile Phe Pro Lys Pro Ser Val Ile His Asp Glu Gly
                405                 410                 415

Ala


<210> SEQ ID NO 35
<211> LENGTH: 415
<212> TYPE: PRT
<213> ORGANISM: HALIOTIS TUBERCULATA

<400> SEQUENCE: 35

Gly His His Gln Ala Asp Glu Tyr Asp Glu Val Val Thr Ala Ala Ser
1               5                   10                  15

His Ile Arg Lys Asn Leu Lys Asp Leu Ser Lys Gly Glu Val Glu Ser
            20                  25                  30

Leu Arg Ser Ala Phe Leu Gln Leu Gln Asn Asp Gly Val Tyr Glu Asn
        35                  40                  45

Ile Ala Lys Phe His Gly Lys Pro Gly Leu Cys Asp Asp Asn Gly Arg
    50                  55                  60

Lys Val Ala Cys Cys Val His Gly Met Pro Thr Phe Pro Gln Trp His
65                  70                  75                  80

Arg Leu Tyr Val Leu Gln Val Glu Asn Ala Leu Leu Glu Arg Gly Ser
                85                  90                  95

Ala Val Ser Val Pro Tyr Trp Asp Trp Thr Glu Thr Phe Thr Glu Leu
            100                 105                 110

Pro Ser Leu Ile Ala Glu Ala Thr Tyr Phe Asn Ser Arg Gln Gln Thr
        115                 120                 125

Phe Asp Pro Asn Pro Phe Phe Arg Gly Lys Ile Ser Phe Glu Asn Ala
    130                 135                 140

Val Thr Thr Arg Asp Pro Gln Pro Glu Leu Tyr Val Asn Arg Tyr Tyr
145                 150                 155                 160

Tyr Gln Asn Val Met Leu Val Phe Glu Gln Asp Asn Tyr Cys Asp Phe
                165                 170                 175

Glu Ile Gln Phe Glu Met Val His Asn Val Leu His Ala Trp Leu Gly
            180                 185                 190

Gly Arg Ala Thr Tyr Ser Ile Ser Ser Leu Asp Tyr Ser Ala Phe Asp
```

-continued

```
        195                 200                 205

Pro Val Phe Phe Leu His His Ala Asn Thr Asp Arg Leu Trp Ala Ile
    210                 215                 220

Trp Gln Glu Leu Gln Arg Tyr Arg Lys Lys Pro Tyr Asn Glu Ala Asp
225                 230                 235                 240

Cys Ala Ile Asn Leu Met Arg Lys Pro Leu His Pro Phe Asp Asn Ser
                245                 250                 255

Asp Leu Asn His Asp Pro Val Thr Phe Lys Tyr Ser Lys Pro Thr Asp
            260                 265                 270

Gly Phe Asp Tyr Gln Asn Asn Phe Gly Tyr Lys Tyr Asp Asn Leu Glu
        275                 280                 285

Phe Asn His Phe Ser Ile Pro Arg Leu Glu Glu Ile Ile Arg Ile Arg
    290                 295                 300

Gln Arg Gln Asp Arg Val Phe Ala Gly Phe Leu Leu His Asn Ile Gly
305                 310                 315                 320

Thr Ser Ala Thr Val Glu Ile Phe Val Cys Val Pro Thr Thr Ser Gly
                325                 330                 335

Glu Gln Asn Cys Glu Asn Lys Ala Gly Thr Phe Ala Val Leu Gly Gly
            340                 345                 350

Glu Thr Glu Met Ala Phe His Phe Asp Arg Leu Tyr Arg Phe Asp Ile
        355                 360                 365

Ser Glu Thr Leu Arg Asp Leu Gly Ile Gln Leu Asp Ser His Asp Phe
    370                 375                 380

Asp Leu Ser Ile Lys Ile Gln Gly Val Asn Gly Ser Tyr Leu Asp Pro
385                 390                 395                 400

His Ile Leu Pro Glu Pro Ser Leu Ile Phe Val Pro Gly Ser Ser
                405                 410                 415


<210> SEQ ID NO 36
<211> LENGTH: 418
<212> TYPE: PRT
<213> ORGANISM: HALIOTIS TUBERCULATA

<400> SEQUENCE: 36

Ser Phe Leu Arg Pro Asp Gly His Ser Asp Asp Ile Leu Val Arg Lys
1               5                   10                  15

Glu Val Asn Ser Leu Thr Thr Arg Glu Thr Ala Ser Leu Ile His Ala
            20                  25                  30

Leu Lys Ser Met Gln Glu Asp His Ser Pro Asp Gly Phe Gln Ala Ile
        35                  40                  45

Ala Ser Phe His Ala Leu Pro Pro Leu Cys Pro Ser Pro Ser Ala Ala
    50                  55                  60

His Arg Tyr Ala Cys Cys Val His Gly Met Ala Thr Phe Pro Gln Trp
65                  70                  75                  80

His Arg Leu Tyr Thr Val Gln Phe Gln Asp Ala Leu Arg Arg His Gly
                85                  90                  95

Ala Thr Val Gly Val Pro Tyr Trp Asp Trp Leu Arg Pro Gln Ser His
            100                 105                 110

Leu Pro Glu Leu Val Thr Met Glu Thr Tyr His Asp Ile Trp Ser Asn
        115                 120                 125

Arg Asp Phe Pro Asn Pro Phe Tyr Gln Ala Asn Ile Glu Phe Glu Gly
    130                 135                 140

Glu Asn Ile Thr Thr Glu Arg Glu Val Ile Ala Asp Lys Leu Phe Val
145                 150                 155                 160
```

-continued

```
Lys Gly Gly His Val Phe Asp Lys Leu Val Leu Gln Thr Ser His Pro
                165                 170                 175

Ser Ala Glu Gln Glu Asn Tyr Cys Asp Phe Glu Ile Gln Phe Glu Ile
            180                 185                 190

Leu His Asn Gly Val His Thr Trp Val Gly Gly Ser Arg Thr Tyr Ser
        195                 200                 205

Ile Gly His Leu His Tyr Ala Phe Tyr Asp Pro Leu Phe Tyr Leu His
    210                 215                 220

His Phe Gln Thr Asp Arg Ile Trp Ala Ile Trp Gln Glu Leu Gln Glu
225                 230                 235                 240

Gln Arg Gly Leu Ser Gly Asp Glu Ala His Cys Ala Leu Glu Gln Met
                245                 250                 255

Arg Glu Pro Leu Lys Pro Phe Ser Phe Gly Ala Pro Tyr Asn Trp Asn
            260                 265                 270

Gln Leu Thr Gln Asp Phe Ser Arg Pro Glu Asp Thr Phe Asp Tyr Arg
        275                 280                 285

Lys Phe Gly Tyr Glu Tyr Asp Asn Leu Glu Phe Leu Gly Met Ser Val
    290                 295                 300

Ala Glu Leu Asp Gln Tyr Ile Ile Glu His Gln Glu Asn Asp Arg Val
305                 310                 315                 320

Phe Ala Gly Phe Leu Leu Ser Gly Phe Gly Gly Ser Ala Ser Val Asn
                325                 330                 335

Phe Gln Val Cys Arg Ala Asp Ser Thr Cys Gln Asp Ala Gly Tyr Phe
            340                 345                 350

Thr Val Leu Gly Gly Ser Ala Glu Met Ala Trp Ala Phe Asp Arg Leu
        355                 360                 365

Tyr Lys Tyr Asp Ile Thr Glu Thr Leu Glu Lys Met His Leu Arg Tyr
    370                 375                 380

Asp Asp Asp Phe Thr Ile Ser Val Ser Leu Thr Ala Asn Asn Gly Thr
385                 390                 395                 400

Val Leu Ser Ser Ser Leu Ile Pro Thr Pro Ser Val Ile Phe Gln Arg
                405                 410                 415

Gly His


<210> SEQ ID NO 37
<211> LENGTH: 416
<212> TYPE: PRT
<213> ORGANISM: HALIOTIS TUBERCULATA

<400> SEQUENCE: 37

Arg Asp Ile Asn Thr Arg Ser Met Ser Pro Asn Arg Val Arg Arg Glu
1               5                   10                  15

Leu Ser Asp Leu Ser Ala Arg Asp Leu Ser Ser Leu Lys Ser Ala Leu
            20                  25                  30

Arg Asp Leu Gln Glu Asp Asp Gly Pro Asn Gly Tyr Gln Ala Leu Ala
        35                  40                  45

Ala Phe His Gly Leu Pro Ala Gly Cys His Asp Ser Arg Gly Asn Glu
    50                  55                  60

Ile Ala Cys Cys Ile His Gly Met Pro Thr Phe Pro Gln Trp His Arg
65                  70                  75                  80

Leu Tyr Thr Leu Gln Leu Glu Met Ala Leu Arg Arg His Gly Ser Ser
                85                  90                  95

Val Ala Ile Pro Tyr Trp Asp Trp Thr Lys Pro Ile Ser Glu Leu Pro
            100                 105                 110
```

-continued

```
Ser Leu Phe Thr Ser Pro Glu Tyr Tyr Asp Pro Trp His Asp Ala Val
        115                 120                 125

Val Asn Asn Pro Phe Ser Lys Gly Phe Val Lys Phe Ala Asn Thr Tyr
    130                 135                 140

Thr Val Arg Asp Pro Gln Glu Met Leu Phe Gln Leu Cys Glu His Gly
145                 150                 155                 160

Glu Ser Ile Leu Tyr Glu Gln Thr Leu Leu Ala Leu Glu Gln Thr Asp
                165                 170                 175

Tyr Cys Asp Phe Glu Val Gln Phe Glu Val Leu His Asn Val Ile His
            180                 185                 190

Tyr Leu Val Gly Gly Arg Gln Thr Tyr Ala Leu Ser Ser Leu His Tyr
        195                 200                 205

Ala Ser Tyr Asp Pro Phe Phe Phe Ile His His Ser Phe Val Asp Lys
    210                 215                 220

Met Trp Val Val Trp Gln Ala Leu Gln Lys Arg Arg Lys Leu Pro Tyr
225                 230                 235                 240

Lys Arg Ala Asp Cys Ala Val Asn Leu Met Thr Lys Pro Met Arg Pro
                245                 250                 255

Phe Asp Ser Asp Met Asn Gln Asn Pro Phe Thr Lys Met His Ala Val
            260                 265                 270

Pro Asn Thr Leu Tyr Asp Tyr Glu Thr Leu Tyr Tyr Ser Tyr Asp Asn
        275                 280                 285

Leu Glu Ile Gly Gly Arg Asn Leu Asp Gln Leu Gln Ala Glu Ile Asp
    290                 295                 300

Arg Ser Arg Ser His Asp Arg Val Phe Ala Gly Phe Leu Leu Arg Gly
305                 310                 315                 320

Ile Gly Thr Ser Ala Asp Val Arg Phe Trp Ile Cys Arg Asn Glu Asn
                325                 330                 335

Asp Cys His Arg Gly Gly Ile Ile Phe Ile Leu Gly Gly Ala Lys Glu
            340                 345                 350

Met Pro Trp Ser Phe Asp Arg Asn Phe Lys Phe Asp Ile Thr His Val
        355                 360                 365

Leu Glu Asn Ala Gly Ile Ser Pro Glu Asp Val Phe Asp Ala Glu Glu
    370                 375                 380

Pro Phe Tyr Ile Lys Val Glu Ile His Ala Val Asn Lys Thr Met Ile
385                 390                 395                 400

Pro Ser Ser Val Ile Pro Ala Pro Thr Ile Ile Tyr Ser Pro Gly Glu
                405                 410                 415


<210> SEQ ID NO 38
<211> LENGTH: 402
<212> TYPE: PRT
<213> ORGANISM: HALIOTIS TUBERCULATA

<400> SEQUENCE: 38

Gly Arg Ala Ala Asp Ser Ala His Ser Ala Asn Ile Ala Gly Ser Gly
1               5                   10                  15

Val Arg Lys Asp Val Thr Thr Leu Thr Val Ser Glu Thr Glu Asn Leu
            20                  25                  30

Arg Gln Ala Leu Gln Gly Val Ile Asp Asp Thr Gly Pro Asn Gly Tyr
        35                  40                  45

Gln Ala Ile Ala Ser Phe His Gly Ser Pro Pro Met Cys Glu Met Asn
    50                  55                  60

Gly Arg Lys Val Ala Cys Cys Ala His Gly Met Ala Ser Phe Pro His
65                  70                  75                  80
```

-continued

```
Trp His Arg Leu Tyr Val Lys Gln Met Glu Asp Ala Leu Ala Asp His
                85                  90                  95

Gly Ser His Ile Gly Ile Pro Tyr Trp Asp Trp Thr Thr Ala Phe Thr
            100                 105                 110

Glu Leu Pro Ala Leu Val Thr Asp Ser Glu Asn Asn Pro Phe His Glu
        115                 120                 125

Gly Arg Ile Asp His Leu Gly Val Thr Thr Ser Arg Ser Pro Arg Asp
    130                 135                 140

Met Leu Phe Asn Asp Pro Glu Gln Gly Ser Glu Ser Phe Phe Tyr Arg
145                 150                 155                 160

Gln Val Leu Leu Ala Leu Glu Gln Thr Asp Tyr Cys Gln Phe Glu Val
                165                 170                 175

Gln Phe Glu Leu Thr His Asn Ala Ile His Ser Trp Thr Gly Gly Arg
            180                 185                 190

Ser Pro Tyr Gly Met Ser Thr Leu Glu Phe Thr Ala Tyr Asp Pro Leu
        195                 200                 205

Phe Trp Leu His His Ser Asn Thr Asp Arg Ile Trp Ala Val Trp Gln
    210                 215                 220

Ala Leu Gln Lys Tyr Arg Gly Leu Pro Tyr Asn Glu Ala His Cys Glu
225                 230                 235                 240

Ile Gln Val Leu Lys Gln Pro Leu Arg Pro Phe Asn Asp Asp Ile Asn
                245                 250                 255

His Asn Pro Ile Thr Lys Thr Asn Ala Arg Pro Ile Asp Ser Phe Asp
            260                 265                 270

Tyr Glu Arg Phe Asn Tyr Gln Tyr Asp Thr Leu Ser Phe His Gly Lys
        275                 280                 285

Ser Ile Pro Glu Leu Asn Asp Leu Leu Glu Glu Arg Lys Arg Glu Glu
    290                 295                 300

Arg Thr Phe Ala Ala Phe Leu Leu Arg Gly Ile Gly Cys Ser Ala Asp
305                 310                 315                 320

Val Val Phe Asp Ile Cys Arg Pro Asn Gly Asp Cys Val Phe Ala Gly
                325                 330                 335

Thr Phe Ala Val Leu Gly Gly Glu Leu Glu Met Pro Trp Ser Phe Asp
            340                 345                 350

Arg Leu Phe Arg Tyr Asp Ile Thr Arg Val Met Asn Gln Leu His Leu
        355                 360                 365

Gln Tyr Asp Ser Asp Phe Ser Phe Arg Val Lys Leu Val Ala Thr Asn
    370                 375                 380

Gly Thr Glu Leu Ser Ser Asp Leu Leu Lys Ser Pro Thr Ile Glu His
385                 390                 395                 400

Glu Leu


<210> SEQ ID NO 39
<211> LENGTH: 515
<212> TYPE: PRT
<213> ORGANISM: HALIOTIS TUBERCULATA
<220> FEATURE:
<221> NAME/KEY: MISC_FEATURE
<222> LOCATION: (425)..(425)
<223> OTHER INFORMATION: Xaa is any naturally occurring amino acid

<400> SEQUENCE: 39

Gly Ala His Arg Gly Pro Val Glu Glu Thr Glu Val Thr Arg Gln His
1               5                   10                  15

Thr Asp Gly Asn Ala His Phe His Arg Lys Glu Val Asp Ser Leu Ser
```

-continued

```
            20                  25                  30

Leu Asp Glu Ala Asn Asn Leu Lys Asn Ala Leu Tyr Lys Leu Gln Asn
        35                  40                  45

Asp His Ser Leu Thr Gly Tyr Glu Ala Ile Ser Gly Tyr His Gly Tyr
    50                  55                  60

Pro Asn Leu Cys Pro Glu Glu Gly Asp Asp Lys Ile Pro Leu Leu Arg
65                  70                  75                  80

Pro Arg Met Gly Ile Phe Pro Tyr Trp His Arg Leu Leu Thr Ile Gln
                85                  90                  95

Leu Glu Arg Ala Leu Glu His Asn Gly Ala Leu Leu Gly Val Pro Tyr
            100                 105                 110

Trp Asp Trp Asn Lys Asp Leu Ser Ser Leu Pro Ala Phe Phe Ser Asp
        115                 120                 125

Ser Ser Asn Asn Asn Pro Tyr Phe Lys Tyr His Ile Ala Gly Val Gly
    130                 135                 140

His Asp Thr Val Arg Glu Pro Thr Ser Leu Ile Tyr Asn Gln Pro Gln
145                 150                 155                 160

Ile His Gly Tyr Asp Tyr Leu Tyr Tyr Leu Ala Leu Thr Thr Leu Glu
                165                 170                 175

Glu Asn Asn Tyr Trp Asp Phe Glu Val Gln Tyr Glu Ile Leu His Asn
            180                 185                 190

Ala Val His Ser Trp Leu Gly Gly Ser Gln Lys Tyr Ser Met Ser Thr
        195                 200                 205

Leu Glu Tyr Ser Ala Phe Asp Pro Val Phe Met Ile Leu His Ser Gly
    210                 215                 220

Leu Asp Arg Leu Trp Ile Ile Trp Gln Glu Leu Gln Lys Ile Arg Arg
225                 230                 235                 240

Lys Pro Tyr Asn Phe Ala Lys Cys Ala Tyr His Met Met Glu Glu Pro
                245                 250                 255

Leu Ala Pro Phe Ser Tyr Pro Ser Ile Asn Gln Asp Glu Phe Thr Arg
            260                 265                 270

Ala Asn Ser Lys Pro Ser Thr Val Phe Asp Ser His Lys Phe Gly Tyr
        275                 280                 285

His Tyr Asp Asn Leu Asn Val Arg Gly His Ser Ile Gln Glu Leu Asn
    290                 295                 300

Thr Ile Ile Asn Asp Leu Arg Asn Thr Asp Arg Ile Tyr Ala Gly Phe
305                 310                 315                 320

Val Leu Ser Gly Ile Gly Thr Ser Ala Ser Val Lys Ile Tyr Leu Arg
                325                 330                 335

Thr Asp Asp Asn Asp Glu Glu Val Gly Thr Phe Thr Val Leu Gly Gly
            340                 345                 350

Glu Arg Glu Met Pro Trp Ala Tyr Glu Arg Val Phe Lys Tyr Asp Ile
        355                 360                 365

Thr Glu Val Ala Asp Arg Leu Lys Ile Lys Leu Trp Gly His Pro Leu
    370                 375                 380

Thr Ser Gly Thr Gly Asp His Ile Leu Thr Asn Gly Ile Gly Gly Lys
385                 390                 395                 400

Gln Glu Pro Thr Gln Ile Leu Ser Ser Ser Thr Asp Leu Pro Ile Met
                405                 410                 415

Thr Thr Met Phe Leu Leu Ser Gln Xaa Gly Arg Asn Leu His Ile Pro
            420                 425                 430

Pro Lys Val Val Val Lys Lys Gly Thr Arg Ile Glu Phe His Pro Val
        435                 440                 445
```

```
Asp Asp Ser Val Thr Arg Pro Val Val Asp Leu Gly Ser Tyr Thr Ala
    450                 455                 460

Leu Phe Asn Cys Val Val Pro Pro Phe Thr Tyr His Gly Phe Glu Leu
465                 470                 475                 480

Asn His Val Tyr Ser Val Lys Pro Gly Asp Tyr Tyr Val Thr Gly Pro
                485                 490                 495

Thr Arg Asp Leu Cys Gln Asn Ala Asp Val Arg Ile His Ile His Val
            500                 505                 510

Glu Asp Glu
        515


<210> SEQ ID NO 40
<211> LENGTH: 322
<212> TYPE: PRT
<213> ORGANISM: MEGATHURA CRENULATA

<400> SEQUENCE: 40

Gly Leu Pro Tyr Trp Asp Trp Thr Glu Pro Met Thr His Ile Pro Gly
1               5                   10                  15

Leu Ala Gly Asn Lys Thr Tyr Val Asp Ser His Gly Ala Ser His Thr
            20                  25                  30

Asn Pro Phe His Ser Ser Val Ile Ala Phe Glu Glu Asn Ala Pro His
        35                  40                  45

Thr Lys Arg Gln Ile Asp Gln Arg Leu Phe Lys Pro Ala Thr Phe Gly
    50                  55                  60

His His Thr Asp Leu Phe Asn Gln Ile Leu Tyr Ala Phe Glu Gln Glu
65                  70                  75                  80

Asp Tyr Cys Asp Phe Glu Val Gln Phe Glu Ile Thr His Asn Thr Ile
                85                  90                  95

His Ala Trp Thr Gly Gly Ser Glu His Phe Ser Met Ser Ser Leu His
            100                 105                 110

Tyr Thr Ala Phe Asp Pro Leu Phe Tyr Phe His His Ser Asn Val Asp
        115                 120                 125

Arg Leu Trp Ala Val Trp Gln Ala Leu Gln Met Arg Arg His Lys Pro
    130                 135                 140

Tyr Arg Ala His Cys Ala Ile Ser Leu Glu His Met His Leu Lys Pro
145                 150                 155                 160

Phe Ala Phe Ser Ser Pro Leu Asn Asn Asn Glu Lys Thr His Ala Asn
                165                 170                 175

Ala Met Pro Asn Lys Ile Tyr Asp Tyr Glu Asn Val Leu His Tyr Thr
            180                 185                 190

Tyr Glu Asp Leu Thr Phe Gly Gly Ile Ser Leu Glu Asn Ile Glu Lys
        195                 200                 205

Met Ile His Glu Asn Gln Gln Glu Asp Arg Ile Tyr Ala Gly Phe Leu
    210                 215                 220

Leu Ala Gly Ile Arg Thr Ser Ala Asn Val Asp Ile Phe Ile Lys Thr
225                 230                 235                 240

Thr Asp Ser Val Gln His Lys Ala Gly Thr Phe Ala Val Leu Gly Gly
                245                 250                 255

Ser Lys Glu Met Lys Trp Gly Phe Asp Arg Val Phe Lys Phe Asp Ile
            260                 265                 270

Thr His Val Leu Lys Asp Leu Asp Leu Thr Ala Asp Gly Asp Phe Glu
        275                 280                 285

Val Thr Val Asp Ile Thr Glu Val Asp Gly Thr Lys Leu Ala Ser Ser
```

```
    290                 295                 300

Leu Ile Pro His Ala Ser Val Ile Arg Glu His Ala Arg Gly Lys Leu
305                 310                 315                 320

Asn Arg


<210> SEQ ID NO 41
<211> LENGTH: 414
<212> TYPE: PRT
<213> ORGANISM: MEGATHURA CRENULATA

<400> SEQUENCE: 41

Val Lys Phe Asp Lys Val Pro Arg Ser Arg Leu Ile Arg Lys Asn Val
1               5                   10                  15

Asp Arg Leu Ser Pro Glu Glu Met Asn Glu Leu Arg Lys Ala Leu Ala
            20                  25                  30

Leu Leu Lys Glu Asp Lys Ser Ala Gly Gly Phe Gln Gln Leu Gly Ala
        35                  40                  45

Phe His Gly Glu Pro Lys Trp Cys Pro Ser Pro Glu Ala Ser Lys Lys
    50                  55                  60

Phe Ala Cys Cys Val His Gly Met Ser Val Phe Pro His Trp His Arg
65                  70                  75                  80

Leu Leu Thr Val Gln Ser Glu Asn Ala Leu Arg Arg His Gly Tyr Asp
                85                  90                  95

Gly Ala Leu Pro Tyr Trp Asp Trp Thr Ser Pro Leu Asn His Leu Pro
            100                 105                 110

Glu Leu Ala Asp His Glu Lys Tyr Val Asp Pro Glu Asp Gly Val Glu
        115                 120                 125

Lys His Asn Pro Trp Phe Asp Gly His Ile Asp Thr Val Asp Lys Thr
    130                 135                 140

Thr Thr Arg Ser Val Gln Asn Lys Leu Phe Glu Gln Pro Glu Phe Gly
145                 150                 155                 160

His Tyr Thr Ser Ile Ala Lys Gln Val Leu Leu Ala Leu Glu Gln Asp
                165                 170                 175

Asn Phe Cys Asp Phe Glu Ile Gln Tyr Glu Ile Ala His Asn Tyr Ile
            180                 185                 190

His Ala Leu Val Gly Gly Ala Gln Pro Tyr Gly Met Ala Ser Leu Arg
        195                 200                 205

Tyr Thr Ala Phe Asp Pro Leu Phe Tyr Leu His His Ser Asn Thr Asp
    210                 215                 220

Arg Ile Trp Ala Ile Trp Gln Ala Leu Gln Lys Tyr Arg Gly Lys Pro
225                 230                 235                 240

Tyr Asn Val Ala Asn Cys Ala Val Thr Ser Met Arg Glu Pro Leu Gln
                245                 250                 255

Pro Phe Gly Leu Ser Ala Asn Ile Asn Thr Asp His Val Thr Lys Glu
            260                 265                 270

His Ser Val Pro Phe Asn Val Phe Asp Tyr Lys Thr Asn Phe Asn Tyr
        275                 280                 285

Glu Tyr Asp Thr Leu Glu Phe Asn Gly Leu Ser Ile Ser Gln Leu Asn
    290                 295                 300

Lys Lys Leu Glu Ala Ile Lys Ser Gln Asp Arg Phe Phe Ala Gly Phe
305                 310                 315                 320

Leu Leu Ser Gly Phe Lys Lys Ser Ser Leu Val Lys Phe Asn Ile Cys
                325                 330                 335

Thr Asp Ser Ser Asn Cys His Pro Ala Gly Glu Phe Tyr Leu Leu Gly
```

-continued

```
            340                 345                 350

Asp Glu Asn Glu Met Pro Trp Ala Tyr Asp Arg Val Phe Lys Tyr Asp
        355                 360                 365

Ile Thr Glu Lys Leu His Asp Leu Lys Leu His Ala Glu Asp His Phe
    370                 375                 380

Tyr Ile Asp Tyr Glu Val Phe Asp Leu Lys Pro Ala Ser Leu Gly Lys
385                 390                 395                 400

Asp Leu Phe Lys Gln Pro Ser Val Ile His Glu Pro Arg Ile
                405                 410


<210> SEQ ID NO 42
<211> LENGTH: 411
<212> TYPE: PRT
<213> ORGANISM: MEGATHURA CRENULATA

<400> SEQUENCE: 42

Gly His His Glu Gly Glu Val Tyr Gln Ala Glu Val Thr Ser Ala Asn
1               5                   10                  15

Arg Ile Arg Lys Asn Ile Glu Asn Leu Ser Leu Gly Glu Leu Glu Ser
            20                  25                  30

Leu Arg Ala Ala Phe Leu Glu Ile Glu Asn Asp Gly Thr Tyr Glu Ser
        35                  40                  45

Ile Ala Lys Phe His Gly Ser Pro Gly Leu Cys Gln Leu Asn Gly Asn
    50                  55                  60

Pro Ile Ser Cys Cys Val His Gly Met Pro Thr Phe Pro His Trp His
65                  70                  75                  80

Arg Leu Tyr Val Val Val Val Glu Asn Ala Leu Leu Lys Lys Gly Ser
                85                  90                  95

Ser Val Ala Val Pro Tyr Trp Asp Trp Thr Lys Arg Ile Glu His Leu
            100                 105                 110

Pro His Leu Ile Ser Asp Ala Thr Tyr Tyr Asn Ser Arg Gln His His
        115                 120                 125

Tyr Glu Thr Asn Pro Phe His His Gly Lys Ile Thr His Glu Asn Glu
    130                 135                 140

Ile Thr Thr Arg Asp Pro Lys Asp Ser Leu Phe His Ser Asp Tyr Phe
145                 150                 155                 160

Tyr Glu Gln Val Leu Tyr Ala Leu Glu Gln Asp Asn Phe Cys Asp Phe
                165                 170                 175

Glu Ile Gln Leu Glu Ile Leu His Asn Ala Leu His Ser Leu Leu Gly
            180                 185                 190

Gly Lys Gly Lys Tyr Ser Met Ser Asn Leu Asp Tyr Ala Ala Phe Asp
        195                 200                 205

Pro Val Phe Phe Leu His His Ala Thr Thr Asp Arg Ile Trp Ala Ile
    210                 215                 220

Trp Gln Asp Leu Gln Arg Phe Arg Lys Arg Pro Tyr Arg Glu Ala Asn
225                 230                 235                 240

Cys Ala Ile Gln Leu Met His Thr Pro Leu Gln Pro Phe Asp Lys Ser
                245                 250                 255

Asp Asn Asn Asp Glu Ala Thr Lys Thr His Ala Thr Pro His Asp Gly
            260                 265                 270

Phe Glu Tyr Gln Asn Ser Phe Gly Tyr Ala Tyr Asp Asn Leu Glu Leu
        275                 280                 285

Asn His Tyr Ser Ile Pro Gln Leu Asp His Met Leu Gln Glu Arg Lys
    290                 295                 300
```

-continued

```
Arg His Asp Arg Val Phe Ala Gly Phe Leu Leu His Asn Ile Gly Thr
305                 310                 315                 320

Ser Ala Asp Gly His Val Phe Val Cys Leu Pro Thr Gly Glu His Thr
                325                 330                 335

Lys Asp Cys Ser His Glu Ala Gly Met Phe Ser Ile Leu Gly Gly Gln
            340                 345                 350

Thr Glu Met Ser Phe Val Phe Asp Arg Leu Tyr Lys Leu Asp Ile Thr
        355                 360                 365

Lys Ala Leu Lys Lys Asn Gly Val His Leu Gln Gly Asp Phe Asp Leu
    370                 375                 380

Glu Ile Glu Ile Thr Ala Val Asn Gly Ser His Leu Asp Ser His Val
385                 390                 395                 400

Ile His Ser Pro Thr Ile Leu Phe Glu Ala Gly
                405                 410


<210> SEQ ID NO 43
<211> LENGTH: 111
<212> TYPE: PRT
<213> ORGANISM: MEGATHURA CRENULATA

<400> SEQUENCE: 43

Asp Ser Ala His Thr Asp Asp Gly His Thr Glu Pro Val Met Ile Arg
1               5                   10                  15

Lys Asp Ile Thr Gln Leu Asp Lys Arg Gln Gln Leu Ser Leu Val Lys
            20                  25                  30

Ala Leu Glu Ser Met Lys Ala Asp His Ser Ser Asp Gly Phe Gln Ala
        35                  40                  45

Ile Ala Ser Phe His Ala Leu Pro Pro Leu Cys Pro Ser Pro Ala Ala
    50                  55                  60

Ser Lys Arg Phe Ala Cys Cys Val His Gly Met Pro Thr Phe Pro Gln
65                  70                  75                  80

Trp His Arg Leu Tyr Thr Val Gln Phe Gln Asp Ser Leu Arg Lys His
                85                  90                  95

Gly Ala Val Val Gly Leu Pro Tyr Trp Asp Trp Thr Leu Pro Arg
            100                 105                 110


<210> SEQ ID NO 44
<211> LENGTH: 317
<212> TYPE: PRT
<213> ORGANISM: MEGATHURA CRENULATA

<400> SEQUENCE: 44

Gly Leu Pro Tyr Trp Asp Trp Thr Met Pro Met Ser His Leu Pro Glu
1               5                   10                  15

Leu Ala Thr Ser Glu Thr Tyr Leu Asp Pro Val Thr Gly Glu Thr Lys
            20                  25                  30

Asn Asn Pro Phe His His Ala Gln Val Ala Phe Glu Asn Gly Val Thr
        35                  40                  45

Ser Arg Asn Pro Asp Ala Lys Leu Phe Met Lys Pro Thr Tyr Gly Asp
    50                  55                  60

His Thr Tyr Leu Phe Asp Ser Met Ile Tyr Ala Phe Glu Gln Glu Asp
65                  70                  75                  80

Phe Cys Asp Phe Glu Val Gln Tyr Glu Leu Thr His Asn Ala Ile His
                85                  90                  95

Ala Trp Val Gly Gly Ser Glu Lys Tyr Ser Met Ser Ser Leu His Tyr
            100                 105                 110
```

-continued

Thr Ala Phe Asp Pro Ile Phe Tyr Leu His His Ser Asn Val Asp Arg
115 120 125

Leu Trp Ala Ile Trp Gln Ala Leu Gln Ile Arg Arg Gly Lys Ser Tyr
130 135 140

Lys Ala His Cys Ala Ser Ser Gln Glu Arg Glu Pro Leu Lys Pro Phe
145 150 155 160

Ala Phe Ser Ser Pro Leu Asn Asn Asn Glu Lys Thr Tyr His Asn Ser
165 170 175

Val Pro Thr Asn Val Tyr Asp Tyr Val Gly Val Leu His Tyr Arg Tyr
180 185 190

Asp Asp Leu Gln Phe Gly Gly Met Thr Met Ser Glu Leu Glu Glu Tyr
195 200 205

Ile His Lys Gln Thr Gln His Asp Arg Thr Phe Ala Gly Phe Phe Leu
210 215 220

Ser Tyr Ile Gly Thr Ser Ala Ser Val Asp Ile Phe Ile Asn Arg Glu
225 230 235 240

Gly His Asp Lys Tyr Lys Val Gly Ser Phe Val Val Leu Gly Gly Ser
245 250 255

Lys Glu Met Lys Trp Gly Phe Asp Arg Met Tyr Lys Tyr Glu Ile Thr
260 265 270

Glu Ala Leu Lys Thr Leu Asn Val Ala Val Asp Asp Gly Phe Ser Ile
275 280 285

Thr Val Glu Ile Thr Asp Val Asp Gly Ser Pro Pro Ser Ala Asp Leu
290 295 300

Ile Pro Pro Pro Ala Ile Ile Phe Glu Arg Gly His Ala
305 310 315

<210> SEQ ID NO 45
<211> LENGTH: 411
<212> TYPE: PRT
<213> ORGANISM: MEGATHURA CRENULATA

<400> SEQUENCE: 45

Asp Ala Lys Asp Phe Gly His Ser Arg Lys Ile Arg Lys Ala Val Asp
1 5 10 15

Ser Leu Thr Val Glu Glu Gln Thr Ser Leu Arg Arg Ala Met Ala Asp
20 25 30

Leu Gln Asp Asp Lys Thr Ser Gly Gly Phe Gln Gln Ile Ala Ala Phe
35 40 45

His Gly Glu Pro Lys Trp Cys Pro Ser Pro Glu Ala Glu Lys Lys Phe
50 55 60

Ala Cys Cys Val His Gly Met Ala Val Phe Pro His Trp His Arg Leu
65 70 75 80

Leu Thr Val Gln Gly Glu Asn Ala Leu Arg Lys His Gly Phe Thr Gly
85 90 95

Gly Leu Pro Tyr Trp Asp Trp Thr Arg Ser Met Ser Ala Leu Pro His
100 105 110

Phe Val Ala Asp Pro Thr Tyr Asn Asp Ala Ile Ser Ser Gln Glu Glu
115 120 125

Asp Asn Pro Trp His His Gly His Ile Asp Ser Val Gly His Asp Thr
130 135 140

Thr Arg Asp Val Arg Asp Asp Leu Tyr Gln Ser Pro Gly Phe Gly His
145 150 155 160

Tyr Thr Asp Ile Ala Gln Gln Val Leu Leu Ala Phe Glu Gln Asp Ser
165 170 175

```
Phe Cys Asp Phe Glu Val Gln Phe Glu Ile Ala His Asn Phe Ile His
            180                 185                 190

Ala Leu Ile Gly Gly Asn Glu Pro Tyr Ser Met Ser Ser Leu Arg Tyr
        195                 200                 205

Thr Thr Tyr Asp Pro Ile Phe Phe Leu His His Ser Ser Thr Asp Arg
    210                 215                 220

Leu Trp Ala Ile Trp Gln Ala Leu Gln Lys Tyr Arg Gly Lys Pro Tyr
225                 230                 235                 240

Asn Thr Ala Asn Cys Ala Ile Ala Ser Met Arg Lys Pro Leu Gln Pro
                245                 250                 255

Phe Gly Leu Asp Ser Val Ile Asn Pro Asp Asp Glu Thr Arg Glu His
            260                 265                 270

Ser Val Pro Phe Arg Val Phe Asp Tyr Lys Asn Asn Phe Asp Tyr Glu
        275                 280                 285

Tyr Glu Ser Leu Ala Phe Asn Gly Leu Ser Ile Ala Gln Leu Asp Arg
    290                 295                 300

Glu Leu Gln Arg Arg Lys Ser His Asp Arg Val Phe Ala Gly Phe Leu
305                 310                 315                 320

Leu His Glu Ile Gly Gln Ser Ala Lys His Asn Val Ser Asp Cys Asp
                325                 330                 335

His Tyr Ala Gly Glu Phe Tyr Ile Leu Gly Asp Glu Ala Glu Met Pro
            340                 345                 350

Trp Arg Tyr Asp Arg Val Tyr Lys Tyr Glu Ile Thr Gln Gln Leu His
        355                 360                 365

Asp Leu Asp Leu His Val Gly Asp Asn Phe Phe Leu Lys Tyr Glu Ala
    370                 375                 380

Phe Asp Leu Asn Gly Gly Ser Leu Gly Gly Ser Ile Phe Ser Gln Pro
385                 390                 395                 400

Ser Val Ile Phe Glu Pro Ala Ala Gly Met Phe
                405                 410


<210> SEQ ID NO 46
<211> LENGTH: 109
<212> TYPE: PRT
<213> ORGANISM: MEGATHURA CRENULATA

<400> SEQUENCE: 46

Gly Ser His Gln Ala Asp Glu Tyr Arg Glu Ala Val Thr Ser Ala Ser
1               5                   10                  15

His Ile Arg Lys Asn Ile Arg Asp Leu Ser Glu Gly Glu Ile Glu Ser
            20                  25                  30

Ile Arg Ser Ala Phe Leu Gln Ile Gln Lys Glu Gly Ile Tyr Glu Asn
        35                  40                  45

Ile Ala Lys Phe His Gly Lys Pro Gly Leu Cys Glu His Asp Gly His
    50                  55                  60

Pro Val Ala Cys Cys Val His Gly Met Pro Thr Phe Pro His Trp His
65                  70                  75                  80

Arg Leu Tyr Val Leu Gln Val Glu Asn Ala Leu Leu Glu Arg Gly Ser
                85                  90                  95

Ala Val Ala Val Pro Tyr Trp Asp Trp Thr Leu Pro Arg
            100                 105


<210> SEQ ID NO 47
<211> LENGTH: 329
<212> TYPE: PRT
```

-continued

<213> ORGANISM: MEGATHURA CRENULATA

<400> SEQUENCE: 47

```
Met Ala Val Phe Pro His Trp His Arg Leu Phe Val Lys Gln Met Glu
1               5                   10                  15

Asp Ala Leu Ala Ala His Gly Ala His Ile Gly Ile Pro Tyr Trp Asp
            20                  25                  30

Trp Thr Ser Ala Phe Ser His Leu Pro Ala Leu Val Thr Asp His Glu
        35                  40                  45

Asn Asn Pro Phe His His Gly His Ile Gly His Leu Asn Val Asp Thr
    50                  55                  60

Ser Arg Ser Pro Arg Asp Met Leu Phe Asn Asp Pro Glu Gln Gly Ser
65                  70                  75                  80

Glu Ser Phe Phe Tyr Arg Gln Val Leu Leu Thr Leu Glu Gln Thr Asp
                85                  90                  95

Phe Cys Gln Phe Glu Val Gln Phe Glu Leu Thr His Asn Ala Ile His
            100                 105                 110

Ser Trp Thr Gly Gly His Thr Pro Tyr Gly Met Ser Ser Leu Glu Tyr
        115                 120                 125

Thr Ala Tyr Asp Pro Leu Phe Tyr Leu His His Ser Asn Thr Asp Arg
    130                 135                 140

Ile Trp Ala Ile Trp Gln Ala Leu Gln Lys Tyr Arg Gly Leu Pro Tyr
145                 150                 155                 160

Asn Ala Ala His Cys Asp Ile Gln Val Leu Lys Gln Pro Leu Lys Pro
                165                 170                 175

Phe Ser Glu Ser Arg Asn Pro Asn Pro Val Thr Arg Ala Asn Ser Arg
            180                 185                 190

Ala Val Asp Ser Phe Asp Tyr Glu Lys Phe Asn Tyr Gln Tyr Asp Thr
        195                 200                 205

Leu Thr Phe His Gly Leu Ser Ile Pro Glu Leu Asp Ala Met Leu Gln
    210                 215                 220

Glu Arg Lys Lys Glu Glu Arg Thr Phe Ala Ala Phe Leu Leu His Gly
225                 230                 235                 240

Phe Gly Ala Ser Ala Asp Val Ser Phe Asp Val Cys Thr Pro Asp Gly
                245                 250                 255

His Cys Ala Phe Ala Gly Thr Phe Ala Val Leu Gly Gly Glu Leu Glu
            260                 265                 270

Met Pro Trp Ser Phe Glu Arg Leu Phe Arg Tyr Asp Ile Thr Lys Val
        275                 280                 285

Leu Lys Gln Met Asn Leu His Tyr Asp Ser Glu Phe His Phe Glu Leu
    290                 295                 300

Lys Ile Val Gly Thr Asp Gly Thr Glu Leu Pro Ser Asp Arg Ile Lys
305                 310                 315                 320

Ser Pro Thr Ile Glu His His Gly Gly
                325
```

<210> SEQ ID NO 48
<211> LENGTH: 103
<212> TYPE: PRT
<213> ORGANISM: MEGATHURA CRENULATA

<400> SEQUENCE: 48

```
Gly His Asp His Ser Glu Arg His Asp Gly Phe Phe Arg Lys Glu Val
1               5                   10                  15

Gly Ser Leu Ser Leu Asp Glu Ala Asn Asp Leu Lys Asn Ala Leu Tyr
```

-continued

```
            20                  25                  30

Lys Leu Gln Asn Asp Gln Gly Pro Asn Gly Tyr Glu Ser Ile Ala Gly
        35                  40                  45

Tyr His Gly Tyr Pro Phe Leu Cys Pro Glu His Gly Glu Asp Gln Tyr
    50                  55                  60

Ala Cys Cys Val His Gly Met Pro Val Phe Pro His Trp His Arg Leu
65                  70                  75                  80

His Thr Ile Gln Phe Glu Arg Ala Leu Lys Glu His Gly Ser His Leu
                85                  90                  95

Gly Leu Pro Tyr Trp Asp Trp
            100
```

<210> SEQ ID NO 49
<211> LENGTH: 1269
<212> TYPE: DNA
<213> ORGANISM: HALIOTIS TUBERCULATA

<400> SEQUENCE: 49

```
ggcttgttca gtttctactc gtcgcccttg tggtgggggc tggagcagac aacgtcgtca     60

gaaaggacgt gagtcacctc acggatgacg aggtgcaagc tctccacggc gccctccatg    120

acgtcactgc atctacaggg cctctgagtt tcgaagacat aacatcttac catgccgcac    180

cagcgtcgtg tgactacaag ggacggaaga tcgcctgctg tgtccacggt atgcccagtt    240

tccccttctg gcacagggca tatgtcgtcc aagccgagcg ggcactgttg tccaaacgga    300

agactgtcgg aatgccttac tgggactgga cgcaaacgct gactcactta ccatctcttg    360

tgactgaacc catctacatt gacagtaaag gtggaaaggc tcaaaccaac tactggtacc    420

gcggcgagat agcgttcatc aataagaaga ctgcgcgagc tgtagatgat cgcctattcg    480

agaaggtgga gcctggtcac tacacacatc ttatggagac tgtcctcgac gctctcgaac    540

aggacgaatt ctgtaaattt gaaatccagt tcgagttggc tcataatgct atccattact    600

tggttggcgg taaatttgaa tattcaatgt caaacttgga atacacctcc tacgacccca    660

tcttcttcct ccaccactcc aacgttgacc gcctcttcgc catctggcag cgtcttcagg    720

aactgcgagg aaagaatccc aatgcaatgg actgtgcaca tgaactcgct caccagcaac    780

tccaaccctt caacagggac agcaatccag tccagctcac aaaggaccac tcgacacctg    840

ctgacctctt tgattacaaa caacttggat acagctacga cagcttaaac ctgaatggaa    900

tgacgccaga acagctgaaa acagaactag acgaacgcca ctccaaagaa cgtgcgtttg    960

caagcttccg actcagtggc tttggggggtt ctgccaacgt tgttgtctat gcatgtgtcc   1020

ctgatgatga tccacgcagt gatgactact gcgagaaagc aggcgacttc ttcattcttg   1080

ggggtcaaag cgaaatgccg tggagattct acagaccctt cttctatgat gtaactgaag   1140

cggtacatca ccttggagtc ccgctaagtg gccactacta tgtgaaaaca gaactcttca   1200

gcgtgaatgg cacagcactt tcacctgatc ttcttcctca accaactgtt gcctaccgac   1260

ctgggaaag                                                            1269
```

<210> SEQ ID NO 50
<211> LENGTH: 569
<212> TYPE: DNA
<213> ORGANISM: HALIOTIS TUBERCULATA

<400> SEQUENCE: 50

```
ggtcttccgt actgggactg gacgcagcat ctgactcaac tcccagatct ggtgtcagac     60
```

-continued

```
cccttgtttg tcgacccgga aggaggaaag gcccatgaca acgcatggta tcgtggaaac    120

atcaagtttg agaataagaa gactgcaaga gctgttgacg atcgcctttt cgagaaggtt    180

ggaccaggag agaatacccg actctttgaa ggaattctcg atgctcttga acaggatgaa    240

ttctgcaact tcgagatcca gtttgagttg gctcacaacg ctatccacta cctggttggc    300

ggccgtcaca cgtactccat gtctcatctc gagttacacc ctcctacgac cccctcttct    360

tcctccatca ctccaacacc ggaccgcatc ttcgccatct gggaacgtct tcaggtactc    420

agaggaaagg accccaacac cgccgactgc gcacacaacc tcatccatga gcccatggaa    480

ccgttccgtc gggactcgaa ccctcttgac ctcaccaggg aaaactccaa accaattgac    540

agctttgatt atgcccacct tggctacca                                      569
```

<210> SEQ ID NO 51
<211> LENGTH: 1246
<212> TYPE: DNA
<213> ORGANISM: HALIOTIS TUBERCULATA

<400> SEQUENCE: 51

```
gttacagagg ccccagctcc ctcctcggat gctcacctcg ccgtcaggaa ggatatcaac     60

catctgacac gcgaggaggt gtacgagctg cgcagagcta tggagagatt ccaggccgac    120

acatccgttg atgggtacca ggctacggtt gagtatcacg gcttacctgc tcgatgtcca    180

ttccccgagg ccacaaatag gttcgcctgt tgcatccacg gcatggcgac attccctcat    240

tggcacagac tgttcgtcac ccaggtggaa gatgctctga tcaggcgagg atcgcctata    300

ggggtcccct actgggactg gactcagcct atggcgcatc tcccaggact tgcagacaac    360

gccacctata gagatcccat cagcggggac agcagacaca acccccttcca cgatgttgaa    420

gttgcctttg aaaatggacg tacagaacgt cacccagata gtagattgtt tgaacaacct    480

ttatttggca aacatacgcg tctcttcgac agtatagtct atgcttttga gcaggaggac    540

ttctgcgatt ttgaagttca atttgagatg acccataata atattcacgc ctggattggt    600

ggcggcgaga agtattccat gtcttctcta cactacacag ccttcgaccc tatcttctac    660

cttcgtcact ccaacactga ccggctctgg gcaatttggc aagcgttgca gatacgaaga    720

aacaggcctt acaaggctca ttgtgcttgg tctgaggaac gccagcctct caaacctttc    780

gccttcagtt ccccactgaa caacaacgaa aaaacctacg aaaactcggt gcccaccaac    840

gtttacgact acgaaggagt ccttggctat acttatgatg acctcaactt cgggggcatg    900

gacctgggtc agcttgagga atacatccag aggcagagac agagagacag gacctttgct    960

ggtttctttc tgtcacatat tggtacatca gcgaatgttg aaatcattat agaccatggg   1020

actcttcata cctccgtggg cacgtttgct gttcttggcg gagagaagga gatgaaatgg   1080

ggatttgacc gtttgtacaa atatgagatt acagatgaac tgaggcaact taatctccgt   1140

gctgatgatg ttttcagcat ctctgttaaa gtaactgatg ttgatggcag tgagctgtcc   1200

tctgaactca tcccatctgc tgctatcatc ttcgaacgaa gccata                  1246
```

<210> SEQ ID NO 52
<211> LENGTH: 1242
<212> TYPE: DNA
<213> ORGANISM: HALIOTIS TUBERCULATA

<400> SEQUENCE: 52

```
gtcaccatca ggctgacgag tacgacgaag ttgtaactgc tgcaagccac atcagaaaga     60

atttaaaaga tctgtcaaag ggagaagtag agagcctaag gtctgccttc ctgcaacttc    120
```

```
agaacgacgg agtctatgag aatattgcca agttccacgg caagcctggg ttgtgtgatg    180
ataacggtcg caaggttgcc tgttgtgtcc atggaatgcc caccttcccc cagtggcaca    240
ggctctatgt cctccaggtg gagaatgctt tgctggagag aggatctgcc gtctctgtgc    300
catactggga ctggactgaa acatttacag agctgccatc tttgattgct gaggctacct    360
atttcaattc ccgtcaacaa acgtttgacc ctaatccttt cttcagaggt aaaatcagtt    420
ttgagaatgc tgttacaaca cgtgatcccc agcctgagct gtacgttaac aggtactact    480
accaaaacgt catgttggtt tttgaacagg acaactactg cgacttcgag atacagtttg    540
agatggttca caatgttctc catgcttggc ttggtggaag agctacttat tctatttctt    600
ctcttgatta ttctgcattc gaccctgtgt ttttccttca ccatgcgaac acagatagat    660
tgtgggccat ctggcaggag ctgcagaggt acaggaagaa gccatacaat gaagcggatt    720
gtgccattaa cctaatgcgc aaacctctac atcccttcga caacagtgat ctcaatcatg    780
atcctgtaac ctttaaatac tcaaaaccca ctgatggctt tgactaccag aacaactttg    840
gatacaagta tgacaacctt gagttcaatc atttcagtat tcccaggctt gaagaaatca    900
ttcgtattag acaacgtcaa gatcgtgtgt ttgcaggatt cctccttcac aacattggga    960
catccgcaac tgttgagata ttcgtctgtg tccctaccac cagcggtgag caaaactgtg   1020
aaaacaaagc cggaacattt gccgtactcg gaggagaaac agagatggcg tttcattttg   1080
acagactcta caggtttgac atcagtgaaa cactgaggga cctcggcata cagctggaca   1140
gccatgactt tgacctcagc atcaagattc aaggagtaaa tggatcctac cttgatccac   1200
acatcctgcc agagccatcc ttgatttttg tgcctggttc aa                      1242
```

<210> SEQ ID NO 53
<211> LENGTH: 1257
<212> TYPE: DNA
<213> ORGANISM: HALIOTIS TUBERCULATA

<400> SEQUENCE: 53

```
gttctttcct gcgtcctgat gggcattcag atgacatcct tgtgagaaaa gaagtgaaca     60
gcctgacaac cagggagact gcatctctga tccatgctct gaaaagtatg caggaagacc    120
attcacctga cgggttccaa gccattgcct ctttccatgc tctgccacca ctctgccctt    180
caccatctgc agctcaccgt tatgcttgct gtgtccacgg catggctaca tttccccagt    240
ggcacagatt gtacactgta cagttccagg atgcactgag gagacatgga gctacggtag    300
gtgtaccgta ttgggattgg ctgcgaccgc agtctcacct accagagctt gtcaccatgg    360
agacatacca tgatatttgg agtaacagag atttccccaa tcctttctac caagccaata    420
ttgagtttga aggagaaaac attacaacag agagagaagt cattgcagac aaactttttg    480
tcaaaggtgg acacgttttt gataaactgg ttcttcaaac aagccatcct agcgctgagc    540
aggaaaacta ctgtgacttt gagattcagt ttgaaattct tcacaacggc gttcacacgt    600
gggtcggagg cagtcgtacc tactctatcg gacatcttca ttacgcattc tacgaccctc    660
ttttctacct tcaccatttc cagacagacc gtatttgggc aatctggcaa gaactccagg    720
aacagagagg gctctcgggt gatgaggctc actgtgctct cgagcaaatg agagaaccat    780
tgaagccttt cagcttcggc gctccttata actggaatca gctcacacag gatttctccc    840
gacccgagga caccttcgac tacaggaagt ttggttatga atatgacaat ttagaattcc    900
tgggaatgtc agttgctgaa ctggatcaat acattattga acatcaagaa aatgatagag    960
```

-continued

```
tattcgctgg gttcctgttg agtggattcg gaggttccgc atcagttaat ttccaggttt   1020

gtagagctga ttccacatgt caggatgctg ggtacttcac cgttcttggt ggcagtgctg   1080

agatggcgtg ggcatttgac aggctttaca aatatgacat tactgaaact ctggagaaaa   1140

tgcaccttcg atatgatgat gacttcacaa tctctgtcag tctgaccgcc aacaacggaa   1200

ctgtcctgag cagcagtcta atcccaacac cgagtgtcat attccagcgg ggacatc      1257
```

<210> SEQ ID NO 54
<211> LENGTH: 1257
<212> TYPE: DNA
<213> ORGANISM: MEGATHURA CRENULATA

<400> SEQUENCE: 54

```
attctgccca cacagatgat ggacacactg aaccagtgat gattcgcaaa gatatcacac     60

aattggacaa gcgtcaacaa ctgtcactgg tgaaagccct cgagtccatg aaagccgacc    120

attcatctga tgggttccag gcaatcgctt ccttccatgc tcttcctcct ctttgtccat    180

caccagctgc ttcaaagagg tttgcgtgct gcgtccatgg catggcaacg ttcccacaat    240

ggcaccgtct gtacacagtc caattccaag attctctcag aaaacatggt gcagtcgttg    300

gacttccgta ctgggactgg accctacctc gttctgaatt accagagctc ctgaccgtct    360

caactattca tgacccggag acaggcagag atataccaaa tccatttatt ggttctaaaa    420

tagagtttga aggagaaaac gtacatacta aaagagatat caatagggat cgtctcttcc    480

agggatcaac aaaaacacat cataactggt ttattgagca agcactgctt gctcttgaac    540

aaaccaacta ctgcgacttc gaggttcagt ttgaaattat gcataatggt gttcatacct    600

gggttggagg caaggagccc tatggaattg gccatctgca ttatgcttcc tatgatccac    660

ttttctacat ccatcactcc caaactgatc gtatttgggc tatatggcaa tcgttgcagc    720

gtttcagagg actttctgga tctgaggcta actgtgctgt aaatctcatg aaaactcctc    780

tgaagccttt cagctttgga gcaccatata atcttaatga tcacacgcat gatttctcaa    840

agcctgaaga tacattcgac taccaaaagt ttggatacat atatgacact ctggaatttg    900

cagggtggtc aattcgtggc attgaccata ttgtccgtaa caggcaggaa cattcaaggg    960

tctttgccgg attcttgctt gaaggatttg gcacctctgc cactgtcgat ttccaggtct   1020

gtcgcacagc gggagactgt gaagatgcag ggtacttcac cgtgttggga ggtgaaaaag   1080

aaatgccttg ggcctttgat cggctttaca agtacgacat aacagaaacc ttagacaaga   1140

tgaaccttcg acatgacgaa atcttccaga ttgaagtaac cattacatcc tacgatggaa   1200

ctgtactcga tagtggcctt attcccacac cgtcaatcat ctatgatcct gctcatc      1257
```

<210> SEQ ID NO 55
<211> LENGTH: 1254
<212> TYPE: DNA
<213> ORGANISM: MEGATHURA CRENULATA

<400> SEQUENCE: 55

```
atgatattag ttcgcaccac ctgtcgctca acaaggttcg tcatgatctg agtacactga     60

gtgagcgaga tattggaagc cttaaatatg ctttgagcag cttgcaggca gatacctcag    120

cagatggttt tgctgccatt gcatccttcc atggtctgcc tgccaaatgt aatgacagcc    180

acaataacga ggtggcatgc tgtatccatg gaatgcctac attcccccac tggcacagac    240

tctacaccct ccaatttgag caagctctaa gaagacatgg ctctagtgta gcagtaccct    300

actgggactg gacaaagcca atacataata ttccacatct gttcacagac aaagaatact    360
```

```
acgatgtctg gagaaataaa gtaatgccaa atccatttgc ccgagggtat gtcccctcac    420

acgatacata cacggtaaga gacgtccaag aaggcctgtt ccacctgaca tcaacgggtg    480

aacactcagc gcttctgaat caagctcttt tggcgctgga acagcacgac tactgcgatt    540

ttgcagtcca gtttgaagtc atgcacaaca caatccatta cctagtggga ggacctcaag    600

tctattcttt gtcatccctt cattatgctt catatgatcc gatcttcttc atacaccact    660

cctttgtaga caaggtttgg gctgtctggc aggctcttca agaaaagaga ggccttccat    720

cagaccgtgc tgactgcgct gttagtctga tgactcagaa catgaggcct ttccattacg    780

aaattaacca taaccagttc accaagaaac atgcagttcc aaatgatgtt ttcaagtacg    840

aactcctggg ttacagatac gacaatctgg aaatcggtgg catgaatttg catgaaattg    900

aaaaggaaat caaagacaaa cagcaccatg tgagagtgtt tgcagggttc ctccttcacg    960

gaattagaac ctcagctgat gtccaattcc agatttgtaa aacatcagaa gattgtcacc   1020

atggaggcca aatcttcgtt cttgggggga ctaaagagat ggcctgggct tataaccgtt   1080

tattcaagta cgatattacc catgctcttc atgacgcaca catcactcca gaagacgtat   1140

tccatccctc tgaaccattc ttcatcaagg tgtcagtgac agccgtcaac ggaacagttc   1200

ttccggcttc aatcctgcat gcaccaacca ttatctatga acctggtctc ggtg         1254
```

<210> SEQ ID NO 56
<211> LENGTH: 509
<212> TYPE: DNA
<213> ORGANISM: MEGATHURA CRENULATA

<400> SEQUENCE: 56

```
accatcacga agatcatcat tcttcttcta tggctggaca tggtgtcaga aaggaaatca     60

acacacttac cactgcagag gtggacaatc tcaaagatgc catgagagcc gtcatggcag    120

accacggtcc aaatggatac caggctatag cagcgttcca tggaaaccca ccaatgtgcc    180

ctatgccaga tggaaagaat tactcgtgtt gtacacatgg catggctact ttcccccact    240

ggcacagact gtacacaaaa cagatggaag atgccttgac cgcccatggt gccagagtcg    300

gccttcctta ctgggacggg acaactgcct ttacagcttt gccaactttt gtcacagatg    360

aagaggacaa tcctttccat catggtcaca tagactattt gggagtggat acaactcggt    420

cgccccgaga caagttgttc aatgatccag agcgaggatc agaatcgttc ttctacaggc    480

aggttctctt ggctttggag cagacagat                                      509
```

<210> SEQ ID NO 57
<211> LENGTH: 943
<212> TYPE: DNA
<213> ORGANISM: MEGATHURA CRENULATA

<400> SEQUENCE: 57

```
ggcctgccct actgggattg gaccatgcca atgagtcatt tgccagaact ggctacaagt     60

gagacctacc tcgatccagt tactggggaa actaaaaaca acccttttcca tcacgcccaa   120

gtggcgtttg aaaatggtgt aacaagcagg aatcctgatg ccaaactttt tatgaaacca    180

acttacggag accacactta cctcttcgac agcatgatct acgcatttga gcaggaagac    240

ttctgcgact ttgaagtcca atatgagctc acgcataatg caatacatgc atgggttgga    300

ggcagtgaaa agtattcaat gtcttctctt cactacactg cttttgatcc tatattttac    360

ctccatcact caaatgttga tcgtctctgg gccatttggc aagctcttca aatcaggaga    420
```

-continued

```
ggcaagtctt acaaggccca ctgcgcctcg tctcaagaaa gagaaccatt aaagcctttt    480

gcattcagtt ccccactgaa caacaacgag aaaacgtacc acaactctgt ccccactaac    540

gtttatgact atgtgggagt tttgcactat cgatatgatg accttcagtt tggcggtatg    600

accatgtcag aacttgagga atatattcac aagcagacac aacatgatag aacctttgca    660

ggattcttcc tttcatatat tggaacatca gcaagcgtag atatcttcat caatcgagaa    720

ggtcatgata aatacaaagt gggaagtttt gtagtacttg gtggatccaa agaaatgaaa    780

tggggctttg atagaatgta caagtatgag atcactgagg ctctgaagac gctgaatgtt    840

gcagtggatg atgggttcag cattactgtt gagatcaccg atgttgatgg atctccccca    900

tctgcagatc tcattccacc tcctgctata atctttgaac gtg                      943
```

<210> SEQ ID NO 58
<211> LENGTH: 1248
<212> TYPE: DNA
<213> ORGANISM: MEGATHURA CRENULATA

<400> SEQUENCE: 58

```
ctgatgccaa agactttggc catagcagaa aaatcaggaa agccgttgat tctctgacag     60

tcgaagaaca aacttcgttg aggcgagcta tggcagatct acaggacgac aaaacatcag    120

ggggtttcca gcagattgca gcattccacg gagaaccaaa atggtgtcca agccccgaag    180

cggagaaaaa atttgcatgc tgtgttcatg gaatggctgt tttccctcac tggcacagat    240

tgctgacagt tcaaggagaa aatgctctga ggaaacatgg ctttactggt ggactgccct    300

actgggactg gactcgatca atgagcgccc ttccacattt tgttgctgat cctacttaca    360

atgatgctat ttccagccag gaagaagata acccatggca tcatggtcac atagactctg    420

ttgggcatga tactacaaga gatgtgcgtg atgatcttta tcaatctcct ggtttcggtc    480

actacacaga tattgcaaaa caagtccttc tggcctttga gcaggacgat ttctgtgatt    540

ttgaggtaca atttgaaatt gcccataatt tcatacatgc tctggttggt ggtaacgaac    600

catacagtat gtcatctttg aggtatacta catacgatcc aatcttcttc ttgcaccgct    660

ccaatacaga ccgactttgg gccatttggc aagctttgca aaaataccgg gggaaaccat    720

acaacactgc aaactgtgcc attgcatcca tgagaaaacc acttcagcca tttggtcttg    780

atagtgtcat aaatccagat gacgaaactc gtgaacattc ggttcctttc cgagtcttcg    840

actacaagaa caacttcgac tatgagtatg agagcctggc atttaatggt ctgtctattg    900

cccaactgga ccgagagttg cagagaagaa agtcacatga cagagtcttt gcaggattcc    960

ttcttcatga aattggacag tctgcactcg tgaaattcta cgtttgcaaa cacaatgtat   1020

ctgactgtga ccattatgct ggagaattct acattttggg agatgaagct gagatgcctt   1080

ggaggtatga ccgtgtgtac aagtacgaga taacacagca gctgcacgat ttagatctac   1140

atgttggaga taatttcttc cttaaatatg aagcctttga tctgaatggc ggaagtcttg   1200

gtggaagtat cttttctcag ccttcggtga ttttcgagcc agctgcag                1248
```

<210> SEQ ID NO 59
<211> LENGTH: 1257
<212> TYPE: DNA
<213> ORGANISM: MEGATHRUA CRENULATA

<400> SEQUENCE: 59

```
gttcacacca ggctgatgaa tatcgtgagg cagtaacaag cgctagccac ataagaaaaa     60

atatccggga cctctcagag ggagaaattg agagcatcag atctgctttc ctccaaattc    120
```

```
aaaaagaggg tatatatgaa aacattgcaa agttccatgg aaaaccagga ctttgtgaac    180
atgatggaca tcctgttgct tgttgtgtcc atggcatgcc cacctttccc cactggcaca    240
gactgtacgt tcttcaggtg gagaatgcgc tcttagaacg agggtctgca gttgctgttc    300
cttactggga ctggaccgag aaagctgact ctctgccatc attaatcaat gatgcaactt    360
atttcaattc acgatcccag acctttgatc ctaatccttt cttcagggga catattgcct    420
tcgagaatgc tgtgacgtcc agagatcctc agccagaact atgggacaat aaggacttct    480
acgagaatgt catgctggct cttgagcaag acaacttctg tgactttgag attcagcttg    540
agctgataca caacgccctt cattctagac ttggaggaag ggctaaatac tccctttcgt    600
ctcttgatta taccgcattt gatcctgtat ttttccttca ccatgcaaac gttgacagaa    660
tctgggccat ctggcaggac ttgcagagat atagaaagaa accatacaat gaggctgact    720
gcgcagtcaa cgagatgcgt aaacctcttc aaccatttaa taacccagaa cttaacagtg    780
attccatgac gcttaaacac aacctcccac aagacagttt tgattatcaa aaccgcttca    840
ggtaccaata tgataacctt caatttaacc acttcagcat acaaaagcta gaccaaacta    900
ttcaggctag aaaacaacac gacagagttt ttgctggctt tattcttcac aacattggga    960
catctgctgt tgtagatatt tatatttgcg ttgaacaagg aggagaacaa aactgcaaga   1020
caaaggcggg ttccttcacg attctggggg gagaaacaga aatgccattc cactttgacc   1080
gcttgtacaa atttgacata acgtctgctc tgcataaact tggtgttccc ttggacggac   1140
atggattcga catcaaagtt gacgtcagag ctgtcaatgg atcgcatctt gatcaacaca   1200
tcctcaacga accgagtctg ctttttgttc ctggtgaacg taagaatata tattatg      1257
```

<210> SEQ ID NO 60
<211> LENGTH: 1239
<212> TYPE: DNA
<213> ORGANISM: MEGATHURA CRENULATA

<400> SEQUENCE: 60

```
atgggctttc acaacataat cttgtgcgaa aagaagtaag ctctcttaca acactggaga     60
aacatttttt gaggaaagct ctcaagaaca tgcaagcaga tgattctcca gacggatatc    120
aagctattgc ttctttccac gctttgcctc ctctttgtcc aagtccatct gctgcacata    180
gacacgcttg ttgcctccat ggtatggcta ccttccctca gtggcacaga ctctacacag    240
ttcagttcga agattctttg aaacgacatg gttctattgt cggacttcca tattgggatt    300
ggctgaaacc gcagtctgca ctccctgatt tggtgacaca ggagacatac gagcacctgt    360
tttcacacaa aaccttccca aatccgttcc tcaaggcaaa tatagaattt gagggagagg    420
gagtaacaac agagagggat gttgatgctg aacacctctt tgcaaaagga aatctggttt    480
acaacaactg gttttgcaat caggcactat atgcactaga acaagaaaat tactgtgact    540
ttgaaataca gttcgaaatt ttgcataatg gaattcattc atgggttgga ggatcaaaga    600
cccattcaat aggtcatctt cattacgcat catacgatcc actgttctat atccaccatt    660
cgcagacaga tcgcatttgg gctatctggc aagctctcca ggagcacaga ggtctttcag    720
ggaaggaagc acactgcgcc ctggagcaaa tgaaagaccc tctcaaacct ttcagctttg    780
gaagtcccta taatttgaac aaacgcactc aagagttctc caagcctgaa gacacatttg    840
attatcaccg attcgggtat gagtatgatt ccctcgaatt tgttggcatg tctgtttcaa    900
gtttacataa ctatataaaa caacaacagg aagctgatag agtcttcgca ggattccttc    960
```

-continued

```
ttaaaggatt tggacaatca gcatccgtat cgtttgatat ctgcagacca gaccagagtt   1020

gccaagaagc tggatacttc tcagttctcg gtggaagttc agaaatgccg tggcagtttg   1080

acaggcttta caagtacgac attacaaaaa cgttgaaaga catgaaactg cgatacgatg   1140

acacatttac catcaaggtt cacataaagg atatagctgg agctgagttg gacagcgatc   1200

tgattccaac tccttctgtt ctccttgaag aaggaaagc                          1239
```

<210> SEQ ID NO 61
<211> LENGTH: 1251
<212> TYPE: DNA
<213> ORGANISM: HALIOTIS TUBERCULATA

<400> SEQUENCE: 61

```
atgggatcaa tgtacgtcac gttggtcgta atcggattcg tatggaacta tctgaactca     60

ccgagagaga tctcgccagc ctgaaatctg caatgaggtc tctacaagct gacgatgggg    120

tgaacggtta tcaagccatt gcatcattcc acggtctccc ggcttcttgt catgatgatg    180

agggacatga gattgcctgt tgtatccacg gaatgccagt attcccacac tggcacaggc    240

tttacaccct gcaaatggac atggctctgt tatctcacgg atctgctgtt gctattccat    300

actgggactg gaccaaacct atcagcaaac tgcctgatct cttcaccagc cctgaatatt    360

acgatccttg gagggatgca gttgtcaata atccatttgc taaaggctac attaaatccg    420

aggacgctta cacggttagg gatcctcagg acattttgta ccacttgcag gacgaaacgg    480

gaacatctgt tttgttagat caaactcttt tagccttaga gcagacagat ttctgtgatt    540

ttgaggttca atttgaggtc gtccataatg ctattcacta cttggtgggt ggtcgacaag    600

tttatgctct ttcttctcaa cactatgctt catatgaccc agccttcttt attcatcact    660

cctttgttga caaaatatgg gcagtctggc aagctctgca aaagaagaga aagcgtccct    720

atcataaagc ggattgtgct cttaacatga tgaccaaacc aatgcgacca tttgcacacg    780

atttcaatca caatggattc acaaaaaatgc acgcagtccc caacactcta tttgactttc    840

aggacctttt ctacacgtat gacaacttag aaattgctgg catgaatgtt aatcagttgg    900

aagcggaaat caaccggcga aaaagccaaa caagagtctt tgccgggttc cttctacatg    960

gcattggaag atcagctgat gtacgatttt ggatttgcaa gacagctgac gactgccacg   1020

catctggcat gatctttatc ttaggaggtt ctaaagagat gcactgggcc tatgacagga   1080

actttaaata cgacatcacc caagctttga aggctcagtc catacaccct gaagatgtgt   1140

ttgacactga tgctcctttc ttcattaaag tggaggtcca tggtgtaaac aagactgctc   1200

tcccatcttc agctatccca gcacctacta taatctactc agctggtgaa g            1251
```

<210> SEQ ID NO 62
<211> LENGTH: 1185
<212> TYPE: DNA
<213> ORGANISM: HALIOTIS TUBERCULATA
<220> FEATURE:
<221> NAME/KEY: misc_feature
<222> LOCATION: (163)..(163)
<223> OTHER INFORMATION: n is a, g, c, or t

<400> SEQUENCE: 62

```
atcatattgc tggcagtgga gtcaggaaag acgtgacgtc tcttaccgca tctgagatag     60

agaacctgag gcatgctctg caaagcgtga tggatgatga tggacccaat ggattccagg    120

caattgctgc ttatcacgga agtcctccca tgtgtcacat gcntgatggt agagacgttg    180

catgttgtac tcatggaatg gcatctttcc ctcactggca cagactgttt gtgaaacaga    240
```

```
tggaggatgc actggctgcg catggagctc acattggcat accatactgg gattggacaa    300

gtgcgtttag tcatctgcct gccctagtga ctgaccacga gcacaatccc ttccaccacg    360

gacatattgc tcatcggaat gtggatacat ctcgatctcc gagagacatg ctgttcaatg    420

accccgaaca cgggtcagaa tcattcttct atagacaggt tctcttggct ctagaacaga    480

cagacttctg ccaatttgaa gttcagtttg aaataacaca caatgcaatc cactcttgga    540

ctggaggaca tactccatat ggaatgtcat cactggaata tacagcatat gatccactct    600

tttatctcca ccattccaac actgatcgta tctgggccat ctggcaggca ctccagaaat    660

acagaggttt tcaatacaac gcagctcatt gcgatatcca ggttctgaaa caacctctta    720

aaccattcag cgagtccagg aatccaaacc cagtcaccag agccaattct agggcagtcg    780

attcatttga ttatgagaga ctcaattatc aatatgacac acttaccttc cacggacatt    840

ctatctcaga acttgatgcc atgcttcaag agagaaagaa ggaagagaga acatttgcag    900

ccttcctgtt gcacggattt ggcgccagtg ctgatgtttc gtttgatgtc tgcacacctg    960

atggtcattg tgcctttgct ggaaccttcg cggtacttgg tggggagctt gagatgccct   1020

ggtcctttga aagattgttc cgttacgata tcacaaaggt tctcaagcag atgaatcttc   1080

actatgattc tgagttccac tttgagttga agattgttgg cacagatgga acagaactgc   1140

catcggatcg tatcaagagc cctaccattg aacaccatgg aggag                   1185


<210> SEQ ID NO 63
<211> LENGTH: 422
<212> TYPE: PRT
<213> ORGANISM: HALIOTIS TUBERCULATA

<400> SEQUENCE: 63

Leu Val Gln Phe Leu Leu Val Ala Leu Val Val Gly Ala Gly Ala Asp
1               5                   10                  15

Asn Val Val Arg Lys Asp Val Ser His Leu Thr Asp Asp Glu Val Gln
            20                  25                  30

Ala Leu His Gly Ala Leu His Asp Val Thr Ala Ser Thr Gly Pro Leu
        35                  40                  45

Ser Phe Glu Asp Ile Thr Ser Tyr His Ala Ala Pro Ala Ser Cys Asp
    50                  55                  60

Tyr Lys Gly Arg Lys Ile Ala Cys Cys Val His Gly Met Pro Ser Phe
65                  70                  75                  80

Pro Phe Trp His Arg Ala Tyr Val Val Gln Ala Glu Arg Ala Leu Leu
                85                  90                  95

Ser Lys Arg Lys Thr Val Gly Met Pro Tyr Trp Asp Trp Thr Gln Thr
            100                 105                 110

Leu Thr His Leu Pro Ser Leu Val Thr Glu Pro Ile Tyr Ile Asp Ser
        115                 120                 125

Lys Gly Gly Lys Ala Gln Thr Asn Tyr Trp Tyr Arg Gly Glu Ile Ala
    130                 135                 140

Phe Ile Asn Lys Lys Thr Ala Arg Ala Val Asp Asp Arg Leu Phe Glu
145                 150                 155                 160

Lys Val Glu Pro Gly His Tyr Thr His Leu Met Glu Thr Val Leu Asp
                165                 170                 175

Ala Leu Glu Gln Asp Glu Phe Cys Lys Phe Glu Ile Gln Phe Glu Leu
            180                 185                 190

Ala His Asn Ala Ile His Tyr Leu Val Gly Gly Lys Phe Glu Tyr Ser
        195                 200                 205
```

```
Met Ser Asn Leu Glu Tyr Thr Ser Tyr Asp Pro Ile Phe Phe Leu His
    210                 215                 220

His Ser Asn Val Asp Arg Leu Phe Ala Ile Trp Gln Arg Leu Gln Glu
225                 230                 235                 240

Leu Arg Gly Lys Asn Pro Asn Ala Met Asp Cys Ala His Glu Leu Ala
                245                 250                 255

His Gln Gln Leu Gln Pro Phe Asn Arg Asp Ser Asn Pro Val Gln Leu
            260                 265                 270

Thr Lys Asp His Ser Thr Pro Ala Asp Leu Phe Asp Tyr Lys Gln Leu
        275                 280                 285

Gly Tyr Ser Tyr Asp Ser Leu Asn Leu Asn Gly Met Thr Pro Glu Gln
    290                 295                 300

Leu Lys Thr Glu Leu Asp Glu Arg His Ser Lys Glu Arg Ala Phe Ala
305                 310                 315                 320

Ser Phe Arg Leu Ser Gly Phe Gly Gly Ser Ala Asn Val Val Val Tyr
                325                 330                 335

Ala Cys Val Pro Asp Asp Asp Pro Arg Ser Asp Asp Tyr Cys Glu Lys
            340                 345                 350

Ala Gly Asp Phe Phe Ile Leu Gly Gly Gln Ser Glu Met Pro Trp Arg
        355                 360                 365

Phe Tyr Arg Pro Phe Phe Tyr Asp Val Thr Glu Ala Val His His Leu
    370                 375                 380

Gly Val Pro Leu Ser Gly His Tyr Tyr Val Lys Thr Glu Leu Phe Ser
385                 390                 395                 400

Val Asn Gly Thr Ala Leu Ser Pro Asp Leu Leu Pro Gln Pro Thr Val
                405                 410                 415

Ala Tyr Arg Pro Gly Lys
            420
```

<210> SEQ ID NO 64
<211> LENGTH: 511
<212> TYPE: PRT
<213> ORGANISM: HALIOTIS TUBERCULATA

<400> SEQUENCE: 64

```
Val His Arg Gly Gly Asn His Glu Asp Glu His His Asp Asp Arg Leu
1               5                   10                  15

Ala Asp Val Leu Ile Arg Lys Glu Val Asp Phe Leu Ser Leu Gln Glu
            20                  25                  30

Ala Asn Ala Ile Lys Asp Ala Leu Tyr Lys Leu Gln Asn Asp Asp Ser
        35                  40                  45

Lys Gly Gly Phe Glu Ala Ile Ala Gly Tyr His Gly Tyr Pro Asn Met
    50                  55                  60

Cys Pro Glu Arg Gly Thr Asp Lys Tyr Pro Cys Cys Val His Gly Met
65                  70                  75                  80

Pro Val Phe Pro His Trp His Arg Leu His Thr Ile Gln Met Glu Arg
                85                  90                  95

Ala Leu Lys Asn His Gly Ser Pro Met Gly Ile Pro Tyr Trp Asp Trp
            100                 105                 110

Thr Lys Lys Met Ser Ser Leu Pro Ser Phe Phe Gly Asp Ser Ser Asn
        115                 120                 125

Asn Asn Pro Phe Tyr Lys Tyr Tyr Ile Arg Gly Val Gln His Glu Thr
    130                 135                 140

Thr Arg Asp Val Asn Gln Arg Leu Phe Asn Gln Thr Lys Phe Gly Glu
```

-continued

```
145                 150                 155                 160

Phe Asp Tyr Leu Tyr Tyr Leu Thr Leu Gln Val Leu Glu Glu Asn Ser
                165                 170                 175

Tyr Cys Asp Phe Glu Val Gln Tyr Glu Ile Leu His Asn Ala Val His
            180                 185                 190

Ser Trp Leu Gly Gly Thr Gly Gln Tyr Ser Met Ser Thr Leu Glu His
        195                 200                 205

Ser Ala Phe Asp Pro Val Phe Met Ile His His Ser Ser Leu Asp Arg
    210                 215                 220

Ile Trp Ile Leu Trp Gln Lys Leu Gln Lys Ile Arg Met Lys Pro Tyr
225                 230                 235                 240

Tyr Ala Leu Asp Cys Ala Gly Asp Arg Leu Met Lys Asp Pro Leu His
                245                 250                 255

Pro Phe Asn Tyr Glu Thr Val Asn Glu Asp Glu Phe Thr Arg Ile Asn
            260                 265                 270

Ser Phe Pro Ser Ile Leu Phe Asp His Tyr Arg Phe Asn Tyr Glu Tyr
        275                 280                 285

Asp Asn Met Arg Ile Arg Gly Gln Asp Ile His Glu Leu Glu Glu Val
    290                 295                 300

Ile Gln Glu Leu Arg Asn Lys Asp Arg Ile Phe Ala Gly Phe Val Leu
305                 310                 315                 320

Ser Gly Leu Arg Ile Ser Ala Thr Val Lys Val Phe Ile His Ser Lys
                325                 330                 335

Asn Asp Thr Ser His Glu Glu Tyr Ala Gly Glu Phe Ala Val Leu Gly
            340                 345                 350

Gly Glu Lys Glu Met Pro Trp Ala Tyr Glu Arg Met Leu Lys Leu Asp
        355                 360                 365

Ile Ser Asp Ala Val His Lys Leu His Val Lys Asp Glu Asp Ile Arg
    370                 375                 380

Phe Arg Val Val Val Thr Ala Tyr Asn Gly Asp Val Val Thr Thr Arg
385                 390                 395                 400

Leu Ser Gln Pro Phe Ile Val His Arg Pro Ala His Val Ala His Asp
                405                 410                 415

Ile Leu Val Ile Pro Val Gly Ala Gly His Asp Leu Pro Pro Lys Val
            420                 425                 430

Val Val Lys Ser Gly Thr Lys Val Glu Phe Thr Pro Ile Asp Ser Ser
        435                 440                 445

Val Asn Lys Ala Met Val Glu Leu Gly Ser Tyr Thr Ala Met Ala Lys
    450                 455                 460

Cys Ile Val Pro Pro Phe Ser Tyr His Gly Phe Glu Leu Asp Lys Val
465                 470                 475                 480

Tyr Ser Val Asp His Gly Asp Tyr Tyr Ile Ala Ala Gly Thr His Ala
                485                 490                 495

Leu Cys Glu Gln Asn Leu Arg Leu His Ile His Val Glu His Glu
            500                 505                 510


<210> SEQ ID NO 65
<211> LENGTH: 197
<212> TYPE: PRT
<213> ORGANISM: HALIOTIS TUBERCULATA

<400> SEQUENCE: 65

Gly Leu Pro Tyr Trp Asp Trp Thr Gln His Leu Thr Gln Leu Pro Asp
1               5                   10                  15
```

-continued

```
Leu Val Ser Asp Pro Leu Phe Val Asp Pro Glu Gly Gly Lys Ala His
            20                  25                  30

Asp Asn Ala Trp Tyr Arg Gly Asn Ile Lys Phe Glu Asn Lys Lys Thr
        35                  40                  45

Ala Arg Ala Val Asp Asp Arg Leu Phe Glu Lys Val Gly Pro Gly Glu
    50                  55                  60

Asn Thr Arg Leu Phe Glu Gly Ile Leu Asp Ala Leu Glu Gln Asp Glu
65                  70                  75                  80

Phe Cys Asn Phe Glu Ile Gln Phe Glu Leu Ala His Asn Ala Ile His
                85                  90                  95

Tyr Leu Val Gly Gly Arg His Thr Tyr Ser Met Ser His Leu Glu Tyr
            100                 105                 110

Thr Ser Tyr Asp Pro Leu Phe Phe Leu His His Ser Asn Pro Asp Arg
        115                 120                 125

Ile Phe Ala Ile Trp Glu Arg Leu Gln Val Leu Arg Gly Lys Asp Pro
    130                 135                 140

Asn Thr Ala Asp Cys Ala His Asn Leu Ile His Glu Pro Met Glu Pro
145                 150                 155                 160

Phe Arg Arg His Glu Pro Met Glu Pro Phe Arg Arg Asp Ser Asn Pro
                165                 170                 175

Leu Asp Leu Thr Arg Glu Asn Ser Lys Pro Ile Asp Ser Phe Asp Tyr
            180                 185                 190

Ala His Leu Gly Tyr
        195
```

<210> SEQ ID NO 66
<211> LENGTH: 415
<212> TYPE: PRT
<213> ORGANISM: HALIOTIS TUBERCULATA

<400> SEQUENCE: 66

```
Val Thr Glu Ala Pro Ala Pro Ser Ser Asp Ala His Leu Ala Val Arg
1               5                   10                  15

Lys Asp Ile Asn His Leu Thr Arg Glu Glu Val Tyr Glu Leu Arg Arg
            20                  25                  30

Ala Met Glu Arg Phe Gln Ala Asp Thr Ser Val Asp Gly Tyr Gln Ala
        35                  40                  45

Thr Val Glu Tyr His Gly Leu Pro Ala Arg Cys Pro Phe Pro Glu Ala
    50                  55                  60

Thr Asn Arg Phe Ala Cys Cys Ile His Gly Met Ala Thr Phe Pro His
65                  70                  75                  80

Trp His Arg Leu Phe Val Thr Gln Val Glu Asp Ala Leu Ile Arg Arg
                85                  90                  95

Gly Ser Pro Ile Gly Val Pro Tyr Trp Asp Trp Thr Gln Pro Met Ala
            100                 105                 110

His Leu Pro Gly Leu Ala Asp Asn Ala Thr Tyr Arg Asp Pro Ile Ser
        115                 120                 125

Gly Asp Ser Arg His Asn Pro Phe His Asp Val Glu Val Ala Phe Glu
    130                 135                 140

Asn Gly Arg Thr Glu Arg His Pro Asp Ser Arg Leu Phe Glu Gln Pro
145                 150                 155                 160

Leu Phe Gly Lys His Thr Arg Leu Phe Asp Ser Ile Val Tyr Ala Phe
                165                 170                 175

Glu Gln Glu Asp Phe Cys Asp Phe Glu Val Gln Phe Glu Met Thr His
            180                 185                 190
```

```
Asn Asn Ile His Ala Trp Ile Gly Gly Gly Glu Lys Tyr Ser Met Ser
        195                 200                 205

Ser Leu His Tyr Thr Ala Phe Asp Pro Ile Phe Tyr Leu Arg His Ser
    210                 215                 220

Asn Thr Asp Arg Leu Trp Ala Ile Trp Gln Ala Leu Gln Ile Arg Arg
225                 230                 235                 240

Asn Arg Pro Tyr Lys Ala His Cys Ala Trp Ser Glu Glu Arg Gln Pro
                245                 250                 255

Leu Lys Pro Phe Ala Phe Ser Ser Pro Leu Asn Asn Asn Glu Lys Thr
            260                 265                 270

Tyr Glu Asn Ser Val Pro Thr Asn Val Tyr Asp Tyr Glu Gly Val Leu
        275                 280                 285

Gly Tyr Thr Tyr Asp Asp Leu Asn Phe Gly Gly Met Asp Leu Gly Gln
    290                 295                 300

Leu Glu Glu Tyr Ile Gln Arg Gln Arg Gln Arg Asp Arg Thr Phe Ala
305                 310                 315                 320

Gly Phe Phe Leu Ser His Ile Gly Thr Ser Ala Asn Val Glu Ile Ile
                325                 330                 335

Ile Asp His Gly Thr Leu His Thr Ser Val Gly Thr Phe Ala Val Leu
            340                 345                 350

Gly Gly Glu Lys Glu Met Lys Trp Gly Phe Asp Arg Leu Tyr Lys Tyr
        355                 360                 365

Glu Ile Thr Asp Glu Leu Arg Gln Leu Asn Leu Arg Ala Asp Asp Val
    370                 375                 380

Phe Ser Ile Ser Val Lys Val Thr Asp Val Asp Gly Ser Glu Leu Ser
385                 390                 395                 400

Ser Glu Leu Ile Pro Ser Ala Ala Ile Ile Phe Glu Arg Ser His
                405                 410                 415
```

<210> SEQ ID NO 67
<211> LENGTH: 414
<212> TYPE: PRT
<213> ORGANISM: HT PRO 20

<400> SEQUENCE: 67

```
Gly His His Gln Ala Asp Glu Tyr Asp Glu Val Val Thr Ala Ala Ser
1               5                   10                  15

His Ile Arg Lys Asn Leu Lys Asp Leu Ser Lys Gly Glu Val Glu Ser
            20                  25                  30

Leu Arg Ser Ala Phe Leu Gln Leu Gln Asn Asp Gly Val Tyr Glu Asn
        35                  40                  45

Ile Ala Lys Phe His Gly Lys Pro Gly Leu Cys Asp Asp Asn Gly Arg
    50                  55                  60

Lys Val Ala Cys Cys Val His Gly Met Pro Thr Phe Pro Gln Trp His
65                  70                  75                  80

Arg Leu Tyr Val Leu Gln Val Glu Asn Ala Leu Leu Glu Arg Gly Ser
                85                  90                  95

Ala Val Ser Val Pro Tyr Trp Asp Trp Thr Glu Thr Phe Thr Glu Leu
            100                 105                 110

Pro Ser Leu Ile Ala Glu Ala Thr Tyr Phe Asn Ser Arg Gln Gln Thr
        115                 120                 125

Phe Asp Pro Asn Pro Phe Phe Arg Gly Lys Ile Ser Phe Glu Asn Ala
    130                 135                 140

Val Thr Thr Arg Asp Pro Gln Pro Glu Leu Tyr Val Asn Arg Tyr Tyr
```

-continued

```
145                 150                 155                 160

Tyr Gln Asn Val Met Leu Val Phe Glu Gln Asp Asn Tyr Cys Asp Phe
                165                 170                 175

Glu Ile Gln Phe Glu Met Val His Asn Val Leu His Ala Trp Leu Gly
            180                 185                 190

Gly Arg Ala Thr Tyr Ser Ile Ser Ser Leu Asp Tyr Ser Ala Phe Asp
        195                 200                 205

Pro Val Phe Phe Leu His His Ala Asn Thr Asp Arg Leu Trp Ala Ile
    210                 215                 220

Trp Gln Glu Leu Gln Arg Tyr Arg Lys Lys Pro Tyr Asn Glu Ala Asp
225                 230                 235                 240

Cys Ala Ile Asn Leu Met Arg Lys Pro Leu His Pro Phe Asp Asn Ser
                245                 250                 255

Asp Leu Asn His Asp Pro Val Thr Phe Lys Tyr Ser Lys Pro Thr Asp
            260                 265                 270

Gly Phe Asp Tyr Gln Asn Asn Phe Gly Tyr Lys Tyr Asp Asn Leu Glu
        275                 280                 285

Phe Asn His Phe Ser Ile Pro Arg Leu Glu Glu Ile Ile Arg Ile Arg
    290                 295                 300

Gln Arg Gln Asp Arg Val Phe Ala Gly Phe Leu Leu His Asn Ile Gly
305                 310                 315                 320

Thr Ser Ala Thr Val Glu Ile Phe Val Cys Val Pro Thr Thr Ser Gly
                325                 330                 335

Glu Gln Asn Cys Glu Asn Lys Ala Gly Thr Phe Ala Val Leu Gly Gly
            340                 345                 350

Glu Thr Glu Met Ala Phe His Phe Asp Arg Leu Tyr Arg Phe Asp Ile
        355                 360                 365

Ser Glu Thr Leu Arg Asp Leu Gly Ile Gln Leu Asp Ser His Asp Phe
    370                 375                 380

Asp Leu Ser Ile Lys Ile Gln Gly Val Asn Gly Ser Tyr Leu Asp Pro
385                 390                 395                 400

His Ile Leu Pro Glu Pro Ser Leu Ile Phe Val Pro Gly Ser
                405                 410
```

<210> SEQ ID NO 68
<211> LENGTH: 419
<212> TYPE: PRT
<213> ORGANISM: HALIOTIS TUBERCULATA

<400> SEQUENCE: 68

```
Ser Ser Phe Leu Arg Pro Asp Gly His Ser Asp Asp Ile Leu Val Arg
1               5                   10                  15

Lys Glu Val Asn Ser Leu Thr Thr Arg Glu Thr Ala Ser Leu Ile His
            20                  25                  30

Ala Leu Lys Ser Met Gln Glu Asp His Ser Pro Asp Gly Phe Gln Ala
        35                  40                  45

Ile Ala Ser Phe His Ala Leu Pro Pro Leu Cys Pro Ser Pro Ser Ala
    50                  55                  60

Ala His Arg Tyr Ala Cys Cys Val His Gly Met Ala Thr Phe Pro Gln
65                  70                  75                  80

Trp His Arg Leu Tyr Thr Val Gln Phe Gln Asp Ala Leu Arg Arg His
                85                  90                  95

Gly Ala Thr Val Gly Val Pro Tyr Trp Asp Trp Leu Arg Pro Gln Ser
            100                 105                 110
```

-continued

```
His Leu Pro Glu Leu Val Thr Met Glu Thr Tyr His Asp Ile Trp Ser
        115                 120                 125

Asn Arg Asp Phe Pro Asn Pro Phe Tyr Gln Ala Asn Ile Glu Phe Glu
    130                 135                 140

Gly Glu Asn Ile Thr Thr Glu Arg Glu Val Ile Ala Asp Lys Leu Phe
145                 150                 155                 160

Val Lys Gly Gly His Val Phe Asp Lys Leu Val Leu Gln Thr Ser His
                165                 170                 175

Pro Ser Ala Glu Gln Glu Asn Tyr Cys Asp Phe Glu Ile Gln Phe Glu
            180                 185                 190

Ile Leu His Asn Gly Val His Thr Trp Val Gly Gly Ser Arg Thr Tyr
        195                 200                 205

Ser Ile Gly His Leu His Tyr Ala Phe Tyr Asp Pro Leu Phe Tyr Leu
    210                 215                 220

His His Phe Gln Thr Asp Arg Ile Trp Ala Ile Trp Gln Glu Leu Gln
225                 230                 235                 240

Glu Gln Arg Gly Leu Ser Gly Asp Glu Ala His Cys Ala Leu Glu Gln
                245                 250                 255

Met Arg Glu Pro Leu Lys Pro Phe Ser Phe Gly Ala Pro Tyr Asn Trp
            260                 265                 270

Asn Gln Leu Thr Gln Asp Phe Ser Arg Pro Glu Asp Thr Phe Asp Tyr
        275                 280                 285

Arg Lys Phe Gly Tyr Glu Tyr Asp Asn Leu Glu Phe Leu Gly Met Ser
    290                 295                 300

Val Ala Glu Leu Asp Gln Tyr Ile Ile Glu His Gln Glu Asn Asp Arg
305                 310                 315                 320

Val Phe Ala Gly Phe Leu Leu Ser Gly Phe Gly Gly Ser Ala Ser Val
                325                 330                 335

Asn Phe Gln Val Cys Arg Ala Asp Ser Thr Cys Gln Asp Ala Gly Tyr
            340                 345                 350

Phe Thr Val Leu Gly Gly Ser Ala Glu Met Ala Trp Ala Phe Asp Arg
        355                 360                 365

Leu Tyr Lys Tyr Asp Ile Thr Glu Thr Leu Glu Lys Met His Leu Arg
    370                 375                 380

Tyr Asp Asp Asp Phe Thr Ile Ser Val Ser Leu Thr Ala Asn Asn Gly
385                 390                 395                 400

Thr Val Leu Ser Ser Ser Leu Ile Pro Thr Pro Ser Val Ile Phe Gln
                405                 410                 415

Arg Gly His


<210> SEQ ID NO 69
<211> LENGTH: 378
<212> TYPE: PRT
<213> ORGANISM: HALIOTIS TUBERCULATA

<400> SEQUENCE: 69

Arg Tyr Gln Ala Thr Ala Glu Tyr His Gly Leu Pro Ala Arg Cys Pro
1               5                   10                  15

Arg Pro Asp Ala Lys Asp Arg Tyr Ala Cys Cys Val His Gly Met Pro
            20                  25                  30

Ile Phe Pro His Trp His Arg Leu Phe Val Thr Gln Val Glu Asp Ala
        35                  40                  45

Leu Val Gly Arg Gly Ala Thr Ile Gly Ile Pro Tyr Trp Asp Trp Thr
    50                  55                  60
```

-continued

```
Glu Pro Met Thr His Ile Pro Gly Leu Ala Gly Asn Lys Thr Tyr Val
65                  70                  75                  80

Asp Ser His Gly Ala Ser His Thr Asn Pro Phe His Ser Ser Val Ile
                85                  90                  95

Ala Phe Glu Glu Asn Ala Pro His Thr Lys Arg Gln Ile Asp Gln Arg
            100                 105                 110

Leu Phe Lys Pro Ala Thr Phe Gly His His Thr Asp Leu Phe Asn Gln
        115                 120                 125

Ile Leu Tyr Ala Phe Glu Gln Glu Asp Tyr Cys Asp Phe Glu Val Gln
    130                 135                 140

Phe Glu Ile Thr His Asn Thr Ile His Ala Trp Thr Gly Gly Ser Glu
145                 150                 155                 160

His Phe Ser Met Ser Ser Leu His Tyr Thr Ala Phe Asp Pro Leu Phe
                165                 170                 175

Tyr Phe His His Ser Asn Val Asp Arg Leu Trp Ala Val Trp Gln Ala
            180                 185                 190

Leu Gln Met Arg Arg His Lys Pro Tyr Arg Ala His Cys Ala Ile Ser
        195                 200                 205

Leu Glu His Met His Leu Lys Pro Phe Ala Phe Ser Ser Pro Leu Asn
    210                 215                 220

Asn Asn Glu Lys Thr His Ala Asn Ala Met Pro Asn Lys Ile Tyr Asp
225                 230                 235                 240

Tyr Glu Asn Val Leu His Tyr Thr Tyr Glu Asp Leu Thr Phe Gly Gly
                245                 250                 255

Ile Ser Leu Glu Asn Ile Glu Lys Met Ile His Glu Asn Gln Gln Glu
            260                 265                 270

Asp Arg Ile Tyr Ala Gly Phe Leu Leu Ala Gly Ile Arg Thr Ser Ala
        275                 280                 285

Asn Val Asp Ile Phe Ile Lys Thr Thr Asp Ser Val Gln His Lys Ala
    290                 295                 300

Gly Thr Phe Ala Val Leu Gly Gly Ser Lys Glu Met Lys Trp Gly Phe
305                 310                 315                 320

Asp Arg Val Phe Lys Phe Asp Ile Thr His Val Leu Lys Asp Leu Asp
                325                 330                 335

Leu Thr Ala Asp Gly Asp Phe Glu Val Thr Val Asp Ile Thr Glu Val
            340                 345                 350

Asp Gly Thr Lys Leu Ala Ser Ser Leu Ile Pro His Ala Ser Val Ile
        355                 360                 365

Arg Glu His Ala Arg Gly Lys Leu Asn Arg
    370                 375
```

<210> SEQ ID NO 70
<211> LENGTH: 419
<212> TYPE: PRT
<213> ORGANISM: MEGATHRUA CRENULATA

<400> SEQUENCE: 70

```
Asp Ser Ala His Thr Asp Asp Gly His Thr Glu Pro Val Met Ile Arg
1               5                   10                  15

Lys Asp Ile Thr Gln Leu Asp Lys Arg Gln Gln Leu Ser Leu Val Lys
            20                  25                  30

Ala Leu Glu Ser Met Lys Ala Asp His Ser Ser Asp Gly Phe Gln Ala
        35                  40                  45

Ile Ala Ser Phe His Ala Leu Pro Pro Leu Cys Pro Ser Pro Ala Ala
    50                  55                  60
```

-continued

```
Ser Lys Arg Phe Ala Cys Cys Val His Gly Met Ala Thr Phe Pro Gln
65                  70                  75                  80

Trp His Arg Leu Tyr Thr Val Gln Phe Gln Asp Ser Leu Arg Lys His
                85                  90                  95

Gly Ala Val Val Gly Leu Pro Tyr Trp Asp Trp Thr Leu Pro Arg Ser
            100                 105                 110

Glu Leu Pro Glu Leu Leu Thr Val Ser Thr Ile His Asp Pro Glu Thr
        115                 120                 125

Gly Arg Asp Ile Pro Asn Pro Phe Ile Gly Ser Lys Ile Glu Phe Glu
    130                 135                 140

Gly Glu Asn Val His Thr Lys Arg Asp Ile Asn Arg Asp Arg Leu Phe
145                 150                 155                 160

Gln Gly Ser Thr Lys Thr His His Asn Trp Phe Ile Glu Gln Ala Leu
                165                 170                 175

Leu Ala Leu Glu Gln Thr Asn Tyr Cys Asp Phe Glu Val Gln Phe Glu
            180                 185                 190

Ile Met His Asn Gly Val His Thr Trp Val Gly Gly Lys Glu Pro Tyr
        195                 200                 205

Gly Ile Gly His Leu His Tyr Ala Ser Tyr Asp Pro Leu Phe Tyr Ile
    210                 215                 220

His His Ser Gln Thr Asp Arg Ile Trp Ala Ile Trp Gln Ser Leu Gln
225                 230                 235                 240

Arg Phe Arg Gly Leu Ser Gly Ser Glu Ala Asn Cys Ala Val Asn Leu
                245                 250                 255

Met Lys Thr Pro Leu Lys Pro Phe Ser Phe Gly Ala Pro Tyr Asn Leu
            260                 265                 270

Asn Asp His Thr His Asp Phe Ser Lys Pro Glu Asp Thr Phe Asp Tyr
        275                 280                 285

Gln Lys Phe Gly Tyr Ile Tyr Asp Thr Leu Glu Phe Ala Gly Trp Ser
    290                 295                 300

Ile Arg Gly Ile Asp His Ile Val Arg Asn Arg Gln Glu His Ser Arg
305                 310                 315                 320

Val Phe Ala Gly Phe Leu Leu Glu Gly Phe Gly Thr Ser Ala Thr Val
                325                 330                 335

Asp Phe Gln Val Cys Arg Thr Ala Gly Asp Cys Glu Asp Ala Gly Tyr
            340                 345                 350

Phe Thr Val Leu Gly Gly Glu Lys Glu Met Pro Trp Ala Phe Asp Arg
        355                 360                 365

Leu Tyr Lys Tyr Asp Ile Thr Glu Thr Leu Asp Lys Met Asn Leu Arg
    370                 375                 380

His Asp Glu Ile Phe Gln Ile Glu Val Thr Ile Thr Ser Tyr Asp Gly
385                 390                 395                 400

Thr Val Leu Asp Ser Gly Leu Ile Pro Thr Pro Ser Ile Ile Tyr Asp
                405                 410                 415

Pro Ala His


<210> SEQ ID NO 71
<211> LENGTH: 418
<212> TYPE: PRT
<213> ORGANISM: MEGATHURA CRENULATA

<400> SEQUENCE: 71

His Asp Ile Ser Ser His His Leu Ser Leu Asn Lys Val Arg His Asp
1               5                   10                  15
```

```
Leu Ser Thr Leu Ser Glu Arg Asp Ile Gly Ser Leu Lys Tyr Ala Leu
            20                  25                  30

Ser Ser Leu Gln Ala Asp Thr Ser Ala Asp Gly Phe Ala Ala Ile Ala
        35                  40                  45

Ser Phe His Gly Leu Pro Ala Lys Cys Asn Asp Ser His Asn Asn Glu
    50                  55                  60

Val Ala Cys Cys Ile His Gly Met Pro Thr Phe Pro His Trp His Arg
65                  70                  75                  80

Leu Tyr Thr Leu Gln Phe Glu Gln Ala Leu Arg Arg His Gly Ser Ser
                85                  90                  95

Val Ala Val Pro Tyr Trp Asp Trp Thr Lys Pro Ile His Asn Ile Pro
            100                 105                 110

His Leu Phe Thr Asp Lys Glu Tyr Tyr Asp Val Trp Arg Asn Lys Val
        115                 120                 125

Met Pro Asn Pro Phe Ala Arg Gly Tyr Val Pro Ser His Asp Thr Tyr
    130                 135                 140

Thr Val Arg Asp Val Gln Glu Gly Leu Phe His Leu Thr Ser Thr Gly
145                 150                 155                 160

Glu His Ser Ala Leu Leu Asn Gln Ala Leu Leu Ala Leu Glu Gln His
                165                 170                 175

Asp Tyr Cys Asp Phe Ala Val Gln Phe Glu Val Met His Asn Thr Ile
            180                 185                 190

His Tyr Leu Val Gly Gly Pro Gln Val Tyr Ser Leu Ser Ser Leu His
        195                 200                 205

Tyr Ala Ser Tyr Asp Pro Ile Phe Phe Ile His His Ser Phe Val Asp
    210                 215                 220

Lys Val Trp Ala Val Trp Gln Ala Leu Gln Glu Lys Arg Gly Leu Pro
225                 230                 235                 240

Ser Asp Arg Ala Asp Cys Ala Val Ser Leu Met Thr Gln Asn Met Arg
                245                 250                 255

Pro Phe His Tyr Glu Ile Asn His Asn Gln Phe Thr Lys Lys His Ala
            260                 265                 270

Val Pro Asn Asp Val Phe Lys Tyr Glu Leu Leu Gly Tyr Arg Tyr Asp
        275                 280                 285

Asn Leu Glu Ile Gly Gly Met Asn Leu His Glu Ile Glu Lys Glu Ile
    290                 295                 300

Lys Asp Lys Gln His His Val Arg Val Phe Ala Gly Phe Leu Leu His
305                 310                 315                 320

Gly Ile Arg Thr Ser Ala Asp Val Gln Phe Gln Ile Cys Lys Thr Ser
                325                 330                 335

Glu Asp Cys His His Gly Gly Gln Ile Phe Val Leu Gly Gly Thr Lys
            340                 345                 350

Glu Met Ala Trp Ala Tyr Asn Arg Leu Phe Lys Tyr Asp Ile Thr His
        355                 360                 365

Ala Leu His Asp Ala His Ile Thr Pro Glu Asp Val Phe His Pro Ser
    370                 375                 380

Glu Pro Phe Phe Ile Lys Val Ser Val Thr Ala Val Asn Gly Thr Val
385                 390                 395                 400

Leu Pro Ala Ser Ile Leu His Ala Pro Thr Ile Ile Tyr Glu Pro Gly
                405                 410                 415

Leu Gly
```

<210> SEQ ID NO 72
<211> LENGTH: 241
<212> TYPE: PRT
<213> ORGANISM: MEGATHURA CRENULATA

<400> SEQUENCE: 72

Asp His His Glu Asp His His Ser Ser Ser Met Ala Gly His Gly Val
1 5 10 15

Arg Lys Glu Ile Asn Thr Leu Thr Thr Ala Glu Val Asp Asn Leu Lys
20 25 30

Asp Ala Met Arg Ala Val Met Ala Asp His Gly Pro Asn Gly Tyr Gln
35 40 45

Ala Ile Ala Ala Phe His Gly Asn Pro Pro Met Cys Pro Met Pro Asp
50 55 60

Gly Lys Asn Tyr Ser Cys Cys Thr His Gly Met Ala Thr Phe Pro His
65 70 75 80

Trp His Arg Leu Tyr Thr Lys Gln Met Glu Asp Ala Leu Thr Ala His
85 90 95

Gly Ala Arg Val Gly Leu Pro Tyr Trp Asp Gly Thr Thr Ala Phe Thr
100 105 110

Ala Leu Pro Thr Phe Val Thr Asp Glu Glu Asp Asn Pro Phe His His
115 120 125

Gly His Ile Asp Tyr Leu Gly Val Asp Thr Thr Arg Ser Pro Arg Asp
130 135 140

Lys Leu Phe Asn Asp Pro Glu Arg Gly Ser Glu Ser Phe Phe Tyr Arg
145 150 155 160

Gln Val Leu Leu Ala Leu Glu Gln Thr Asp Phe Cys Gln Phe Glu Val
165 170 175

Gln Phe Glu Ile Thr His Asn Ala Ile His Ser Trp Thr Gly Gly Leu
180 185 190

Thr Pro Tyr Gly Met Ser Thr Leu Glu Tyr Thr Thr Tyr Asp Pro Leu
195 200 205

Phe Trp Leu His His Ala Asn Thr Asp Arg Ile Trp Ala Ile Trp Gln
210 215 220

Ala Leu Gln Glu Tyr Arg Gly Leu Pro Tyr Asp His Ala Asn Cys Glu
225 230 235 240

Ile

<210> SEQ ID NO 73
<211> LENGTH: 98
<212> TYPE: PRT
<213> ORGANISM: MEGATHURA CRENULATA

<400> SEQUENCE: 73

Lys His His Glu Lys His His Glu Asp His His Glu Asp Ile Leu Val
1 5 10 15

Arg Lys Asn Ile His Ser Leu Ser His His Glu Ala Glu Glu Leu Arg
20 25 30

Asp Ala Leu Tyr Lys Leu Gln Asn Asp Glu Ser His Gly Gly Tyr Glu
35 40 45

His Ile Ala Gly Phe His Gly Tyr Pro Asn Leu Cys Pro Glu Lys Gly
50 55 60

Asp Glu Lys Tyr Pro Cys Cys Val His Gly Met Ser Ile Phe Pro His
65 70 75 80

Trp His Arg Leu His Thr Ile Gln Leu Glu Arg Ala Leu Lys Lys His
85 90 95

```
Gly Ser

<210> SEQ ID NO 74
<211> LENGTH: 314
<212> TYPE: PRT
<213> ORGANISM: MEGATHURA CRENULATA

<400> SEQUENCE: 74

Gly Leu Pro Tyr Trp Asp Trp Thr Met Pro Met Ser His Leu Pro Glu
1               5                   10                  15

Leu Ala Thr Ser Glu Thr Tyr Leu Asp Pro Val Thr Gly Glu Thr Lys
            20                  25                  30

Asn Asn Pro Phe His His Ala Gln Val Ala Phe Glu Asn Gly Val Thr
        35                  40                  45

Ser Arg Asn Pro Asp Ala Lys Leu Phe Met Lys Pro Thr Tyr Gly Asp
    50                  55                  60

His Thr Tyr Leu Phe Asp Ser Met Ile Tyr Ala Phe Glu Gln Glu Asp
65                  70                  75                  80

Phe Cys Asp Phe Glu Val Gln Tyr Glu Leu Thr His Asn Ala Ile His
                85                  90                  95

Ala Trp Val Gly Gly Ser Glu Lys Tyr Ser Met Ser Ser Leu His Tyr
            100                 105                 110

Thr Ala Phe Asp Pro Ile Phe Tyr Leu His His Ser Asn Val Asp Arg
        115                 120                 125

Leu Trp Ala Ile Trp Gln Ala Leu Gln Ile Arg Arg Gly Lys Ser Tyr
    130                 135                 140

Lys Ala His Cys Ala Ser Ser Gln Glu Arg Glu Pro Leu Lys Pro Phe
145                 150                 155                 160

Ala Phe Ser Ser Pro Leu Asn Asn Asn Glu Lys Thr Tyr His Asn Ser
                165                 170                 175

Val Pro Thr Asn Val Tyr Asp Tyr Val Gly Val Leu His Tyr Arg Tyr
            180                 185                 190

Asp Asp Leu Gln Phe Gly Gly Met Thr Met Ser Glu Leu Glu Glu Tyr
        195                 200                 205

Ile His Lys Gln Thr Gln His Asp Arg Thr Phe Ala Gly Phe Phe Leu
    210                 215                 220

Ser Tyr Ile Gly Thr Ser Ala Ser Val Asp Ile Phe Ile Asn Arg Glu
225                 230                 235                 240

Gly His Asp Lys Tyr Lys Val Gly Ser Phe Val Val Leu Gly Gly Ser
                245                 250                 255

Lys Glu Met Lys Trp Gly Phe Asp Arg Met Tyr Lys Tyr Glu Ile Thr
            260                 265                 270

Glu Ala Leu Lys Thr Leu Asn Val Ala Val Asp Asp Gly Phe Ser Ile
        275                 280                 285

Thr Val Glu Ile Thr Asp Val Asp Gly Ser Pro Pro Ser Ala Asp Leu
    290                 295                 300

Ile Pro Pro Pro Ala Ile Ile Phe Glu Arg
305                 310

<210> SEQ ID NO 75
<211> LENGTH: 416
<212> TYPE: PRT
<213> ORGANISM: MEGATHURA CRENULATA

<400> SEQUENCE: 75
```

-continued

```
Ala Asp Ala Lys Asp Phe Gly His Ser Arg Lys Ile Arg Lys Ala Val
1               5                   10                  15

Asp Ser Leu Thr Val Glu Glu Gln Thr Ser Leu Arg Arg Ala Met Ala
            20                  25                  30

Asp Leu Gln Asp Asp Lys Thr Ser Gly Gly Phe Gln Gln Ile Ala Ala
        35                  40                  45

Phe His Gly Glu Pro Lys Trp Cys Pro Ser Pro Glu Ala Glu Lys Lys
    50                  55                  60

Phe Ala Cys Cys Val His Gly Met Ala Val Phe Pro His Trp His Arg
65                  70                  75                  80

Leu Leu Thr Val Gln Gly Glu Asn Ala Leu Arg Lys His Gly Phe Thr
                85                  90                  95

Gly Gly Leu Pro Tyr Trp Asp Trp Thr Arg Ser Met Ser Ala Leu Pro
            100                 105                 110

His Phe Val Ala Asp Pro Thr Tyr Asn Asp Ala Ile Ser Ser Gln Glu
        115                 120                 125

Glu Asp Asn Pro Trp His His Gly His Ile Asp Ser Val Gly His Asp
    130                 135                 140

Thr Thr Arg Asp Val Arg Asp Asp Leu Tyr Gln Ser Pro Gly Phe Gly
145                 150                 155                 160

His Tyr Thr Asp Ile Ala Lys Gln Val Leu Leu Ala Phe Glu Gln Asp
                165                 170                 175

Asp Phe Cys Asp Phe Glu Val Gln Phe Glu Ile Ala His Asn Phe Ile
            180                 185                 190

His Ala Leu Val Gly Gly Asn Glu Pro Tyr Ser Met Ser Ser Leu Arg
        195                 200                 205

Tyr Thr Thr Tyr Asp Pro Ile Phe Phe Leu His Arg Ser Asn Thr Asp
    210                 215                 220

Arg Leu Trp Ala Ile Trp Gln Ala Leu Gln Lys Tyr Arg Gly Lys Pro
225                 230                 235                 240

Tyr Asn Thr Ala Asn Cys Ala Ile Ala Ser Met Arg Lys Pro Leu Gln
                245                 250                 255

Pro Phe Gly Leu Asp Ser Val Ile Asn Pro Asp Asp Glu Thr Arg Glu
            260                 265                 270

His Ser Val Pro Phe Arg Val Phe Asp Tyr Lys Asn Asn Phe Asp Tyr
        275                 280                 285

Glu Tyr Glu Ser Leu Ala Phe Asn Gly Leu Ser Ile Ala Gln Leu Asp
    290                 295                 300

Arg Glu Leu Gln Arg Arg Lys Ser His Asp Arg Val Phe Ala Gly Phe
305                 310                 315                 320

Leu Leu His Glu Ile Gly Gln Ser Ala Leu Val Lys Phe Tyr Val Cys
                325                 330                 335

Lys His Asn Val Ser Asp Cys Asp His Tyr Ala Gly Glu Phe Tyr Ile
            340                 345                 350

Leu Gly Asp Glu Ala Glu Met Pro Trp Arg Tyr Asp Arg Val Tyr Lys
        355                 360                 365

Tyr Glu Ile Thr Gln Gln Leu His Asp Leu Asp Leu His Val Gly Asp
    370                 375                 380

Asn Phe Phe Leu Lys Tyr Glu Ala Phe Asp Leu Asn Gly Gly Ser Leu
385                 390                 395                 400

Gly Gly Ser Ile Phe Ser Gln Pro Ser Val Ile Phe Glu Pro Ala Ala
                405                 410                 415
```

-continued

```
<210> SEQ ID NO 76
<211> LENGTH: 419
<212> TYPE: PRT
<213> ORGANISM: MEGATHURA CRENULATA

<400> SEQUENCE: 76

Gly Ser His Gln Ala Asp Glu Tyr Arg Glu Ala Val Thr Ser Ala Ser
1               5                   10                  15

His Ile Arg Lys Asn Ile Arg Asp Leu Ser Glu Gly Glu Ile Glu Ser
            20                  25                  30

Ile Arg Ser Ala Phe Leu Gln Ile Gln Lys Glu Gly Ile Tyr Glu Asn
        35                  40                  45

Ile Ala Lys Phe His Gly Lys Pro Gly Leu Cys Glu His Asp Gly His
    50                  55                  60

Pro Val Ala Cys Cys Val His Gly Met Pro Thr Phe Pro His Trp His
65                  70                  75                  80

Arg Leu Tyr Val Leu Gln Val Glu Asn Ala Leu Leu Glu Arg Gly Ser
                85                  90                  95

Ala Val Ala Val Pro Tyr Trp Asp Trp Thr Glu Lys Ala Asp Ser Leu
            100                 105                 110

Pro Ser Leu Ile Asn Asp Ala Thr Tyr Phe Asn Ser Arg Ser Gln Thr
        115                 120                 125

Phe Asp Pro Asn Pro Phe Phe Arg Gly His Ile Ala Phe Glu Asn Ala
    130                 135                 140

Val Thr Ser Arg Asp Pro Gln Pro Glu Leu Trp Asp Asn Lys Asp Phe
145                 150                 155                 160

Tyr Glu Asn Val Met Leu Ala Leu Glu Gln Asp Asn Phe Cys Asp Phe
                165                 170                 175

Glu Ile Gln Leu Glu Leu Ile His Asn Ala Leu His Ser Arg Leu Gly
            180                 185                 190

Gly Arg Ala Lys Tyr Ser Leu Ser Ser Leu Asp Tyr Thr Ala Phe Asp
        195                 200                 205

Pro Val Phe Phe Leu His His Ala Asn Val Asp Arg Ile Trp Ala Ile
    210                 215                 220

Trp Gln Asp Leu Gln Arg Tyr Arg Lys Lys Pro Tyr Asn Glu Ala Asp
225                 230                 235                 240

Cys Ala Val Asn Glu Met Arg Lys Pro Leu Gln Pro Phe Asn Asn Pro
                245                 250                 255

Glu Leu Asn Ser Asp Ser Met Thr Leu Lys His Asn Leu Pro Gln Asp
            260                 265                 270

Ser Phe Asp Tyr Gln Asn Arg Phe Arg Tyr Gln Tyr Asp Asn Leu Gln
        275                 280                 285

Phe Asn His Phe Ser Ile Gln Lys Leu Asp Gln Thr Ile Gln Ala Arg
    290                 295                 300

Lys Gln His Asp Arg Val Phe Ala Gly Phe Ile Leu His Asn Ile Gly
305                 310                 315                 320

Thr Ser Ala Val Val Asp Ile Tyr Ile Cys Val Glu Gln Gly Gly Glu
                325                 330                 335

Gln Asn Cys Lys Thr Lys Ala Gly Ser Phe Thr Ile Leu Gly Gly Glu
            340                 345                 350

Thr Glu Met Pro Phe His Phe Asp Arg Leu Tyr Lys Phe Asp Ile Thr
        355                 360                 365

Ser Ala Leu His Lys Leu Gly Val Pro Leu Asp Gly His Gly Phe Asp
    370                 375                 380
```

-continued

```
Ile Lys Val Asp Val Arg Ala Val Asn Gly Ser His Leu Asp Gln His
385                 390                 395                 400

Ile Leu Asn Glu Pro Ser Leu Leu Phe Val Pro Gly Glu Arg Lys Asn
                405                 410                 415

Ile Tyr Tyr


<210> SEQ ID NO 77
<211> LENGTH: 413
<212> TYPE: PRT
<213> ORGANISM: MEGATHURA CRENULATA

<400> SEQUENCE: 77

Asp Gly Leu Ser Gln His Asn Leu Val Arg Lys Glu Val Ser Ser Leu
1               5                   10                  15

Thr Thr Leu Glu Lys His Phe Leu Arg Lys Ala Leu Lys Asn Met Gln
            20                  25                  30

Ala Asp Asp Ser Pro Asp Gly Tyr Gln Ala Ile Ala Ser Phe His Ala
        35                  40                  45

Leu Pro Pro Leu Cys Pro Ser Pro Ser Ala Ala His Arg His Ala Cys
    50                  55                  60

Cys Leu His Gly Met Ala Thr Phe Pro Gln Trp His Arg Leu Tyr Thr
65                  70                  75                  80

Val Gln Phe Glu Asp Ser Leu Lys Arg His Gly Ser Ile Val Gly Leu
                85                  90                  95

Pro Tyr Trp Asp Trp Leu Lys Pro Gln Ser Ala Leu Pro Asp Leu Val
            100                 105                 110

Thr Gln Glu Thr Tyr Glu His Leu Phe Ser His Lys Thr Phe Pro Asn
        115                 120                 125

Pro Phe Leu Lys Ala Asn Ile Glu Phe Glu Gly Glu Gly Val Thr Thr
    130                 135                 140

Glu Arg Asp Val Asp Ala Glu His Leu Phe Ala Lys Gly Asn Leu Val
145                 150                 155                 160

Tyr Asn Asn Trp Phe Cys Asn Gln Ala Leu Tyr Ala Leu Glu Gln Glu
                165                 170                 175

Asn Tyr Cys Asp Phe Glu Ile Gln Phe Glu Ile Leu His Asn Gly Ile
            180                 185                 190

His Ser Trp Val Gly Gly Ser Lys Thr His Ser Ile Gly His Leu His
        195                 200                 205

Tyr Ala Ser Tyr Asp Pro Leu Phe Tyr Ile His His Ser Gln Thr Asp
    210                 215                 220

Arg Ile Trp Ala Ile Trp Gln Ala Leu Gln Glu His Arg Gly Leu Ser
225                 230                 235                 240

Gly Lys Glu Ala His Cys Ala Leu Glu Gln Met Lys Asp Pro Leu Lys
                245                 250                 255

Pro Phe Ser Phe Gly Ser Pro Tyr Asn Leu Asn Lys Arg Thr Gln Glu
            260                 265                 270

Phe Ser Lys Pro Glu Asp Thr Phe Asp Tyr His Arg Phe Gly Tyr Glu
        275                 280                 285

Tyr Asp Ser Leu Glu Phe Val Gly Met Ser Val Ser Ser Leu His Asn
    290                 295                 300

Tyr Ile Lys Gln Gln Gln Glu Ala Asp Arg Val Phe Ala Gly Phe Leu
305                 310                 315                 320

Leu Lys Gly Phe Gly Gln Ser Ala Ser Val Ser Phe Asp Ile Cys Arg
                325                 330                 335
```

```
Pro Asp Gln Ser Cys Gln Glu Ala Gly Tyr Phe Ser Val Leu Gly Gly
            340                 345                 350

Ser Ser Glu Met Pro Trp Gln Phe Asp Arg Leu Tyr Lys Tyr Asp Ile
        355                 360                 365

Thr Lys Thr Leu Lys Asp Met Lys Leu Arg Tyr Asp Asp Thr Phe Thr
    370                 375                 380

Ile Lys Val His Ile Lys Asp Ile Ala Gly Ala Glu Leu Asp Ser Asp
385                 390                 395                 400

Leu Ile Pro Thr Pro Ser Val Leu Leu Glu Glu Gly Lys
                405                 410


<210> SEQ ID NO 78
<211> LENGTH: 417
<212> TYPE: PRT
<213> ORGANISM: MEGATHURA CRENULATA

<400> SEQUENCE: 78

His Gly Ile Asn Val Arg His Val Gly Arg Asn Arg Ile Arg Met Glu
1               5                   10                  15

Leu Ser Glu Leu Thr Glu Arg Asp Leu Ala Ser Leu Lys Ser Ala Met
            20                  25                  30

Arg Ser Leu Gln Ala Asp Asp Gly Val Asn Gly Tyr Gln Ala Ile Ala
        35                  40                  45

Ser Phe His Gly Leu Pro Ala Ser Cys His Asp Asp Glu Gly His Glu
    50                  55                  60

Ile Ala Cys Cys Ile His Gly Met Pro Val Phe Pro His Trp His Arg
65                  70                  75                  80

Leu Tyr Thr Leu Gln Met Asp Met Ala Leu Leu Ser His Gly Ser Ala
                85                  90                  95

Val Ala Ile Pro Tyr Trp Asp Trp Thr Lys Pro Ile Ser Lys Leu Pro
            100                 105                 110

Asp Leu Phe Thr Ser Pro Glu Tyr Tyr Asp Pro Trp Arg Asp Ala Val
        115                 120                 125

Val Asn Asn Pro Phe Ala Lys Gly Tyr Ile Lys Ser Glu Asp Ala Tyr
    130                 135                 140

Thr Val Arg Asp Pro Gln Asp Ile Leu Tyr His Leu Gln Asp Glu Thr
145                 150                 155                 160

Gly Thr Ser Val Leu Leu Asp Gln Thr Leu Leu Ala Leu Glu Gln Thr
                165                 170                 175

Asp Phe Cys Asp Phe Glu Val Gln Phe Glu Val Val His Asn Ala Ile
            180                 185                 190

His Tyr Leu Val Gly Gly Arg Gln Val Tyr Ala Leu Ser Ser Gln His
        195                 200                 205

Tyr Ala Ser Tyr Asp Pro Ala Phe Phe Ile His His Ser Phe Val Asp
    210                 215                 220

Lys Ile Trp Ala Val Trp Gln Ala Leu Gln Lys Lys Arg Lys Arg Pro
225                 230                 235                 240

Tyr His Lys Ala Asp Cys Ala Leu Asn Met Met Thr Lys Pro Met Arg
                245                 250                 255

Pro Phe Ala His Asp Phe Asn His Asn Gly Phe Thr Lys Met His Ala
            260                 265                 270

Val Pro Asn Thr Leu Phe Asp Phe Gln Asp Leu Phe Tyr Thr Tyr Asp
        275                 280                 285

Asn Leu Glu Ile Ala Gly Met Asn Val Asn Gln Leu Glu Ala Glu Ile
    290                 295                 300
```

```
Asn Arg Arg Lys Ser Gln Thr Arg Val Phe Ala Gly Phe Leu Leu His
305                 310                 315                 320

Gly Ile Gly Arg Ser Ala Asp Val Arg Phe Trp Ile Cys Lys Thr Ala
                325                 330                 335

Asp Asp Cys His Ala Ser Gly Met Ile Phe Ile Leu Gly Gly Ser Lys
            340                 345                 350

Glu Met His Trp Ala Tyr Asp Arg Asn Phe Lys Tyr Asp Ile Thr Gln
        355                 360                 365

Ala Leu Lys Ala Gln Ser Ile His Pro Glu Asp Val Phe Asp Thr Asp
    370                 375                 380

Ala Pro Phe Phe Ile Lys Val Glu Val His Gly Val Asn Lys Thr Ala
385                 390                 395                 400

Leu Pro Ser Ser Ala Ile Pro Ala Pro Thr Ile Ile Tyr Ser Ala Gly
                405                 410                 415

Glu


<210> SEQ ID NO 79
<211> LENGTH: 395
<212> TYPE: PRT
<213> ORGANISM: MEGATHURA CRENULATA
<220> FEATURE:
<221> NAME/KEY: MISC_FEATURE
<222> LOCATION: (55)..(55)
<223> OTHER INFORMATION: X is any naturally occurring amino acid

<400> SEQUENCE: 79

Asp His Ile Ala Gly Ser Gly Val Arg Lys Asp Val Thr Ser Leu Thr
1               5                   10                  15

Ala Ser Glu Ile Glu Asn Leu Arg His Ala Leu Gln Ser Val Met Asp
            20                  25                  30

Asp Asp Gly Pro Asn Gly Phe Gln Ala Ile Ala Ala Tyr His Gly Ser
        35                  40                  45

Pro Pro Met Cys His Met Xaa Asp Gly Arg Asp Val Ala Cys Cys Thr
    50                  55                  60

His Gly Met Ala Ser Phe Pro His Trp His Arg Leu Phe Val Lys Gln
65                  70                  75                  80

Met Glu Asp Ala Leu Ala Ala His Gly Ala His Ile Gly Ile Pro Tyr
                85                  90                  95

Trp Asp Trp Thr Ser Ala Phe Ser His Leu Pro Ala Leu Val Thr Asp
            100                 105                 110

His Glu His Asn Pro Phe His His Gly His Ile Ala His Arg Asn Val
        115                 120                 125

Asp Thr Ser Arg Ser Pro Arg Asp Met Leu Phe Asn Asp Pro Glu His
    130                 135                 140

Gly Ser Glu Ser Phe Phe Tyr Arg Gln Val Leu Leu Ala Leu Glu Gln
145                 150                 155                 160

Thr Asp Phe Cys Gln Phe Glu Val Gln Phe Glu Ile Thr His Asn Ala
                165                 170                 175

Ile His Ser Trp Thr Gly Gly His Thr Pro Tyr Gly Met Ser Ser Leu
            180                 185                 190

Glu Tyr Thr Ala Tyr Asp Pro Leu Phe Tyr Leu His His Ser Asn Thr
        195                 200                 205

Asp Arg Ile Trp Ala Ile Trp Gln Ala Leu Gln Lys Tyr Arg Gly Phe
    210                 215                 220

Gln Tyr Asn Ala Ala His Cys Asp Ile Gln Val Leu Lys Gln Pro Leu
```

-continued

```
225                 230                 235                 240

Lys Pro Phe Ser Glu Ser Arg Asn Pro Asn Pro Val Thr Arg Ala Asn
                245                 250                 255

Ser Arg Ala Val Asp Ser Phe Asp Tyr Glu Arg Leu Asn Tyr Gln Tyr
            260                 265                 270

Asp Thr Leu Thr Phe His Gly His Ser Ile Ser Glu Leu Asp Ala Met
        275                 280                 285

Leu Gln Glu Arg Lys Lys Glu Glu Arg Thr Phe Ala Ala Phe Leu Leu
    290                 295                 300

His Gly Phe Gly Ala Ser Ala Asp Val Ser Phe Asp Val Cys Thr Pro
305                 310                 315                 320

Asp Gly His Cys Ala Phe Ala Gly Thr Phe Ala Val Leu Gly Gly Glu
                325                 330                 335

Leu Glu Met Pro Trp Ser Phe Glu Arg Leu Phe Arg Tyr Asp Ile Thr
            340                 345                 350

Lys Val Leu Lys Gln Met Asn Leu His Tyr Asp Ser Glu Phe His Phe
        355                 360                 365

Glu Leu Lys Ile Val Gly Thr Asp Gly Thr Glu Leu Pro Ser Asp Arg
    370                 375                 380

Ile Lys Ser Pro Thr Ile Glu His His Gly Gly
385                 390                 395


<210> SEQ ID NO 80
<211> LENGTH: 1266
<212> TYPE: DNA
<213> ORGANISM: HALIOTIS TUBERCULATA

<400> SEQUENCE: 80

cttgttcagt ttctactcgt cgcccttgtg gtgggggctg gagcagacaa cgtcgtcaga      60

aaggacgtga gtcacctcac ggatgacgag gtgcaagctc tccacggcgc cctccatgac     120

gtcactgcat ctacagggcc tctgagtttc gaagacataa catcttacca tgccgcacca     180

gcgtcgtgtg actacaaggg acggaagatc gcctgctgtg tccacggtat gcccagtttc     240

cccttctggc acagggcata tgtcgtccaa gccgagcggg cactgttgtc caaacggaag     300

actgtcggaa tgccttactg ggactggacg caaacgctga ctcacttacc atctcttgtg     360

actgaaccca tctacattga cagtaaaggt ggaaaggctc aaaccaacta ctggtaccgc     420

ggcgagatag cgttcatcaa taagaagact gcgcgagctg tagatgatcg cctattcgag     480

aaggtggagc ctggtcacta cacacatctt atggagactg tcctcgacgc tctcgaacag     540

gacgaattct gtaaatttga aatccagttc gagttggctc ataatgctat ccattacttg     600

gttggcggta aatttgaata ttcaatgtca aacttggaat acacctccta cgaccccatc     660

ttcttcctcc accactccaa cgttgaccgc ctcttcgcca tctggcagcg tcttcaggaa     720

ctgcgaggaa agaatcccaa tgcaatggac tgtgcacatg aactcgctca ccagcaactc     780

caacccttca acagggacag caatccagtc cagctcacaa aggaccactc gacacctgct     840

gacctctttg attacaaaca acttggatac agctacgaca gcttaaacct gaatggaatg     900

acgccagaac agctgaaaac agaactagac gaacgccact ccaaagaacg tgcgtttgca     960

agcttccgac tcagtggctt tgggggttct gccaacgttg ttgtctatgc atgtgtccct    1020

gatgatgatc cacgcagtga tgactactgc gagaaagcag gcgacttctt cattcttggg    1080

ggtcaaagcg aaatgccgtg gagattctac agacccttct tctatgatgt aactgaagcg    1140

gtacatcacc ttggagtccc gctaagtggc cactactatg tgaaaacaga actcttcagc    1200
```

gtgaatggca cagcactttc acctgatctt cttcctcaac caactgttgc ctaccgacct 1260
gggaaa 1266

<210> SEQ ID NO 81
<211> LENGTH: 1257
<212> TYPE: DNA
<213> ORGANISM: HALIOTIS TUBERCULATA

<400> SEQUENCE: 81
ggtcaccttg acccacctgt gcatcatcgc cacgatgacg atcttattgt tcgaaaaaat 60
atagatcatt tgactcgtga agaggaatac gagctaagga tggctctgga gagattccag 120
gccgacacat ccgttgatgg gtaccaggct acagtagagt accatggcct tcctgctcgt 180
tgtccacgac cagatgcaaa agtcaggttc gcctgttgta tgcatggcat ggcatccttc 240
cctcactggc accggctgtt cgttacccag gtggaagatg ctcttgtacg gcgtggatcg 300
cctatcggtg ttccttattg ggactggaca aaacctatga ctcaccttcc agacttggca 360
tcaaatgaga cgtacgtaga cccgtatgga catacacatc ataatccatt cttcaatgca 420
aatatatctt ttgaggaggg acaccatcac acgagcagga tgatagattc gaaactgttt 480
gccccagtcg cttttgggga gcattcccat ctgtttgatg gaatcctgta cgcatttgag 540
caggaagatt tctgcgactt tgagattcag tttgagttag tccataattc tattcatgcg 600
tggataggcg gttccgaaga ttactccatg gccaccctgc attacacagc ctttgacccc 660
attttctacc ttcatcattc caatgtcgat cgtctatggg caatctggca agctcttcaa 720
atcaggagac acaagccata tcaagcccac tgtgcacagt ctgtggaaca gttgccaatg 780
aagccatttg ctttcccatc acctcttaac aacaacgaga agacacatag tcattcagtc 840
ccgactgaca tttatgacta cgaggaagtg ctgcactaca gctacgatga tctaacgttt 900
ggtgggatga accttgaaga aatagaagaa gctatacatc tcagacaaca gcatgaacga 960
gtcttcgcgg gatttctcct tgctggaata ggaacatctg cacttgttga cattttcata 1020
aataaaccgg ggaaccaacc actcaaagct ggagatattg ccattcttgg tggtgccaag 1080
gaaatgcctt gggcgtttga ccgcttgtat aaggtcgaaa taactgactc attgaagaca 1140
ctttctctcg atgtcgatgg agattatgaa gtcactttta aaattcatga tatgcacgga 1200
aacgctcttg atacggacct gattccacac gcagcagttg tttctgagcc agctcac 1257

<210> SEQ ID NO 82
<211> LENGTH: 1242
<212> TYPE: DNA
<213> ORGANISM: HALIOTIS TUBERCULATA

<400> SEQUENCE: 82
cctacctttg aggatgaaaa gcacagctta cgaatcagaa aaaatgtcga cagcttgact 60
cctgaagaaa caaatgaact gcgtaaagcc ctggagcttc ttgaaaatga tcatactgca 120
ggtggattca atcagcttgg cgccttccat ggagagccta aatggtgccc taatcctgaa 180
gcggagcaca aggttgcatg ctgtgttcat ggcatggctg ttttccctca ttggcacagg 240
cttcttgctc tccaggcgga gaatgctctt agaaagcatg ggtacagtgg tgctctacca 300
tactgggatt ggactcgccc cctttcccaa cttcctgatc tggttagtca tgagcagtat 360
acagatcctt ccgaccatca cgtgaagcat aacccgtggt tcaatggcca catcgataca 420
gtaaatcagg ataccaccag aagcgtacgg gaggatcttt atcaacaacc tgaatttgga 480

```
catttcacgg atattgctca acaagtcctc ttagcattag aacaagatga cttctgttcg    540

tttgaagtgc agtatgagat ttcccataat tttatccatg cacttgtagg aggaaccgac    600

gcttatggca tggcatcgct gagatataca gcatacgatc caatcttttt cttgcatcat    660

tcaaacaccg acaggatctg ggctatttgg caatccctgc aaaaatacag aggcaaaccg    720

tacaacactg ccaactgcgc catagaatct atgagaaggc cctgcaacc atttggacta    780

agcagtgcca ttaaccctga cagaatcacc agagagcatg ctatcccgtt tgatgtcttc    840

aactatagag ataaccttca ttacgtatat gataccctgg aatttaatgg tttgtcgatt    900

tcacaacttg atagagagct ggaaaaaatc aagagtcacg aaagagtatt tgctggattc    960

ttgctgtcgg ggattaaaaa atctgctctt gtgaaattcg aagtttgtac tccacctgat   1020

aattgtcata aagcagggga gttttatcta ctcggggacg aaaacgagat ggcttgggcc   1080

tatgaccgac ttttcaagta tgatattact caggttctgg aagcaaacca tctacacttc   1140

tatgatcatc tcttcattcg ctacgaagtc tttgatctta aggagtgag tttgggaact   1200

gacctgttcc acactgcaaa tgtggtacat gattccggca ca                        1242
```

<210> SEQ ID NO 83
<211> LENGTH: 1239
<212> TYPE: DNA
<213> ORGANISM: HALIOTIS TUBERCULATA

<400> SEQUENCE: 83

```
ggcacccgtg atcgtgataa ctacgttgaa gaagttactg ggccagtca tatcaggaag      60

aatttgaacg acctcaatac cggagaaatg gaaagcctta gagctgcttt cctgcatatt    120

caggacgacg gaacatatga atctattgcc cagtaccatg gcaaaccagg caaatgtcaa    180

ttgaatgatc ataatattgc gtgttgtgtc catggtatgc ctaccttccc ccagtggcac    240

agactgtatg tggttcaggt ggagaatgct ctcctaaaca ggggatctgg tgtggctgtt    300

ccttactggg agtggactgc tcccatagac catctacctc atttcattga tgatgcaaca    360

tacttcaatt cccgacaaca gcggtacgac cctaaccctt tcttcagggg aaaggttact    420

tttgaaaacg cagtcacaac aagggaccca caagccgggc tcttcaactc agattatatg    480

tatgagaatg ttttacttgc actggagcag gaaaattatt gtgactttga aattcagttt    540

gagcttgttc ataacgcact tcattccatg ctgggaggta aagggcagta ctccatgtcc    600

tccctggact attctgcgtt tgatcccgtc ttcttcctac atcatgccaa cacggacaga    660

ctgtgggcaa tctggcagga actacaaaga ttccgagaac tgccttatga agaagcgaac    720

tgtgcaatca acctcatgca tcaaccactg aagccgttca gtgatccaca tgagaatcac    780

gacaatgtca ctttgaaata ctcaaaacca caggacggat tcgactacca gaaccacttc    840

ggatacaagt atgacaacct tgagttccat cacttatcta tcccaagtct tgatgctacc    900

ctgaagcaaa ggagaaatca cgacagagtg tttgcgggct tccttcttca taacatagga    960

acttctgctg acataactat ctacatatgt ctgcctgacg gacggcgtgg caatgactgc   1020

agtcatgagg cgggaacatt ctatatcctc ggaggcgaaa cagagatgcc ttttatcttt   1080

gaccgtttgt ataaatttga aatcaccaaa ccactgcaac agttaggagt caagctgcat   1140

ggtggagttt tcgaactgga gcttgagatc aaggcataca acggttccta tctggatccc   1200

catacctttg atccaactat catctttgaa cctggaaca                           1239
```

<210> SEQ ID NO 84
<211> LENGTH: 1260

<212> TYPE: DNA
<213> ORGANISM: HALIOTIS TUBERCULATA

<400> SEQUENCE: 84
gatacccata tcttggacca cgaccatgag gaagagatac ttgtcaggaa gaatataatt 60
gatttgagcc caagggagag ggtttctcta gtcaaagctt tgcaaagaat gaagaatgat 120
cgctccgctg atgggtacca agccattgcc tctttccatg ccctgccacc actctgtccc 180
aatccatctg cagctcaccg ttatgcttgc tgtgtccatg gcatggctac atttccccag 240
tggcacagac tgtacactgt tcaggttcag gatgccctga ggagacatgg ttcacttgtt 300
ggtattcctt actgggactg gacaaaacca gtcaacgagt tacccgagct tctttcttca 360
gcaacatttt atcatccaat ccggaatatt aatatttcaa atccattcct cggggctgac 420
atagaatttg aaggaccggg cgttcataca gagaggcaca taaatactga gcgcctgttt 480
cacagtgggg atcatgacgg ataccacaac tggttcttcg aaactgttct ctttgctttg 540
gaacaggaag attactgcga ttttgaaata caatttgaga tagcccataa tggcatccac 600
acatggattg gtggaagcgc agtatatggc atgggacacc ttcactatgc atcatatgat 660
ccaattttct acatccacca ttcacagacg gacagaatat gggctatttg gcaagagctg 720
cagaagtaca ggggtctatc tggttcggaa gcaaactgtg ccattgaaca tatgagaaca 780
cccttgaagc ctttcagctt tgggccaccc tacaatttga atagtcatac gcaagaatat 840
tcaaagcctg aggacacgtt tgactataag aagtttggat acagatatga tagtctggaa 900
ttggaggggc gatcaatttc tcgcattgat gaacttatcc agcagagaca ggagaaagac 960
agaacttttg cagggttcct ccttaaaggt tttggtacat ccgcatctgt gtcattgcaa 1020
gtttgcagag ttgatcacac ctgtaaagat gcgggctatt tcactattct gggaggatca 1080
gccgaaatgc catgggcatt cgacaggctt tataagtatg acattactaa aactcttcac 1140
gacatgaacc tgaggcacga ggacactttc tctatagacg taactatcac gtcttacaat 1200
ggaacagtac tctcgggaga cctcattcag acgccctcca ttatatttgt acctggacgc 1260

<210> SEQ ID NO 85
<211> LENGTH: 1251
<212> TYPE: DNA
<213> ORGANISM: HALIOTIS TUBERCULATA

<400> SEQUENCE: 85
cataaactca actcacggaa acatacacct aacagagtcc gccatgagct aagtagcctt 60
agttcccgtg acatagcaag cttgaaggca gctttgacaa gccttcaaca tgataatggg 120
actgatggtt atcaagctat tgctgccttc catggcgttc ctgcgcagtg ccacgagcca 180
tctggacgtg agatcgcctg ttgcatccac ggcatggcga cgtttcctca ctggcaccgg 240
ttgtacactc tgcagttgga gcaagcgctg cgcagacacg ggtccagtgt tgctgttcca 300
tactgggact ggaccaagcc aatcaccgaa ctgccacaca ttctgacaga cggagaatat 360
tatgacgttt ggcaaaatgc cgtcttggcc aatccgtttg caagaggtta tgtgaaaatt 420
aaagatgcat ttacggtgag aaatgtccag gaaagtctgt tcaaaatgtc aagttttgga 480
aagcactcgc ttctgtttga ccaggctttg ttggctcttg aacaaactga ctactgtgac 540
ttcgaagttc agtttgaagt gatgcataac acgatccatt atctcgtagg agggcgtcaa 600
acgtacgcct tctcctctct cgagtattcc tcatacgatc caatcttctt tattcaccac 660
tcgtttgttg acaaaatatg ggctgtatgg caagaactgc aaagcaggag acatctacag 720

-continued

```
tttagaacag ctgattgtgc tgtgggcctc atgggtcagg caatgaggcc tttcaacaag    780

gatttcaacc acaactcgtt caccaagaag cacgcagtcc ctaatacagt atttgattat    840

gaagatcttg gctataacta tgacaacctt gaaatcagtg gtttaaactt aaatgagatc    900

gaggcgttaa tagcaaaacg caagtcacat gctagagtct ttgctgggtt cctgttgttt    960

ggattaggaa cttcggctga tatacatctg gaaatttgca agacatcgga aaactgccat   1020

gatgctggtg tgattttcat ccttggaggt tctgcagaga tgcattgggc atacaaccgc   1080

ctctacaagt atgacattac agaagcattg caggaatttg acatcaaccc tgaagatgtt   1140

ttccatgctg atgaaccatt tttcctgagg ctgtcggttg ttgctgtgaa tggaactgtc   1200

attccatcgt ctcatcttca ccagccaacg ataatctatg aaccaggcga a            1251
```

<210> SEQ ID NO 86
<211> LENGTH: 1209
<212> TYPE: DNA
<213> ORGANISM: HALIOTIS TUBERCULATA

<400> SEQUENCE: 86

```
gatcaccatg acgaccatca gtcgggaagc atagcaggat ccggggtccg caaggacgtg     60

aacaccttga ctaaggctga gaccgacaac ctgagggagg cgctgtgggg tgtcatggca    120

gaccacggtc ccaatggctt tcaagctatt gctgctttcc atggaaaacc agctttgtgt    180

cccatgcctg atggccacaa ctactcatgt tgtactcacg gcatggctac cttcccacac    240

tggcatcgcc tctacaccaa gcagatggag gatgcaatga gggcgcatgg gtctcatgtc    300

ggcctgccct actgggactg gactgctgcc ttcacccacc tgccaacact ggtcaccgac    360

acggacaaca acccccttcca acatggacac attgattatc tcaatgtcag cacaactcga    420

tctccccgag acatgctgtt caacgacccc gagcatggat cagagtcgtt cttctacaga    480

caagtcctct tagctctgga acaaactgat ttctgcaaat tcgaagttca gtttgagata    540

acccacaatg ccatccattc ctggacaggt ggccacagcc cctacggaat gtccactctc    600

gacttcactg cctacgatcc tctcttctgg cttcaccact ccaacaccga cagaatctgg    660

gctgtctggc aagctttgca agaatacaga ggacttccat acaaccatgc caattgtgag    720

atccaggcaa tgaaaacgcc cctgaggcct ttcagtgacg atatcaacca caacccagtc    780

acaaaggcta acgcgaagcc attagatgtg ttcgagtata atcggttgag cttccagtac    840

gacaacctca tcttccatgg atacagtatt ccggaacttg atcgcgtgct tgaagaaaga    900

aaggaggagg acagaatatt tgctgccttc cttctcagtg gaatcaagcg tagtgctgat    960

gtagtgttcg acatatgcca gccagaacac gaatgtgtgt tcgcagggac ttttgcgatt   1020

ttgggagggg agctagaaat gccctggtcc ttcgacagac tgttccgcta tgatatcacc   1080

aaggtgatga agcagctaca cctgaggcat gactctgact ttaccttcag ggtgaagatt   1140

gtcggcaccg acgaccacga gcttccttca gacagtgtca aagcaccaac tattgaattt   1200

gaaccgggc                                                           1209
```

<210> SEQ ID NO 87
<211> LENGTH: 1536
<212> TYPE: DNA
<213> ORGANISM: HALIOTIS TUBERCULATA

<400> SEQUENCE: 87

```
gtgcacagag gcggaaacca cgaagatgaa caccatgatg acagactcgc agatgtcctg     60

atcaggaaag aagttgactt cctctccctg caagaggcca acgcaattaa ggatgcactg    120
```

-continued

```
tacaagctcc agaatgacga cagtaaaggg ggctttgagg ccatagctgg ctatcacggg    180
tatcctaata tgtgtccaga aagaggtacc gacaagtatc cctgctgtgt ccacggaatg    240
cccgtgttcc cccactggca ccgcctgcat accattcaga tggagagagc tctgaaaaac    300
catggctctc caatgggcat tccttactgg gattggacaa agaagatgtc gagtcttcca    360
tctttctttg gagattccag caacaacaac cctttctaca aatattacat ccggggcgtg    420
cagcacgaaa caaccaggga cattaatcag agactcttta atcaaaccaa gtttggtgaa    480
tttgattacc tatattacct aactctgcaa gtcctggagg aaaactcgta ctgtgacttt    540
gaagttcagt atgagatcct ccataacgcc gtccactcct ggcttggagg aactggaaag    600
tattccatgt ctaccctgga gcattcggcc tttgaccctg tcttcatgat tcaccactcg    660
agtttggata gaatctggat cctttggcag aagttgcaaa agataagaat gaagccttac    720
tacgcattgg attgtgctgg cgacagactt atgaaagacc ccctgcatcc cttcaactac    780
gaaaccgtta atgaagatga attcacccgc atcaactctt tcccaagcat actgtttgac    840
cactacaggt tcaactatga atacgataac atgagaatca ggggtcagga catacatgaa    900
cttgaagagg taattcagga attaagaaac aaagatcgca tatttgctgg ttttgttttg    960
tcgggcttac ggatatcagc tacagtgaaa gtattcattc attcgaaaaa cgatacaagt   1020
cacgaagaat atgcaggaga atttgcagtt ttgggaggtg agaaggagat gccgtgggca   1080
tatgaaagaa tgctgaaatt ggacatctcc gatgctgtac acaagcttca cgtgaaagat   1140
gaagacatcc gttttagagt ggttgttact gcctacaacg gtgacgttgt taccaccagg   1200
ctgtctcagc cattcatcgt ccaccgtcca gcccatgtgg ctcacgacat cttggtaatc   1260
ccagtaggtg cgggccatga ccttccgcct aaagtcgtag taaagagcgg caccaaagtc   1320
gagtttacac caatagattc gtcggtgaac aaagcaatgg tggagctggg cagctatact   1380
gctatggcta aatgcatcgt tccccctttc tcttaccacg gctttgaact ggacaaagtc   1440
tacagcgtcg atcacggaga ctactacatt gctgcaggta cccacgcgtt gtgtgagcag   1500
aacctcaggc tccacatcca cgtggaacac gagtag                             1536
```

<210> SEQ ID NO 88
<211> LENGTH: 591
<212> TYPE: DNA
<213> ORGANISM: HALIOTIS TUBERCULATA

<400> SEQUENCE: 88

```
ggtcttccgt actgggactg gacgcagcat ctgactcaac tcccagatct ggtgtcagac     60
cccttgtttg tcgacccgga aggaggaaag gcccatgaca acgcatggta tcgtggaaac    120
atcaagtttg agaataagaa gactgcaaga gctgttgacg atcgcctttt cgagaaggtt    180
ggaccaggag agaataccccg actctttgaa ggaattctcg atgctcttga acaggatgaa    240
ttctgcaact tcgagatcca gtttgagttg gctcacaacg ctatccacta cctggttggc    300
ggccgtcaca cgtactccat gtctcatctc gagtacacct cctacgaccc cctcttcttc    360
ctccatcact ccaacccgga ccgcatcttc gccatctggg aacgtcttca ggtactcaga    420
ggaaaggacc ccaacaccgc cgactgcgca cacaacctca tccatgagcc catggaaccg    480
ttccgtcggc atgagcccat ggaaccgttc cgtcgggact cgaaccctct tgacctcacc    540
agggaaaact ccaaaccaat tgacagcttt gattatgccc accttggcta c             591
```

<210> SEQ ID NO 89

<211> LENGTH: 1245
<212> TYPE: DNA
<213> ORGANISM: HALIOTIS TUBERCULATA

<400> SEQUENCE: 89

```
gttacagagg ccccagctcc ctcctcggat gctcacctcg ccgtcaggaa ggatatcaac     60
catctgacac gcgaggaggt gtacgagctg cgcagagcta tggagagatt ccaggccgac    120
acatccgttg atgggtacca ggctacggtt gagtatcacg gcttacctgc tcgatgtcca    180
ttccccgagg ccacaaatag gttcgcctgt tgcatccacg gcatggcgac attccctcat    240
tggcacagac tgttcgtcac ccaggtggaa gatgctctga tcaggcgagg atcgcctata    300
ggggtcccct actgggactg gactcagcct atggcgcatc tcccaggact tgcagacaac    360
gccacctata gagatcccat cagcggggac agcagacaca accccttcca cgatgttgaa    420
gttgcctttg aaaatggacg tacagaacgt cacccagata gtagattgtt tgaacaacct    480
ttatttggca aacatacgcg tctcttcgac agtatagtct atgcttttga gcaggaggac    540
ttctgcgatt ttgaagttca atttgagatg acccataata atattcacgc ctggattggt    600
ggcggcgaga agtattccat gtcttctcta cactacacag ccttcgaccc tatcttctac    660
cttcgtcact ccaacactga ccggctctgg gcaatttggc aagcgttgca gatacgaaga    720
aacaggcctt acaaggctca ttgtgcttgg tctgaggaac gccagcctct caaacctttc    780
gccttcagtt ccccactgaa caacaacgaa aaaacctacg aaaactcggt gcccaccaac    840
gtttacgact acgaaggagt ccttggctat acttatgatg acctcaactt cgggggcatg    900
gacctgggtc agcttgagga atacatccag aggcagagac agagagacag gacctttgct    960
ggtttctttc tgtcacatat tggtacatca gcgaatgttg aaatcattat agaccatggg   1020
actcttcata cctccgtggg cacgtttgct gttcttggcg gagagaagga gatgaaatgg   1080
ggatttgacc gtttgtacaa atatgagatt acagatgaac tgaggcaact taatctccgt   1140
gctgatgatg ttttcagcat ctctgttaaa gtaactgatg ttgatggcag tgagctgtcc   1200
tctgaactca tcccatctgc tgctatcatc ttcgaacgaa gccat                   1245
```

<210> SEQ ID NO 90
<211> LENGTH: 1251
<212> TYPE: DNA
<213> ORGANISM: HALIOTIS ASSIMILIS

<400> SEQUENCE: 90

```
attgaccatc aggacccgca tcatgacaca atcattagga aaaatgttga taatcttaca     60
cccgaggaaa ttaattctct gaggcgggca atggcagacc ttcaatcaga caaaaaccgcc   120
ggtggattcc agcaaattgc tgcttttcac ggggaaccca aatggtgccc aagtcccgat    180
gctgagaaga agttctcctg ctgtgtccat ggaatggctg tcttccctca ctggcacaga    240
ctcctgaccg tgcaaggcga gaatgccctg agaaagcatg gatgtctcgg agctctcccc    300
tactgggact ggactcggcc cctgtctcac ctacctgatt tggttttggt aagtagcaga    360
actacaccga tgccatattc caccgtggaa gcccgaaacc cctggtacag cggccatatt    420
gatacagttg gtgttgacac aacaagaagc gtccgtcaag aactgtatga agctcctgga    480
tttggccatt atactggggt cgctaagcaa gtgcttctgg ctttggagca ggatgacttc    540
tgtgattttg aagtccagtt tgagatagct cacaatttca ttcacgctct tgtcggcgga    600
agcgagccat atggtatggc gtcactccgt tacactactt atgatccaat tttctacctc    660
catcattcta acactgacag actctgggct atatggcagg ctctacaaaa gtacaggggc    720
```

-continued

```
aaaccttaca attccgccaa ctgcgccatt gcttctatga gaaaacccct acaacccttt    780

ggtctgactg atgagatcaa cccggatgat gagacaagac agcatgctgt tcctttcagt    840

gtctttgatt acaagaacaa cttcaattat gaatatgaca cccttgactt caacggacta    900

tcaatctccc agctggaccg tgaactgtca cggagaaagt ctcatgacag agtatttgcc    960

ggatttttgc tgcatggtat tcagcagtct gcactagtta aattctttgt ctgcaaatca   1020

gatgatgact gtgaccacta tgctggtgaa ttctacatcc ttggtgatga agctgaaatg   1080

ccatggggct atgatcgtct ttacaaatat gagatcactg agcagctcaa tgccctggat   1140

ctacacatcg gagatagatt cttcatcaga tacgaagcgt ttgatcttca tggtacaagt   1200

cttggaagca acatcttccc caaaccttct gtcatacatg acgaaggggc a            1251
```

<210> SEQ ID NO 91
<211> LENGTH: 1242
<212> TYPE: DNA
<213> ORGANISM: HALIOTIS TUBERCULATA

<400> SEQUENCE: 91

```
ggtcaccatc aggctgacga gtacgacgaa gttgtaactg ctgcaagcca catcagaaag     60

aatttaaaag atctgtcaaa gggagaagta gagagcctaa ggtctgcctt cctgcaactt    120

cagaacgacg gagtctatga gaatattgcc aagttccacg gcaagcctgg gttgtgtgat    180

gataacggtc gcaaggttgc ctgttgtgtc catggaatgc ccaccttccc ccagtggcac    240

aggctctatg tcctccaggt ggagaatgct ttgctggaga gaggatctgc cgtctctgtg    300

ccatactggg actggactga aacatttaca gagctgccat ctttgattgc tgaggctacc    360

tatttcaatt cccgtcaaca aacgtttgac cctaatcctt tcttcagagg taaaatcagt    420

tttgagaatg ctgttacaac acgtgatccc cagcctgagc tgtacgttaa caggtactac    480

taccaaaacg tcatgttggt ttttgaacag gacaactact gcgacttcga gatacagttt    540

gagatggttc acaatgttct ccatgcttgg cttggtggaa gagctactta ttctatttct    600

tctcttgatt attctgcatt cgaccctgtg tttttccttc accatgcgaa cacagataga    660

ttgtgggcca tctggcagga gctgcagagg tacaggaaga agccatacaa tgaagcggat    720

tgtgccatta acctaatgcg caaacctcta catcccttcg acaacagtga tctcaatcat    780

gatcctgtaa cctttaaata ctcaaaaccc actgatggct ttgactacca gaacaacttt    840

ggatacaagt atgacaacct tgagttcaat catttcagta ttcccaggct tgaagaaatc    900

attcgtatta gacaacgtca agatcgtgtg tttgcaggat tcctccttca caacattggg    960

acatccgcaa ctgttgagat attcgtctgt gtccctacca ccagcggtga gcaaaactgt   1020

gaaaacaaag ccggaacatt tgccgtactc ggaggagaaa cagagatggc gtttcatttt   1080

gacagactct acaggtttga catcagtgaa acactgaggg acctcggcat acagctggac   1140

agccatgact ttgacctcag catcaagatt caaggagtaa atggatccta ccttgatcca   1200

cacatcctgc cagagccatc cttgattttt gtgcctggtt ca                      1242
```

<210> SEQ ID NO 92
<211> LENGTH: 1257
<212> TYPE: DNA
<213> ORGANISM: HALIOTIS TUBERCULATA

<400> SEQUENCE: 92

```
agttctttcc tgcgtcctga tgggcattca gatgacatcc ttgtgagaaa agaagtgaac     60
```

-continued

```
agcctgacaa ccagggagac tgcatctctg atccatgctc tgaaaagtat gcaggaagac    120
cattcacctg acgggttcca agccattgcc tctttccatg ctctgccacc actctgccct    180
tcaccatctg cagctcaccg ttatgcttgc tgtgtccacg gcatggctac atttccccag    240
tggcacagat tgtacactgt acagttccag gatgcactga ggagacatgg agctacggta    300
ggtgtaccgt attgggattg gctgcgaccg cagtctcacc taccagagct tgtcaccatg    360
gagacatacc atgatatttg gagtaacaga gatttcccca atcctttcta ccaagccaat    420
attgagtttg aaggagaaaa cattacaaca gagagagaag tcattgcaga caaacttttt    480
gtcaaaggtg gacacgtttt tgataaactg gttcttcaaa caagccatcc tagcgctgag    540
caggaaaact actgtgactt tgagattcag tttgaaattc ttcacaacgg cgttcacacg    600
tgggtcggag gcagtcgtac ctactctatc ggacatcttc attacgcatt ctacgaccct    660
cttttctacc ttcaccattt ccagacagac cgtatttggg caatctggca agaactccag    720
gaacagagag ggctctcggg tgatgaggct cactgtgctc tcgagcaaat gagagaacca    780
ttgaagcctt tcagcttcgg cgctccttat aactggaatc agctcacaca ggatttctcc    840
cgacccgagg acaccttcga ctacaggaag tttggttatg aatatgacaa tttagaattc    900
ctgggaatgt cagttgctga actggatcaa tacattattg aacatcaaga aaatgataga    960
gtattcgctg ggttcctgtt gagtggattc ggaggttccg catcagttaa tttccaggtt   1020
tgtagagctg attccacatg tcaggatgct gggtacttca ccgttcttgg tggcagtgct   1080
gagatggcgt gggcatttga caggctttac aaatatgaca ttactgaaac tctggagaaa   1140
atgcaccttc gatatgatga tgacttcaca atctctgtca gtctgaccgc caacaacgga   1200
actgtcctga gcagcagtct aatcccaaca ccgagtgtca tattccagcg gggacat      1257
```

<210> SEQ ID NO 93
<211> LENGTH: 1248
<212> TYPE: DNA
<213> ORGANISM: HALIOTIS TUBERCULATA

<400> SEQUENCE: 93

```
cgtgacataa ataccaggag catgtcaccg aaccgtgttc gccgtgagct gagcgatctg     60
tctgcgaggg acctgtctag tctcaagtct gctctgcgag acctacagga ggatgatggc    120
cccaacggat accaggctct tgcagccttc catgggctac cagcaggctg ccatgatagc    180
cggggaaatg agatcgcatg ttgcattcac gggatgccga ccttccccca gtggcacaga    240
ctgtacaccc tgcagttgga gatggctctg aggagacatg gatcatctgt cgccatcccc    300
tactgggact ggacaaagcc tatctccgaa ctcccctcgc tcttcaccag ccctgagtat    360
tatgacccat ggcatgatgc tgtggtaaac aacccattct ccaaaggttt tgtcaaattt    420
gcaaatacct acacagtaag agacccacag gagatgctgt tccagctttg tgaacatgga    480
gagtcaatcc tctatgagca aactcttctt gctcttgagc aaaccgacta ctgtgatttt    540
gaggtacagt ttgaggtcct ccataacgtg atccactacc ttgttggtgg acgtcagacc    600
tacgcattgt cttctctgca ttatgcctcc tacgacccat tcttctttat acaccattcc    660
tttgtggata agatgtgggt agtatggcaa gctcttcaaa agaggaggaa acttccatac    720
aagcgagctg actgtgctgt caacctaatg actaaaccaa tgaggccatt tgactccgat    780
atgaatcaga acccattcac aaagatgcac gcagttccca acacactcta tgactacgag    840
acactgtact acagctacga taatctcgaa ataggtggca ggaatctcga ccagcttcag    900
gctgaaattg acagaagcag aagccacgat cgcgtttttg ctggattctt gcttcgtgga    960
```

```
atcggaactt ctgctgatgt caggttttgg atttgtagaa atgaaaatga ctgccacagg   1020

ggtggaataa ttttcatctt aggtggagcc aaggaaatgc catggtcatt tgacagaaac   1080

ttcaagtttg atatcaccca tgtactcgag aatgctggca ttagcccaga ggacgtgttt   1140

gatgctgagg agccatttta tatcaaggtt gagatccatg ctgttaacaa gaccatgata   1200

ccgtcgtctg tgatcccagc cccaactatc atctattctc ctggggaa                1248
```

<210> SEQ ID NO 94
<211> LENGTH: 1206
<212> TYPE: DNA
<213> ORGANISM: HALIOTIS TUBERCULATA

<400> SEQUENCE: 94

```
ggtcgcgctg ctgacagtgc gcactctgcc aacattgctg gctctggggt gaggaaggac     60

gtcacgaccc tcactgtgtc tgagaccgag aacctaagac aggctcttca aggtgtcatc    120

gatgatactg gtcccaatgg ttaccaagca atagcatcct tccacggaag tcctccaatg    180

tgcgagatga acggccgcaa ggttgcctgt tgtgctcacg gtatggcctc cttcccacac    240

tggcacagac tgtatgtgaa gcagatggaa gatgccctgg ctgaccacgg gtcacatatc    300

ggcatccctt actgggactg gacaactgcc ttcacagagt tacccgccct tgtcacagac    360

tccgagaaca atcccttcca tgagggtcgc attgatcatc tcggtgtaac cacgtcacgt    420

tcccccagag acatgctgtt taacgaccca gagcaaggat cagagtcgtt cttctataga    480

caagtcctcc tggctttgga gcagactgac tactgccagt tcgaagtcca gtttgagctg    540

acccacaacg ccattcactc ctggacaggt ggacgtagcc cttacggaat gtcgaccctc    600

gagttcacag cctacgatcc tctcttctgg cttcaccact ccaacaccga cagaatctgg    660

gctgtctggc aagcactgca gaaataccga ggactcccat acaacgaagc acactgtgaa    720

atccaggttc tgaaacagcc cttgaggcca ttcaacgatg acatcaacca caatccaatc    780

accaagacta atgccaggcc tatcgattca tttgattatg agaggtttaa ctatcagtat    840

gacaccctta gcttccatgg taagagcatc cctgaactga atgacctgct cgaggaaaga    900

aaaagagaag agagaacatt tgctgccttc cttcttcgtg gaatcggttg cagtgctgat    960

gtcgtctttg acatctgccg gcccaatggt gactgtgtct ttgcaggaac ctttgctgtg   1020

ctgggagggg agctagaaat gccttggtcc ttcgacagac tgttccgcta tgacatcacc   1080

agagtcatga atcagctcca tctccagtat gattcagatt tcagtttcag ggtgaagctt   1140

gttgccacca atggcactga gctttcatca gaccttctca agtcaccaac aattgaacat   1200

gaactt                                                              1206
```

<210> SEQ ID NO 95
<211> LENGTH: 1548
<212> TYPE: DNA
<213> ORGANISM: HALIOTIS TUBERCULATA
<220> FEATURE:
<221> NAME/KEY: misc_feature
<222> LOCATION: (1275)..(1275)
<223> OTHER INFORMATION: n is a, g, c, or t

<400> SEQUENCE: 95

```
ggagcccaca gaggaccagt tgaagaaaca gaagtcactc gccaacatac tgacggcaat     60

gcacactttc atcgtaagga agttgattcg ctgtccctgg atgaagcaaa caacttgaag    120

aatgcccttt acaagctaca gaacgaccac agtctaacgg gatacgaagc aatctctggt    180
```

-continued

```
taccatggat accccaatct gtgtccggaa gaaggcgatg acaaaatacc cctgctgcgt    240

ccccggatgg gcatctttcc ttactggcac agactcttga ccattcaact ggaaagagct    300

cttgagcaca atggtgcact gcttggtgtt ccttactggg actggaacaa ggacctgtcg    360

tcactgccgg cgttcttctc cgactccagc aacaacaatc cctacttcaa gtaccacatc    420

gccggtgttg gtcacgacac cgtcagagag ccaactagtc ttatatataa ccagccccaa    480

atccatggtt atgattatct ctattaccta gcattgacca cgcttgaaga aaacaattac    540

tgggactttg aggttcagta tgagatcctc cacaacgccg tccactcctg gcttggagga    600

tcccagaagt attccatgtc taccctggag tattcggcct ttgaccctgt ctttatgatc    660

cttcactcgg gtctagacag actttggatc atctggcaag aacttcagaa gatcaggaga    720

aagccctaca acttcgctaa atgtgcttat catatgatgg aagagccact ggcgcccttc    780

agctatccat ctatcaacca ggacgagttc acccgtgcca actccaagcc ttctacagtt    840

tttgacagcc ataagttcgg ctaccattac gataacctga atgttagagg tcacagcatc    900

caagaactca acacaatcat caatgacttg agaaacacag acagaatcta cgcaggattt    960

gttttgtcag gcatcggtac gtctgctagt gtcaagatct atctccgaac agatgacaat   1020

gacgaagaag ttggaacttt cactgtcctg ggaggagaga gggaaatgcc atgggcctac   1080

gagcgagttt tcaagtatga catcacagag gttgcagata gacttaaaat taagttatgg   1140

ggacaccctt taacttccgg aactggagat cacatcctta cgaatggaat cggtggtaaa   1200

caagagccta cccaaatcct ttcatcatct acagacctgc caatcatgac tacgatgttc   1260

ttgttatccc agtanggaag aaaccttcac atccctccca aagttgtcgt caagaaaggc   1320

acccgcatcg agttccaccc agtcgatgat tcagttacga gaccagttgt tgatcttgga   1380

agctacactg cactcttcaa ctgtgtggta ccaccgttca cataccacgg attcgaactg   1440

aaccacgtct attctgtcaa gcctggtgac tactatgtta ctggacccac gagagacctt   1500

tgccagaatg cagatgtcag gattcatatc catgttgagg atgagtaa                1548
```

```
<210> SEQ ID NO 96
<211> LENGTH: 966
<212> TYPE: DNA
<213> ORGANISM: MEGATHURA CRENULATA

<400> SEQUENCE: 96

ggcctaccgt actgggactg gactgaaccc atgacacaca ttccgggtct ggcaggaaac     60

aaaacttatg tggattctca tggtgcatcc cacacaaatc cttttcatag ttcagtgatt    120

gcatttgaag aaaatgctcc ccacaccaaa agacaaatag atcaaagact ctttaaaccc    180

gctacctttg gacaccacac agacctgttc aaccagattt tgtatgcctt tgaacaagaa    240

gattactgtg actttgaagt ccaatttgag attacccata acacgattca cgcttggaca    300

ggaggaagcg aacatttctc aatgtcgtcc ctacattaca cagctttcga tcctttgttt    360

tactttcacc attctaacgt tgatcgtctt tgggccgttt ggcaagcctt acagatgaga    420

cggcataaac cctacagggc ccactgcgcc atatctctgg aacatatgca tctgaaacca    480

ttcgcctttt catctcccct taacaataac gaaaagactc atgccaatgc catgccaaac    540

aagatctacg actatgaaaa tgtcctccat tacacatacg aagatttaac atttggaggc    600

atctctctgg aaaacataga aaagatgatc cacgaaaacc agcaagaaga cagaatatat    660

gccggttttc tcctggctgg catacgtact tcagcaaatg ttgatatctt cattaaaact    720

accgattccg tgcaacataa ggctggaaca tttgcagtgc tcggtggaag caaggaaatg    780
```

aagtggggat ttgatcgcgt tttcaagttt gacatcacgc acgttttgaa agatctcgat 840
ctcactgctg atggcgattt cgaagttact gttgacatca ctgaagtcga tggaactaaa 900
cttgcatcca gtcttattcc acatgcttct gtcattcgtg agcatgcacg tggtaagctg 960
aataga 966

<210> SEQ ID NO 97
<211> LENGTH: 1242
<212> TYPE: DNA
<213> ORGANISM: MEGATHURA CRENULATA

<400> SEQUENCE: 97
gttaaatttg acaaagtgcc aaggagtcgt cttattcgaa aaaatgtaga ccgtttgagc 60
cccgaggaga tgaatgaact tcgtaaagcc ctagccttac tgaaagagga caaaagtgcc 120
ggtggatttc agcagcttgg tgcattccat ggggagccaa aatggtgtcc tagtcccgaa 180
gcatctaaaa aatttgcctg ctgtgttcac ggcatgtctg tgttccctca ctggcatcga 240
ctgttgacgg ttcagagtga aaatgctttg agacgacatg gctacgatgg agctttgccg 300
tactgggatt ggacctctcc tcttaatcac cttcccgaac tggcagatca tgagaagtac 360
gtcgaccctg aagatggggt agagaagcat aacccttggt tcgatggtca tatagataca 420
gtcgacaaaa caacaacaag aagtgttcag aataaactct tcgaacagcc tgagtttggt 480
cattatacaa gcattgccaa acaagtactg ctagcgttgg aacaggacaa tttctgtgac 540
tttgaaatcc aatatgagat tgcccataac tacatccatg cacttgtagg aggcgctcag 600
ccttatggta tggcatcgct tcgctacact gcttttgatc cactattcta cttgcatcac 660
tctaatacag atcgtatatg ggcaatatgg caggctttac agaagtacag aggaaaaccg 720
tacaacgttg ctaactgtgc tgttacatcg atgagagaac ctttgcaacc atttggcctc 780
tctgccaata tcaacacaga ccatgtaacc aaggagcatt cagtgccatt caacgttttt 840
gattacaaga ccaatttcaa ttatgaatat gacactttgg aatttaacgg tctctcaatc 900
tctcagttga ataaaaagct cgaagcgata aagagccaag acaggttctt tgcaggcttc 960
ctgttatctg gtttcaagaa atcatctctt gttaaattca atatttgcac cgatagcagc 1020
aactgtcacc ccgctggaga gttttacctt ctgggtgatg aaaacgagat gccatgggca 1080
tacgatagag tcttcaaata tgacataacc gaaaaactcc acgatctaaa gctgcatgca 1140
gaagaccact tctacattga ctatgaagta tttgacctta aaccagcaag cctgggaaaa 1200
gatttgttca agcagccttc agtcattcat gaaccaagaa ta 1242

<210> SEQ ID NO 98
<211> LENGTH: 1236
<212> TYPE: DNA
<213> ORGANISM: MEGATHURA CRENULATA

<400> SEQUENCE: 98
ggtcaccatg aaggcgaagt atatcaagct gaagtaactt ctgccaaccg tattcgaaaa 60
aacattgaaa atctgagcct tggtgaactc gaaagtctga gagctgcctt cctggaaatt 120
gaaaacgatg gaacttacga atcaatagct aaattccatg gtagccctgg tttgtgccag 180
ttaaatggta accccatctc ttgttgtgtc catggcatgc caactttccc tcactggcac 240
agactgtacg tggttgtcgt tgagaatgcc ctcctgaaaa aaggatcatc tgtagctgtt 300
ccctattggg actggacaaa acgaatcgaa catttacctc acctgatttc agacgccact 360

```
tactacaatt ccaggcaaca tcactatgag acaaacccat tccatcatgg caaaatcaca    420

cacgagaatg aaatcactac tagggatccc aaggacagcc tcttccattc agactacttt    480

tacgagcagg tcctttacgc cttggagcag gataacttct gtgatttcga gattcagttg    540

gagatattac acaatgcatt gcattcttta cttggtggca aaggtaaata ttccatgtca    600

aaccttgatt acgctgcttt tgatcctgtg ttcttccttc atcacgcaac gactgacaga    660

atctgggcaa tctggcaaga ccttcagagg ttccgaaaac ggccataccg agaagcgaat    720

tgcgctatcc aattgatgca cacgccactc cagccgtttg ataagagcga caacaatgac    780

gaggcaacga aaacgcatgc cactccacat gatggttttg aatatcaaaa cagctttggt    840

tatgcttacg ataatctgga actgaatcac tactcgattc ctcagcttga tcacatgctg    900

caagaaagaa aaaggcatga cagagtattc gctggcttcc tccttcacaa tattggaaca    960

tctgccgatg gccatgtatt tgtatgtctc ccaactgggg aacacacgaa ggactgcagt   1020

catgaggctg gtatgttctc catcttaggc ggtcaaacgg agatgtcctt tgtatttgac   1080

agactttaca aacttgacat aactaaagcc ttgaaaaaga acggtgtgca cctgcaaggg   1140

gatttcgatc tggaaattga gattacggct gtgaatggat ctcatctaga cagtcatgtc   1200

atccactctc ccactatact gtttgaggcc ggaaca                            1236
```

<210> SEQ ID NO 99
<211> LENGTH: 1257
<212> TYPE: DNA
<213> ORGANISM: MEGATHURA CRENULATA

<400> SEQUENCE: 99

```
gattctgccc acacagatga tggacacact gaaccagtga tgattcgcaa agatatcaca     60

caattggaca agcgtcaaca actgtcactg gtgaaagccc tcgagtccat gaaagccgac    120

cattcatctg atgggttcca ggcaatcgct tccttccatg ctcttcctcc tctttgtcca    180

tcaccagctg cttcaaagag gtttgcgtgc tgcgtccatg gcatggcaac gttcccacaa    240

tggcaccgtc tgtacacagt ccaattccaa gattctctca gaaaacatgg tgcagtcgtt    300

ggacttccgt actgggactg gaccctacct cgttctgaat taccagagct cctgaccgtc    360

tcaactattc atgacccgga gacaggcaga gatataccaa atccatttat tggttctaaa    420

atagagtttg aaggagaaaa cgtacatact aaaagagata tcaataggga tcgtctcttc    480

cagggatcaa caaaaacaca tcataactgg tttattgagc aagcactgct tgctcttgaa    540

caaaccaact actgcgactt cgaggttcag tttgaaatta tgcataatgg tgttcatacc    600

tgggttggag gcaaggagcc ctatggaatt ggccatctgc attatgcttc ctatgatcca    660

cttttctaca tccatcactc ccaaactgat cgtatttggg ctatatggca atcgttgcag    720

cgtttcagag gactttctgg atctgaggct aactgtgctg taaatctcat gaaaactcct    780

ctgaagcctt tcagctttgg agcaccatat aatcttaatg atcacacgca tgatttctca    840

aagcctgaag atacattcga ctaccaaaag tttggataca tatatgacac tctggaattt    900

gcagggtggt caattcgtgg cattgaccat attgtccgta acaggcagga acattcaagg    960

gtctttgccg gattcttgct tgaaggattt ggcacctctg ccactgtcga tttccaggtc   1020

tgtcgcacag cgggagactg tgaagatgca gggtacttca ccgtgttggg aggtgaaaaa   1080

gaaatgcctt gggcctttga tcggctttac aagtacgaca taacagaaac cttagacaag   1140

atgaaccttc gacatgacga aatcttccag attgaagtaa ccattacatc ctacgatgga   1200

actgtactcg atagtggcct tattcccaca ccgtcaatca tctatgatcc tgctcat      1257
```

<210> SEQ ID NO 100
<211> LENGTH: 1254
<212> TYPE: DNA
<213> ORGANISM: MEGATHURA CRENULATA

<400> SEQUENCE: 100

```
catgatatta gttcgcacca cctgtcgctc aacaaggttc gtcatgatct gagtacactg     60
agtgagcgag atattggaag ccttaaatat gctttgagca gcttgcaggc agatacctca    120
gcagatggtt ttgctgccat tgcatccttc catggtctgc ctgccaaatg taatgacagc    180
cacaataacg aggtggcatg ctgtatccat ggaatgccta cattccccca ctggcacaga    240
ctctacaccc tccaatttga gcaagctcta agaagacatg gctctagtgt agcagtaccc    300
tactgggact ggacaaagcc aatacataat attccacatc tgttcacaga caaagaatac    360
tacgatgtct ggagaaataa agtaatgcca aatccatttg cccgagggta tgtcccctca    420
cacgatacat acacggtaag agacgtccaa gaaggcctgt tccacctgac atcaacgggt    480
gaacactcag cgcttctgaa tcaagctctt ttggcgctgg aacagcacga ctactgcgat    540
tttgcagtcc agtttgaagt catgcacaac acaatccatt acctagtggg aggacctcaa    600
gtctattctt tgtcatccct tcattatgct tcatatgatc cgatcttctt catacaccac    660
tcctttgtag acaaggtttg ggctgtctgg caggctcttc aagaaaagag aggccttcca    720
tcagaccgtg ctgactgcgc tgttagtctg atgactcaga acatgaggcc tttccattac    780
gaaattaacc ataaccagtt caccaagaaa catgcagttc caaatgatgt tttcaagtac    840
gaactcctgg gttacagata cgacaatctg gaaatcggtg gcatgaattt gcatgaaatt    900
gaaaaggaaa tcaaagacaa acagcaccat gtgagagtgt ttgcagggtt cctccttcac    960
ggaattagaa cctcagctga tgtccaattc cagatttgta aaacatcaga agattgtcac   1020
catggaggcc aaatcttcgt tcttgggggg actaaagaga tggcctgggc ttataaccgt   1080
ttattcaagt acgatattac ccatgctctt catgacgcac acatcactcc agaagacgta   1140
ttccatccct ctgaaccatt cttcatcaag gtgtcagtga cagccgtcaa cggaacagtt   1200
cttccggctt caatcctgca tgcaccaacc attatctatg aacctggtct cggt         1254
```

<210> SEQ ID NO 101
<211> LENGTH: 510
<212> TYPE: DNA
<213> ORGANISM: MEGATHURA CRENULATA

<400> SEQUENCE: 101

```
gaccatcacg aagatcatca ttcttcttct atggctggac atggtgtcag aaaggaaatc     60
aacacactta ccactgcaga ggtggacaat ctcaaagatg ccatgagagc cgtcatggca    120
gaccacggtc caaatggata ccaggctata gcagcgttcc atggaaaccc accaatgtgc    180
cctatgccag atggaaagaa ttactcgtgt tgtacacatg gcatggctac tttcccccac    240
tggcacagac tgtacacaaa acagatggaa gatgccttga ccgcccatgg tgccagagtc    300
ggccttcctt actgggacgg gacaactgcc tttacagctt tgccaacttt tgtcacagat    360
gaagaggaca atcctttcca tcatggtcac atagactatt tgggagtgga tacaactcgg    420
tcgccccgag acaagttgtt caatgatcca gagcgaggat cagaatcgtt cttctacagg    480
caggttctct tggctttgga gcagacagat                                     510
```

<210> SEQ ID NO 102

<211> LENGTH: 942
<212> TYPE: DNA
<213> ORGANISM: MEGATHURA CRENULATA

<400> SEQUENCE: 102

```
ggcctgccct actgggattg gaccatgcca atgagtcatt tgccagaact ggctacaagt     60
gagacctacc tcgatccagt tactggggaa actaaaaaca accctttcca tcacgcccaa    120
gtggcgtttg aaaatggtgt aacaagcagg aatcctgatg ccaaactttt tatgaaacca    180
acttacggag accacactta cctcttcgac agcatgatct acgcatttga gcaggaagac    240
ttctgcgact ttgaagtcca atatgagctc acgcataatg caatacatgc atgggttgga    300
ggcagtgaaa agtattcaat gtcttctctt cactacactg cttttgatcc tatattttac    360
ctccatcact caaatgttga tcgtctctgg gccatttggc aagctcttca aatcaggaga    420
ggcaagtctt acaaggccca ctgcgcctcg tctcaagaaa gagaaccatt aaagcctttt    480
gcattcagtt ccccactgaa caacaacgag aaaacgtacc acaactctgt ccccactaac    540
gtttatgact atgtgggagt tttgcactat cgatatgatg accttcagtt tggcggtatg    600
accatgtcag aacttgagga atatattcac aagcagacac aacatgatag aacctttgca    660
ggattcttcc tttcatatat tggaacatca gcaagcgtag atatcttcat caatcgagaa    720
ggtcatgata aatacaaagt gggaagtttt gtagtacttg gtggatccaa agaaatgaaa    780
tggggctttg atagaatgta caagtatgag atcactgagg ctctgaagac gctgaatgtt    840
gcagtggatg atgggttcag cattactgtt gagatcaccg atgttgatgg atctccccca    900
tctgcagatc tcattccacc tcctgctata atctttgaac gt                       942
```

<210> SEQ ID NO 103
<211> LENGTH: 1248
<212> TYPE: DNA
<213> ORGANISM: MEGATHURA CRENULATA

<400> SEQUENCE: 103

```
gctgatgcca aagactttgg ccatagcaga aaaatcagga aagccgttga ttctctgaca     60
gtcgaagaac aaacttcgtt gaggcgagct atggcagatc tacaggacga caaaaacatca    120
gggggtttcc agcagattgc agcattccac ggagaaccaa aatggtgtcc aagccccgaa    180
gcggagaaaa aatttgcatg ctgtgttcat ggaatggctg ttttccctca ctggcacaga    240
ttgctgacag ttcaaggaga aaatgctctg aggaaacatg gctttactgg tggactgccc    300
tactgggact ggactcgatc aatgagcgcc cttccacatt ttgttgctga tcctacttac    360
aatgatgcta tttccagcca ggaagaagat aacccatggc atcatggtca catagactct    420
gttgggcatg atactacaag agatgtgcgt gatgatcttt atcaatctcc tggtttcggt    480
cactacacag atattgcaaa acaagtcctt ctggcctttg agcaggacga tttctgtgat    540
tttgaggtac aatttgaaat tgcccataat ttcatacatg ctctggttgg tggtaacgaa    600
ccatacagta tgtcatcttt gaggtatact acatacgatc caatcttctt cttgcaccgc    660
tccaatacag accgactttg ggccatttgg caagctttgc aaaaataccg gggggaaacca    720
tacaacactg caaactgtgc cattgcatcc atgagaaaac cacttcagcc atttggtctt    780
gatagtgtca taaatccaga tgacgaaact cgtgaacatt cggttccttt ccgagtcttc    840
gactacaaga acaacttcga ctatgagtat gagagcctgg catttaatgg tctgtctatt    900
gcccaactgg accgagagtt gcagagaaga aagtcacatg acagagtctt tgcaggattc    960
cttcttcatg aaattggaca gtctgcactc gtgaaattct acgtttgcaa acacaatgta   1020
```

-continued

```
tctgactgtg accattatgc tggagaattc tacattttgg gagatgaagc tgagatgcct   1080

tggaggtatg accgtgtgta caagtacgag ataacacagc agctgcacga tttagatcta   1140

catgttggag ataatttctt ccttaaatat gaagcctttg atctgaatgg cggaagtctt   1200

ggtggaagta tcttttctca gccttcggtg attttcgagc cagctgca                1248
```

```
<210> SEQ ID NO 104
<211> LENGTH: 1257
<212> TYPE: DNA
<213> ORGANISM: MEGATHURA CRENULATA

<400> SEQUENCE: 104

ggttcacacc aggctgatga atatcgtgag gcagtaacaa gcgctagcca cataagaaaa     60

aatatccggg acctctcaga gggagaaatt gagagcatca gatctgcttt cctccaaatt    120

caaaaagagg gtatatatga aacattgcaa aagttccatg gaaaaccagg actttgtgaa    180

catgatggac atcctgttgc ttgttgtgtc catggcatgc ccacctttcc ccactggcac    240

agactgtacg ttcttcaggt ggagaatgcg ctcttagaac gagggtctgc agttgctgtt    300

ccttactggg actggaccga gaaagctgac tctctgccat cattaatcaa tgatgcaact    360

tatttcaatt cacgatccca gacctttgat cctaatcctt tcttcagggg acatattgcc    420

ttcgagaatg ctgtgacgtc cagagatcct cagccagaac tatgggacaa taaggacttc    480

tacgagaatg tcatgctggc tcttgagcaa gacaacttct gtgactttga gattcagctt    540

gagctgatac acaacgccct tcattctaga cttggaggaa gggctaaata ctccctttcg    600

tctcttgatt ataccgcatt tgatcctgta tttttccttc accatgcaaa cgttgacaga    660

atctgggcca tctggcagga cttgcagaga tatagaaaga aaccatacaa tgaggctgac    720

tgcgcagtca acgagatgcg taaacctctt caaccattta ataacccaga acttaacagt    780

gattccatga cgcttaaaca caacctccca caagacagtt ttgattatca aaaccgcttc    840

aggtaccaat atgataacct tcaatttaac cacttcagca tacaaaagct agaccaaact    900

attcaggcta gaaaacaaca cgacagagtt tttgctggct ttattcttca caacattggg    960

acatctgctg ttgtagatat ttatatttgc gttgaacaag gaggagaaca aaactgcaag   1020

acaaaggcgg gttccttcac gattctgggg ggagaaacag aaatgccatt ccactttgac   1080

cgcttgtaca aatttgacat aacgtctgct ctgcataaac ttggtgttcc cttggacgga   1140

catggattcg acatcaaagt tgacgtcaga gctgtcaatg gatcgcatct tgatcaacac   1200

atcctcaacg aaccgagtct gctttttgtt cctggtgaac gtaagaatat atattat      1257
```

```
<210> SEQ ID NO 105
<211> LENGTH: 1239
<212> TYPE: DNA
<213> ORGANISM: MEGATHURA CRENULATA

<400> SEQUENCE: 105

gatgggcttt cacaacataa tcttgtgcga aaagaagtaa gctctcttac aacactggag     60

aaacattttt tgaggaaagc tctcaagaac atgcaagcag atgattctcc agacggatat    120

caagctattg cttctttcca cgctttgcct cctctttgtc caagtccatc tgctgcacat    180

agacacgctt gttgcctcca tggtatggct accttccctc agtggcacag actctacaca    240

gttcagttcg aagattcttt gaaacgacat ggttctattg tcggacttcc atattgggat    300

tggctgaaac cgcagtctgc actccctgat ttggtgacac aggagacata cgagcacctg    360
```

-continued

```
ttttcacaca aaaccttccc aaatccgttc ctcaaggcaa atatagaatt tgagggagag    420

ggagtaacaa cagagaggga tgttgatgct gaacacctct ttgcaaaagg aaatctggtt    480

tacaacaact ggttttgcaa tcaggcacta tatgcactag aacaagaaaa ttactgtgac    540

tttgaaatac agttcgaaat tttgcataat ggaattcatt catgggttgg aggatcaaag    600

acccattcaa taggtcatct tcattacgca tcatacgatc cactgttcta tatccaccat    660

tcgcagacag atcgcatttg ggctatctgg caagctctcc aggagcacag aggtctttca    720

gggaaggaag cacactgcgc cctggagcaa atgaaagacc ctctcaaacc tttcagcttt    780

ggaagtccct ataatttgaa caaacgcact caagagttct ccaagcctga agacacattt    840

gattatcacc gattcgggta tgagtatgat tccctcgaat ttgttggcat gtctgtttca    900

agtttacata actatataaa acaacaacag gaagctgata gagtcttcgc aggattcctt    960

cttaaaggat ttggacaatc agcatccgta tcgtttgata tctgcagacc agaccagagt   1020

tgccaagaag ctggatactt ctcagttctc ggtggaagtt cagaaatgcc gtggcagttt   1080

gacaggcttt acaagtacga cattacaaaa acgttgaaag acatgaaact gcgatacgat   1140

gacacattta ccatcaaggt tcacataaag gatatagctg gagctgagtt ggacagcgat   1200

ctgattccaa ctccttctgt tctccttgaa gaaggaaag                          1239
```

<210> SEQ ID NO 106
<211> LENGTH: 1251
<212> TYPE: DNA
<213> ORGANISM: MEGATHURA CRENULATA

<400> SEQUENCE: 106

```
catgggatca atgtacgtca cgttggtcgt aatcggattc gtatggaact atctgaactc     60

accgagagag atctcgccag cctgaaatct gcaatgaggt ctctacaagc tgacgatggg    120

gtgaacggtt atcaagccat tgcatcattc cacggtctcc cggcttcttg tcatgatgat    180

gagggacatg agattgcctg ttgtatccac ggaatgccag tattcccaca ctggcacagg    240

ctttacaccc tgcaaatgga catggctctg ttatctcacg gatctgctgt tgctattcca    300

tactgggact ggaccaaacc tatcagcaaa ctgcctgatc tcttcaccag ccctgaatat    360

tacgatcctt ggagggatgc agttgtcaat aatccatttg ctaaaggcta cattaaatcc    420

gaggacgctt acacggttag ggatcctcag gacattttgt accacttgca ggacgaaacg    480

ggaacatctg ttttgttaga tcaaactctt ttagccttag agcagacaga tttctgtgat    540

tttgaggttc aatttgaggt cgtccataat gctattcact acttggtggg tggtcgacaa    600

gtttatgctc tttcttctca acactatgct tcatatgacc cagccttctt tattcatcac    660

tcctttgttg acaaaatatg ggcagtctgg caagctctgc aaaagaagag aaagcgtccc    720

tatcataaag cggattgtgc tcttaacatg atgaccaaac caatgcgacc atttgcacac    780

gatttcaatc acaatggatt cacaaaaatg cacgcagtcc ccaacactct atttgacttt    840

caggaccttt tctacacgta tgacaactta gaaattgctg gcatgaatgt taatcagttg    900

gaagcggaaa tcaaccggcg aaaaagccaa acaagagtct ttgccgggtt ccttctacat    960

ggcattggaa gatcagctga tgtacgattt tggatttgca agacagctga cgactgccac   1020

gcatctggca tgatctttat cttaggaggt tctaaagaga tgcactgggc ctatgacagg   1080

aactttaaat acgacatcac ccaagctttg aaggctcagt ccatacaccc tgaagatgtg   1140

tttgacactg atgctccttt cttcattaaa gtggaggtcc atggtgtaaa caagactgct   1200

ctcccatctt cagctatccc agcacctact ataatctact cagctggtga a            1251
```

<210> SEQ ID NO 107
<211> LENGTH: 1185
<212> TYPE: DNA
<213> ORGANISM: MEGATHURA CRENULATA
<220> FEATURE:
<221> NAME/KEY: misc_feature
<222> LOCATION: (164)..(164)
<223> OTHER INFORMATION: n is a, g, c, or t

<400> SEQUENCE: 107

```
gatcatattg ctggcagtgg agtcaggaaa gacgtgacgt ctcttaccgc atctgagata     60
gagaacctga ggcatgctct gcaaagcgtg atggatgatg atggacccaa tggattccag    120
gcaattgctg cttatcacgg aagtcctccc atgtgtcaca tgcntgatgg tagagacgtt    180
gcatgttgta ctcatggaat ggcatctttc cctcactggc acagactgtt tgtgaaacag    240
atggaggatg cactggctgc gcatggagct cacattggca taccatactg ggattggaca    300
agtgcgttta gtcatctgcc tgccctagtg actgaccacg agcacaatcc cttccaccac    360
ggacatattg ctcatcggaa tgtggataca tctcgatctc cgagagacat gctgttcaat    420
gaccccgaac acgggtcaga atcattcttc tatagacagg ttctcttggc tctagaacag    480
acagacttct gccaatttga agttcagttt gaaataacac acaatgcaat ccactcttgg    540
actggaggac atactccata tggaatgtca tcactggaat atacagcata tgatccactc    600
ttttatctcc accattccaa cactgatcgt atctgggcca tctggcaggc actccagaaa    660
tacagaggtt ttcaatacaa cgcagctcat tgcgatatcc aggttctgaa acaacctctt    720
aaaccattca gcgagtccag gaatccaaac ccagtcacca gagccaattc tagggcagtc    780
gattcatttg attatgagag actcaattat caatatgaca cacttacctt ccacggacat    840
tctatctcag aacttgatgc catgcttcaa gagagaaaga aggaagagag aacatttgca    900
gccttcctgt tgcacggatt tggcgccagt gctgatgttt cgtttgatgt ctgcacacct    960
gatggtcatt gtgcctttgc tggaaccttc gcggtacttg gtggggagct tgagatgccc   1020
tggtcctttg aaagattgtt ccgttacgat atcacaaagg ttctcaagca gatgaatctt   1080
cactatgatt ctgagttcca ctttgagttg aagattgttg gcacagatgg aacagaactg   1140
ccatcggatc gtatcaagag ccctaccatt gaacaccatg gagga                   1185
```

<210> SEQ ID NO 108
<211> LENGTH: 309
<212> TYPE: DNA
<213> ORGANISM: MEGATHURA CRENULATA

<400> SEQUENCE: 108

```
ggtcacgatc acagtgaacg tcacgatgga tttttcagga aggaagtcgg ttccctgtcc     60
ctggatgaag ccaatgacct taaaaatgca ctgtacaagc tgcagaatga tcagggtccc    120
aatggatatg aatcaatagc cggttaccat ggctatccat tcctctgccc tgaacatggt    180
gaagaccagt acgcatgctg tgtccacgga atgcctgtat ttccacattg gcacagactt    240
catacaatcc agtttgagag agctctcaaa gaacatggtt ctcatttggg tctgccatac    300
tgggactgg                                                            309
```

NUCLEIC ACID MOLECULE COMPRISING A NUCLEIC ACID SEQUENCE WHICH CODES FOR A HAEMOCYANIN

CROSS-REFERENCE TO RELATED APPLICATIONS

This is a division of application Ser. No. 09/936,852 filed Jul. 3, 2002 now U.S. Pat. No. 7,125,556, which application claims benefit of PCT application PCT/EP00/02410 filed 17 Mar. 2000 that claimed benefit of German application No. 199 39 578.0 filed 20 Aug. 1999 and German application No. 199 11 971.6 filed 17 Mar. 1999.

BACKGROUND OF THE INVENTION

The present invention relates to a nucleic acid molecule comprising a nucleic acid sequence which codes for a haemocyanin, a haemocyanin domain or a fragment with the immunological properties of at least one domain of haemocyanin, constructs which comprise this, host cells which comprise the nucleic acid sequences or the constructs, processes for the preparation of haemocyanin polypeptides, and recombinant haemocyanin polypeptides.

Haemocyanin is a blue copper protein which occurs in a freely dissolved form in the blood of numerous molluscs and arthropods and transports oxygen. Of the molluscs, the cephalopods, chitons, most gastropods and some bivalves contain haemocyanin. Among the arthropods, haemocyanin is typical of arachnids, xiphosurans, malacostracan crustaceans and *Scutigera*. Numerous species of insects contain proteins which are derived from haemocyanin. Haemocyanins are present in the extracellular medium and float in the haemolymph.

While arthropod haemocyanin has a maximum diameter of 25 nm under an electron microscope and a subunit has a molecular weight of 75,000 Da, mollusc cyanins are much larger. Thus e.g. the haemocyanin of *Megathura* has a diameter of 35 nm and is composed of 2 subunits. Each subunit has a molecular weight of approx. 400,000 Da and is divided into eight oxygen-binding domains, each of which has a molecular weight of approx. 50,000. The domains differ immunologically. These domains can be liberated from the subunit by limited proteolysis.

The haemocyanin of gastropods visible under an electron microscope has a molecular weight of approx. 8 million Da and is a di-decamer. In contrast to this, the haemocyanin of cephalopods is arranged as an isolated decamer, which also differs significantly from the haemocyanin of gastropods in the quaternary structure.

The haemocyanin of the Californian keyhole limpet *Megathura crenulata* is of particular immunological interest. The haemocyanin is therefore also called keyhole limpet haemocyanin (KLH). Haemocyanins are very potent antigens. Immunization of a vertebrate leads to a non-specific activation of the immune system which to date is not very well understood. By the general activation of the immune system, it is then possible also to achieve an immune reaction to other foreign structures which have previously been tolerated. KLH is used above all as a hapten carrier in order thus to achieve the formation of antibodies against the hapten.

In addition to *Megathura crenulata*, the abalone *Haliotis tuberculata* also belongs to the Archaegastropoda group, which is relatively old in respect of evolution. It is known that *Haliotis* also produces haemocyanin.

KLH is a mixture of two different haemocyanins, which are called KLH1 and KLH2. The subunit of KLH1 is a 390 kDa polypeptide which consists of eight globular domains called 1a to 1h according to their sequence in the subunit. On the other hand, KLH2 has a molecular weight of 350 kDa and according to the most recent data also contains 8 domains, called 2a to 2h. In vivo every type of subunit forms homo-oligomers, while no hetero-oligomers have been observed.

Amino-terminal, internal and carboxy-terminal domains have been obtained by limited proteolysis and crossed immunoelectrophoresis of the subunit of KLH1 and KLH2, and their amino-terminal sequences has been determined (Söhngen et al., Eur. J. Biochem. 248 (1997), 602-614; Gebauer et al., Zoology 98(1994), 51-68). However, the resulting sequences do not allow designing of sequence-specific primers and/or probes which promise success for hybridization with genomic DNA. Although both KLH types have been known since 1991 and 1994 respectively, it has so far not been possible to clarify the primary structure.

At the DNA level, in respect of molluscs only the cDNA sequence of the haemocyanin subunit from the cephalopod *Octopus dofleini* is so far known (Miller et al., J. Mol. Biol. 278 (1998), 827-842). *Octopus dofleini* is phylogenetically very far removed from the archaegastropods. A haemocyanin gene sequence from molluscs is so far not known at all.

As described by Miller at al. supra, it is difficult both to isolate a single functional domain (functional unit=domain; also called functional domain) and to obtain tissue which is suitable for purification of mRNA for cDNA sequencing.

There is a further difficulty in the analysis of the haemocyanin from *Megathura crenulata* in that the test animals must have reached an age of 4 to 8 years for haemolymph to be taken from them in the first place. After the haemolymph has been taken, haemocyanin is not subsequently produced in these animals. It is not yet known how haemocyanin synthesis could be stimulated. Furthermore, culture of *Megathura* is extremely expensive, since special flow basins are required for this.

BRIEF SUMMARY OF THE INVENTION

It is therefore an object of the present invention to provide means and ways in order to be able to produce haemocyanin and/or domains thereof in a sufficient amount and inexpensively. This includes the further object of providing a process with which this haemocyanin can be prepared.

This object is achieved according to the invention by a nucleic acid molecule comprising a nucleic acid sequence which codes for a haemocyanin, a haemocyanin domain or a functional fragment thereof with the immunological properties of at least one domain of a haemocyanin, the nucleic acid sequence being selected from (a) nucleic acid sequences which are selected from the group consisting of the DNA sequences shown below or the corresponding RNA sequences or which contain these:

SEQ ID NO:1 (HtH1 domain a+signal peptide),
SEQ ID NO:2 (HtH1 domain b),
SEQ ID NO:3 (HtH1 domain c),
SEQ ID NO:4 (HtH1 domain d),
SEQ ID NO:5 (HtH1 domain e),
SEQ ID NO:6 (HtH1 domain f),
SEQ ID NO:7 (HtH1 domain g),
SEQ ID NO: 8 (HtH1 domain h),
SEQ ID NO:9 (partial HtH2 domain b),
SEQ ID NO:10 (HtH2 domain c),
SEQ ID NO:11 (HtH2 domain d), SEQ ID NO:12 (HtH2 domain e),
SEQ ID NO:13 (HtH2 domain f),
SEQ ID NO:14 (HtH2 domain g),
SEQ ID NO:15 (HtH2 domain h),
SEQ ID NO:16 (partial KLH1 domain b),
SEQ ID NO:17 (KLH1 domain c),
SEQ ID NO:18 (KLH1 domain d),
SEQ ID NO:19 (partial KLH1 domain e),
SEQ ID NO:20 (KLH2 domain b),
SEQ ID NO:21 (KLH2 domain c),
SEQ ID NO:22 (partial KLH2 domain d),
SEQ ID NO:23 (KLH2 domain g),
SEQ ID NO:24 (partial KLH2 domain h),
SEQ ID NO:49 (HtH1 domain a'+signal peptide),
SEQ ID NO:50 (partial HtH2 domain a),
SEQ ID NO:51 (HtH2 domain b'),
SEQ ID NO:52 (HtH2 domain d'),
SEQ ID NO:53 (HtH2 domain e'),
SEQ ID NO:54 (KLH1 domain e'),
SEQ ID NO:55 (KLH1 domain f),
SEQ ID NO:56 (KLH1 domain g),
SEQ ID NO:57 (KLH2 domain b'),
SEQ ID NO:58 (KLH2 domain c'),
SEQ ID NO:59 (KLH2 domain d'),
SEQ ID NO:60 (KLH1 domain e),
SEQ ID NO:61 (KLH2 domain f),
SEQ ID NO:62 (KLH2 domain g'),
SEQ ID NO:80 (HtH1 domain a"+signal peptide),
SEQ ID NO:81 (HtH1 domain b"),
SEQ ID NO:82 (HtH1 domain c"),
SEQ ID NO:83 (HtH1 domain d"),
SEQ ID NO:84 (HtH1 domain e"),
SEQ ID NO:85 (HtH1 domain f"),
SEQ ID NO:86 (HtH1 domain g"),
SEQ ID NO:87 (HtH1 domain h"),
SEQ ID NO:88 (partial HtH2 domain a"),
SEQ ID NO:89 (HtH2 domain b"),
SEQ ID NO:90 (HtH2 domain c"),
SEQ ID NO:91 (HtH2 domain d"),
SEQ ID NO:92 (HtH2 domain e"),
SEQ ID NO:93 (HtH2 domain f"),
SEQ ID NO:94 (HtH2 domain g"),
SEQ ID NO:95 (HtH2 domain h"),
SEQ ID NO:96 (partial KLH1 domain b"),
SEQ ID NO:97 (KLH1 domain c"),
SEQ ID NO:98 (KLH1 domain d"),
SEQ ID NO:99 (KLH1 domain e"),
SEQ ID NO:100 (KLH1 domain f"),
SEQ ID NO:101 (KLH1 domain g"),
SEQ ID NO:102 (KLH2 domain b"),
SEQ ID NO:103 (KLH2 domain c"),
SEQ ID NO:104 (KLH2 domain d"),
SEQ ID NO:105 (KLH2 domain e"),
SEQ ID NO:106 (KLH2 domain f"),
SEQ ID NO:107 (KLH2 domain g"),
SEQ ID NO:108 (partial KLH2 domain h"), b) nucleic acid sequences which hybridize with the counter-strand of a nucleic acid sequence according to (a) and code for a polypeptide which has the immunological properties of at least one domain of a haemocyanin;

(c) nucleic acid sequences which on the basis of the genetic code are degenerated to the DNA sequences defined under (a) and (b) and code for a polypeptide which has the immunological properties of at least one domain of a haemocyanin;

(d) nucleic acid sequences which hybridize with one of the nucleic acid sequences described under (a) to (c) and the counter-strand of which codes for a polypeptide which has the immunological properties of at least one domain of a haemocyanin;

(e) nucleic acid sequences which are at least 60% homologous to one of the nucleic acid sequences described under (a);

(f) variants of the sequences described under (a) to (e), the variants containing additions, deletions, insertions or inversions and coding for a polypeptide which has the immunological properties of at least one domain of haemocyanin; and (g) combinations of several of the DNA sequences described under (a) to (f).

Some terms are explained in more detail below in order to clarify how they are to be understood in connection with the present application.

The term "haemocyanin" as used below in the description includes complete haemocyanin, haemocyanin domains and/or fragments, haemocyanin mutants and fusion proteins. In respect of fusion proteins, these include, in particular, those in which the fusion comprises haemocyanin and antigens.

"Domains" are understood as meaning functional partial sequences of the haemocyanin subunits which can be separated from one another, for example, by limited proteolysis. They can furthermore have different immunological properties.

The "immunological properties of at least one domain of haemocyanin" means the property of a polypeptide of inducing, in the same manner as at least one domain of haemocyanin, an immunological response of the recipient immunized with the polypeptide. "Immunological response" here is understood as meaning T and/or B cell responses to haemocyanin epitopes, such as, for example, an antibody production. The immunological reaction can be observed, for example, by immunization of a mammal, such as e.g. a mouse, a rat or a rabbit, with the corresponding polypeptide and comparison of the immune response to the polypeptide used for the immunization with the immune response to natural haemocyanins.

According to the invention, the term "antigen" includes both haptens and weak and potent antigens. Haptens are characterized in that they are substances of low molecular weight (less than 4,000 Da), but without being coupled to a carrier molecule are not capable of inducing an immunological reaction. Weak antigens are substances which can themselves already induce an immunological reaction and of which the potential to be able to induce an immunological reaction can be increased further by coupling with a carrier molecule at the protein and/or DNA level.

"His tag" means a sequence of at least 6 histidine amino acids which, by corresponding cloning and fusion with an expressible sequence, leads to a fusion protein which has at least 6 His residues on the $NH_2$ terminus and can easily be purified by complexing with an $Ni^{2+}$ column.

"Cloning" is intended to include all cloning methods known in the prior art which could be employed here but which are not all described in detail because they belong to the obvious hand tools of the skilled person.

"Variants" of a nucleic acid sequences include additions, deletions, insertions or inversions and code for a polypeptide which has the immunological properties of at least one domain of a haemocyanin. Variants can be synthetic or natural. Allelic variants are an example of natural variants.

"Recombinant expression in a suitable host cell" is to be understood as meaning all the expression methods known in the prior art in known expression systems which could be employed here but which are not all described in detail because they belong to the obvious hand tools of the skilled person.

The nucleic acid sequence contained in the nucleic acid molecule according to the invention can be genomic DNA, cDNA or synthetic DNA, synthetic DNA sequences also being understood as meaning those which comprise modified internucleoside bonds. The nucleic acid sequences can furthermore be RNA sequences, which may be necessary e.g. for expression by means of recombinant vector systems. The nucleic acid sequences according to (b) are obtainable, for example, by using a detectably marked probe which corresponds to one of the sequences described under (a) or a fragment, or a counter-strand thereof for screening cDNA/genomic DNA libraries from molluscs or arthropods. The mRNA on which the cDNA library is based is preferably to be obtained from mollusc tissues which express haemocyanin to a particularly high degree, such as e.g. mantle tissue from gastropods and branchial gland tissue from cephalopods.

Positive cDNA/genomic DNA clones are identified by standard methods. Cf. Maniatis et al., Molecular Cloning (1989) Cold Spring Harbor Laboratory Press.

In a preferred embodiment, the hybridization described under (b) or (d) is carried out under stringent conditions. Stringent hybridization conditions are e.g. 68° C. overnight in 0.5×SSC; 1% blocking reagent (Boehringer Mannheim); 0.1% sodium lauryl sarcosinate and subsequent washing with 2×SSC; 0.1% SDS.

In a preferred embodiment, nucleic acid sequences which are at least 60% homologous to one of the nucleic acid sequences described under (a) are provided. The nucleic acid sequences are preferably at least 80% homologous to one of the nucleic acid sequences described under (a). The nucleic acid sequences are particularly preferably at least 90% homologous to one of the nucleic acid sequences described under (a). In particular, the nucleic acid sequences are at least 95% homologous to one of the nucleic acid sequences described under (a).

According to the invention, the term "homology" means homology at the DNA level, which can be determined by known methods, e.g. computer-assisted sequence comparisons (Basic local alignment search tool, S. F. Altschul et al., J. Mol. Biol. 215 (1990), 403-410).

The term "homology" known to the skilled person describes the degree to which two or more nucleic acid molecules are related, this being determined by the concordance between the sequences. The percentage of "homology" is obtained from the percentage of identical regions in two or more sequences, taking into account gaps or other sequence peculiarities.

The homology of nucleic acid molecules which are related to one another can be determined with the aid of known methods. As a rule, special computer programs with algorithms which take account of the particular requirements are employed.

Preferred methods for the determination of homology initially produce the greatest concordance between the sequences analysed. Computer programs for determination of the homology between two sequences include, but are not limited to, the GCG program package, including GAP (Devereux, J., et al., Nucleic Acids Research 12 (12): 387 (1984); Genetics Computer Group University of Wisconsin, Madison, (Wis.)); BLASTP, BLASTN and FASTA (Altschul, S. et al., J. Mol. Biol. 215:403-410 (1990)). The BLASTX program can be obtained from the National Centre for Biotechnology Information (NCBI) and from other sources (BLAST Handbook, Altschul S., et al., NCB NLM NIH Bethesda MD 20894; Altschul, S., et al., J. Mol. Biol. 215:403-410 (1990)). The known Smith Waterman algorithm can also be used for determining homologies.

Preferred parameters for the comparison of nucleic acid sequences include the following:

| | |
|---|---|
| Algorithm: | Needeman and Wunsch, J. Mol. Biol 48: 443-453 (1970) |
| Comparison matrix: | Concordance (matches) = +10<br>Non-concordance (mismatch) = 0 |
| Gap penalty: | 50 |
| Gap length penalty: | 3 |

The GAP program is also suitable for use with the above parameters. The above parameters are the default parameters for nucleic acid sequence comparisons.

Further algorithms, gap opening penalties, gap extension penalties and comparison matrices by way of example, including those mentioned in the Program Handbook, Wisconsin Package, version 9, September 1997, can be used. The choice depends on the comparison to be made and furthermore on whether the comparison is to be made between sequence pairs, in which case GAP or Best Fit are preferred, or between a sequence and a comprehensive sequence databank, in which case FASTA or BLAST are preferred.

A concordance of 60% determined with the abovementioned algorithm is designated 60% homology in the context of this application. The same applies accordingly to higher degrees of homology.

In a preferred embodiment, the DNA sequence according to the invention is a combination of several of the DNA sequences described under (a) to (f), which can be obtain by fusion and optionally cloning, which are known to the skilled person. These combinations are of particular interest, since they are particularly immunogenic. Combinations which contain several or all of the domains in the sequence (a to h) which occurs naturally in the subunit are particularly preferred. Embodiments in which the nucleic acid sequences which code for the domains are coupled to one another directly in frame are particularly preferred.

Constructs which comprise the nucleic acid molecules according to the invention are furthermore provided. In a preferred embodiment, the construct according to the invention comprises a promoter which is suitable for expression, the nucleic acid sequence being under the control of the promoter. The choice of promoter depends on the expression system used for expression. Generally, constitutive promoters are preferred, but inducible promoters, such as e.g. the metallothionein promoter, are also possible.

In a further preferred embodiment, the construct furthermore comprises an antigen-coding nucleic acid sequence which is bonded directly to the haemocyanin nucleic acid according to the invention. The antigen-coding sequence can be located both 5' and 3' relative to the haemocyanin sequence or also on both ends. It either follows the haemocyanin sequence directly in the same reading frame, or is coupled to it by a nucleic acid linker, the reading frame being preserved. By fusion of the antigen-coding sequence with the haemocyanin sequence the formation of a fusion protein in which the antigen-coding sequence is bonded covalently to the haemocyanin sequence is intended. The antigen according to the invention is a medically relevant antigen, which is selected, for example, from: tumour antigens, virus antigens and antigens of bacterial or parasitic pathogens. Tumour antigens can be, for example, Rb and p53. The virus antigens preferably originate from immunologically relevant viruses, such as e.g. influenza virus, hepatitis virus and HIV. Pathogen antigens are, inter alia, those from mammalian pathogens, in particular organisms which are pathogenic to humans, such as e.g. Plasmodium. Bacterial antigens can originate e.g. from *Klebsiella, Pseudomonas, E. coli, Vibrio cholerae, Chlamydia, Streptococci* or *Staphylococci.*

In another preferred embodiment, the construct furthermore comprises at least a part of a vector, in particular regulatory regions, the vector being selected from: bacteriophages, such as □ derivatives, adenoviruses, vaccinia viruses, baculoviruses, SV40 viruses and retroviruses, preferably MoMuLV (Moloney murine leukaemia virus).

A construct which additionally comprises a His tag-coding DNA sequence, which, when expressed, leads to the formation of a fusion protein with a His tag on the $NH_2$ terminus of the haemocyanin, facilitating purification of the protein on a nickel column by chelate formation, is furthermore preferred.

The invention furthermore provides host cells which contain the construct and which are suitable for expression of the construct. Numerous prokaryotic and eukaryotic expression systems are known in the prior art, the host cells being selected, for example, from prokaryotic cells, such as *E. coli* or *B. subtilis*, from eukaryotic cells, such as yeast cells, plant cells, insect cells and mammalian cells, e.g. CHO cells, COS cells or HeLa cells, and derivatives thereof. For example certain CHO production lines of which the glycosylation patterns are altered compared with CHO cells are known in the prior art. The haemocyanins obtained using glycosylation-deficient or glycosylation-reduced host cells possibly have additional epitopes which are otherwise not accessible to the immune system of the recipient in the case of complete glycosylation, so that haemocyanins with a reduced glycosylation under certain circumstances have an increased immunogenicity. From plant cells transformed with the construct according to the invention it is possible to produce transgenic plants or plant cell cultures which produce haemocyanin polypeptides, for example tobacco, potato, tomato, sugar beet, soya bean, coffee, pea, bean, rape, cotton, rice or maize plants or plant cell cultures.

The present invention also relates to a process for the preparation of a haemocyanin polypeptide. For this, the nucleic acid molecule according to the invention and/or the construct is expressed in a suitable host cell and the protein is isolated from the host cell or the medium by means of conventional processes.

Numerous processes for expression of DNA sequences are known to the skilled person; compare Recombinant Gene Expression Protocols in Methods in Molecular Biology, volume 62, Humana Press Totowa New Jersey (1995). The expression can be both constitutive and inducible, inducers such as, for example, IPTG and $Zn^{2+}$ being known to the skilled person. If a His tag has been fused on to the $NH_2$ terminus of the haemocyanin, the haemocyanin prepared can be purified by chelate formation on a nickel column. Processes for the purification of haemocyanin, in particular KLH, are to be found in Harris et al., Micron 26 (1995), 201-212. The haemocyanin is preferably purified by ion exchange chromatography and/or gel filtration chromatography. The procedure for these measures is known to the skilled person.

In another preferred embodiment, the haemocyanin prepared according to the invention is modified. The modifications include di-, oligo- and polymerization of the monomeric starting substance, for example by crosslinking, e.g. by means of dicyclohexylcarbodiimide or pegylation or association (self assembly). The di-, oligo- and polymers prepared in this way can be separated from one another by gel filtration. The formation of decamers, didecamers or multidecamers is intended in particular. Further modifications include side chain modifications, for example of ε-amino-lysine residues of the haemocyanin, or amino- or carboxy-terminal modifications. Modification of the haemocyanin by covalent bonding to an antigen is particularly preferred, it being possible for the antigen to be reacted stoichiometrically or non-stoichiometrically with the haemocyanin. The antigen is preferably selected from tumour antigens, virus antigens and pathogen antigens, as mentioned above. Further modifications include post-translational events, e.g. glycosylation or partial or complete deglycosylation of the protein.

In a preferred embodiment, the haemocyanin obtained by recombinant expression in prokaryotes or glycosylation-deficient eukaryotes is non-glycosylated. Haemocyanin which is glycosylated by recombinant expression in eukaryotes which are capable of glycosylation, such as yeast cells, plant cells, insect cells or mammalian cells, such as CHO cells or HeLa cells, is also possible according to the invention.

Haemocyanin polypeptides which comprise an amino acid sequence, the amino acid sequence being coded by one or more of the nucleic acid molecules according to the invention, are provided in another embodiment, Haemocyanin polypeptides which comprise at least one amino acid sequence selected from the following group:

SEQ ID NO:25 (HtH1 domain a+signal peptide),
SEQ ID NO:26 (HtH1 domain b),
SEQ ID NO:27 (HtH1 domain c),
SEQ ID NO:28 (HtH1 domain d),
SEQ ID NO:29 (HtH1 domain e),
SEQ ID NO:30 (HtH1 domain f),
SEQ ID NO:31 (HtH1 domain g),
SEQ ID NO:32 (HtH1 domain h),
SEQ ID NO:33 (partial HtH2 domain b),
SEQ ID NO:34 (HtH2 domain c),
SEQ ID NO:35 (HtH2 domain d),
SEQ ID NO:36 (HtH2 domain e),
SEQ ID NO:37 (HtH2 domain f),
SEQ ID NO:38 (HtH2 domain g),
SEQ ID NO:39 (HtH2 domain h),
SEQ ID NO:40 (partial KLH1 domain b),
SEQ ID NO:41 (KLH1 domain c),
SEQ ID NO:42 (partial KLH1 domain d),
SEQ ID NO:43 (partial KLH1 domain e),
SEQ ID NO:44 (KLH2 domain b),
SEQ ID NO:45 (KLH2 domain c),
SEQ ID NO:46 (partial KLH2 domain d),
SEQ ID NO:47 (KLH2 domain g),
SEQ ID NO:48 (partial KLH2 domain h),
SEQ ID NO:63 (HtH1 domain a'+signal peptide),
SEQ ID NO:64 (HtH1 domain h'),
SEQ ID NO:65 (partial HtH2 domain a),
SEQ ID NO:66 (HtH2 domain b'),
SEQ ID NO:67 (HtH2 domain d'),
SEQ ID NO:68 (HtH2 domain e'),
SEQ ID NO:69 (partial KLH1 domain b'),
SEQ ID NO:70 (KLH1 domain e'),
SEQ ID NO:71 (KLH1 domain f),
SEQ ID NO:72 (KLH1 domain g),
SEQ ID NO:73 (KLH1 domain h),
SEQ ID NO:74 (KLH2 domain b'), SEQ ID NO:75 (KLH2 domain c'),
SEQ ID NO:76 (KLH2 domain d'),
SEQ ID NO:77 (KLH2 domain e),
SEQ ID NO:78 (KLH2 domain f),
SEQ ID NO:79 (KLH2 domain g'), or a fragment of one of these sequences which has the immunological properties of at least one domain of haemocyanin are preferred.

The invention also includes haemocyanin polypeptides of which the sequence shows at least 60% or 70%, preferably at least 80%, particularly preferably at least 90% or 95% homology to one of the amino acid sequences according to SEQ ID NO:25 to 48 and SEQ ID NO:63 to 79 over a partial region of at least 90 amino acids.

In this connection, the expression "at least 70%, preferably at least 80%, particularly preferably at least 90% homology" relates to concordance at the amino acid sequence level, which can be determined by known methods, e.g. computer-assisted sequence comparisons (Basic local alignment search tool, S. F. Altschul et al., J. Mol. Biol. 215 (1990), 403-410).

The term "homology" known to the skilled person describes here the degree to which two or more polypeptide molecules are related, this being determined by the concordance between the sequences, concordance being understood as meaning both identical concordance and conservative amino acid exchange. The percentage of "homology" is obtained from the percentage of regions in concordance in two or more sequences, taking into account gaps or other sequence peculiarities.

The expression "conservative amino acid exchange" relates to an exchange of an amino acid residue for another amino acid residue, where the exchange does not lead to a change in polarity or charge. An example of a conservative amino acid exchange is the exchange of a non-polar amino acid residue for another non-polar amino acid residue.

The homology of polypeptide molecules which are related to one another can be determined with the aid of known methods. As a rule, special computer programs with algorithms which take account of the particular requirements are employed. Preferred methods for the determination of homology initially produce the greatest concordance between the sequences analysed. Computer programs for determination of the homology between two sequences include, but are not limited to, the GCG program package, including GAP (Devereux, J., et al., Nucleic Acids Research 12 (12): 387 (1984); Genetics Computer Group University of Wisconsin, Madison, (Wis.)); BLASTP, BLASTN and FASTA (Altschul, S. et al., J. Molec. Biol. 215:403/410 (1990)). The BLAST X program can be obtained from the National Centre for Biotechnology Information (NCBI) and from other sources (BLAST Handbook, Altschul S., et al., NCB NLM NIH Bethesda MD 20894; Altschul, S., et al., J. Mol. 215:403/410 (1990)). The known Smith Waterman algorithm can also be used for determining homology.

Preferred parameters for the sequence comparison include the following:

| | |
|---|---|
| Algorithm: | Needleman and Wunsch, J. Mol. Biol 48: 443-453 (1970) |
| Comparison matrix: | BLOSUM 62 of Henikoff and Henikoff, Proc. Natl. Acad. Sci. USA 89: 10915-10919 (1992) |
| Gap penalty: | 12 |
| Gap length penalty: | 4 |
| Similarity threshold: | 0 |

The GAP program is also suitable for use with the above parameters. The above parameters are the standard parameters (default parameters) for amino acid sequence comparisons where gaps at the ends do not reduce the homology value. If sequences are very short compared with the reference sequence, it may furthermore be necessary to increase the expected value to up to 100,000 and where appropriate to reduce the word size down to 2.

Further algorithms, gap opening penalties, gap extension penalties and comparison matrices by way of example, including those mentioned in the Program-Handbuch, Wisconsin-Paket [Program Handbook, Wisconsin Package], version 9, September 1997, can be used. The choice depends on the comparison to be made and furthermore on whether the comparison is to be made between sequence pairs, in which case GAP or best fit are preferred, or between a sequence and a comprehensive sequence database, in which case FASTA or BLAST are preferred.

A concordance of 60% determined with the above mentioned algorithm is designated 60% homology in the context of this Application. The same applies accordingly to higher degrees of homology.

In another embodiment, the invention provides haemocyanin polypeptides which are obtainable by the recombinant preparation method or modifications thereof.

Preferred haemocyanin polypeptides are those which comprise each of the sequences SEQ ID NO: 25 to 32, it being possible for the sequence with SEQ ID NO:25 to be replaced by SEQ ID NO:63 and/or SEQ ID NO:32 to be replaced by SEQ ID NO:64. Haemocyanin polypeptides which are also preferred are those which comprise either the sequences SEQ ID NO: 33 to 39 or the sequences SEQ ID NO:65, 66, 34-39, it being possible for SEQ ID NO:35 to be replaced by SEQ ID NO:67 and/or SEQ ID NO:36 to be replaced by SEQ ID NO:68. These haemocyanin polypeptides are particularly preferably haemocyanin 1 or 2 from *Haliotis tuberculata.*

Haemocyanin 1 from *Haliotis tuberculata*, which has an apparent molecular weight of 370 kDa in SDS-PAGE under reducing conditions, is particularly preferred. Haemocyanin 2 from *Haliotis tuberculata*, which has an apparent molecular weight of 370 kDa in SDS-PAGE under reducing conditions, is furthermore particularly preferred. The haemocyanins are obtainable from whole haemocyanin from *Haliotis tuberculata* by the selective dissociation process described in the examples.

Haemocyanin polypeptides which are furthermore preferred are those which comprise each of the sequences SEQ ID NO: 40 to 43 or the sequences SEQ ID NO:40 to 43 and SEQ ID NO:71 to 73, it being possible in each case for the sequence with SEQ ID NO:40 to be replaced by SEQ ID NO:66 and/or SEQ ID NO:43 to be replaced by SEQ ID NO:70. Haemocyanin polypeptides which are also preferred are those which comprise either each of the sequences SEQ ID NO: 44 to 48 or the sequences SEQ ID NO:44 to 46, 77, 78, 47, 48, it being possible in each case for the sequence with SEQ ID NO:44 to be replaced by SEQ ID NO:74, SEQ ID NO:45 to be replaced by SEQ ID NO:75, SEQ ID NO:46 to be replaced by SEQ ID NO:76 and/or SEQ ID NO:47 to be replaced by SEQ ID NO:79.

These haemocyanin polypeptides are particularly preferably complete haemocyanin 1 (KLH1) or 2 (KLH2) from *Megathura crenulata.*

Non-glycosylated and glycosylated haemocyanin polypeptide obtainable by expression in host cells which are capable or incapable of glycosylation is furthermore provided. Depending on the envisaged use of the haemocyanin polypeptide, the glycosylation pattern of yeast, in particular methylotrophic yeast, of plant cells or of COS or HeLa cells can be preferred.

The invention furthermore relates to pharmaceutical compositions which comprise the nucleic acid molecules according to the invention and physiologically tolerated additives known in the prior art. The pharmaceutical compositions are preferably employed for non-specific immunostimulation in the form of a gene therapy, haemocyanin polypeptides being expressed after transformation with a suitable vector and serving to antigenize the tissue.

In particular, the invention provides the use of a nucleic acid molecule according to the invention which is bonded to an antigen-coding DNA sequence for specific immunization against this antigen. Without being bound to this theory, the immunization here is based on non-specific stimulation of the immune system by haemocyanin polypeptide epitopes and more extensive specific immunization by recognition of antigen epitopes by the immune system.

Such an immunization is particularly valuable in respect of pathogen antigens, and especially in respect of tumour antigens. The usability of the pharmaceutical composition according to the invention for treatment of tumour diseases also results from the cross-reactivity of the haemocyanin-specific antibodies with carbohydrate residues, which occur on the surface of tumours, such as e.g. the Thomsen-Friedenreich antigen, which occurs in the majority of human tumours, such as epithelial carcinomas, ovarian carcinoma, colorectal carcinoma, mammary carcinoma, bronchial carcinoma and bladder carcinoma.

The pharmaceutical compositions according to the invention can furthermore be employed for treatment of parasitic diseases, such as schistosomiasis, and for prevention of cocaine abuse.

Pharmaceutical compositions which comprise a haemocyanin polypeptide according to the invention in combination with one or more physiologically tolerated additives are provided as a further embodiment of the present invention. As already mentioned above, such a haemocyanin polypeptide can consist of a complete haemocyanin subunit, of one or more domains and of one or more fragments of such domains, provided that these fragments still have the immunological properties of at least one domain of a haemocyanin. Such a pharmaceutical composition is suitable e.g. as an antiparasitic composition, antivirus composition or antitumour composition due to either the non-specific immunostimulation, which is to be attributed solely to the haemocyanin, or due to the specific immune reaction to antigens associated with the haemocyanin. It can thus be employed e.g. for treatment of schistosomiasis, epithelial carcinomas, ovarian carcinoma, colorectal carcinoma, mammary carcinoma, bronchial carcinoma and bladder carcinomas, but is also suitable for treatment of high blood pressure. The treatment of high blood pressure is achieved by carrying out an immunization with the aid of haemocyanin-β-adrenergic receptor peptide constructs and/or fusion proteins.

In another embodiment, the pharmaceutical compositions according to the invention are used as vaccines. They can thus make a valuable contribution to the prophylaxis of diseases caused by known pathogens. This applies in particular to pharmaceutical compositions in which a haemocyanin polypeptide is coupled to a virus, virus constituent, killed bacteria, bacteria constituents, in particular surface proteins from virus or bacteria envelopes, DNA, DNA constituents, inorganic or organic molecules, e.g. carbohydrates, peptides and/or glycoproteins.

According to another preferred embodiment, the pharmaceutical composition according to the invention is used for prevention of cocaine abuse.

Liposomes are particularly suitable for administration both of the nucleic acid molecules according to the invention and of the haemocyanin polypeptides. The present invention accordingly relates to liposomes which comprise a nucleic acid molecule according to the invention, a construct according to the invention or a haemocyanin polypeptide according to the invention.

Various methods for the preparation of liposomes which can be used for pharmaceutical purposes are known to the skilled person. The selectivity of the liposomes comprising the nucleic acid molecules or haemocyanin polypeptides according to the invention can be increased by the additional incorporation into the liposome of cell recognition molecules, which bind selectively to target cells. Receptor ligands which bind to receptors of the target cells or, especially in the case of tumours, antibodies directed against surface antigens of the particular target cells envisaged are particularly suitable for this.

The haemocyanin polypeptides according to the invention are furthermore envisaged as carrier molecules for medicaments, such as e.g. cytostatics. The increase in the molecular weight prolongs the physiological half-life of the medicaments considerably since the loss due to ultrafiltration in the kidneys is significantly reduced.

The vaccines are formulated by methods known to the skilled person; in some embodiments the additional use of adjuvants, such as e.g. Freund's adjuvant or polysaccharides, is envisaged.

The invention furthermore provides antibodies which react specifically with the haemocyanin polypeptide according to the invention and are obtainable by immunization of a test animal with a haemocyanin polypeptide. Polyclonal antibodies can be obtained by immunization, for example, of rabbits and subsequent isolation of antisera. Monoclonal antibodies can be obtained by standard methods by immunization of e.g. mice, isolation and immortalization of the spleen cells and cloning of the hybridomas which produce antibodies specific for haemocyanin.

A screening method for identification of tumour-specific DNA in a cell is furthermore provided, this comprising the steps:

a) bringing cell DNA and/or cell protein into contact with a probe comprising the nucleic acid molecule according to the invention and/or the antibody according to the invention and b) detecting the specific binding.

The tumour to be detected is preferably a bladder carcinoma, epithelial carcinoma, ovarian carcinoma, mammary carcinoma, bronchial carcinoma or colorectal carcinoma.

It is intended to illustrate the invention with the following figures and examples, but not to limit this in any way. Further embodiments, which are also included, are accessible to the skilled person on the basis of the description and the examples.

BRIEF DESCRIPTION OF THE SEVERAL VIEWS OF THE DRAWING(S)

FIG. 1 shows the characterization and purification of *Haliotis tuberculata* haemocyanin (HtH):

(a) Electron microscopy of negatively stained whole HtH, which has been purified by ultracentrifugation of cell-free haemolymph;

(b) SDS polyacrylamide gel electrophoresis (7.5% polyacrylamide) of HtH1 compared with KLH (MW 370 kDa);

(c) Native polyacrylamide gel electrophoresis (5% polyacrylamide) of the HtH subunit preparation, the anode being at the lower edge;

(d) Crossed immunoelectrophoresis of the two HtH subunits using anti-HtH antibodies from the rabbit;

(e) Electron microscopy of the remaining HtH1 didecamers (white arrows) after selective dissociation of HtH2 (black arrows);

(f) Elution profile of the gel filtration chromatography (Biogel A15m) in the presence of ammonium molybdate/polyethylene glycol solution (pH 5.9) after selective dissociation of HtH2 into its subunit and subsequent concentration of HtH1 by ultracentrifugation;

(g) Native polyacrylamide gel electrophoresis (6.5% polyacrylamide) of HtH1 and HtH2 subunits purified by gel chromatography compared with the starting material;

(h,i) Crossed immunoelectrophoresis of chromatographically purified HtH subunits; and (j,m) Crossed immunoelectrophoresis of the purified HtH subunits using anti-KLH antibodies from the rabbit which are specific for KLH1 and KLH2.

FIG. 2 shows the analysis of the subunit organization of HtH1, anti-HtH1 antibodies from the rabbit having been used for the immunoelectrophoresis and the anode being on the left-hand side;

(a) Crossed immunoelectrophoresis after limited proteolysis of HtH1 with the aid of elastase;

(b) SDS polyacrylamide gel electrophoresis (7.5% polyacrylamide) of the elastase-cleaved HtH1 subunit;

(c,d,g-j,l,n,p) Crossed immunoelectrophoresis of the elastase cleavage products of the HtH1 subunit;

(e) Crossed immunoelectrophoresis after limited proteolysis of HtH1 with the aid of V8 protease;

(f) SDS polyacrylamide gel electrophoresis (7.5% polyacrylamide) of the V8 protease-cleaved HtH1 subunit;

(k,m,o) Crossed immunoelectrophoresis after limited proteolysis of HtH1 with the aid of the three stated proteases.

FIG. 3 shows the separation of proteolytic cleavage products of the subunit HtH1 with the aid of HPLC.

FIG. 4 shows the cDNA sequence of HtH1 in combination with the intron structure.

FIG. 5 shows the primary structure deduced for HtH1.

FIG. 6 shows the cDNA sequence of HtH2 in combination with the intron structure.

FIG. 7 shows the primary structure deduced for HtH2.

FIG. 8 shows the cDNA sequence of KLH1 in combination with the intron structure.

FIG. 9 shows the primary structure deduced for KLH1.

FIG. 10 shows the cDNA sequence of KLH2 in combination with the intron structure.

FIG. 11 shows the primary structure deduced for KLH2.

EXAMPLES

Material and Methods

1. Preparation of the Haemolymph and Isolation of Haemocyanin

Individuals of the European abalone *Haliotis tuberculata* from the French Atlantic coast region were provided by S.M.E.L (Blainville sur Mer, France) and Biosyn (Fellbach, Germany). The animals were kept in a 300 l sea-water aquarium at 17° C. and fed with brown algae. For removal of the haemolymph, the abalones were placed on ice in a closed plastic bag. After one hour, large volumes of haemolymph had been secreted through their skin. It emerged that the haemocyanin obtained by this process is identical to the haemocyanin which could be collected by cutting a hollow in the foot of cooled-down sea snails using a scalpel blade. The blood cells were separated from the haemolymph by centrifugation at 800 g for 30 min at 4° C. The whole haemocyanin was then immediately sedimented by preparative ultracentrifugation at 30,000 g for 4 hours at 4° C. The supernatant was discarded and the blue haemocyanin pellet was suspended overnight in "stabilization buffer" (0.05 M Tris, 5 mM $CaCl_2$, 5 mM $MgCl_2$, 0.15 M NaCl, 1 mM PMSF, pH 7.4) and stored at 4° C.

Using the process described by Harris et al., 1995, supra, intact HtH1 was obtained from the whole HtH by selective dissociation of HtH2 in ammonium molybdate/polyethylene glycol (1%/0.2%) solution, pH 5.9 and subsequent ultracentrifugation. The partly purified HtH1 pellet formed was dissolved and purified to homogeneity by gel filtration on a Biogel A15m device. The last step resulted in small amounts of purified HtH2. Native HtH1 and HtH2 was dissociated quantitatively into the subunits by dialysis against "dissociation buffer" (0.13 M glycine/NaOH, pH 9.6) at 4° C. overnight; the presence of EDTA was not necessary. 1 mM PMSF was added at each stage of the purification to inhibit proteolysis.

2. Electron Microscopy

Conventional "negative staining" was carried out by the individual drop method (Harris and Horne in Harris, J. R. (editors) Electron microscopy in biology, (1991), IRL Press Oxford, p. 203-228). Carbon carrier films were initially subjected to glow discharge for 20 seconds to render them hydrophilic and adsorptive for the protein. The protein samples are allowed to adsorb on to the carbon films for 60 seconds. The buffer salts are then removed by sequential washing with four successive 20 μl drops of water. Finally, the gratings are negatively stained with a 20 μl drop of 5% aqueous ammonium molybdate containing 1% trehalose (pH 7.0) and left to dry at room temperature. A Zeiss EM 900 transmission electron microscope is used for the electron microscopy analysis.

3. Polyacrylamide Gel Electrophoresis and Immunoelectrophoresis

SDS polyacrylamide gel electrophoresis (SDS-PAGE) was carried out by the method of Laemmli (Nature 227 (1970), 670-685). An alkaline system according to Markl et al. (1979) J. Comp. Physiol. 133 B, 167-175 with a 0.33 M Tris/borate, pH 9.6 as the gel buffer and 0.065 M Tris/borate, pH 9.6 as the electrode buffer was used for the native PAGE. Crossed and "crossed-line" immunoelectrophoresis (IE) were carried out in accordance with Weeke (Scand. J. Immunol. 2 (1973), Suppl. 1, 47-56) or Kroll (Scand. J. Immunol. 2, Suppl. 1 (1973), 79-81). Rabbit antibodies against dissociated whole HtH and purified HtH1 were produced by Charles River Deutschland (Kisslegg, Germany). The immunization process was carried out in accordance with Markl and Winter (J. Comp. Physiol. 159B (1989), 139-151).

4. Limited Proteolysis and Isolation of the Fragments

The limited proteolysis was carried out at 37° C. in 0.13 M glycine/NaOH, pH 9.6 by addition of one of the following enzymes (Sigma, Deisenhofen, Germany), which were dissolved in 0.1 M $NH_4HCO_3$, pH 8.0: *Staphylococcus aureus* V8 protease type XVII (8400), papain type II from papaya milk (P-3125), bovine pancreas elastase type IV (E-0258), chymotrypsin and trypsin. The haemocyanin concentration was between 1 and 10 mg/ml. The final concentration of the enzyme was 2% (weight/weight). The proteolysis was ended after 5 hours by freezing to −20° C. The HPLC process was carried out on a device from Applied Biosystems (BAI, Bensheim, Germany) equipped with a model 1000S Diode Array detector. The proteolytic fragments were introduced on to a small Mono-Q anion exchanger column (Pharmacia, Freiburg, Germany), which had been equilibrated with 0.02 M Tris/HCl, pH 8.0, and were eluted with a linear sodium chloride gradient (0.0 M-0.5 M CaCl) in the same buffer at a flow rate of 1 ml/min. Alternatively, the proteolytic fragments were isolated by cutting out the bands from native PAGE gels (Markl et al., 1979) J. Comp. Physiol. 133 B, 167-175, after they had first been inversely stained with the Roti-White system (Roth, Karlsruhe, Germany) in accordance with Fernandez-Patron et al. (1995) Anal. Biochem. 224, 203-211. For subsequent cleavage with a second enzyme, the fragments isolated were first dialysed overnight against 0.13 M glycine/NaOH, pH 9.6 to remove NaCl.

5. Amino Acid Sequence Analysis

The proteins obtained by the HPLC process were denatured in SDS-containing sample buffer and separated by SDS-PAGE (Laemmli, 1970, supra; 7.5% polyacrylamide). To prevent blocking of the $NH_2$ terminus, 0.6% (weight/weight) thioglycollic acid was added to the cathode buffer (Walsh et al., Biochemistry 27 (1988), 6867-6876). The protein bands were transferred by electro-transfer to ProBlot membranes (Applied Biosystems, Germany) in a vertical blotting chamber (25 mM borate buffer, pH 8.8, containing 2 mM EDTA; 10 min/100 mA, 15 min/200 mA, 12 h/300 mA). Detection of the individual polypeptides on the membranes was carried out with Ponceau S stain. The polypeptide bands of interest were cut out and sequenced in a 477A protein sequencing device from Applied Biosystems. The amounts of polypeptides applied to the sequencing device were in the lower pmo1 range.

6. cDNA Cloning and Sequence Analysis

A lambda-cDNA expression library was established from poly($A^+$)-RNA from *Haliotis* mantle tissue using the vector Lambda ZAP Express® in accordance with the manufacturer's instructions (Stratagene, Heidelberg, Germany). The clones were isolated using HtH-specific rabbit antibodies. The nucleotide sequencing was carried out on both strands using the Taq Dye deoxy Terminator® system. The sequences were arranged with the software CLUSTAL W (1.7)® and TREEVIEW® (Thompson et al., Nucl. Acids Res. 22 (1994), 4673-4680).

Example 1

Isolation of HtH and Separation of Two Different Types (HtH1 and HtH2)

The haemolymph was obtained from adult abalones. The blood cells were removed by centrifugation and the haemocyanin was then sedimented by ultracentrifugation. The blue haemocyanin pellet was dissolved again in "stabilization buffer" (pH 7.4) and examined by electron microscopy (FIG. 1*a*). It comprised mainly typical di-decamers, accompanied by a small content of decamers and tridecamers. Denaturing in 2% SDS in the presence of reducing substances and subsequent SDS-PAGE separation resulted in a single band, which corresponded to the polypeptide with an apparent molecular weight of 370 kDa, which is only slightly below the apparent subunit weight of KLH (FIG. 1*b*). Complete dissociation of the oligomers and of the di-decamers into the native polypeptides (subunits) was achieved by overnight dialysis of HtH against "dissociation buffer" (pH 9.6). The native PAGE method, which was used on these samples, showed a main and a secondary component (FIG. 1*c*). Crossed immunoelectrophoresis (crossed IE) using polyclonal rabbit antibodies generated against purified whole HtH showed two components which are immunologically different but show the classical reaction of being partly immunologically identical (FIG. 1*d*). Their preparative isolation (FIG. 1*e-i*) showed that they are subunits of two different HtH types, called HtH1 and HtH2, and the patterns of the native PAGE and crossed IE methods could be assigned to each individually (FIG. 1*c, d*).

The separation of HtH1 and HtH2 was carried out by the method of selective dissociation according to Harris et al., 1995, supra. In ammonium molybdate/polyethylene glycol, HtH1 in the oligomer state (di-decamer) was completely stable, while HtH2 dissociated completely into the subunits (FIG. 1*e*). This allowed quantitative sedimentation of HtH1 in an ultracentrifuge, while the majority of the HtH2 remained in the supernatant. Large amounts of HtH1 were purified to homogeneity from the redissolved pellet by gel filtration chromatography, which also resulted in small amounts of pure HtH2 (FIG. 1*f*). The fractions were investigated by native PAGE (FIG. 1*g*) and crossed IE (FIG. 1*h, i*). The process of selective dissociation of HtH2 removed all the tri-decamer from the samples, which suggests that the latter are built up from HtH2, but not from HtH1 (FIG. 1*e*). The selective dissociation behaviour of HtH2 and also the ability to form aggregates which are larger than in vivo di-decamers correspond to the properties of KLH2. Conversely, the stability of HtH1 under these conditions and its inability to assemble into aggregates larger than di-decamers resemble the behaviour of KLH1. This feature of being related is demonstrated further by the reaction of anti-KLH1 and anti-KLH2 antibodies against the two HtH types (FIG. 1*j-m*).

Example 2

Analysis of the Organization of the HtH1 Subunit

The eight functional units (FUs, often called "functional domains") which form a mollusc haemocyanin subunit differ in primary structure and show no immunological cross-reactivity, as emerged from crossed IE. In the case of the purified HtH1 subunit (FIG. 1*g, h*), small concentrations of five different proteases (elastase, V8 protease, papain, trypsin and chymotrypsin) which had cleaved the peptide bonds between adjacent FUs of KLH1 and KLH2 were used (Gebauer et al., 1994, supra, Söhngen et al., 1997, supra). The cleavage products were investigated by crossed IE and SDS-PAGE (FIG. 2). Elastase treatment produces eight individual FUs, deduced from the number of different immunoprecipitation peaks in the crossed IE (FIG. 2*a*) and with the apparent molecular weight of approx. 50 kDa of the main portion of the cleavage products in SDS-PAGE (FIG. 2*b*). A further precipitation peak was recognized as FU dimer, which was formed by incomplete cleavage of the segment ab (FIG. 2*a*). By an HPLC process with a Mono-Q column (FIG. 3*a*), two of the elastase cleavage products were obtained in a sufficient purity to allow their clear assignment to two of the eight precipitation peaks (FIG. 2*c, d*) by "crossed-line IE". The other four proteases had different cleavage patterns, which comprised mixtures of individual FUs and larger fragments containing two, three or more FUs (e.g. FIG. 2*e, f*). Many of them were concentrated to a sufficient amount by the HPLC process (FIG. 3*b-e*) to allow their identification in their corresponding SDS-PAGE and crossed IE patterns. A number of these components were sequenced N-terminally by blot transfer of SDS gels on ProBlot® membranes (Table 1). The results were compared with the N-terminal sequences which had been obtained from the apparently orthologous protein in *Megathura crenulata*, KLH1 (Table I), the complete FU arrangement of which is available (Söhngen et al., 1997, supra; cf. FIG. 5*b*). The result of the entire batch led to the determination of the complete FU arrangement within the HtH1 subunit (FIG. 2*a*).

In particular, cleavage of the HtH1 subunit (1-abcdefgh) with V8 protease resulted in four precipitation peaks in the crossed IE (FIG. 2*e*). The SDS-PAGE showed five different fragments (FIG. 2*f*): 220 kDa (5 FUs), 185 kDa (4 FUs), 100 kDa (2 FUs), 55 kDa (1 FU) and 46 kDa (1 FU). The 100 kDa fragment was isolated by the HPLC method (FIG. 3*b*) and identified by N-terminal sequencing as 1-ab, since the sequence was identical to that of the intact subunit (Table I). In the "crossed-line" IE process, 1-ab fused with three precipitation peaks of the elastase cleavage pattern. On the basis of the evaluation, they represent fragments 1-ab, 1-a and 1-b (FIG. 2*g*). However, it remained unclear which peak represents 1-a and which 1-b. In a second step, the 1-ab purified by HPLC was cleaved by elastase into its component FUs, from which one could be eluted by the native PAGE gel strip method and was assigned to the elastase pattern by the "crossed-line" IE method (FIG. 2*h*) and sequenced N-terminally. This component had the same N-terminal sequence as the whole subunit and was therefore identical to 1-a. The second FU of the 100 kDa fragment is thus 1-b (FIG. 2*a*; Table I). HPLC-purified 1-c and 1-h were also obtained (FIG. 3*b*), identified by N-terminal sequence similarities with the corresponding FUs in KLH1 (Table I) and assigned by the "crossed-line" IE method to their corresponding precipitation peaks in the elastase pattern (FIGS. 2*i, j*). 1-a, 1-b, 1-c and 1-h were furthermore identified (FIG. 2*a*). Using papain for subunit cleavage, five different peaks were obtained in the crossed IE method (FIG. 2*k*). A 100 kDa fragment (2 FUs) was purified from such a sample by the HPLC method (FIG. 3*c*), and, according to the "crossed-line" IE method, contained the FU 1-h already identified and one of the four FUs still not identified and therefore must be 1-gh (FIG. 2*k*, 3*c*). In fact, this fragment had an N-terminal sequence which showed similarities with KLH1-g (Table I). For further confirmation, the HPLC-purified fragment 1-gh was cleaved into its constituent FUs with elastase, from which 1-g was purified and identified by N-terminal sequencing. It was assigned to its peak in the elastase cleavage patter by the "crossed-line" IE method (FIG. 2*l*).

The 220 kDa fragment from the V8 protease cleavage (FIG. 2*e, f*) was purified by HPLC (FIG. 3*b*) and in the "crossed-line" IE method fused with 1-h, 1-g and three peaks of the elastase cleavage pattern which have not yet been identified. The 185 kDa fragment was furthermore obtained in a sufficient purity (FIG. 2*e, f*; 3*b*), and it was shown that it comprised the same components with the exception of 1-h. This suggested that the 22 kDa and the 185 kDa fragment are 1-defgh and 1-defg respectively. In fact, the N-terminal sequence was practically identical and furthermore showed similarity with KLH1-d (Table I). Cleavage of the HtH1 subunit with trypsin resulted in a large number of components in the molecular weight range of one or two FUs (FIG. 2*m*). Several of the components were concentrated in HPLC fractions (FIG. 3*d*). A 100 kDa fragment proved to be particularly useful since it had the same N-terminal sequence as the fragment 1-defg from the v8 protease cleavage (Table I); the 100 kDa fragment should therefore be 1-de. In the "crossed-line" IE method, this component fused with two of the three FU peaks of the elastase cleavage pattern not yet identified (FIG. 2*n*), which should therefore be 1-d and 1-e, and thus left a single possibility for 1-f. The "crossed-line" IE method also showed that FU 1-f was furthermore present in the 1-de fraction (FIG. 2*n*). The identification of 1-f was confirmed by cleavage of the subunit with chymotrypsin (FIG. 2*o*) and a subsequent HPLC process (FIG. 3*e*). This cleavage gave, inter alia, a 95 kDa fragment (2 FUs) which fused with 1-g and a second peak (FIG. 2*p*) in the "crossed-line" IE method and could therefore be either 1-gh (which could be ruled out since 1-h had already been identified) or 1-fg (which seems appropriate on the basis of the further peak in question, which was identical to the remaining candidate). In fact, this fragment showed a new N-terminal sequence which is similar to KLH1-f in a certain manner. The last problem was now to assign the two remaining FU peaks to 1-d and 1-e. This was achieved using HPLC-isolated FUs from samples in which the subunit had been cleaved with elastase. (FIG. 2*c, d*; 3*a*). The more acidic component in the crossed IE method was deduced as 1-d from its N-terminal sequence, which is identical to that of 1-defgh (FIG. 2*c*, Table I), while the more basic component of the 1-d/1-g pair had a new N-terminal sequence (Table I) and therefore had to be 1-e (FIG. 2*a*). The structure of the functional units of subunit HtH1 was thus clarified.

Example 3

Comparison of the molecular weights and N-terminal sequences of the biochemically isolated functional units (FUs) from HtH1 and KLH1. The various FUs, each with an intact binuclear copper-binding site, were liberated from their larger unit as globular segments by limited proteolysis; cf. the section "Isolation and analysis of the units from HtH1". The KLH1 data were obtained from Söhngen et al., supra. The assignment as an actual unit was done on the basis of the molecular weight and the immunological properties (cf. FIG. 2). The unusually low molecular weight of isolated HtH1-d could means that a large peptide was split off C-terminally.

TABLE 1

| Functional unit | Weight (kDa) | N-terminal sequence |
|---|---|---|
| HtH1-a | 53 | DNV**VRK**DVSH**L**TDDEVQ |
| KLH1-a | 50 | ENL**VRK**DVER**L** |
| HtH1-b | 48 | ? |
| KLH1-b | 45 | ? |
| HtH1-c | 46 | FEDEKHSLR**IRK**NVDS**L**TPEENTNERLR |
| KLH1-c | 45 | KVPRSRL**IRK**NVDR**L**TPSE |
| HtH1-d | 40 | VEEVTGASH**IRK**NLND**L**NTGEM |
| KLH1-d | 50 | EVTSANR**IRK**NIEN**L**S |
| HtH1-e | 49 | ILDHDHEEEIL**VRK**NIID**L**SP |
| KLH1-e | 50 | ? |
| HtH1-f | 50 | KLNSRKHTPNR**VRH**ELSS**L**SSRDIASLKA |
| KLH1-f | 45 | HHLSXNK**VRH**DLST**L** |
| HtH1-g | 45 | DHQSGSIAGSG**VRK**DVNT**L**TKAETDNLRE |
| KLH1-g | 45 | SSMAGHF**VRK**DINT**L**TP |
| HtH1-h | 55 | DEHHDDRLADVL**IRK**EVDF**L**SLQEANAIKD |
| KLH1-h | 60 | HEDHHEDIL**VRK**NIHS**L** |

Example 4

Cloning of Haemocyanin cDNA

1. For cloning the cDNA of haemocyanin, mRNA was isolated from the mantle tissue of the particular mollusc. The first cDNA strand was obtained by reverse transcription with Oligo(dT) as a primer. The second strand was obtained conventional synthesis with random primers. The cDNA obtained in this way was cloned in a lambda expression vector to form a cDNA expression library. Using an anti-haemocyanin antibody, the library was searched under suitable conditions, positive clones being obtained. These positive clones were isolated, sequenced and characterized.

2. A cDNA probe was prepared from the N-terminal region of a positive clone obtained, and the cDNA library was searched with this. The positive clones obtained were in turn isolated, sequenced and characterized.

3. To obtain sequences arranged still further to 5', another expression library was established from cDNA, this being obtained with the aid of a combination of haemocyanin-specific and "random" primers. This cDNA library was searched with cDNA probes which correspond to the "N-terminal" regions of the positive clones obtained under (2.). The positive clones obtained were isolated, sequenced and characterized.

Example 5

Cloning of Haemocyanin Genes

Genomic DNA was isolated by standard methods. The PCR reaction was carried out with the aid of haemocyanin-specific primers in order to amplify the gene sections of the haemocyanins of interest. The amplification products obtained were cloned in a suitable vector (for example pGem T or pGem T easy (Promega, Mannheim) sequenced and characterized.

Example 6

Recombinant Expression of Haemocyanin

A PCR reaction was carried out with a cDNA clone which contains the coding sequence for HtH-1d in order to amplify specifically the coding sequence of the domain 1d. Synthetically prepared oligonucleotides were used as primers.

Primer 1 (upstream) comprises six nucleotides of the end of the domain HtH-1c, an SacI cleavage site and 12 nucleotides of the end of the domain HtH-1d.

Primer 2 (downstream) comprises six nucleotides of the start of the domain HtH-1e, an SalI cleavage site and an HtH1-d-specific sequence.

PCR conditions: 2 min 95° C.

30 sec 95° C.

30 sec 55° C.

1 min 72° C.

35 cycles 10 min 72° C.

The amplification product was cloned in the pGEM T easy PCR cloning vector (Promega) in XL-1 Blue (Stratagene). After isolation of the recombinant plasmid and restriction with SacI and SalI, the cDNA of domain 1d could be isolated. The expression vector pQE30 (Qiagen) was also restricted with the corresponding enzymes.

The ligation was then carried out between the HtH-1d-cDNA (restricted with SacI and SalI) and pQE (restricted with SacI and SalI). Directed cloning of the cDNA which codes for HtH-1d in an expression vector is thus possible. The expression of HtH1-d in pQE in XL-1 Blue is carried out in accordance with the manufacturer's instructions. The expression of further HtH1, HtH2 or KLH1 or KLH2 domains can be carried out analogously.

The invention claimed is:

1. An isolated nucleic acid molecule comprising a nucleic acid sequence that codes for a Keyhole Limpit Hemocyanin 1 (KLH1) polypeptide, wherein said nucleic acid sequence is selected from the group consisting of:

(a) a DNA sequence or the corresponding RNA sequence selected from the group consisting of:

SEQ ID NO:16 (partial KLH1 domain b),
SEQ ID NO:17 (KLH1 domain c),
SEQ ID NO:18 (KLH1 domain d),
SEQ ID NO:19 (partial KLH1 domain e),
SEQ ID NO:54 (KLH1 domain e'),
SEQ ID NO:55 (KLH1 domain f),
SEQ ID NO:56 (KLH1 domain g),
SEQ ID NO:96 (partial KLH1 domain b"),
SEQ ID NO:97 (KLH1 domain c"),
SEQ ID NQ:98 (KLH1 domain d"),
SEQ ID NO:99 (KLH1 domain e"),
SEQ ID NO:100 (KLH1 domain f"),
SEQ ID NO:101 (KLH1 domain g"), and nucleic acid sequences which have at least 90% sequence identity to one of the nucleic acid sequence described under (a).

2. The isolated nucleic acid molecule according to claim 1 that hybridizes under stringent hybridization conditions of 0.55×SSC; 1% blocking reagent; 0.1% sodium dodecyl sulfate (SDS) at about 68° C. overnight.

3. The isolated nucleic acid molecule according to claim 1, characterized in that the nucleic acid molecule described under (b) has at least 95 identity to one of the nucleic acid sequences described under (a).

4. The isolated nucleic acid molecule according to claim 1, characterized in that it is a deoxyribonucleic acid molecule.

5. A construct comprising a nucleic acid molecule according to claim 1.

6. The construct according to claim 5, further comprising a promoter that is suitable for expression control, the nucleic acid sequence that codes for said KLH1 polypeptide being under the control of the promoter.

7. The construct according to claim 5, further comprising a nucleic acid sequence that codes for an antigen and is coupled directly to the nucleic acid sequence that codes for said KLH1 polypeptide.

8. The construct according to claim 7, wherein the antigen is selected from the group consisting of: a tumour antigens, a virus antigen and an ancigen of a bacterial or a parasitic pathogen.

9. The construct according to claim 5, wherein the construct comprises at least a part of a vector, the vector being selected from the group consisting of: a bacteriophag, an adenoviruse, a vaccinia viruse, a baculoviruse, a SV4Q virus and a retroviruse.

10. The construct according to claim 5, wherein the construct further comprises a His tag-coding nucleic acid sequence and the expression of the construct leads to the formation of a fusion protein with a His tag.

11. A isolated host cell containing a construct according to claim 5, wherein the host cell is a prokaryotic or eukaryotic cell suitable for expression of the construct.

12. The host cell according to claim 11, characterized in that the prokaryotic host cell is *E. coil* or *Bacillus subtilis.*

13. The host cell according to claim 11, characterized in that the eukaryotic host cell is selected from the group consisting of a yeast cells, a plant cell, an insect cell and a mammalian cell.

14. A process for the preparation of a haemocyanin KLH1 polypeptide, wherein a nucleic acid molecule according to claim 1 is expressed in a suitable host cell and the protein is isolated.

15. The process according to claim 14, characterized in that the haemocyanin KLH1 polypeptide prepared is modified naturally or chemically.

16. The process according to claim 15, characterized in that the modification is a cross-linking or a covalent bonding to an antigen.

17. The process according to claim 14, characterized in that the expression is carried out in a host cell that is a prokaryotic or eukaryotic cell suitable for expression.

18. A composition, comprising a nucleic acid molecule according to claim 1 and a physiologically tolerated additives.

19. The host cell according to claim 11, characterized in that the eukaryotic host cell is a mammalian cell that is a CHO cell, a COS cell or a HeLa cell.

20. A process for the preparation of a haemocyanin KLH1 polypeptide, wherein a construct according to claim 5 is expressed in a suitable host cell and the protein is isolated.

21. The process according to claim 14, characterized in that the haemocyanin KLH1 polypeptide prepared is modified naturally or chemically.

22. The process according to claim 21, characterized in that the modification is a cross-linking or a covalent bonding to an antigen.

23. A composition, comprising a construct according to claim 5 and a physiologically tolerated additive.

24. The composition according to claim 23, characterized in that it is adapted for use for gene therapy treatment of a tumour.

25. An isolated polynucleotide that encodes a haemocyanin Keyhole Limpit Hemocyanin 1 (KLH1) polypeptide comprising, a) at least one amino acid sequence selected from the group consisting of:

SEQ ID NO:40 (partial KLH1 domain b),
SEQ ID NO:41 (KLH1 domain c),
SEQ ID NO:42 (partial KLH1 domain d),
SEQ ID NO:43 (partial KLH1 domain e),
SEQ ID NO:69 (partial KLH1 domain b'),
SEQ ID NO:70 (KLH1 domain e'),
SEQ ID NO:71 (KLH1 domain f),
SEQ ID NO:72 (KLH1 domain g), and
SEQ ID NO:73 (KLH1 domain h), b) or a sequence that is least 90% identical to one of the amino acid sequences of SEQ ID NOs 40-43 or 69-73.

26. An isolated polynucleotide according to claim 25, characterized in that the encoded hemocyanin KLH1 polypeptide comprises either the sequences SEQ ID No: 40 to 43 or the sequence SEQ ID No: 40 to 43 and 71 to 73 and is KLH1 from *Megathura crenulata.*

27. An isolated polynucleotide according to claim 25, wherein said polynucleotide has 90% or greater identity to a nucleotide sequence encoding one of the amino acid sequences set forth in SEQ ID NOs 40-43 or 69-73.

28. An isolated polynucleotide capable of hybridizing to a polynucleotide of claim 27 under stringent hybridization conditions of 0.5×SSC; 1% blocking reagent; 0.1% sodium lauryl sarconsinate and subsequent washing with 2×SSC and 0.1% sodium dodecyl sulfate (SDS) at about 68° C. overnight.

29. The construct according to claim 5 that is a recombinant expression vector.

30. The process according to claim 14, wherein the polynucleotide is linked to an inducible promoter.

31. An isolated polynucleotide according to claim 25, characterized in that the encoded hemocyanin KLH1 polypeptide comprises either the following sequences consecutively: a) SEQ ID Nos: 69, 41, 42, 43 or b) SEQ ID Nos: 69, 41, 42, 70 and 71 to 73 and is KLH1 from *Megathura crenulata*.

* * * * *